US012065647B2

(12) United States Patent
Fishilevich et al.

(10) Patent No.: US 12,065,647 B2
(45) Date of Patent: Aug. 20, 2024

(54) SHORT/SMALL HAIRPIN RNA MOLECULES

(71) Applicants: DOW AGROSCIENCES LLC, Indianapolis, IN (US); QUEENSLAND UNIVERSITY OF TECHNOLOGY, Brisbane (AU)

(72) Inventors: Elane Fishilevich, Indianapolis, IN (US); Kenneth Narva, Indianapolis, IN (US); Xiaozeng Yang, Indianapolis, IN (US); Meghan L. Frey, Indianapolis, IN (US); Murugesan Rangasamy, Indianapolis, IN (US); Wendy Lo, Indianapolis, IN (US); Premchand Gandra, Indianapolis, IN (US); Peter Michael Waterhouse, Newton (AU)

(73) Assignees: DOW AGROSCIENCES LLC, Indianapolis, IN (US); QUEENSLAND UNIVERSITY OF TECHNOLOGY, Brisbane (AU)

(*) Notice: Subject to any disclaimer, the term of this patent is extended or adjusted under 35 U.S.C. 154(b) by 0 days.

(21) Appl. No.: 16/971,893

(22) PCT Filed: Feb. 22, 2019

(86) PCT No.: PCT/AU2019/050146
§ 371 (c)(1),
(2) Date: Aug. 21, 2020

(87) PCT Pub. No.: WO2019/161449
PCT Pub. Date: Aug. 29, 2019

(65) Prior Publication Data
US 2021/0254058 A1 Aug. 19, 2021

Related U.S. Application Data

(60) Provisional application No. 62/773,355, filed on Nov. 30, 2018, provisional application No. 62/633,720, filed on Feb. 22, 2018.

(51) Int. Cl.
C12N 15/113 (2010.01)
A01N 63/60 (2020.01)
C12N 15/82 (2006.01)

(52) U.S. Cl.
CPC ............ C12N 15/113 (2013.01); A01N 63/60 (2020.01); C12N 15/8218 (2013.01); C12N 15/8286 (2013.01); C12N 2310/14 (2013.01); C12N 2310/531 (2013.01)

(58) Field of Classification Search
None
See application file for complete search history.

(56) References Cited

U.S. PATENT DOCUMENTS

| | | | |
|---|---|---|---|
| 8,283,460 B2 | 10/2012 | Ge et al. | |
| 8,410,334 B2* | 4/2013 | Allen | C12N 15/8285 800/286 |
| 2006/0223777 A1 | 10/2006 | Vermeulen et al. | |
| 2013/0291188 A1* | 10/2013 | Bogaert | C12N 15/113 435/418 |
| 2020/0071713 A1* | 3/2020 | Sayre | C12N 15/8218 |

FOREIGN PATENT DOCUMENTS

| | | |
|---|---|---|
| WO | 2008147837 A1 | 12/2008 |
| WO | 2012092544 A3 | 7/2012 |
| WO | 2015084254 A1 | 6/2015 |
| WO | 2016100333 A1 | 6/2016 |
| WO | 2016/134377 A1 | 8/2016 |
| WO | 2017/011771 A1 | 1/2017 |

OTHER PUBLICATIONS

Zeng et al. The EMBO Journal 24, 138-148 (Year: 2005).*
Kozak et al. Proc. Natl. Acad. Sci USA vol. 83 pp. 2850-2854 (Year: 1986).*
Gu et al. Cell 151:900-911, pp. 1-22 (Year: 2012).*
Sheng et al. Front. Bioeng Biotechnol. 8:940, pp. 1-8 (Year: 2020).*
Ni et al. Nature Methods vol. 8, pp. 405-409 (Year: 2011).*
Ni et al. Nature Methods, vol. 8, pp. 405-409, Supplementary information, pp. 1-21 (Year: 2011).*
Song et al. "CAF-1 is essential for *Drosophila* development and involved in the maintenance of epigenetic memory", Developmental Biology, vol. 311, No. 1, pp. 213-222.
Tsutsumi et al. "Recognition of the pre-miRNA structure by *Drosophila* Dicer-1", Nat. Struct. Mol. Biol. vol. 18, No. 10, pp. 1153-1158.
Chang et al. "Generation of Transgenic *Drosophila* Expressing shRNAs in the miR-1 Backbone", Cold Spring Harbour Protocols, vol. 2014, No. 5, XP55846061, DOI: 10.1101/pdb.prot080762.
Yogindran et al. "Artificial miRNA-mediated silencing of ecdysone receptor (EcR) affects larval development and pogenesis in Helicoverpa armigera", Insects Biochemistry and Molecular Biology, vol. 77, pp. 21-30.
International Search Report and Written Opinion, ISA/AU, PCT/AU2019/050146, May 2, 2019, 16 pgs.
Bofill-De Ros, X. et al., "Guidelines for the optimal design of miRNA-based shRNAs," Methods, 2016, vol. 103, pp. 157-166.
Chen, S.-L. et al., "Display female-specific doublsex RNA interference in early generations of transformed oriental fruit fly, *Bactrocera dorsalis* (Hendel)," Pest Management Science, 2011, vol. 67, pp. 466-473.

(Continued)

*Primary Examiner* — Brian Whiteman
(74) *Attorney, Agent, or Firm* — Faegre Drinker Biddle & Reath LLP

(57) ABSTRACT

This disclosure concerns compositions and methods for novel RNA inhibition molecules (e.g., small/short hairpin RNA (shRNA) molecules), polynucleotides encoding such molecules, use of such novel RNA inhibition molecules to inhibit a target gene by suppressing the expression of the mRNA of the target gene, and for application such as the of control insect pests, and transgenic plants that produce, and are protected, by these novel RNA inhibition molecules are described.

12 Claims, 4 Drawing Sheets

Specification includes a Sequence Listing.

(56) References Cited

OTHER PUBLICATIONS

Gu, J. et al., "Development of an Efficient Recombinant Mosquito Densovirus-Mediated RNA Interference System and Its Preliminary Application in Mosquito Control," PLoS One, 2011, vol. 6, No. 6, e21329.

Haley, B., et al., "A simplified miRNA-based gene silencing method for *Drosophila melanogaster*," Developmental Biology, 2008, vol. 321, No. 2, pp. 482-490.

International Preliminary Report on Patentability received for PCT Patent Application No. PCT/AU2019/050146, mailed on Sep. 3, 2020, 11 pages.

International Search Report and Written Opinion received for PCT Patent Application No. PCT/AU2019/050146, mailed on May 2, 2019, 16 pages.

\* cited by examiner

SEQUENCE LISTING

```
<160> NUMBER OF SEQ ID NOS: 421

<210> SEQ ID NO 1
<211> LENGTH: 60
<212> TYPE: DNA
<213> ORGANISM: artificial sequence
<220> FEATURE:
<223> OTHER INFORMATION: IRRNA.27482.8: shRNA targeting WCR COPI? mRNA
      based on Diabrotica virgifera virgifera pre-miR-1 (60 nt)

<400> SEQUENCE: 1
```
ctggtgctga tgacagacac atagtgttat taatcgtatt gtctgtcatc agcaccagag     60

<210> SEQ ID NO 2
<211> LENGTH: 60
<212> TYPE: DNA
<213> ORGANISM: artificial sequence
<220> FEATURE:
<223> OTHER INFORMATION: IRRNA.27480.2: shRNA targeting WCR COPI? mRNA
      based on Drosophila melanogaster pre-miR-1 (60 nt)

<400> SEQUENCE: 2
ctggtgctga tgacagacaa tagttatatt caagcatatt gtctgtcatc agcaccagag     60

<210> SEQ ID NO 3
<211> LENGTH: 59
<212> TYPE: DNA
<213> ORGANISM: artificial sequence
<220> FEATURE:
<223> OTHER INFORMATION: IRRNA.28297.1: shRNA targeting WCR COPI? mRNA
      based on Diabrotica virgifera virgifera pre-bantam (59 nt)

<400> SEQUENCE: 3
tctggtgctg atgacagact aagatggttt tgattcttgt ctgtcatcag caccagagg      59

<210> SEQ ID NO 4
<211> LENGTH: 60
<212> TYPE: DNA
<213> ORGANISM: artificial sequence
<220> FEATURE:
<223> OTHER INFORMATION: IRRNA.28298.1: shRNA targeting WCR COPI? mRNA
      based on Tribolium castaneum pre-bantam (60 nt)

<400> SEQUENCE: 4
tctggtgctg atgacagacc aaagatatat ttgattcttg tctgtcatca gcaccagagg    60

<210> SEQ ID NO 5
<211> LENGTH: 60
<212> TYPE: DNA
<213> ORGANISM: artificial sequence
<220> FEATURE:
<223> OTHER INFORMATION: IRRNA.28299.1: shRNA targeting WCR COPI? mRNA
      based on Drosophila melanogaster pre-bantam (60 nt)

<400> SEQUENCE: 5
tctggtgctg atgacagaca actgtttttc atacaagttg tctgtcatca gcaccagagg    60

<210> SEQ ID NO 6
<211> LENGTH: 58
<212> TYPE: DNA
<213> ORGANISM: artificial sequence
<220> FEATURE:
<223> OTHER INFORMATION: IRRNA.25074.6: shRNA targeting WCR COPI? mRNA
      based on Tribolium castaneum pre-miR-1 (57 nt)

<400> SEQUENCE: 6
ctggtgctga tgacagacaa tagtgcttta aacgtattgt ctgtcatcag caccagag      58

<210> SEQ ID NO 7
<211> LENGTH: 60
<212> TYPE: DNA
<213> ORGANISM: Diabrotica virgifera virgifera

<400> SEQUENCE: 7
ccgtacttcc ttactatccc atagtgttat taatcgtatg gaatgtaaag aagtatggag    60

<210> SEQ ID NO 8

```
<211> LENGTH: 58
<212> TYPE: DNA
<213> ORGANISM: Tribolium castaneum

<400> SEQUENCE: 8
ccgtgcttcc ttacttccca tagtgcttta aacgtatgga atgtaaagaa gtatggag      58

<210> SEQ ID NO 9
<211> LENGTH: 60
<212> TYPE: DNA
<213> ORGANISM: Drosophila melanogaster

<400> SEQUENCE: 9
ccatgcttcc ttgcattcaa tagttatatt caagcatatg gaatgtaaag aagtatggag    60

<210> SEQ ID NO 10
<211> LENGTH: 59
<212> TYPE: DNA
<213> ORGANISM: Diabrotica virgifera virgifera

<400> SEQUENCE: 10
ctggttttca cagtgatttg cagatggttt tgattctgag atcattgtga aagctgttt     59

<210> SEQ ID NO 11
<211> LENGTH: 60
<212> TYPE: DNA
<213> ORGANISM: Tribolium castaneum

<400> SEQUENCE: 11
ctggttttca cagtgatttg acagatatat ttgattctga gatcattgtg aaagctgatt    60

<210> SEQ ID NO 12
<211> LENGTH: 60
<212> TYPE: DNA
<213> ORGANISM: Drosophila melanogaster

<400> SEQUENCE: 12
ccggttttcg atttggtttg actgtttttc atacaagtga gatcattttg aaagctgatt    60

<210> SEQ ID NO 13
<211> LENGTH: 66
<212> TYPE: DNA
<213> ORGANISM: Artificial Sequence
<220> FEATURE:
<223> OTHER INFORMATION: Loop sequence GeCan_1577

<400> SEQUENCE: 13
cacaaggcgg tgactgtcac agtactgtta agtcaagagc acggagtggc atttcgttgc    60
gttgtg                                                               66

<210> SEQ ID NO 14
<211> LENGTH: 17
<212> TYPE: DNA
<213> ORGANISM: artificial sequence
<220> FEATURE:
<223> OTHER INFORMATION: Loop sequence WCR_miR-8

<400> SEQUENCE: 14 cttttttgagc attctaa                                                  17

<210> SEQ ID NO 15
<211> LENGTH: 17
<212> TYPE: DNA
<213> ORGANISM: artificial sequence
```

```
<220> FEATURE:
<223> OTHER INFORMATION: Loop sequence WCR_miR-315a

<400> SEQUENCE: 15
gtgatttttg taggctt                                                  17

<210> SEQ ID NO 16
<211> LENGTH: 16
<212> TYPE: DNA
<213> ORGANISM: artificial sequence
<220> FEATURE:
<223> OTHER INFORMATION: Loop sequence WCR_miR-2779b

<400> SEQUENCE: 16
tactatcggc aaagct                                                   16

<210> SEQ ID NO 17
<211> LENGTH: 15
<212> TYPE: DNA
<213> ORGANISM: artificial sequence
<220> FEATURE:
<223> OTHER INFORMATION: Loop sequence GeCan_0699

<400> SEQUENCE: 17
tgttattaat gtaga                                                    15

<210> SEQ ID NO 18
<211> LENGTH: 46
<212> TYPE: DNA
<213> ORGANISM: artificial sequence
<220> FEATURE:
<223> OTHER INFORMATION: Loop sequence GeCan_0031

<400> SEQUENCE: 18
tttttcctaa cattttatta tataataaaa tgttaggaaa aattaa                  46

<210> SEQ ID NO 19
<211> LENGTH: 46
<212> TYPE: DNA
<213> ORGANISM: artificial sequence
<220> FEATURE:
<223> OTHER INFORMATION: Loop sequence GeCan_0462

<400> SEQUENCE: 19
attttcttca acattattaa cagtaaacaa atgttctaat ctttct                  46

<210> SEQ ID NO 20
<211> LENGTH: 31
<212> TYPE: DNA
<213> ORGANISM: artificial sequence
<220> FEATURE:
<223> OTHER INFORMATION: Loop sequence GeCan_1516

<400> SEQUENCE: 20
ggaatgttaa cactattaat cttgatgtaa g                                  31

<210> SEQ ID NO 21
<211> LENGTH: 18
<212> TYPE: DNA
<213> ORGANISM: Artificial sequence
<220> FEATURE:
<223> OTHER INFORMATION: Loop sequence GeCan_0999

<400> SEQUENCE: 21 ttgttttga agagttca                                                  18
```

```
<210> SEQ ID NO 22
<211> LENGTH: 17
<212> TYPE: DNA
<213> ORGANISM: artificial sequence
<220> FEATURE:
<223> OTHER INFORMATION: Loop sequence GeCan_0630

<400> SEQUENCE: 22
ttggttattt tatttgc                                                    17

<210> SEQ ID NO 23
<211> LENGTH: 20
<212> TYPE: DNA
<213> ORGANISM: artificial sequence
<220> FEATURE:
<223> OTHER INFORMATION: Loop sequence GeCan_1495

<400> SEQUENCE: 23
gtgaattgtg aatgtggaat                                                 20

<210> SEQ ID NO 24
<211> LENGTH: 21
<212> TYPE: DNA
<213> ORGANISM: artificial sequence
<220> FEATURE:
<223> OTHER INFORMATION: Loop sequence GeCan_1144

<400> SEQUENCE: 24
tggctcatcg tgcgcgagaa t                                               21

<210> SEQ ID NO 25
<211> LENGTH: 22
<212> TYPE: DNA
<213> ORGANISM: artificial sequence
<220> FEATURE:
<223> OTHER INFORMATION: Loop sequence GeCan_0260

<400> SEQUENCE: 25
ttgacgcagc tgtcaaaggt ca                                              22

<210> SEQ ID NO 26
<211> LENGTH: 21
<212> TYPE: DNA
<213> ORGANISM: Artificial sequence
<220> FEATURE:
<223> OTHER INFORMATION: Loop sequence WCR_miR-263a

<400> SEQUENCE: 26
ggatattttt taactgcccg t                                               21

<210> SEQ ID NO 27
<211> LENGTH: 14
<212> TYPE: DNA
<213> ORGANISM: artificial sequence
<220> FEATURE:
<223> OTHER INFORMATION: Loop sequence GeCan_0767

<400> SEQUENCE: 27
cctattggtt gcct                                                       14

<210> SEQ ID NO 28
<211> LENGTH: 52
<212> TYPE: DNA
<213> ORGANISM: artificial sequence
<220> FEATURE:
<223> OTHER INFORMATION: Loop sequence GeCan_0250
```

```
<400> SEQUENCE: 28
cggtaccgtc ttagaagaat ggttaaccat tcttctaaga cggtaccgac ac       52

<210> SEQ ID NO 29
<211> LENGTH: 14
<212> TYPE: DNA
<213> ORGANISM: artificial sequence
<220> FEATURE:
<223> OTHER INFORMATION: Loop sequence  WCR_miR-252

<400> SEQUENCE: 29
acatttgatc tcct                                                  14

<210> SEQ ID NO 30
<211> LENGTH: 15
<212> TYPE: DNA
<213> ORGANISM: artificial sequence
<220> FEATURE:
<223> OTHER INFORMATION: Loop sequence WCR_miR-193

<400> SEQUENCE: 30
aatatagagt tctac                                                 15

<210> SEQ ID NO 31
<211> LENGTH: 9
<212> TYPE: DNA
<213> ORGANISM: artificial sequence
<220> FEATURE:
<223> OTHER INFORMATION: Loop sequence GeCan_0925

<400> SEQUENCE: 31 ccggggtca                                                         9

<210> SEQ ID NO 32
<211> LENGTH: 40
<212> TYPE: DNA
<213> ORGANISM: artificial sequence
<220> FEATURE:
<223> OTHER INFORMATION: Loop sequence GeCan_0074

<400> SEQUENCE: 32
ctcagatgta ccacttgcaa gtggtacatc tgaggctgcc                      40

<210> SEQ ID NO 33
<211> LENGTH: 12
<212> TYPE: DNA
<213> ORGANISM: artificial sequence
<220> FEATURE:
<223> OTHER INFORMATION: Loop sequence GeCan_1252

<400> SEQUENCE: 33
taagttgcgt ag                                                    12

<210> SEQ ID NO 34
<211> LENGTH: 17
<212> TYPE: DNA
<213> ORGANISM: artificial sequence
<220> FEATURE:
<223> OTHER INFORMATION: Loop Sequence WCR_miR-133b

<400> SEQUENCE: 34 tttttttgttt gttattt                                              17

<210> SEQ ID NO 35
```

```
<211> LENGTH: 15
<212> TYPE: DNA
<213> ORGANISM: Artificial Sequence
<220> FEATURE:
<223> OTHER INFORMATION: Loop Sequence GeCan_1557

<400> SEQUENCE: 35
cctgattggt catat                                                      15

<210> SEQ ID NO 36
<211> LENGTH: 60
<212> TYPE: DNA
<213> ORGANISM: artificial sequence
<220> FEATURE:
<223> OTHER INFORMATION: Loop sequence GeCan_0092

<400> SEQUENCE: 36
ctgaacagtt tatattttta atcgatcatg atcgattaaa aatataaact gttcagtaca     60

<210> SEQ ID NO 37
<211> LENGTH: 17
<212> TYPE: DNA
<213> ORGANISM: artificial sequence
<220> FEATURE:
<223> OTHER INFORMATION: Loop sequence WCR_miR-279b

<400> SEQUENCE: 37
atgagttttt aattgtg                                                    17

<210> SEQ ID NO 38
<211> LENGTH: 16
<212> TYPE: DNA
<213> ORGANISM: artificial sequence
<220> FEATURE:
<223> OTHER INFORMATION: Loop sequence WCR_miR-2779e

<400> SEQUENCE: 38
taagttcggc tcagct                                                     16

<210> SEQ ID NO 39
<211> LENGTH: 22
<212> TYPE: DNA
<213> ORGANISM: artificial sequence
<220> FEATURE:
<223> OTHER INFORMATION: Loop sequence GeCan_1532

<400> SEQUENCE: 39
aaaattgaaa agaaatagtt tt                                              22

<210> SEQ ID NO 40
<211> LENGTH: 21
<212> TYPE: DNA
<213> ORGANISM: artificial sequence
<220> FEATURE:
<223> OTHER INFORMATION: Loop sequence GeCan_1102

<400> SEQUENCE: 40
ttgaagtccg tttaggttca g                                               21

<210> SEQ ID NO 41
<211> LENGTH: 11
<212> TYPE: DNA
<213> ORGANISM: artificial sequence
<220> FEATURE:
<223> OTHER INFORMATION: Loop sequence WCR_miR-2a

<400> SEQUENCE: 41
```

```
ttatcgttct a                                                              11

<210> SEQ ID NO 42
<211> LENGTH: 9
<212> TYPE: DNA
<213> ORGANISM: artificial sequence
<220> FEATURE:
<223> OTHER INFORMATION: Loop sequence GeCan_0309

<400> SEQUENCE: 42 agatggctc                                                                  9

<210> SEQ ID NO 43
<211> LENGTH: 32
<212> TYPE: DNA
<213> ORGANISM: artificial sequence
<220> FEATURE:
<223> OTHER INFORMATION: Loop sequence GeCan_0070

<400> SEQUENCE: 43
caaatataaa gtttaaactt tatatttggg gt                                       32

<210> SEQ ID NO 44
<211> LENGTH: 19
<212> TYPE: DNA
<213> ORGANISM: artificial sequence
<220> FEATURE:
<223> OTHER INFORMATION: Loop sequence WCR_miR-3049

<400> SEQUENCE: 44
ttttgtgttt gattaagtc                                                      19

<210> SEQ ID NO 45
<211> LENGTH: 16
<212> TYPE: DNA
<213> ORGANISM: artificial sequence
<220> FEATURE:
<223> OTHER INFORMATION: Loop sequence GeCan_0839

<400> SEQUENCE: 45
gaaaattttt gaaggt                                                         16

<210> SEQ ID NO 46
<211> LENGTH: 27
<212> TYPE: DNA
<213> ORGANISM: artificial sequence
<220> FEATURE:
<223> OTHER INFORMATION: Loop sequence GeCan_0756

<400> SEQUENCE: 46
cagtccttat ccaatggatt gggtcct                                             27

<210> SEQ ID NO 47
<211> LENGTH: 31
<212> TYPE: DNA
<213> ORGANISM: artificial sequence
<220> FEATURE:
<223> OTHER INFORMATION: Loop sequence GeCan_1584

<400> SEQUENCE: 47
ggaatgttaa tactattaat cttgatgtaa g                                        31

<210> SEQ ID NO 48
<211> LENGTH: 13
<212> TYPE: DNA
```

```
<213> ORGANISM: artificial sequence
<220> FEATURE:
<223> OTHER INFORMATION: Loop sequence GeCan_1061

<400> SEQUENCE: 48
tatttgaccg agt                                                        13

<210> SEQ ID NO 49
<211> LENGTH: 14
<212> TYPE: DNA
<213> ORGANISM: artificial sequence
<220> FEATURE:
<223> OTHER INFORMATION: Loop sequence GeCan_0346

<400> SEQUENCE: 49
aaaaacttct tttg                                                       14

<210> SEQ ID NO 50
<211> LENGTH: 30
<212> TYPE: DNA
<213> ORGANISM: Artificial sequence
<220> FEATURE:
<223> OTHER INFORMATION: Loop Sequence GeCan_0929

<400> SEQUENCE: 50
aatgagtacg gaagaaaatc tgacttcaac                                      30

<210> SEQ ID NO 51
<211> LENGTH: 20
<212> TYPE: DNA
<213> ORGANISM: artificial sequence
<220> FEATURE:
<223> OTHER INFORMATION: Loop sequence WCR_miR-993

<400> SEQUENCE: 51
gtagttattt atatcagaag                                                 20

<210> SEQ ID NO 52
<211> LENGTH: 68
<212> TYPE: DNA
<213> ORGANISM: artificial sequence
<220> FEATURE:
<223> OTHER INFORMATION: Loop sequence GeCan_0904

<400> SEQUENCE: 52
gcatacgaga atttgaacct tagaacttaa aaattaagtg aaggttcaaa tcctctacag     60
catgtaga                                                              68

<210> SEQ ID NO 53
<211> LENGTH: 40
<212> TYPE: DNA
<213> ORGANISM: artificial sequence
<220> FEATURE:
<223> OTHER INFORMATION: Loop sequence GeCan_0096

<400> SEQUENCE: 53
tagttttaag tttgtaatat tacaaactta aaactatttc                           40

<210> SEQ ID NO 54
<211> LENGTH: 22
<212> TYPE: DNA
<213> ORGANISM: artificial sequence
<220> FEATURE:
<223> OTHER INFORMATION: Loop sequence GeCan_0991

<400> SEQUENCE: 54
```

```
aaaattgaaa agaaatagtt tt                                          22

<210> SEQ ID NO 55
<211> LENGTH: 17
<212> TYPE: DNA
<213> ORGANISM: artificial sequence
<220> FEATURE:
<223> OTHER INFORMATION: Loop sequence GeCan_1426

<400> SEQUENCE: 55
ttaatgtatt tttatca                                                17

<210> SEQ ID NO 56
<211> LENGTH: 15
<212> TYPE: DNA
<213> ORGANISM: artificial sequence
<220> FEATURE:
<223> OTHER INFORMATION: Loop sequence GeCan_0717

<400> SEQUENCE: 56
tcttgtttag tgcca                                                  15

<210> SEQ ID NO 57
<211> LENGTH: 12
<212> TYPE: DNA
<213> ORGANISM: artificial sequence
<220> FEATURE:
<223> OTHER INFORMATION: Loop sequence WCR_miR-2944c

<400> SEQUENCE: 57
attgttatcg ta                                                     12

<210> SEQ ID NO 58
<211> LENGTH: 22
<212> TYPE: DNA
<213> ORGANISM: artificial sequence
<220> FEATURE:
<223> OTHER INFORMATION: Loop sequence GeCan_0990

<400> SEQUENCE: 58
aaaattgaaa agaaatagtt tt                                          22

<210> SEQ ID NO 59
<211> LENGTH: 50
<212> TYPE: DNA
<213> ORGANISM: artificial sequence
<220> FEATURE:
<223> OTHER INFORMATION: Loop sequence GeCan_0122

<400> SEQUENCE: 59
tattaattgt cgaatcttgt catatgacaa gattcgacaa ttaatactaa             50

<210> SEQ ID NO 60
<211> LENGTH: 19
<212> TYPE: DNA
<213> ORGANISM: artificial sequence
<220> FEATURE:
<223> OTHER INFORMATION: Loop sequence WCR_miR-932

<400> SEQUENCE: 60
gtttaaggca acagtctgc                                              19

<210> SEQ ID NO 61
<211> LENGTH: 18
<212> TYPE: DNA
```

```
<213> ORGANISM: artificial sequence
<220> FEATURE:
<223> OTHER INFORMATION: Loop sequence GeCan_0722

<400> SEQUENCE: 61
catgttttga ttctgaga                                                     18

<210> SEQ ID NO 62
<211> LENGTH: 18
<212> TYPE: DNA
<213> ORGANISM: artificial sequence
<220> FEATURE:
<223> OTHER INFORMATION: Loop sequence WCR_miR-305a

<400> SEQUENCE: 62
ggtatgttag tttcccga                                                     18

<210> SEQ ID NO 63
<211> LENGTH: 17
<212> TYPE: DNA
<213> ORGANISM: artificial sequence
<220> FEATURE:
<223> OTHER INFORMATION: Loop sequence GeCan_0536

<400> SEQUENCE: 63
aaatatttga tcgagtt                                                      17

<210> SEQ ID NO 64
<211> LENGTH: 18
<212> TYPE: DNA
<213> ORGANISM: artificial sequence
<220> FEATURE:
<223> OTHER INFORMATION: Loop sequence GeCan_1319

<400> SEQUENCE: 64
agagtatttg gtcctgct                                                     18

<210> SEQ ID NO 65
<211> LENGTH: 76
<212> TYPE: DNA
<213> ORGANISM: artificial sequence
<220> FEATURE:
<223> OTHER INFORMATION: Loop sequence GeCan_0591

<400> SEQUENCE: 65
ctggtatcac aacctctgtt agatttttta tctggatcca gataaaaaat ctaacagagg       60
ttgtgatacc agatga                                                       76

<210> SEQ ID NO 66
<211> LENGTH: 25
<212> TYPE: DNA
<213> ORGANISM: artificial sequence
<220> FEATURE:
<223> OTHER INFORMATION: Loop sequence GeCan_0484

<400> SEQUENCE: 66
ggggctatca ttagagctta ttcga                                             25

<210> SEQ ID NO 67
<211> LENGTH: 31
<212> TYPE: DNA
<213> ORGANISM: artificial sequence
<220> FEATURE:
<223> OTHER INFORMATION: Loop sequence GeCan_1296

<400> SEQUENCE: 67
```

```
ggaatgttaa cactattaat cttgatgtaa g                                  31

<210> SEQ ID NO 68
<211> LENGTH: 9
<212> TYPE: DNA
<213> ORGANISM: artificial sequence
<220> FEATURE:
<223> OTHER INFORMATION: Loop sequence GeCan_0238

<400> SEQUENCE: 68 gacgtttct                                                            9

<210> SEQ ID NO 69
<211> LENGTH: 25
<212> TYPE: DNA
<213> ORGANISM: artificial sequence
<220> FEATURE:
<223> OTHER INFORMATION: Loop sequence GeCan_1512

<400> SEQUENCE: 69
tgatacatct aaactgcatc aatgg                                         25

<210> SEQ ID NO 70
<211> LENGTH: 57
<212> TYPE: DNA
<213> ORGANISM: artificial sequence
<220> FEATURE:
<223> OTHER INFORMATION: Loop sequence GeCan_0600

<400> SEQUENCE: 70
tcaatcccta atgaacccca cggatgaacc ccgtgaggtt cattagggat tgaaccc       57

<210> SEQ ID NO 71
<211> LENGTH: 19
<212> TYPE: DNA
<213> ORGANISM: artificial sequence
<220> FEATURE:
<223> OTHER INFORMATION: Loop sequence GeCan_1218

<400> SEQUENCE: 71 gtttttatt tggaaaact                                                 19

<210> SEQ ID NO 72
<211> LENGTH: 13
<212> TYPE: DNA
<213> ORGANISM: artificial sequence
<220> FEATURE:
<223> OTHER INFORMATION: Loop sequence GeCan_1183

<400> SEQUENCE: 72
gtggttttat gca                                                      13

<210> SEQ ID NO 73
<211> LENGTH: 20
<212> TYPE: DNA
<213> ORGANISM: artificial sequence
<220> FEATURE:
<223> OTHER INFORMATION: Loop sequence WCR_miR-317b

<400> SEQUENCE: 73
cataaattag aacagtgaac                                               20

<210> SEQ ID NO 74
<211> LENGTH: 14
<212> TYPE: DNA
```

<213> ORGANISM: artificial sequence
<220> FEATURE:
<223> OTHER INFORMATION: Loop sequence GeCan_1334

<400> SEQUENCE: 74
gttttttttt tatt                                                    14

<210> SEQ ID NO 75
<211> LENGTH: 17
<212> TYPE: DNA
<213> ORGANISM: artificial sequence
<220> FEATURE:
<223> OTHER INFORMATION: Loop sequence WCR_miR-989

<400> SEQUENCE: 75
aatattgaga acacgtg                                                 17

<210> SEQ ID NO 76
<211> LENGTH: 12
<212> TYPE: DNA
<213> ORGANISM: artificial sequence
<220> FEATURE:
<223> OTHER INFORMATION: Loop sequence GeCan_0131

<400> SEQUENCE: 76
acgcgtttct ca                                                      12

<210> SEQ ID NO 77
<211> LENGTH: 19
<212> TYPE: DNA
<213> ORGANISM: artificial sequence
<220> FEATURE:
<223> OTHER INFORMATION: Loop sequence WCR_miR-970

<400> SEQUENCE: 77
agtgtgattg atagctatc                                               19

<210> SEQ ID NO 78
<211> LENGTH: 12
<212> TYPE: DNA
<213> ORGANISM: artificial sequence
<220> FEATURE:
<223> OTHER INFORMATION: Loop sequence WCR_miR-2944b

<400> SEQUENCE: 78
tattgttatc gt                                                      12

<210> SEQ ID NO 79
<211> LENGTH: 11
<212> TYPE: DNA
<213> ORGANISM: artificial sequence
<220> FEATURE:
<223> OTHER INFORMATION: Loop sequence GeCan_0020

<400> SEQUENCE: 79
gtcgtgaatt a                                                       11

<210> SEQ ID NO 80
<211> LENGTH: 84
<212> TYPE: DNA
<213> ORGANISM: artificial sequence
<220> FEATURE:
<223> OTHER INFORMATION: Loop sequence GeCan_0726

<400> SEQUENCE: 80
atggcatcgt ttaccatgtg acgaagtaca atttgttagt taataatcca ttgtcatccc   60 agcgcccta tgatgttatc ccag                                          84

<210> SEQ ID NO 81
<211> LENGTH: 56
<212> TYPE: DNA
<213> ORGANISM: artificial sequence
<220> FEATURE:
<223> OTHER INFORMATION: Loop sequence GeCan_0316

<400> SEQUENCE: 81
acttcacttc actaaatttt ttcccattgg gggactttct gaagtgcgaa ataatt      56

<210> SEQ ID NO 82
<211> LENGTH: 20
<212> TYPE: DNA
<213> ORGANISM: artificial sequence
<220> FEATURE:
<223> OTHER INFORMATION: Loop sequence WCR_miR-750a

<400> SEQUENCE: 82
aacatttcag aaagtgccag                                              20

<210> SEQ ID NO 83
<211> LENGTH: 17
<212> TYPE: DNA
<213> ORGANISM: artificial sequence
<220> FEATURE:
<223> OTHER INFORMATION: Loop sequence GeCan_0764

<400> SEQUENCE: 83
gttttttagg agacata                                                 17

<210> SEQ ID NO 84
<211> LENGTH: 29
<212> TYPE: DNA
<213> ORGANISM: artificial sequence
<220> FEATURE:
<223> OTHER INFORMATION: Loop sequence WCR_miR-277b

<400> SEQUENCE: 84
cgttaaaggt tctgattgaa gtctgtaaa                                    29

<210> SEQ ID NO 85
<211> LENGTH: 14
<212> TYPE: DNA
<213> ORGANISM: artificial sequence
<220> FEATURE:
<223> OTHER INFORMATION: Loop sequence WCR_miR-276

<400> SEQUENCE: 85
tgatttctat tgta                                                    14

<210> SEQ ID NO 86
<211> LENGTH: 19
<212> TYPE: DNA
<213> ORGANISM: artificial sequence
<220> FEATURE:
<223> OTHER INFORMATION: Loop sequence WCR_miR-1175

<400> SEQUENCE: 86
ctttgtttag aatagtgag                                               19

<210> SEQ ID NO 87
<211> LENGTH: 18
<212> TYPE: DNA

```
<213> ORGANISM: artificial sequence
<220> FEATURE:
<223> OTHER INFORMATION: Loop sequence CGTCACTTGCACTCTCAC

<400> SEQUENCE: 87
cgtcacttgc actctcac                                                    18

<210> SEQ ID NO 88
<211> LENGTH: 51
<212> TYPE: DNA
<213> ORGANISM: artificial sequence
<220> FEATURE:
<223> OTHER INFORMATION: Loop sequence GeCan_0623

<400> SEQUENCE: 88
cgctgtctct cggctcggct gtggcagctg tgcattcgtg cagcgctagg a               51

<210> SEQ ID NO 89
<211> LENGTH: 8
<212> TYPE: DNA
<213> ORGANISM: artificial sequence
<220> FEATURE:
<223> OTHER INFORMATION: Loop sequence GeCan_0342

<400> SEQUENCE: 89 ttaaccag                                                                8

<210> SEQ ID NO 90
<211> LENGTH: 31
<212> TYPE: DNA
<213> ORGANISM: artificial sequence
<220> FEATURE:
<223> OTHER INFORMATION: Loop sequence GeCan_0231

<400> SEQUENCE: 90
caatcaacca tcttcgggtt gattgggtcc t                                     31

<210> SEQ ID NO 91
<211> LENGTH: 44
<212> TYPE: DNA
<213> ORGANISM: artificial sequence
<220> FEATURE:
<223> OTHER INFORMATION: Loop sequence GeCan_0401

<400> SEQUENCE: 91
caatcaagta gtcatcgttg accgaaaatg gttgattggg tcct                       44

<210> SEQ ID NO 92
<211> LENGTH: 19
<212> TYPE: DNA
<213> ORGANISM: artificial sequence
<220> FEATURE:
<223> OTHER INFORMATION: Loop sequence GeCan_1543

<400> SEQUENCE: 92 cggttttta ctccgttca                                                    19

<210> SEQ ID NO 93
<211> LENGTH: 14
<212> TYPE: DNA
<213> ORGANISM: artificial sequence
<220> FEATURE:
<223> OTHER INFORMATION: Loop sequence GeCan_1280

<400> SEQUENCE: 93 tgttttttt tatt                                                         14
```

<210> SEQ ID NO 94
<211> LENGTH: 13
<212> TYPE: DNA
<213> ORGANISM: artificial sequence
<220> FEATURE:
<223> OTHER INFORMATION: Loop sequence GeCan_1279

<400> SEQUENCE: 94
tggttttttt att                                                        13

<210> SEQ ID NO 95
<211> LENGTH: 13
<212> TYPE: DNA
<213> ORGANISM: artificial sequence
<220> FEATURE:
<223> OTHER INFORMATION: Loop sequence WCR_miR-307b

<400> SEQUENCE: 95
gaactttatc cat                                                        13

<210> SEQ ID NO 96
<211> LENGTH: 5
<212> TYPE: DNA
<213> ORGANISM: Artificial Sequence
<220> FEATURE:
<223> OTHER INFORMATION: Loop sequence GeCan_0544

<400> SEQUENCE: 96 aaatt                                                                  5

<210> SEQ ID NO 97
<211> LENGTH: 23
<212> TYPE: DNA
<213> ORGANISM: artificial sequence
<220> FEATURE:
<223> OTHER INFORMATION: Loop sequence GeCan_1189

<400> SEQUENCE: 97
tatctatcca gtaaataaat gca                                             23

<210> SEQ ID NO 98
<211> LENGTH: 8
<212> TYPE: DNA
<213> ORGANISM: artificial sequence
<220> FEATURE:
<223> OTHER INFORMATION: Loop sequence GeCan_0594

<400> SEQUENCE: 98 gcgaaatc                                                               8

<210> SEQ ID NO 99
<211> LENGTH: 19
<212> TYPE: DNA
<213> ORGANISM: artificial sequence
<220> FEATURE:
<223> OTHER INFORMATION: Loop sequence WCR_miR-11

<400> SEQUENCE: 99
gtgtcactat tattcacat                                                  19

<210> SEQ ID NO 100
<211> LENGTH: 15
<212> TYPE: DNA
<213> ORGANISM: artificial sequence
<220> FEATURE:

```
<223> OTHER INFORMATION: Loop sequence WCR_miR-2765

<400> SEQUENCE: 100
gtacatttga atgcc                                                    15

<210> SEQ ID NO 101
<211> LENGTH: 41
<212> TYPE: DNA
<213> ORGANISM: artificial sequence
<220> FEATURE:
<223> OTHER INFORMATION: Loop sequence GeCan_1077

<400> SEQUENCE: 101
ggaatcggta tgcttttcga taatttcgcg gcaaaatggt a                       41

<210> SEQ ID NO 102
<211> LENGTH: 15
<212> TYPE: DNA
<213> ORGANISM: artificial sequence
<220> FEATURE:
<223> OTHER INFORMATION: Loop sequence WCR_miR-13b

<400> SEQUENCE: 102
tttttatcag tggta                                                    15

<210> SEQ ID NO 103
<211> LENGTH: 16
<212> TYPE: DNA
<213> ORGANISM: artificial sequence
<220> FEATURE:
<223> OTHER INFORMATION: Loop sequence GeCan_1084

<400> SEQUENCE: 103
ttttattaga ttgtgg                                                   16

<210> SEQ ID NO 104
<211> LENGTH: 16
<212> TYPE: DNA
<213> ORGANISM: artificial sequence
<220> FEATURE:
<223> OTHER INFORMATION: Loop sequence GeCan_0951

<400> SEQUENCE: 104
gtcacttgca ctctca                                                   16

<210> SEQ ID NO 105
<211> LENGTH: 35
<212> TYPE: DNA
<213> ORGANISM: artificial sequence
<220> FEATURE:
<223> OTHER INFORMATION: Loop sequence GeCan_0805

<400> SEQUENCE: 105
gcctattcaa gagaggctag gatcagctaa tttgt                              35

<210> SEQ ID NO 106
<211> LENGTH: 16
<212> TYPE: DNA
<213> ORGANISM: artificial sequence
<220> FEATURE:
<223> OTHER INFORMATION: Loop sequence WCR_miR-71

<400> SEQUENCE: 106
gttcatattt tttgtc                                                   16
```

```
<210> SEQ ID NO 107
<211> LENGTH: 17
<212> TYPE: DNA
<213> ORGANISM: artificial sequence
<220> FEATURE:
<223> OTHER INFORMATION: Loop sequence GeCan_0856

<400> SEQUENCE: 107
tcttttatgc attccaa                                                17

<210> SEQ ID NO 108
<211> LENGTH: 29
<212> TYPE: DNA
<213> ORGANISM: artificial sequence
<220> FEATURE:
<223> OTHER INFORMATION: Loop sequence GeCan_0220

<400> SEQUENCE: 108
aatccaggct ggtcgcctat tgattgttt                                   29

<210> SEQ ID NO 109
<211> LENGTH: 16
<212> TYPE: DNA
<213> ORGANISM: artificial sequence
<220> FEATURE:
<223> OTHER INFORMATION: Loop sequence WCR_miR-92b

<400> SEQUENCE: 109
ttgttaaggt tcaaat                                                 16

<210> SEQ ID NO 110
<211> LENGTH: 20
<212> TYPE: DNA
<213> ORGANISM: artificial sequence
<220> FEATURE:
<223> OTHER INFORMATION: Loop sequence WCR_miR-6012

<400> SEQUENCE: 110
atgttatttt cagtcatttc                                             20

<210> SEQ ID NO 111
<211> LENGTH: 30
<212> TYPE: DNA
<213> ORGANISM: artificial sequence
<220> FEATURE:
<223> OTHER INFORMATION: Loop sequence GeCan_1072

<400> SEQUENCE: 111
caggaaagca acaggaaatc ctgcatttct                                  30

<210> SEQ ID NO 112
<211> LENGTH: 32
<212> TYPE: DNA
<213> ORGANISM: artificial sequence
<220> FEATURE:
<223> OTHER INFORMATION: Loop sequence GeCan_0932

<400> SEQUENCE: 112
tggaccactt tttccgcacg gtggtcggga at                               32

<210> SEQ ID NO 113
<211> LENGTH: 17
<212> TYPE: DNA
<213> ORGANISM: artificial sequence
<220> FEATURE:
<223> OTHER INFORMATION: Loop sequence GeCan_1212
```

<400> SEQUENCE: 113
gctatatttg tgttgcc    17

<210> SEQ ID NO 114
<211> LENGTH: 31
<212> TYPE: DNA
<213> ORGANISM: artificial sequence
<220> FEATURE:
<223> OTHER INFORMATION: Loop sequence GeCan_0066

<400> SEQUENCE: 114
ggcaaaagaa aaccagatta aagtgccatt t    31

<210> SEQ ID NO 115
<211> LENGTH: 20
<212> TYPE: DNA
<213> ORGANISM: artificial sequence
<220> FEATURE:
<223> OTHER INFORMATION: Loop sequence GeCan_1107

<400> SEQUENCE: 115
aaaaatatcg aaactattgc    20

<210> SEQ ID NO 116
<211> LENGTH: 13
<212> TYPE: DNA
<213> ORGANISM: artificial sequence
<220> FEATURE:
<223> OTHER INFORMATION: Loop sequence GeCan_1054

<400> SEQUENCE: 116
gtggttttaa gca    13

<210> SEQ ID NO 117
<211> LENGTH: 17
<212> TYPE: DNA
<213> ORGANISM: artificial sequence
<220> FEATURE:
<223> OTHER INFORMATION: Loop sequence GeCan_1500

<400> SEQUENCE: 117
ggcaaaatta tagcgtc    17

<210> SEQ ID NO 118
<211> LENGTH: 32
<212> TYPE: DNA
<213> ORGANISM: artificial sequence
<220> FEATURE:
<223> OTHER INFORMATION: Loop sequence GeCan_0897

<400> SEQUENCE: 118
acgtacttag agtggaacaa gtatgaacgt cc    32

<210> SEQ ID NO 119
<211> LENGTH: 17
<212> TYPE: DNA
<213> ORGANISM: artificial sequence
<220> FEATURE:
<223> OTHER INFORMATION: Loop sequence WCR_miR-971

<400> SEQUENCE: 119
ctactgttat tcgtttg    17

<210> SEQ ID NO 120
<211> LENGTH: 8

```
<212> TYPE: DNA
<213> ORGANISM: artificial sequence
<220> FEATURE:
<223> OTHER INFORMATION: Loop sequence GeCan_0365

<400> SEQUENCE: 120 caaaactc                                                                  8

<210> SEQ ID NO 121
<211> LENGTH: 17
<212> TYPE: DNA
<213> ORGANISM: artificial sequence
<220> FEATURE:
<223> OTHER INFORMATION: Loop sequence GeCan_0438

<400> SEQUENCE: 121
tcttcctttc tcttttt                                                       17

<210> SEQ ID NO 122
<211> LENGTH: 75
<212> TYPE: DNA
<213> ORGANISM: artificial sequence
<220> FEATURE:
<223> OTHER INFORMATION: Loop sequence GeCan_1485

<400> SEQUENCE: 122
ccaatcaacc atcttcagtc aacgatgact actaagttag tagtcatcgt tgaccgaaga        60
tggttgattg ggtca                                                         75

<210> SEQ ID NO 123
<211> LENGTH: 14
<212> TYPE: DNA
<213> ORGANISM: artificial sequence
<220> FEATURE:
<223> OTHER INFORMATION: Loop sequence GeCan_0742

<400> SEQUENCE: 123
gttaattgaa gtgc                                                          14

<210> SEQ ID NO 124
<211> LENGTH: 27
<212> TYPE: DNA
<213> ORGANISM: artificial sequence
<220> FEATURE:
<223> OTHER INFORMATION: Loop sequence GeCan_0755

<400> SEQUENCE: 124
ccaatccatt ggataaggac tgggtcc                                            27

<210> SEQ ID NO 125
<211> LENGTH: 13
<212> TYPE: DNA
<213> ORGANISM: artificial sequence
<220> FEATURE:
<223> OTHER INFORMATION: Loop sequence WCR_miR-2b

<400> SEQUENCE: 125
taattggctc gta                                                           13

<210> SEQ ID NO 126
<211> LENGTH: 17
<212> TYPE: DNA
<213> ORGANISM: artificial sequence
<220> FEATURE:
<223> OTHER INFORMATION: Loop sequence WCR_miR-13a
```

```
<400> SEQUENCE: 126
cttttatttc aagatat                                                    17

<210> SEQ ID NO 127
<211> LENGTH: 8
<212> TYPE: DNA
<213> ORGANISM: artificial sequence
<220> FEATURE:
<223> OTHER INFORMATION: Loop sequence GeCan_0289

<400> SEQUENCE: 127 gcttcctg                                                               8

<210> SEQ ID NO 128
<211> LENGTH: 47
<212> TYPE: DNA
<213> ORGANISM: artificial sequence
<220> FEATURE:
<223> OTHER INFORMATION: Loop sequence GeCan_0463

<400> SEQUENCE: 128
gtttggagta tgtgaaacta ggaacgatac tgactggagc attagga                   47

<210> SEQ ID NO 129
<211> LENGTH: 57
<212> TYPE: DNA
<213> ORGANISM: artificial sequence
<220> FEATURE:
<223> OTHER INFORMATION: Loop sequence GeCan_0601

<400> SEQUENCE: 129
caatccctaa tgaacctcac ggggttcatc cgtggggttc attagggatt gaacccc        57

<210> SEQ ID NO 130
<211> LENGTH: 35
<212> TYPE: DNA
<213> ORGANISM: artificial sequence
<220> FEATURE:
<223> OTHER INFORMATION: Loop sequence GeCan_1464

<400> SEQUENCE: 130
gcgcctggga gtgggagtcc tgcgtcagcc cgacc                                35

<210> SEQ ID NO 131
<211> LENGTH: 19
<212> TYPE: DNA
<213> ORGANISM: artificial sequence
<220> FEATURE:
<223> OTHER INFORMATION: Loop sequence GeCan_1316

<400> SEQUENCE: 131
gtatattagc ttcagtttg                                                  19

<210> SEQ ID NO 132
<211> LENGTH: 20
<212> TYPE: DNA
<213> ORGANISM: artificial sequence
<220> FEATURE:
<223> OTHER INFORMATION: Loop sequence WCR_miR-317a

<400> SEQUENCE: 132
catacattag aacagtgaac                                                 20

<210> SEQ ID NO 133
<211> LENGTH: 76
```

```
<212> TYPE: DNA
<213> ORGANISM: artificial sequence
<220> FEATURE:
<223> OTHER INFORMATION: Loop sequence GeCan_0592

<400> SEQUENCE: 133
tggtatcaca acctctgtta gattttttat ctggatccag ataaaaaatc taacagaggt    60
tgtgatacca gatgat                                                    76

<210> SEQ ID NO 134
<211> LENGTH: 16
<212> TYPE: DNA
<213> ORGANISM: artificial sequence
<220> FEATURE:
<223> OTHER INFORMATION: Loop sequence GeCan_1415

<400> SEQUENCE: 134
ttttattaga ttgtgg                                                    16

<210> SEQ ID NO 135
<211> LENGTH: 31
<212> TYPE: DNA
<213> ORGANISM: artificial sequence
<220> FEATURE:
<223> OTHER INFORMATION: Loop sequence GeCan_1339

<400> SEQUENCE: 135
gaatgttaac actattaatc ttgatgtaag t                                   31

<210> SEQ ID NO 136
<211> LENGTH: 11
<212> TYPE: DNA
<213> ORGANISM: artificial sequence
<220> FEATURE:
<223> OTHER INFORMATION: Loop sequence GeCan_0889

<400> SEQUENCE: 136
atttgaacgt t                                                         11

<210> SEQ ID NO 137
<211> LENGTH: 82
<212> TYPE: DNA
<213> ORGANISM: artificial sequence
<220> FEATURE:
<223> OTHER INFORMATION: Loop sequence GeCan_0634

<400> SEQUENCE: 137
gcgtcagaac gtgacgtgaa tggcgtgacg tgaatgacgt gtcatttacg tgacgtgaat    60
ggcgtgacgt gagacgctct gc                                             82

<210> SEQ ID NO 138
<211> LENGTH: 36
<212> TYPE: DNA
<213> ORGANISM: artificial sequence
<220> FEATURE:
<223> OTHER INFORMATION: Loop sequence GeCan_0098

<400> SEQUENCE: 138
ttcaaaacag ttttccggaa aactgttttg aatttg                              36

<210> SEQ ID NO 139
<211> LENGTH: 22
<212> TYPE: DNA
<213> ORGANISM: artificial sequence
<220> FEATURE:
```

<223> OTHER INFORMATION: Loop sequence GeCan_1531

<400> SEQUENCE: 139
aaaattgaaa agaaatagtt tt				22

<210> SEQ ID NO 140
<211> LENGTH: 15
<212> TYPE: DNA
<213> ORGANISM: artificial sequence
<220> FEATURE:
<223> OTHER INFORMATION: Loop sequence GeCan_0354

<400> SEQUENCE: 140
tcgcggcaaa atggt				15

<210> SEQ ID NO 141
<211> LENGTH: 14
<212> TYPE: DNA
<213> ORGANISM: artificial sequence
<220> FEATURE:
<223> OTHER INFORMATION: Loop sequence WCR_miR-275b

<400> SEQUENCE: 141
atcatttgct agtc				14

<210> SEQ ID NO 142
<211> LENGTH: 17
<212> TYPE: DNA
<213> ORGANISM: artificial sequence
<220> FEATURE:
<223> OTHER INFORMATION: Loop sequence WCR_miR-980

<400> SEQUENCE: 142
gtatcaataa acagcta				17

<210> SEQ ID NO 143
<211> LENGTH: 39
<212> TYPE: DNA
<213> ORGANISM: artificial sequence
<220> FEATURE:
<223> OTHER INFORMATION: Loop sequence GeCan_0646

<400> SEQUENCE: 143
tctttgagtt ccattaatcc tttaaaactc aagaaaatt				39

<210> SEQ ID NO 144
<211> LENGTH: 16
<212> TYPE: DNA
<213> ORGANISM: artificial sequence
<220> FEATURE:
<223> OTHER INFORMATION: Loop sequence WCR_miR-3477b

<400> SEQUENCE: 144 gttgttttt tccca				16

<210> SEQ ID NO 145
<211> LENGTH: 84
<212> TYPE: DNA
<213> ORGANISM: artificial sequence
<220> FEATURE:
<223> OTHER INFORMATION: Loop sequence WCR_miR-2514c

<400> SEQUENCE: 145
tgtttcgggc tgttgagggg aggggagatc gcaacaggtg ggcggttctg ctcctcttcg				60 acgttcgaaa cgcttttaat tcat				84

```
<210> SEQ ID NO 146
<211> LENGTH: 18
<212> TYPE: DNA
<213> ORGANISM: artificial sequence
<220> FEATURE:
<223> OTHER INFORMATION: Loop sequence WCR_miR-7

<400> SEQUENCE: 146
ttctgttttt attaacaa                                                18

<210> SEQ ID NO 147
<211> LENGTH: 48
<212> TYPE: DNA
<213> ORGANISM: artificial sequence
<220> FEATURE:
<223> OTHER INFORMATION: Loop sequence GeCan_0261

<400> SEQUENCE: 147
tttctggttg ggaagtgttg tacaccattt cccaaccaga aatattat                48

<210> SEQ ID NO 148
<211> LENGTH: 47
<212> TYPE: DNA
<213> ORGANISM: artificial sequence
<220> FEATURE:
<223> OTHER INFORMATION: Loop sequence GeCan_0282

<400> SEQUENCE: 148
tggccccaaa tttagtattg aacctatact aaatttgggg ccaagag                 47

<210> SEQ ID NO 149
<211> LENGTH: 28
<212> TYPE: DNA
<213> ORGANISM: artificial sequence
<220> FEATURE:
<223> OTHER INFORMATION: Loop sequence GeCan_0125

<400> SEQUENCE: 149
ccgaaaggcc gcggcctttc ggtgattg                                      28

<210> SEQ ID NO 150
<211> LENGTH: 15
<212> TYPE: DNA
<213> ORGANISM: artificial sequence
<220> FEATURE:
<223> OTHER INFORMATION: Loop sequence GeCan_0447

<400> SEQUENCE: 150
atctccgagt tagga                                                    15

<210> SEQ ID NO 151
<211> LENGTH: 23
<212> TYPE: DNA
<213> ORGANISM: artificial sequence
<220> FEATURE:
<223> OTHER INFORMATION: Loop sequence GeCan_1191

<400> SEQUENCE: 151
tatttatcct gtagataaat aca                                           23

<210> SEQ ID NO 152
<211> LENGTH: 17
<212> TYPE: DNA
<213> ORGANISM: artificial sequence
<220> FEATURE:
```

```
<223> OTHER INFORMATION: Loop sequence GeCan_1101

<400> SEQUENCE: 152
gttggttatt ttatttg                                                  17

<210> SEQ ID NO 153
<211> LENGTH: 17
<212> TYPE: DNA
<213> ORGANISM: artificial sequence
<220> FEATURE:
<223> OTHER INFORMATION: Loop sequence GeCan_0743

<400> SEQUENCE: 153
cgaattaata tttattt                                                  17

<210> SEQ ID NO 154
<211> LENGTH: 16
<212> TYPE: DNA
<213> ORGANISM: artificial sequence
<220> FEATURE:
<223> OTHER INFORMATION: Loop sequence WCR_miR-927

<400> SEQUENCE: 154
gtcaatataa atggca                                                   16

<210> SEQ ID NO 155
<211> LENGTH: 9
<212> TYPE: DNA
<213> ORGANISM: artificial sequence
<220> FEATURE:
<223> OTHER INFORMATION: Loop sequence GeCan_0265

<400> SEQUENCE: 155 accttaaaa                                                            9

<210> SEQ ID NO 156
<211> LENGTH: 17
<212> TYPE: DNA
<213> ORGANISM: artificial sequence
<220> FEATURE:
<223> OTHER INFORMATION: Loop sequence WCR_miR-283

<400> SEQUENCE: 156
tggttgttga tcccaga                                                  17

<210> SEQ ID NO 157
<211> LENGTH: 30
<212> TYPE: DNA
<213> ORGANISM: artificial sequence
<220> FEATURE:
<223> OTHER INFORMATION: Loop sequence GeCan_1125

<400> SEQUENCE: 157
gcaggaaagc aacaggaaat cctgcatttc                                    30

<210> SEQ ID NO 158
<211> LENGTH: 18
<212> TYPE: DNA
<213> ORGANISM: artificial sequence
<220> FEATURE:
<223> OTHER INFORMATION: Loop sequence GeCan_1299

<400> SEQUENCE: 158
agaaataccg aaactatt                                                 18
```

-continued

```
<210> SEQ ID NO 159
<211> LENGTH: 19
<212> TYPE: DNA
<213> ORGANISM: artificial sequence
<220> FEATURE:
<223> OTHER INFORMATION: Loop sequence GeCan_0787

<400> SEQUENCE: 159
gtaaaatgtt acaatacaa                                                    19

<210> SEQ ID NO 160
<211> LENGTH: 84
<212> TYPE: DNA
<213> ORGANISM: artificial sequence
<220> FEATURE:
<223> OTHER INFORMATION: Loop sequence WCR_miR-2514d

<400> SEQUENCE: 160
gtgtttcggg ctgttgaggg gaggggagat cgcaacaggt gggcggttct gctcctcttc       60
gacgttcgaa acgcttttaa ttca                                              84

<210> SEQ ID NO 161
<211> LENGTH: 16
<212> TYPE: DNA
<213> ORGANISM: artificial sequence
<220> FEATURE:
<223> OTHER INFORMATION: Loop sequence GeCan_1366

<400> SEQUENCE: 161
attttattat actgca                                                       16

<210> SEQ ID NO 162
<211> LENGTH: 41
<212> TYPE: DNA
<213> ORGANISM: artificial sequence
<220> FEATURE:
<223> OTHER INFORMATION: Loop sequence GeCan_1071

<400> SEQUENCE: 162
caagcatcta aatttaaaac ctttagggtt ttcatttgga a                           41

<210> SEQ ID NO 163
<211> LENGTH: 50
<212> TYPE: DNA
<213> ORGANISM: artificial sequence
<220> FEATURE:
<223> OTHER INFORMATION: Loop sequence GeCan_0798

<400> SEQUENCE: 163
caatcaacca tcttctgaag atggtaagta aagatggttg attgggtcgt                  50

<210> SEQ ID NO 164
<211> LENGTH: 16
<212> TYPE: DNA
<213> ORGANISM: artificial sequence
<220> FEATURE:
<223> OTHER INFORMATION: Loop sequence WCR_miR-1000

<400> SEQUENCE: 164
tgtcttgtat ttactg                                                       16

<210> SEQ ID NO 165
<211> LENGTH: 9
<212> TYPE: DNA
<213> ORGANISM: artificial sequence
<220> FEATURE:
```

<223> OTHER INFORMATION: Loop sequence GeCan_0267

<400> SEQUENCE: 165 gacgtttct                                                                                          9

<210> SEQ ID NO 166
<211> LENGTH: 16
<212> TYPE: DNA
<213> ORGANISM: artificial sequence
<220> FEATURE:
<223> OTHER INFORMATION: Loop sequence WCR_miR-3477a

<400> SEQUENCE: 166
ggttgttttt ttcccc                                                                                 16

<210> SEQ ID NO 167
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 167
ttttcttcaa cattattaac agtaaacaaa tgttctaatc tttcta                                                 46

<210> SEQ ID NO 168
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 168
ttttcttcaa cattattaac agtaaacaaa tgttctaatc tttcta                                                 46

<210> SEQ ID NO 169
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 169
ttttcttcaa cattattaac agtaaacaaa tgttctaatc tttcta                                                 46

<210> SEQ ID NO 170
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 170
ttttcttcaa cattattaac agtaaacaaa tgttctaatc tttcta                                                 46

<210> SEQ ID NO 171
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 171
ttttcttcaa cattattaac agtaaacaaa tgttctaatc tttcta                                                 46

-continued

```
<210> SEQ ID NO 172
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 172 tttcttcaa cattattaac agtaaacaaa tgttctaatc tttcta                46

<210> SEQ ID NO 173
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 173 tttcttcaa cattattaac agtaaacaaa tgttctaatc tttcta                46

<210> SEQ ID NO 174
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 174 tttcttcaa cattattaac agtaaacaaa tgttctaatc tttcta                46

<210> SEQ ID NO 175
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 175 tttcttcaa cattattaac agtaaacaaa tgttctaatc tttcta                46

<210> SEQ ID NO 176
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 176 tttcttcaa cattattaac agtaaacaaa tgttctaatc tttcta                46

<210> SEQ ID NO 177
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 177 tttcttcaa cattattaac agtaaacaaa tgttctaatc tttcta                46

<210> SEQ ID NO 178
<211> LENGTH: 46
<212> TYPE: DNA
<213> ORGANISM: artificial sequence
<220> FEATURE:
<223> OTHER INFORMATION: Loop sequence  GeCan_1099
```

<400> SEQUENCE: 178
ttttcttcaa cattattaac agtaaacaaa tgttctaatc tttcta                         46

<210> SEQ ID NO 179
<211> LENGTH: 46
<212> TYPE: DNA
<213> ORGANISM: artificial sequence
<220> FEATURE:
<223> OTHER INFORMATION: Loop sequence GeCan_1099

<400> SEQUENCE: 179
ttttcttcaa cattattaac agtaaacaaa tgttctaatc tttcta                         46

<210> SEQ ID NO 180
<211> LENGTH: 52
<212> TYPE: DNA
<213> ORGANISM: Artificial sequence
<220> FEATURE:
<223> OTHER INFORMATION: Loop sequence GeCan_1020

<400> SEQUENCE: 180
cgtttgacaa gccgaacttc gagctcaagc cggcttgtct cttgcgagcc aa                  52

<210> SEQ ID NO 181
<211> LENGTH: 19
<212> TYPE: DNA
<213> ORGANISM: artificial sequence
<220> FEATURE:
<223> OTHER INFORMATION: Loop sequence WCR_miR-137

<400> SEQUENCE: 181
cacatatttg gggatgtta                                                       19

<210> SEQ ID NO 182
<211> LENGTH: 21
<212> TYPE: DNA
<213> ORGANISM: artificial sequence
<220> FEATURE:
<223> OTHER INFORMATION: Loop sequence GeCan_1219

<400> SEQUENCE: 182
gttcttcctt ttgaataagt t                                                    21

<210> SEQ ID NO 183
<211> LENGTH: 17
<212> TYPE: DNA
<213> ORGANISM: artificial sequence
<220> FEATURE:
<223> OTHER INFORMATION: Loop sequence WCR_miR-133a

<400> SEQUENCE: 183 tttttttgttt gttattt                                                        17

<210> SEQ ID NO 184
<211> LENGTH: 16
<212> TYPE: DNA
<213> ORGANISM: artificial sequence
<220> FEATURE:
<223> OTHER INFORMATION: Loop sequence WCR_miR-263b

<400> SEQUENCE: 184
gattgtcttg aatcgt                                                          16

<210> SEQ ID NO 185
<211> LENGTH: 16

```
<212> TYPE: DNA
<213> ORGANISM: artificial sequence
<220> FEATURE:
<223> OTHER INFORMATION: Loop sequence GeCan_0881

<400> SEQUENCE: 185
ttgatttgat tttaaa                                                 16

<210> SEQ ID NO 186
<211> LENGTH: 16
<212> TYPE: DNA
<213> ORGANISM: artificial sequence
<220> FEATURE:
<223> OTHER INFORMATION: Loop sequence GeCan_1492

<400> SEQUENCE: 186
ttgcatccat ggaaac                                                 16

<210> SEQ ID NO 187
<211> LENGTH: 9
<212> TYPE: DNA
<213> ORGANISM: artificial sequence
<220> FEATURE:
<223> OTHER INFORMATION: Loop sequence GeCan_0882

<400> SEQUENCE: 187 tgagcaaaa                                                          9

<210> SEQ ID NO 188
<211> LENGTH: 19
<212> TYPE: DNA
<213> ORGANISM: artificial sequence
<220> FEATURE:
<223> OTHER INFORMATION: Loop sequence WCR_miR-12

<400> SEQUENCE: 188
tagagttgtg aaactacct                                              19

<210> SEQ ID NO 189
<211> LENGTH: 19
<212> TYPE: DNA
<213> ORGANISM: artificial sequence
<220> FEATURE:
<223> OTHER INFORMATION: Loop sequence WCR_miR-3849

<400> SEQUENCE: 189
gtttaagttc gagtcaacg                                              19

<210> SEQ ID NO 190
<211> LENGTH: 15
<212> TYPE: DNA
<213> ORGANISM: artificial sequence
<220> FEATURE:
<223> OTHER INFORMATION: Loop sequence GeCan_1038

<400> SEQUENCE: 190
tctttagtat ccatc                                                  15

<210> SEQ ID NO 191
<211> LENGTH: 61
<212> TYPE: DNA
<213> ORGANISM: artificial sequence
<220> FEATURE:
<223> OTHER INFORMATION: Loop sequence GeCan_0390

<400> SEQUENCE: 191
```

```
acgaaaccta atagaaaata atatttgtct ttaatatcat tttctattag gtttcgtgtt    60
a                                                                    61

<210> SEQ ID NO 192
<211> LENGTH: 39
<212> TYPE: DNA
<213> ORGANISM: artificial sequence
<220> FEATURE:
<223> OTHER INFORMATION: Loop sequence GeCan_0402

<400> SEQUENCE: 192
acctgtggtt ggctaaacac gtccatacca caggtcatt                           39

<210> SEQ ID NO 193
<211> LENGTH: 28
<212> TYPE: DNA
<213> ORGANISM: artificial sequence
<220> FEATURE:
<223> OTHER INFORMATION: Loop sequence GeCan_0857

<400> SEQUENCE: 193
caggaaagca acaggatcct gcgtttct                                       28

<210> SEQ ID NO 194
<211> LENGTH: 20
<212> TYPE: DNA
<213> ORGANISM: artificial sequence
<220> FEATURE:
<223> OTHER INFORMATION: Loop sequence GeCan_0556

<400> SEQUENCE: 194
tgggttaatc aagacacatc                                                20

<210> SEQ ID NO 195
<211> LENGTH: 15
<212> TYPE: DNA
<213> ORGANISM: artificial sequence
<220> FEATURE:
<223> OTHER INFORMATION: Loop sequence WCR_miR-iab-4

<400> SEQUENCE: 195
gtgtcttctg tccgg                                                     15

<210> SEQ ID NO 196
<211> LENGTH: 32
<212> TYPE: DNA
<213> ORGANISM: artificial sequence
<220> FEATURE:
<223> OTHER INFORMATION: Loop sequence GeCan_0142

<400> SEQUENCE: 196
taggaaatca caatattgtg atttcctata ca                                  32

<210> SEQ ID NO 197
<211> LENGTH: 26
<212> TYPE: DNA
<213> ORGANISM: artificial sequence
<220> FEATURE:
<223> OTHER INFORMATION: Loop sequence GeCan_1263

<400> SEQUENCE: 197
tcgttacctc cactagctcg gccata                                         26

<210> SEQ ID NO 198
<211> LENGTH: 21
```

<212> TYPE: DNA
<213> ORGANISM: artificial sequence
<220> FEATURE:
<223> OTHER INFORMATION: Loop sequence GeCan_1143

<400> SEQUENCE: 198
tggctcatcg tgcgcgagaa t                                        21

<210> SEQ ID NO 199
<211> LENGTH: 11
<212> TYPE: DNA
<213> ORGANISM: artificial sequence
<220> FEATURE:
<223> OTHER INFORMATION: Loop sequence GeCan_0964

<400> SEQUENCE: 199
tttcaatccg g                                                   11

<210> SEQ ID NO 200
<211> LENGTH: 39
<212> TYPE: DNA
<213> ORGANISM: artificial sequence
<220> FEATURE:
<223> OTHER INFORMATION: Loop sequence GeCan_0275

<400> SEQUENCE: 200
tgcagcattt tgacctgcag gatcaaaatg ctgcaagcg                     39

<210> SEQ ID NO 201
<211> LENGTH: 22
<212> TYPE: DNA
<213> ORGANISM: artificial sequence
<220> FEATURE:
<223> OTHER INFORMATION: Loop sequence GeCan_1527

<400> SEQUENCE: 201
aaaattgaaa agaaatagtt tt                                       22

<210> SEQ ID NO 202
<211> LENGTH: 78
<212> TYPE: DNA
<213> ORGANISM: artificial sequence
<220> FEATURE:
<223> OTHER INFORMATION: Loop sequence GeCan_0451

<400> SEQUENCE: 202
ttgtttaata tggatattat tatggaactg tatgttaggc actacttatc tcaggttatg    60
tgttatatta tttggaat                                                 78

<210> SEQ ID NO 203
<211> LENGTH: 18
<212> TYPE: DNA
<213> ORGANISM: artificial sequence
<220> FEATURE:
<223> OTHER INFORMATION: Loop sequence WCR_miR-9a

<400> SEQUENCE: 203 gtattttta tttcataa                                             18

<210> SEQ ID NO 204
<211> LENGTH: 15
<212> TYPE: DNA
<213> ORGANISM: artificial sequence
<220> FEATURE:
<223> OTHER INFORMATION: Loop sequence WCR_miR-281a

```
<400> SEQUENCE: 204
atatatttta cactg                                              15

<210> SEQ ID NO 205
<211> LENGTH: 8
<212> TYPE: DNA
<213> ORGANISM: artificial sequence
<220> FEATURE:
<223> OTHER INFORMATION: Loop sequence GeCan_1378

<400> SEQUENCE: 205 ttaggcgt                                                       8

<210> SEQ ID NO 206
<211> LENGTH: 16
<212> TYPE: DNA
<213> ORGANISM: artificial sequence
<220> FEATURE:
<223> OTHER INFORMATION: Loop sequence GeCan_1182

<400> SEQUENCE: 206 gtgttttat tacgca                                              16

<210> SEQ ID NO 207
<211> LENGTH: 21
<212> TYPE: DNA
<213> ORGANISM: artificial sequence
<220> FEATURE:
<223> OTHER INFORMATION: Loop sequence GeCan_0310

<400> SEQUENCE: 207
cagttgtgac caaatgatgg a                                       21

<210> SEQ ID NO 208
<211> LENGTH: 57
<212> TYPE: DNA
<213> ORGANISM: artificial sequence
<220> FEATURE:
<223> OTHER INFORMATION: Loop sequence GeCan_1260

<400> SEQUENCE: 208
caatccctaa tgaacctcac ggggttcatc cgtggggttc attagggatt gaacccc  57

<210> SEQ ID NO 209
<211> LENGTH: 19
<212> TYPE: DNA
<213> ORGANISM: artificial sequence
<220> FEATURE:
<223> OTHER INFORMATION: Loop sequence GeCan_1448

<400> SEQUENCE: 209
gtatattaac tgcagtttc                                          19

<210> SEQ ID NO 210
<211> LENGTH: 18
<212> TYPE: DNA
<213> ORGANISM: artificial sequence
<220> FEATURE:
<223> OTHER INFORMATION: Loop sequence WCR_miR-9b

<400> SEQUENCE: 210
gtatttttaa catcataa                                           18

<210> SEQ ID NO 211
<211> LENGTH: 9
```

```
<212> TYPE: DNA
<213> ORGANISM: artificial sequence
<220> FEATURE:
<223> OTHER INFORMATION: Loop sequence GeCan_0777

<400> SEQUENCE: 211 tgtgagata                                                            9

<210> SEQ ID NO 212
<211> LENGTH: 43
<212> TYPE: DNA
<213> ORGANISM: artificial sequence
<220> FEATURE:
<223> OTHER INFORMATION: Loop sequence GeCan_0504

<400> SEQUENCE: 212
ggagctgata ctgttgccat gttggcaagt acatggctcg ctg                     43

<210> SEQ ID NO 213
<211> LENGTH: 20
<212> TYPE: DNA
<213> ORGANISM: artificial sequence
<220> FEATURE:
<223> OTHER INFORMATION: Loop sequence GeCan_1493

<400> SEQUENCE: 213
gtgaattgtg aatctagaat                                               20

<210> SEQ ID NO 214
<211> LENGTH: 25
<212> TYPE: DNA
<213> ORGANISM: artificial sequence
<220> FEATURE:
<223> OTHER INFORMATION: Loop sequence GeCan_1506

<400> SEQUENCE: 214
ataacttatc aatggtcatc ttttt                                         25

<210> SEQ ID NO 215
<211> LENGTH: 21
<212> TYPE: DNA
<213> ORGANISM: artificial sequence
<220> FEATURE:
<223> OTHER INFORMATION: Loop sequence GeCan_0293

<400> SEQUENCE: 215
gaggttgtga taccagatga t                                             21

<210> SEQ ID NO 216
<211> LENGTH: 25
<212> TYPE: DNA
<213> ORGANISM: artificial sequence
<220> FEATURE:
<223> OTHER INFORMATION: Loop sequence GeCan_0221

<400> SEQUENCE: 216
tattatagat cttataatat aattg                                         25

<210> SEQ ID NO 217
<211> LENGTH: 24
<212> TYPE: DNA
<213> ORGANISM: artificial sequence
<220> FEATURE:
<223> OTHER INFORMATION: Loop sequence GeCan_0953

<400> SEQUENCE: 217
```

-continued

```
taactttata gtctttatat agac                                          24

<210> SEQ ID NO 218
<211> LENGTH: 18
<212> TYPE: DNA
<213> ORGANISM: artificial sequence
<220> FEATURE:
<223> OTHER INFORMATION: Loop sequence WCR_miR-10

<400> SEQUENCE: 218
tgatattagg cgacaaat                                                 18

<210> SEQ ID NO 219
<211> LENGTH: 10
<212> TYPE: DNA
<213> ORGANISM: artificial sequence
<220> FEATURE:
<223> OTHER INFORMATION: Loop sequence WCR_miR-998

<400> SEQUENCE: 219
aagttgcgta                                                          10

<210> SEQ ID NO 220
<211> LENGTH: 43
<212> TYPE: DNA
<213> ORGANISM: artificial sequence
<220> FEATURE:
<223> OTHER INFORMATION: Loop sequence GeCan_0198

<400> SEQUENCE: 220
gcagttggtg aactattagt aactccaaac agtgcagctt caa                     43

<210> SEQ ID NO 221
<211> LENGTH: 15
<212> TYPE: DNA
<213> ORGANISM: artificial sequence
<220> FEATURE:
<223> OTHER INFORMATION: Loop sequence GeCan_0508

<400> SEQUENCE: 221
tatatttgaa cgtac                                                    15

<210> SEQ ID NO 222
<211> LENGTH: 16
<212> TYPE: DNA
<213> ORGANISM: artificial sequence
<220> FEATURE:
<223> OTHER INFORMATION: Loop sequence GeCan_1405

<400> SEQUENCE: 222
tcacgtatct ttgtaa                                                   16

<210> SEQ ID NO 223
<211> LENGTH: 48
<212> TYPE: DNA
<213> ORGANISM: artificial sequence
<220> FEATURE:
<223> OTHER INFORMATION: Loop sequence GeCan_0329

<400> SEQUENCE: 223
atgccaatat ttttgaagat gaacaccttc aaaatattg gcatcatt                 48

<210> SEQ ID NO 224
<211> LENGTH: 54
<212> TYPE: DNA
<213> ORGANISM: artificial sequence
```

```
<220> FEATURE:
<223> OTHER INFORMATION: Loop sequence GeCan_1401

<400> SEQUENCE: 224
tgggaggaat cagcgggcac gttattagat gtgttgctgc ctcctgatga ccta        54

<210> SEQ ID NO 225
<211> LENGTH: 20
<212> TYPE: DNA
<213> ORGANISM: artificial sequence
<220> FEATURE:
<223> OTHER INFORMATION: Loop sequence GeCan_0281

<400> SEQUENCE: 225
acattctaat atagacaata                                              20

<210> SEQ ID NO 226
<211> LENGTH: 55
<212> TYPE: DNA
<213> ORGANISM: artificial sequence
<220> FEATURE:
<223> OTHER INFORMATION: Loop sequence GeCan_0409

<400> SEQUENCE: 226
tctcactctt actcattggg aaggtacttc tcaatgagta agagtgagat agatg       55

<210> SEQ ID NO 227
<211> LENGTH: 22
<212> TYPE: DNA
<213> ORGANISM: artificial sequence
<220> FEATURE:
<223> OTHER INFORMATION: Loop sequence GeCan_1530

<400> SEQUENCE: 227
aaaattgaac agaaatagtt tt                                           22

<210> SEQ ID NO 228
<211> LENGTH: 46
<212> TYPE: DNA
<213> ORGANISM: artificial sequence
<220> FEATURE:
<223> OTHER INFORMATION: Loop sequence GeCan_0382

<400> SEQUENCE: 228
ggaatgactt tgtgattaag gccttaatca caaagtcatt ccaaat                 46

<210> SEQ ID NO 229
<211> LENGTH: 29
<212> TYPE: DNA
<213> ORGANISM: artificial sequence
<220> FEATURE:
<223> OTHER INFORMATION: Loop sequence GeCan_0458

<400> SEQUENCE: 229
ctgacctgag cgggagcaga aggcctacc                                    29

<210> SEQ ID NO 230
<211> LENGTH: 14
<212> TYPE: DNA
<213> ORGANISM: artificial sequence
<220> FEATURE:
<223> OTHER INFORMATION: Loop sequence GeCan_1488

<400> SEQUENCE: 230
ggcttaaggc gtgg                                                    14
```

<210> SEQ ID NO 231
<211> LENGTH: 18
<212> TYPE: DNA
<213> ORGANISM: artificial sequence
<220> FEATURE:
<223> OTHER INFORMATION: Loop sequence GeCan_0762

<400> SEQUENCE: 231
gttttttagg agacataa                                                 18

<210> SEQ ID NO 232
<211> LENGTH: 17
<212> TYPE: DNA
<213> ORGANISM: artificial sequence
<220> FEATURE:
<223> OTHER INFORMATION: Loop sequence GeCan_1333

<400> SEQUENCE: 232
ttggttatct tattttc                                                  17

<210> SEQ ID NO 233
<211> LENGTH: 28
<212> TYPE: DNA
<213> ORGANISM: artificial sequence
<220> FEATURE:
<223> OTHER INFORMATION: Loop sequence GeCan_0038

<400> SEQUENCE: 233
ttattgtcat cgacagtatc cttactaa                                      28

<210> SEQ ID NO 234
<211> LENGTH: 12
<212> TYPE: DNA
<213> ORGANISM: artificial sequence
<220> FEATURE:
<223> OTHER INFORMATION: Loop sequence WCR_miR-2944a

<400> SEQUENCE: 234
attgttatcg ta                                                       12

<210> SEQ ID NO 235
<211> LENGTH: 30
<212> TYPE: DNA
<213> ORGANISM: artificial sequence
<220> FEATURE:
<223> OTHER INFORMATION: Loop sequence GeCan_1275

<400> SEQUENCE: 235
atgactccaa taagagtcga aaatcgtcga                                    30

<210> SEQ ID NO 236
<211> LENGTH: 17
<212> TYPE: DNA
<213> ORGANISM: artificial sequence
<220> FEATURE:
<223> OTHER INFORMATION: Loop sequence WCR_bantam

<400> SEQUENCE: 236
atggttttga ttctgag                                                  17

<210> SEQ ID NO 237
<211> LENGTH: 47
<212> TYPE: DNA
<213> ORGANISM: artificial sequence
<220> FEATURE:
<223> OTHER INFORMATION: Loop sequence GeCan_1587

```
<400> SEQUENCE: 237
gcgacaactg aaactgccgc cctgcagttg ccgcctgccg cctgccg          47

<210> SEQ ID NO 238
<211> LENGTH: 15
<212> TYPE: DNA
<213> ORGANISM: artificial sequence
<220> FEATURE:
<223> OTHER INFORMATION: Loop sequence GeCan_1317

<400> SEQUENCE: 238
atattagctt cagtt                                              15

<210> SEQ ID NO 239
<211> LENGTH: 27
<212> TYPE: DNA
<213> ORGANISM: artificial sequence
<220> FEATURE:
<223> OTHER INFORMATION: Loop sequence GeCan_0533

<400> SEQUENCE: 239
ttatttataa caattaataa attattt                                 27

<210> SEQ ID NO 240
<211> LENGTH: 16
<212> TYPE: DNA
<213> ORGANISM: artificial sequence
<220> FEATURE:
<223> OTHER INFORMATION: Loop sequence GeCan_0689

<400> SEQUENCE: 240
aaatatgaaa agtacc                                             16

<210> SEQ ID NO 241
<211> LENGTH: 9
<212> TYPE: DNA
<213> ORGANISM: artificial sequence
<220> FEATURE:
<223> OTHER INFORMATION: Loop sequence GeCan_0266

<400> SEQUENCE: 241 cgtcgtttc                                                      9

<210> SEQ ID NO 242
<211> LENGTH: 42
<212> TYPE: DNA
<213> ORGANISM: artificial sequence
<220> FEATURE:
<223> OTHER INFORMATION: Loop sequence GeCan_1542

<400> SEQUENCE: 242
ctgagatcgg gccgcccaag gggacgggct gtcccacagt tg                42

<210> SEQ ID NO 243
<211> LENGTH: 23
<212> TYPE: DNA
<213> ORGANISM: artificial sequence
<220> FEATURE:
<223> OTHER INFORMATION: Loop sequence GeCan_0704

<400> SEQUENCE: 243
aagttgtgat gaaattatgg aca                                     23

<210> SEQ ID NO 244
```

```
<211> LENGTH: 17
<212> TYPE: DNA
<213> ORGANISM: artificial sequence
<220> FEATURE:
<223> OTHER INFORMATION: Loop sequence GeCan_1424

<400> SEQUENCE: 244
gaattaatgt atcagta                                                   17

<210> SEQ ID NO 245
<211> LENGTH: 17
<212> TYPE: DNA
<213> ORGANISM: artificial sequence
<220> FEATURE:
<223> OTHER INFORMATION: Loop sequence GeCan_1477

<400> SEQUENCE: 245
cgcagtttcg cggttcg                                                   17

<210> SEQ ID NO 246
<211> LENGTH: 29
<212> TYPE: DNA
<213> ORGANISM: artificial sequence
<220> FEATURE:
<223> OTHER INFORMATION: Loop sequence WCR_miR-277a

<400> SEQUENCE: 246
cgttaaaggt tctgattgaa gtctgtaaa                                      29

<210> SEQ ID NO 247
<211> LENGTH: 16
<212> TYPE: DNA
<213> ORGANISM: artificial sequence
<220> FEATURE:
<223> OTHER INFORMATION: Loop sequence GeCan_0656

<400> SEQUENCE: 247
gtataccaaa tttat                                                     16

<210> SEQ ID NO 248
<211> LENGTH: 57
<212> TYPE: DNA
<213> ORGANISM: artificial sequence
<220> FEATURE:
<223> OTHER INFORMATION: Loop sequence GeCan_1259

<400> SEQUENCE: 248
tcaatcccta atgaacccca cggatgaacc ccgtgaggtt cattagggat tgaaccc       57

<210> SEQ ID NO 249
<211> LENGTH: 15
<212> TYPE: DNA
<213> ORGANISM: artificial sequence
<220> FEATURE:
<223> OTHER INFORMATION: Loop sequence GeCan_1454

<400> SEQUENCE: 249
tatattagct tcagt                                                     15

<210> SEQ ID NO 250
<211> LENGTH: 10
<212> TYPE: DNA
<213> ORGANISM: artificial sequence
<220> FEATURE:
<223> OTHER INFORMATION: Loop sequence WCR_miR-2779c

<400> SEQUENCE: 250
```

```
taatttatca                                                              10

<210> SEQ ID NO 251
<211> LENGTH: 14
<212> TYPE: DNA
<213> ORGANISM: artificial sequence
<220> FEATURE:
<223> OTHER INFORMATION: Loop sequence WCR_miR-275a

<400> SEQUENCE: 251
atcatttgct agtc                                                         14

<210> SEQ ID NO 252
<211> LENGTH: 36
<212> TYPE: DNA
<213> ORGANISM: artificial sequence
<220> FEATURE:
<223> OTHER INFORMATION: Loop sequence GeCan_0099

<400> SEQUENCE: 252
tcaaaacagt tttccggaaa actgttttga atttgg                                 36

<210> SEQ ID NO 253
<211> LENGTH: 29
<212> TYPE: DNA
<213> ORGANISM: artificial sequence
<220> FEATURE:
<223> OTHER INFORMATION: Loop sequence GeCan_0394

<400> SEQUENCE: 253
cggagtgacg tttcgttgcg ttgtgccgt                                         29

<210> SEQ ID NO 254
<211> LENGTH: 13
<212> TYPE: DNA
<213> ORGANISM: artificial sequence
<220> FEATURE:
<223> OTHER INFORMATION: Loop sequence GeCan_0753

<400> SEQUENCE: 254
atgtaagcaa att                                                          13

<210> SEQ ID NO 255
<211> LENGTH: 19
<212> TYPE: DNA
<213> ORGANISM: artificial sequence
<220> FEATURE:
<223> OTHER INFORMATION: Loop sequence GeCan_0651

<400> SEQUENCE: 255
tcggttattt actccgttc                                                    19

<210> SEQ ID NO 256
<211> LENGTH: 46
<212> TYPE: DNA
<213> ORGANISM: artificial sequence
<220> FEATURE:
<223> OTHER INFORMATION: Loop sequence GeCan_0312

<400> SEQUENCE: 256
aagagcagct tgacttggaa ggagtggaaa agctgctctt ccatat                      46

<210> SEQ ID NO 257
<211> LENGTH: 17
<212> TYPE: DNA
```

```
<213> ORGANISM: artificial sequence
<220> FEATURE:
<223> OTHER INFORMATION: Loop sequence GeCan_0691

<400> SEQUENCE: 257
cgtttttact ccgttca                                                  17

<210> SEQ ID NO 258
<211> LENGTH: 28
<212> TYPE: DNA
<213> ORGANISM: artificial sequence
<220> FEATURE:
<223> OTHER INFORMATION: Loop sequence GeCan_0525

<400> SEQUENCE: 258
ataacgcaga accctggatt aagatcgt                                      28

<210> SEQ ID NO 259
<211> LENGTH: 64
<212> TYPE: DNA
<213> ORGANISM: artificial sequence
<220> FEATURE:
<223> OTHER INFORMATION: Loop sequence GeCan_0426

<400> SEQUENCE: 259 aggattttc atgatataat tggattctaa ttagaatcca attatatcat gaaaaatcct    60
gaag                                                                64

<210> SEQ ID NO 260
<211> LENGTH: 48
<212> TYPE: DNA
<213> ORGANISM: artificial sequence
<220> FEATURE:
<223> OTHER INFORMATION: Loop sequence GeCan_0655

<400> SEQUENCE: 260
ggaatgttaa cactattact cttgatgtaa gtttctgata tgatttaa                48

<210> SEQ ID NO 261
<211> LENGTH: 12
<212> TYPE: DNA
<213> ORGANISM: artificial sequence
<220> FEATURE:
<223> OTHER INFORMATION: Loop sequence WCR_miR-2c

<400> SEQUENCE: 261
tttactttca ta                                                       12

<210> SEQ ID NO 262
<211> LENGTH: 84
<212> TYPE: DNA
<213> ORGANISM: artificial sequence
<220> FEATURE:
<223> OTHER INFORMATION: Loop sequence WCR_miR-2514a

<400> SEQUENCE: 262
tgtttcgggc tgttgagggg agggagatc gcaacaggtg ggcggttctg ctcctcttcg    60
acgttcgaaa cgcttttaat tcat                                          84

<210> SEQ ID NO 263
<211> LENGTH: 47
<212> TYPE: DNA
<213> ORGANISM: artificial sequence
<220> FEATURE:
<223> OTHER INFORMATION: Loop sequence GeCan_0957
```

```
<400> SEQUENCE: 263
ggcttggctg tggcttgcac atgcaaacct atgcctgggc cttgcac                    47

<210> SEQ ID NO 264
<211> LENGTH: 8
<212> TYPE: DNA
<213> ORGANISM: artificial sequence
<220> FEATURE:
<223> OTHER INFORMATION: Loop sequence GeCan_0276

<400> SEQUENCE: 264 tggtcata                                                                8

<210> SEQ ID NO 265
<211> LENGTH: 19
<212> TYPE: DNA
<213> ORGANISM: artificial sequence
<220> FEATURE:
<223> OTHER INFORMATION: Loop sequence GeCan_0226

<400> SEQUENCE: 265
gtcgtatcca aaacatata                                                   19

<210> SEQ ID NO 266
<211> LENGTH: 31
<212> TYPE: DNA
<213> ORGANISM: artificial sequence
<220> FEATURE:
<223> OTHER INFORMATION: Loop sequence GeCan_0078

<400> SEQUENCE: 266
gcaaaagaaa accaggttaa agtgccattt a                                     31

<210> SEQ ID NO 267
<211> LENGTH: 18
<212> TYPE: DNA
<213> ORGANISM: artificial sequence
<220> FEATURE:
<223> OTHER INFORMATION: Loop sequence WCR_miR-929

<400> SEQUENCE: 267
gttacttatt agcgactc                                                    18

<210> SEQ ID NO 268
<211> LENGTH: 18
<212> TYPE: DNA
<213> ORGANISM: artificial sequence
<220> FEATURE:
<223> OTHER INFORMATION: Loop sequence WCR_miR-279a

<400> SEQUENCE: 268 ggtttttttgc attcgtga                                                   18

<210> SEQ ID NO 269
<211> LENGTH: 51
<212> TYPE: DNA
<213> ORGANISM: artificial sequence
<220> FEATURE:
<223> OTHER INFORMATION: Loop sequence GeCan_1266

<400> SEQUENCE: 269
agcgtcccgc ataggttt gatgcaaacc tctattcgga aagctaaagc g                 51

<210> SEQ ID NO 270
```

```
<211> LENGTH: 52
<212> TYPE: DNA
<213> ORGANISM: artificial sequence
<220> FEATURE:
<223> OTHER INFORMATION: Loop sequence WCR_miR-1001b

<400> SEQUENCE: 270
gtctatcttg ttttgtacaa taattattgt acaaacaag atagacacag ct              52

<210> SEQ ID NO 271
<211> LENGTH: 40
<212> TYPE: DNA
<213> ORGANISM: artificial sequence
<220> FEATURE:
<223> OTHER INFORMATION: Loop sequence GeCan_0033

<400> SEQUENCE: 271
ttctaacttt aattattata ataattaaag ttagaatatc                           40

<210> SEQ ID NO 272
<211> LENGTH: 16
<212> TYPE: DNA
<213> ORGANISM: artificial sequence
<220> FEATURE:
<223> OTHER INFORMATION: Loop sequence GeCan_0996

<400> SEQUENCE: 272
gtgtatttac ctcgac                                                     16

<210> SEQ ID NO 273
<211> LENGTH: 41
<212> TYPE: DNA
<213> ORGANISM: artificial sequence
<220> FEATURE:
<223> OTHER INFORMATION: Loop sequence GeCan_1034

<400> SEQUENCE: 273
ggaatcggta tgcttttcga taatttcgcg gcaaaatggt a                         41

<210> SEQ ID NO 274
<211> LENGTH: 16
<212> TYPE: DNA
<213> ORGANISM: artificial sequence
<220> FEATURE:
<223> OTHER INFORMATION: Loop sequence WCR_miR-124c

<400> SEQUENCE: 274
tcaatatttt gtcata                                                     16

<210> SEQ ID NO 275
<211> LENGTH: 18
<212> TYPE: DNA
<213> ORGANISM: artificial sequence
<220> FEATURE:
<223> OTHER INFORMATION: Loop sequence GeCan_0555

<400> SEQUENCE: 275
tcacttttta ctccgttc                                                   18

<210> SEQ ID NO 276
<211> LENGTH: 17
<212> TYPE: DNA
<213> ORGANISM: artificial sequence
<220> FEATURE:
<223> OTHER INFORMATION: Loop sequence WCR_miR-995

<400> SEQUENCE: 276
```
ctttatttaa atcgtag                                                          17

<210> SEQ ID NO 277
<211> LENGTH: 25
<212> TYPE: DNA
<213> ORGANISM: artificial sequence
<220> FEATURE:
<223> OTHER INFORMATION: Loop sequence GeCan_0271

<400> SEQUENCE: 277
gtattattgt caataatact ggaac                                                 25

<210> SEQ ID NO 278
<211> LENGTH: 18
<212> TYPE: DNA
<213> ORGANISM: artificial sequence
<220> FEATURE:
<223> OTHER INFORMATION: Loop sequence GeCan_0052

<400> SEQUENCE: 278
tttgtttaaa caaaaggc                                                         18

<210> SEQ ID NO 279
<211> LENGTH: 15
<212> TYPE: DNA
<213> ORGANISM: artificial sequence
<220> FEATURE:
<223> OTHER INFORMATION: Loop sequence GeCan_0994

<400> SEQUENCE: 279
tatatttgaa cgtat                                                            15

<210> SEQ ID NO 280
<211> LENGTH: 15
<212> TYPE: DNA
<213> ORGANISM: artificial sequence
<220> FEATURE:
<223> OTHER INFORMATION: Loop sequence WCR_miR-184

<400> SEQUENCE: 280
tatttcgacg actgg                                                            15

<210> SEQ ID NO 281
<211> LENGTH: 31
<212> TYPE: DNA
<213> ORGANISM: artificial sequence
<220> FEATURE:
<223> OTHER INFORMATION: Loop sequence GeCan_0428

<400> SEQUENCE: 281
gaatgttaac actattaatt ttgatgtaag t                                          31

<210> SEQ ID NO 282
<211> LENGTH: 23
<212> TYPE: DNA
<213> ORGANISM: artificial sequence
<220> FEATURE:
<223> OTHER INFORMATION: Loop sequence GeCan_0943

<400> SEQUENCE: 282
tttgactctt attggagtca tca                                                   23

<210> SEQ ID NO 283
<211> LENGTH: 31
<212> TYPE: DNA

-continued

```
<213> ORGANISM: artificial sequence
<220> FEATURE:
<223> OTHER INFORMATION: Loop sequence GeCan_1546

<400> SEQUENCE: 283
gaatgttaac actattaatc ttgatgtaag t                              31

<210> SEQ ID NO 284
<211> LENGTH: 30
<212> TYPE: DNA
<213> ORGANISM: artificial sequence
<220> FEATURE:
<223> OTHER INFORMATION: Loop sequence GeCan_1205

<400> SEQUENCE: 284
gcaggaaagc aacaggaaat cctgcatttc                                30

<210> SEQ ID NO 285
<211> LENGTH: 25
<212> TYPE: DNA
<213> ORGANISM: artificial sequence
<220> FEATURE:
<223> OTHER INFORMATION: Loop sequence GeCan_1028

<400> SEQUENCE: 285
ttacagtttc attattggac tattc                                     25

<210> SEQ ID NO 286
<211> LENGTH: 28
<212> TYPE: DNA
<213> ORGANISM: artificial sequence
<220> FEATURE:
<223> OTHER INFORMATION: Loop sequence GeCan_0124

<400> SEQUENCE: 286
accgaaaggc cgcggccttt cggtgatt                                  28

<210> SEQ ID NO 287
<211> LENGTH: 21
<212> TYPE: DNA
<213> ORGANISM: artificial sequence
<220> FEATURE:
<223> OTHER INFORMATION: Loop sequence GeCan_0375

<400> SEQUENCE: 287
ttaactataa cagttaaatc a                                         21

<210> SEQ ID NO 288
<211> LENGTH: 46
<212> TYPE: DNA
<213> ORGANISM: artificial sequence
<220> FEATURE:
<223> OTHER INFORMATION: Loop sequence GeCan_0158

<400> SEQUENCE: 288
taatccttac cttttaatct gcagattaaa aggtaaggat tactta              46

<210> SEQ ID NO 289
<211> LENGTH: 30
<212> TYPE: DNA
<213> ORGANISM: artificial sequence
<220> FEATURE:
<223> OTHER INFORMATION: Loop sequence GeCan_0507

<400> SEQUENCE: 289
gcagggaagc aacataaaat cctgcatttc                                30
```

```
<210> SEQ ID NO 290
<211> LENGTH: 16
<212> TYPE: DNA
<213> ORGANISM: artificial sequence
<220> FEATURE:
<223> OTHER INFORMATION: Loop sequence WCR_miR-29

<400> SEQUENCE: 290
atttgattta attcta                                                       16

<210> SEQ ID NO 291
<211> LENGTH: 40
<212> TYPE: DNA
<213> ORGANISM: artificial sequence
<220> FEATURE:
<223> OTHER INFORMATION: Loop sequence GeCan_0072

<400> SEQUENCE: 291
cctcagatgt accacttgca agtggtacat ctgaggctgc                             40

<210> SEQ ID NO 292
<211> LENGTH: 66
<212> TYPE: DNA
<213> ORGANISM: artificial sequence
<220> FEATURE:
<223> OTHER INFORMATION: Loop sequence GeCan_0861

<400> SEQUENCE: 292
gagctcctct acatataaac cattggttcg tcgaaggtga gcgctgagcg ggagcaccaa       60
cgtatc                                                                  66

<210> SEQ ID NO 293
<211> LENGTH: 17
<212> TYPE: DNA
<213> ORGANISM: artificial sequence
<220> FEATURE:
<223> OTHER INFORMATION: Loop sequence WCR_miR-2796

<400> SEQUENCE: 293
cagaatagac ggttgta                                                      17

<210> SEQ ID NO 294
<211> LENGTH: 15
<212> TYPE: DNA
<213> ORGANISM: artificial sequence
<220> FEATURE:
<223> OTHER INFORMATION: Loop sequence WCR_miR-219

<400> SEQUENCE: 294
gtggtaatga tcaag                                                        15

<210> SEQ ID NO 295
<211> LENGTH: 22
<212> TYPE: DNA
<213> ORGANISM: artificial sequence
<220> FEATURE:
<223> OTHER INFORMATION: Loop sequence GeCan_1528

<400> SEQUENCE: 295
aaaattgaaa agaaatagtt tt                                                22

<210> SEQ ID NO 296
<211> LENGTH: 51
<212> TYPE: DNA
```

```
<213> ORGANISM: artificial sequence
<220> FEATURE:
<223> OTHER INFORMATION: Loop sequence GeCan_0645

<400> SEQUENCE: 296
ccaatcaacc atcttcggtc ctaagatgac cgaagatggt taattgggtc c          51

<210> SEQ ID NO 297
<211> LENGTH: 21
<212> TYPE: DNA
<213> ORGANISM: artificial sequence
<220> FEATURE:
<223> OTHER INFORMATION: Loop sequence GeCan_0730

<400> SEQUENCE: 297
ttcttccttt tgaataagtt t                                            21

<210> SEQ ID NO 298
<211> LENGTH: 31
<212> TYPE: DNA
<213> ORGANISM: artificial sequence
<220> FEATURE:
<223> OTHER INFORMATION: Loop sequence GeCan_0983

<400> SEQUENCE: 298
ggaatgttaa cactattaat cttgatgtaa g                                 31

<210> SEQ ID NO 299
<211> LENGTH: 14
<212> TYPE: DNA
<213> ORGANISM: artificial sequence
<220> FEATURE:
<223> OTHER INFORMATION: Loop sequence GeCan_1164

<400> SEQUENCE: 299
ggaatttgta tgta                                                    14

<210> SEQ ID NO 300
<211> LENGTH: 18
<212> TYPE: DNA
<213> ORGANISM: artificial sequence
<220> FEATURE:
<223> OTHER INFORMATION: Loop sequence GeCan_0421

<400> SEQUENCE: 300
gtgcaccaga atcgtcgt                                                18

<210> SEQ ID NO 301
<211> LENGTH: 60
<212> TYPE: DNA
<213> ORGANISM: artificial sequence
<220> FEATURE:
<223> OTHER INFORMATION: Loop sequence GeCan_1502

<400> SEQUENCE: 301
ctgttggact taggtacgac ctttctaaag aagatggtac cattacagcc accgacagct  60

<210> SEQ ID NO 302
<211> LENGTH: 12
<212> TYPE: DNA
<213> ORGANISM: artificial sequence
<220> FEATURE:
<223> OTHER INFORMATION: Loop sequence GeCan_0905

<400> SEQUENCE: 302
aattagcatg tt                                                      12
```

```
<210> SEQ ID NO 303
<211> LENGTH: 17
<212> TYPE: DNA
<213> ORGANISM: artificial sequence
<220> FEATURE:
<223> OTHER INFORMATION: Loop sequence WCR_miR-34

<400> SEQUENCE: 303
tgatacttga accacga                                                    17

<210> SEQ ID NO 304
<211> LENGTH: 18
<212> TYPE: DNA
<213> ORGANISM: artificial sequence
<220> FEATURE:
<223> OTHER INFORMATION: Loop sequence GeCan_0702

<400> SEQUENCE: 304
gttttgacaa aatttgga                                                   18

<210> SEQ ID NO 305
<211> LENGTH: 19
<212> TYPE: DNA
<213> ORGANISM: artificial sequence
<220> FEATURE:
<223> OTHER INFORMATION: Loop sequence GeCan_0677

<400> SEQUENCE: 305
cgtatattaa ctgcagttt                                                  19

<210> SEQ ID NO 306
<211> LENGTH: 19
<212> TYPE: DNA
<213> ORGANISM: artificial sequence
<220> FEATURE:
<223> OTHER INFORMATION: Loop sequence GeCan_0949

<400> SEQUENCE: 306
cgtatattaa ctgcagttt                                                  19

<210> SEQ ID NO 307
<211> LENGTH: 18
<212> TYPE: DNA
<213> ORGANISM: artificial sequence
<220> FEATURE:
<223> OTHER INFORMATION: Loop sequence WCR_miR-9c

<400> SEQUENCE: 307
agtatttttt atttcata                                                   18

<210> SEQ ID NO 308
<211> LENGTH: 36
<212> TYPE: DNA
<213> ORGANISM: artificial sequence
<220> FEATURE:
<223> OTHER INFORMATION: Loop sequence GeCan_0017

<400> SEQUENCE: 308
ttttcctata tatatatata tatataggaa aagaag                                36

<210> SEQ ID NO 309
<211> LENGTH: 23
<212> TYPE: DNA
<213> ORGANISM: artificial sequence
<220> FEATURE:
```

<223> OTHER INFORMATION: Loop sequence GeCan_1190

<400> SEQUENCE: 309
tatctatcca gtaaataaat gca                                    23

<210> SEQ ID NO 310
<211> LENGTH: 19
<212> TYPE: DNA
<213> ORGANISM: artificial sequence
<220> FEATURE:
<223> OTHER INFORMATION: Loop sequence WCR_miR-100

<400> SEQUENCE: 310
tcttttttta acactcacg                                         19

<210> SEQ ID NO 311
<211> LENGTH: 40
<212> TYPE: DNA
<213> ORGANISM: artificial sequence
<220> FEATURE:
<223> OTHER INFORMATION: Loop sequence GeCan_0454

<400> SEQUENCE: 311
aggtgttttc aatgccaaac agtggcttgt tggccgtata                  40

<210> SEQ ID NO 312
<211> LENGTH: 79
<212> TYPE: DNA
<213> ORGANISM: artificial sequence
<220> FEATURE:
<223> OTHER INFORMATION: Loop sequence GeCan_1109

<400> SEQUENCE: 312
gatacagcca gtttcataat tattgagtac caatttcaaa tggtgaacaa tgatggtcaa   60
aaactatgtt aatttccac                                         79

<210> SEQ ID NO 313
<211> LENGTH: 11
<212> TYPE: DNA
<213> ORGANISM: artificial sequence
<220> FEATURE:
<223> OTHER INFORMATION: Loop sequence WCR_miR-2779a

<400> SEQUENCE: 313
ctaataccaa a                                                 11

<210> SEQ ID NO 314
<211> LENGTH: 72
<212> TYPE: DNA
<213> ORGANISM: artificial sequence
<220> FEATURE:
<223> OTHER INFORMATION: Loop sequence GeCan_1311

<400> SEQUENCE: 314
atttatttaa acgcaacagc aagtgacagt aggtaggtaa atgacttgtt gttgcgttta   60
gtaaatttca at                                                72

<210> SEQ ID NO 315
<211> LENGTH: 66
<212> TYPE: DNA
<213> ORGANISM: artificial sequence
<220> FEATURE:
<223> OTHER INFORMATION: Loop sequence GeCan_1578

<400> SEQUENCE: 315
cacaaggcgg tgactgtcac agtactgtta agtcaagagc acggagtggc atttcgttgc    60
gttgtg                                                              66

<210> SEQ ID NO 316
<211> LENGTH: 16
<212> TYPE: DNA
<213> ORGANISM: artificial sequence
<220> FEATURE:
<223> OTHER INFORMATION: Loop sequence WCR_miR-2779d

<400> SEQUENCE: 316
taagttcggc tcagct                                                   16

<210> SEQ ID NO 317
<211> LENGTH: 18
<212> TYPE: DNA
<213> ORGANISM: artificial sequence
<220> FEATURE:
<223> OTHER INFORMATION: Loop sequence GeCan_0339

<400> SEQUENCE: 317
ccttgatagt caagcata                                                 18

<210> SEQ ID NO 318
<211> LENGTH: 22
<212> TYPE: DNA
<213> ORGANISM: artificial sequence
<220> FEATURE:
<223> OTHER INFORMATION: Loop sequence GeCan_0333

<400> SEQUENCE: 318
caatcaacca tcttcgggtc ct                                            22

<210> SEQ ID NO 319
<211> LENGTH: 12
<212> TYPE: DNA
<213> ORGANISM: artificial sequence
<220> FEATURE:
<223> OTHER INFORMATION: Loop sequence GeCan_0692

<400> SEQUENCE: 319
atatttcatc ga                                                       12

<210> SEQ ID NO 320
<211> LENGTH: 18
<212> TYPE: DNA
<213> ORGANISM: artificial sequence
<220> FEATURE:
<223> OTHER INFORMATION: Loop sequence GeCan_0903

<400> SEQUENCE: 320
tttttatttt atattaga                                                 18

<210> SEQ ID NO 321
<211> LENGTH: 52
<212> TYPE: DNA
<213> ORGANISM: artificial sequence
<220> FEATURE:
<223> OTHER INFORMATION: Loop sequence WCR_miR-1001a

<400> SEQUENCE: 321
tgtctatctt gttttgtaca ataattattg tacaaaacaa gatagacaca gc           52

<210> SEQ ID NO 322

-continued

```
<211> LENGTH: 17
<212> TYPE: DNA
<213> ORGANISM: artificial sequence
<220> FEATURE:
<223> OTHER INFORMATION: Loop sequence GeCan_1300

<400> SEQUENCE: 322
ttggcaggca acgtttg                                                  17

<210> SEQ ID NO 323
<211> LENGTH: 84
<212> TYPE: DNA
<213> ORGANISM: artificial sequence
<220> FEATURE:
<223> OTHER INFORMATION: Loop sequence WCR_miR-2514b

<400> SEQUENCE: 323
tgtttcgggc tgttgagggg aggggagatc gcaacaggtg ggcggttctg ctcctcttcg   60
acgttcgaaa cgcttttaat tcat                                         84

<210> SEQ ID NO 324
<211> LENGTH: 15
<212> TYPE: DNA
<213> ORGANISM: artificial sequence
<220> FEATURE:
<223> OTHER INFORMATION: Loop sequence WCR_miR-2788

<400> SEQUENCE: 324
agtatttgaa ttgca                                                    15

<210> SEQ ID NO 325
<211> LENGTH: 14
<212> TYPE: DNA
<213> ORGANISM: artificial sequence
<220> FEATURE:
<223> OTHER INFORMATION: Loop sequence GeCan_1505

<400> SEQUENCE: 325
ttattggaat tcaa                                                     14

<210> SEQ ID NO 326
<211> LENGTH: 12
<212> TYPE: DNA
<213> ORGANISM: artificial sequence
<220> FEATURE:
<223> OTHER INFORMATION: Loop sequence GeCan_0130

<400> SEQUENCE: 326
aacgcgtttc tc                                                       12

<210> SEQ ID NO 327
<211> LENGTH: 16
<212> TYPE: DNA
<213> ORGANISM: artificial sequence
<220> FEATURE:
<223> OTHER INFORMATION: Loop sequence WCR_miR-124a

<400> SEQUENCE: 327
tcaataattt gtcata                                                   16

<210> SEQ ID NO 328
<211> LENGTH: 30
<212> TYPE: DNA
<213> ORGANISM: artificial sequence
<220> FEATURE:
<223> OTHER INFORMATION: Loop sequence GeCan_1123
```

<400> SEQUENCE: 328
gcaggaaagc aacaggaaat cctgcgtttc                                30

<210> SEQ ID NO 329
<211> LENGTH: 218
<212> TYPE: DNA
<213> ORGANISM: artificial sequence
<220> FEATURE:
<223> OTHER INFORMATION: Loop sequence WCR_miR-2779f

<400> SEQUENCE: 329
cttcgaaagt gtctttttt taaaaacgtt tacgtcagta ggggccaacc tttattgatt  60
cagaaggaaa taatgaattt cctgtagtcg gctgtatacc ataaatttta tcaaaaactc 120
ctttataaaa ggtacatttt ctaggggcgg tccgataagt actaagtact tagtcttcaa 180
aatgagaacg gaaattttc ggccttcgag ccggaaaa                         218

<210> SEQ ID NO 330
<211> LENGTH: 14
<212> TYPE: DNA
<213> ORGANISM: artificial sequence
<220> FEATURE:
<223> OTHER INFORMATION: Loop sequence WCR_miR-981

<400> SEQUENCE: 330
gtactttact ggtt                                                 14

<210> SEQ ID NO 331
<211> LENGTH: 62
<212> TYPE: DNA
<213> ORGANISM: artificial sequence
<220> FEATURE:
<223> OTHER INFORMATION: Loop sequence GeCan_0068

<400> SEQUENCE: 331
ggcatgtttt ctattagacc tcttcaaacg tttgaagagg tctaatagaa aacatgccaa  60
ag                                                               62

<210> SEQ ID NO 332
<211> LENGTH: 32
<212> TYPE: DNA
<213> ORGANISM: artificial sequence
<220> FEATURE:
<223> OTHER INFORMATION: Loop sequence GeCan_0071

<400> SEQUENCE: 332
aaatataaag tttaaacttt atatttgggg tt                              32

<210> SEQ ID NO 333
<211> LENGTH: 17
<212> TYPE: DNA
<213> ORGANISM: artificial sequence
<220> FEATURE:
<223> OTHER INFORMATION: Loop sequence GeCan_0884

<400> SEQUENCE: 333
agtataaaag aaacttg                                               17

<210> SEQ ID NO 334
<211> LENGTH: 9
<212> TYPE: DNA
<213> ORGANISM: artificial sequence
<220> FEATURE:

-continued

<223> OTHER INFORMATION: Loop sequence GeCan_1580

<400> SEQUENCE: 334 ctgtctctt                                                                                      9

<210> SEQ ID NO 335
<211> LENGTH: 15
<212> TYPE: DNA
<213> ORGANISM: artificial sequence
<220> FEATURE:
<223> OTHER INFORMATION: Loop sequence WCR_miR-92c

<400> SEQUENCE: 335
tggtatttga tcata                                                                              15

<210> SEQ ID NO 336
<211> LENGTH: 38
<212> TYPE: DNA
<213> ORGANISM: artificial sequence
<220> FEATURE:
<223> OTHER INFORMATION: Loop sequence GeCan_0836

<400> SEQUENCE: 336
acccctgcga ttatccctaa tgcggataac tcgggcgc                                                     38

<210> SEQ ID NO 337
<211> LENGTH: 15
<212> TYPE: DNA
<213> ORGANISM: artificial sequence
<220> FEATURE:
<223> OTHER INFORMATION: Loop sequence GeCan_0547

<400> SEQUENCE: 337
tctcttagtt aggac                                                                              15

<210> SEQ ID NO 338
<211> LENGTH: 16
<212> TYPE: DNA
<213> ORGANISM: artificial sequence
<220> FEATURE:
<223> OTHER INFORMATION: Loop sequence GeCan_1433

<400> SEQUENCE: 338
tgtataccaa atttta                                                                             16

<210> SEQ ID NO 339
<211> LENGTH: 16
<212> TYPE: DNA
<213> ORGANISM: artificial sequence
<220> FEATURE:
<223> OTHER INFORMATION: Loop sequence WCR_miR-14

<400> SEQUENCE: 339 tttttttaata tagtca                                                                            16

<210> SEQ ID NO 340
<211> LENGTH: 64
<212> TYPE: DNA
<213> ORGANISM: artificial sequence
<220> FEATURE:
<223> OTHER INFORMATION: Loop sequence GeCan_0252

<400> SEQUENCE: 340
attatccaat gcttgacaag taatgtcgat atcgacatta cttgtcaagc attggataat        60
atta                                                                                          64

<210> SEQ ID NO 341
<211> LENGTH: 17
<212> TYPE: DNA
<213> ORGANISM: artificial sequence
<220> FEATURE:
<223> OTHER INFORMATION: Loop sequence GeCan_1483

<400> SEQUENCE: 341
acgaattaat atttatc                                                        17

<210> SEQ ID NO 342
<211> LENGTH: 13
<212> TYPE: DNA
<213> ORGANISM: artificial sequence
<220> FEATURE:
<223> OTHER INFORMATION: Loop sequence WCR_miR-307a

<400> SEQUENCE: 342
aactttatcc atc                                                            13

<210> SEQ ID NO 343
<211> LENGTH: 22
<212> TYPE: DNA
<213> ORGANISM: artificial sequence
<220> FEATURE:
<223> OTHER INFORMATION: Loop sequence GeCan_0992

<400> SEQUENCE: 343
aaaattgaaa agaaatagtt tt                                                  22

<210> SEQ ID NO 344
<211> LENGTH: 18
<212> TYPE: DNA
<213> ORGANISM: artificial sequence
<220> FEATURE:
<223> OTHER INFORMATION: Loop sequence WCR_miR-282

<400> SEQUENCE: 344
ggtggaatga aatggaca                                                       18

<210> SEQ ID NO 345
<211> LENGTH: 11
<212> TYPE: DNA
<213> ORGANISM: artificial sequence
<220> FEATURE:
<223> OTHER INFORMATION: Loop sequence GeCan_0311

<400> SEQUENCE: 345
tacagattat c                                                              11

<210> SEQ ID NO 346
<211> LENGTH: 17
<212> TYPE: DNA
<213> ORGANISM: artificial sequence
<220> FEATURE:
<223> OTHER INFORMATION: Loop sequence WCR_miR-92a

<400> SEQUENCE: 346 gtgttttga ctaatat                                                         17

<210> SEQ ID NO 347
<211> LENGTH: 18
<212> TYPE: DNA
<213> ORGANISM: artificial sequence
<220> FEATURE:

<223> OTHER INFORMATION: Loop sequence GeCan_1460

<400> SEQUENCE: 347
ctatattagg tacagtca                                          18

<210> SEQ ID NO 348
<211> LENGTH: 75
<212> TYPE: DNA
<213> ORGANISM: artificial sequence
<220> FEATURE:
<223> OTHER INFORMATION: Loop sequence GeCan_1397

<400> SEQUENCE: 348
actagttatc gggaagttta tctaatagat tacatgtaaa tctctcagat aaacttcccg    60
ataactagtt actcg                                             75

<210> SEQ ID NO 349
<211> LENGTH: 62
<212> TYPE: DNA
<213> ORGANISM: artificial sequence
<220> FEATURE:
<223> OTHER INFORMATION: Loop sequence GeCan_0069

<400> SEQUENCE: 349
gcatgttttc tattagacct cttcaaacgt tgaagaggt ctaatagaaa acatgccaaa    60
ga                                                           62

<210> SEQ ID NO 350
<211> LENGTH: 13
<212> TYPE: DNA
<213> ORGANISM: artificial sequence
<220> FEATURE:
<223> OTHER INFORMATION: Loop sequence WCR_miR-210

<400> SEQUENCE: 350
ttctatttaa ctc                                               13

<210> SEQ ID NO 351
<211> LENGTH: 21
<212> TYPE: DNA
<213> ORGANISM: Artificial Sequence
<220> FEATURE:
<223> OTHER INFORMATION: Loop sequence GeCan_1110

<400> SEQUENCE: 351
gcatactcta gcaatcttcc t                                      21

<210> SEQ ID NO 352
<211> LENGTH: 18
<212> TYPE: DNA
<213> ORGANISM: artificial sequence
<220> FEATURE:
<223> OTHER INFORMATION: Loop sequence WCR_miR-305b

<400> SEQUENCE: 352
gtatgttagt ttcccgac                                          18

<210> SEQ ID NO 353
<211> LENGTH: 64
<212> TYPE: DNA
<213> ORGANISM: artificial sequence
<220> FEATURE:
<223> OTHER INFORMATION: Loop sequence GeCan_0253

<400> SEQUENCE: 353

```
ttatccaatg cttgacaagt aatgtcgata tcgacattac ttgtcaagca ttggataata    60
ttat                                                                 64

<210> SEQ ID NO 354
<211> LENGTH: 16
<212> TYPE: DNA
<213> ORGANISM: artificial sequence
<220> FEATURE:
<223> OTHER INFORMATION: Loop sequence GeCan_0974

<400> SEQUENCE: 354
gagaatgtga atctag                                                    16

<210> SEQ ID NO 355
<211> LENGTH: 56
<212> TYPE: DNA
<213> ORGANISM: artificial sequence
<220> FEATURE:
<223> OTHER INFORMATION: Loop sequence GeCan_0595

<400> SEQUENCE: 355
ccaatcagcc atcttcaatc aacgatgact actaagtaag atggttgatt gggtcc        56

<210> SEQ ID NO 356
<211> LENGTH: 25
<212> TYPE: DNA
<213> ORGANISM: artificial sequence
<220> FEATURE:
<223> OTHER INFORMATION: Loop sequence WCR_let-7

<400> SEQUENCE: 356
aggattacac cattttggag tactg                                          25

<210> SEQ ID NO 357
<211> LENGTH: 52
<212> TYPE: DNA
<213> ORGANISM: artificial sequence
<220> FEATURE:
<223> OTHER INFORMATION: Loop sequence GeCan_0363

<400> SEQUENCE: 357
ataatatcaa tctatatatt aaatattta attatagatt gatattattg gt             52

<210> SEQ ID NO 358
<211> LENGTH: 9
<212> TYPE: DNA
<213> ORGANISM: artificial sequence
<220> FEATURE:
<223> OTHER INFORMATION: Loop sequence GeCan_0719

<400> SEQUENCE: 358 aaaagactg                                                             9

<210> SEQ ID NO 359
<211> LENGTH: 78
<212> TYPE: DNA
<213> ORGANISM: artificial sequence
<220> FEATURE:
<223> OTHER INFORMATION: Loop sequence GeCan_1180

<400> SEQUENCE: 359
gatacagcca gtttcaaatt attgagtacc aatttcaaat ggtgaacaat gatggtcaaa    60
aactatgtta atttccac                                                  78
```

```
<210> SEQ ID NO 360
<211> LENGTH: 16
<212> TYPE: DNA
<213> ORGANISM: artificial sequence
<220> FEATURE:
<223> OTHER INFORMATION: Loop sequence WCR_miR-965

<400> SEQUENCE: 360 tttttagga gacata                                                      16

<210> SEQ ID NO 361
<211> LENGTH: 50
<212> TYPE: DNA
<213> ORGANISM: artificial sequence
<220> FEATURE:
<223> OTHER INFORMATION: Loop sequence GeCan_0123

<400> SEQUENCE: 361
attaattgtc gaatcttgtc atatgacaag attcgacaat taatactaat               50

<210> SEQ ID NO 362
<211> LENGTH: 10
<212> TYPE: DNA
<213> ORGANISM: Artificial sequence
<220> FEATURE:
<223> OTHER INFORMATION: Loop sequence GeCan_0931

<400> SEQUENCE: 362
acgagtggtc                                                            10

<210> SEQ ID NO 363
<211> LENGTH: 19
<212> TYPE: DNA
<213> ORGANISM: Artificial sequence
<220> FEATURE:
<223> OTHER INFORMATION: Loop sequence GeCan_1429

<400> SEQUENCE: 363
gctactgtta ttcgtttgg                                                  19

<210> SEQ ID NO 364
<211> LENGTH: 15
<212> TYPE: DNA
<213> ORGANISM: artificial sequence
<220> FEATURE:
<223> OTHER INFORMATION: Loop sequence GeCan_0995

<400> SEQUENCE: 364
tatatttgaa cgtac                                                      15

<210> SEQ ID NO 365
<211> LENGTH: 24
<212> TYPE: DNA
<213> ORGANISM: artificial sequence
<220> FEATURE:
<223> OTHER INFORMATION: Loop sequnce GeCan_0725

<400> SEQUENCE: 365
ttcctttatg acgtgtcatt ccag                                            24

<210> SEQ ID NO 366
<211> LENGTH: 14
<212> TYPE: DNA
<213> ORGANISM: artificial sequence
<220> FEATURE:
<223> OTHER INFORMATION: Loop sequence GeCan_0824
```

```
<400> SEQUENCE: 366
gttgttttga aagt                                                    14

<210> SEQ ID NO 367
<211> LENGTH: 9
<212> TYPE: DNA
<213> ORGANISM: artificial sequence
<220> FEATURE:
<223> OTHER INFORMATION: Loop sequence GeCan_0879

<400> SEQUENCE: 367 tagtctgga                                                           9

<210> SEQ ID NO 368
<211> LENGTH: 16
<212> TYPE: DNA
<213> ORGANISM: artificial sequence
<220> FEATURE:
<223> OTHER INFORMATION: Loop sequence GeCan_0119

<400> SEQUENCE: 368
attttattat actgca                                                  16

<210> SEQ ID NO 369
<211> LENGTH: 31
<212> TYPE: DNA
<213> ORGANISM: artificial sequence
<220> FEATURE:
<223> OTHER INFORMATION: Loop sequence GeCan_0297

<400> SEQUENCE: 369
tgaaaacctc acatattgga tttcaatggc c                                 31

<210> SEQ ID NO 370
<211> LENGTH: 22
<212> TYPE: DNA
<213> ORGANISM: artificial sequence
<220> FEATURE:
<223> OTHER INFORMATION: Loop sequence GeCan_1529

<400> SEQUENCE: 370
aaaattgaaa agaaatagtt tt                                           22

<210> SEQ ID NO 371
<211> LENGTH: 30
<212> TYPE: DNA
<213> ORGANISM: artificial sequence
<220> FEATURE:
<223> OTHER INFORMATION: Loop sequence GeCan_0399

<400> SEQUENCE: 371
gcaggaaagc aacaggacat cctgcatttc                                   30

<210> SEQ ID NO 372
<211> LENGTH: 40
<212> TYPE: DNA
<213> ORGANISM: artificial sequence
<220> FEATURE:
<223> OTHER INFORMATION: Loop sequence GeCan_0034

<400> SEQUENCE: 372
tctaacttta attattataa taattaaagt tagaatatca                        40

<210> SEQ ID NO 373
```

```
<211> LENGTH: 64
<212> TYPE: DNA
<213> ORGANISM: artificial sequence
<220> FEATURE:
<223> OTHER INFORMATION: Loop sequence GeCan_0184

<400> SEQUENCE: 373
ccgcgctgta cgaaagctga cggtatgccg cggcataccg tcagctttcg tacagcgcgg    60
taga                                                                64

<210> SEQ ID NO 374
<211> LENGTH: 16
<212> TYPE: DNA
<213> ORGANISM: artificial sequence
<220> FEATURE:
<223> OTHER INFORMATION: Loop sequence WCR_miR-1a

<400> SEQUENCE: 374
gtgttattaa tcgtat                                                   16

<210> SEQ ID NO 375
<211> LENGTH: 64
<212> TYPE: DNA
<213> ORGANISM: artificial sequence
<220> FEATURE:
<223> OTHER INFORMATION: Loop sequence GeCan_0680

<400> SEQUENCE: 375
gaattttccc acggtggtct agaaccggtg tgccgattct gggccagaat attccgacgg    60
tggc                                                                64

<210> SEQ ID NO 376
<211> LENGTH: 18
<212> TYPE: DNA
<213> ORGANISM: artificial sequence
<220> FEATURE:
<223> OTHER INFORMATION: Loop sequence GeCan_1216

<400> SEQUENCE: 376
cgtatattaa ctgcagta                                                 18

<210> SEQ ID NO 377
<211> LENGTH: 30
<212> TYPE: DNA
<213> ORGANISM: artificial sequence
<220> FEATURE:
<223> OTHER INFORMATION: Loop sequence GeCan_0434

<400> SEQUENCE: 377
caggaaagca acaagaaatc ctgcatttct                                    30

<210> SEQ ID NO 378
<211> LENGTH: 31
<212> TYPE: DNA
<213> ORGANISM: artificial sequence
<220> FEATURE:
<223> OTHER INFORMATION: Loop sequence GeCan_0935

<400> SEQUENCE: 378
ggaatgttaa cactattaat cttgatgtaa g                                  31

<210> SEQ ID NO 379
<211> LENGTH: 32
<212> TYPE: DNA
<213> ORGANISM: artificial sequence
```

```
<220> FEATURE:
<223> OTHER INFORMATION: Loop sequence GeCan_0039

<400> SEQUENCE: 379
aactcactga gttataactc agtgagtttt gt                                      32

<210> SEQ ID NO 380
<211> LENGTH: 44
<212> TYPE: DNA
<213> ORGANISM: artificial sequence
<220> FEATURE:
<223> OTHER INFORMATION: Loop sequence GeCan_0343

<400> SEQUENCE: 380
ctattaattt tagaaacagc agtatctata attaatagta aaag                         44

<210> SEQ ID NO 381
<211> LENGTH: 15
<212> TYPE: DNA
<213> ORGANISM: artificial sequence
<220> FEATURE:
<223> OTHER INFORMATION: Loop sequence WCR_miR-281b

<400> SEQUENCE: 381
tatattttac actgt                                                        15

<210> SEQ ID NO 382
<211> LENGTH: 15
<212> TYPE: DNA
<213> ORGANISM: artificial sequence
<220> FEATURE:
<223> OTHER INFORMATION: Loop sequence GeCan_0917

<400> SEQUENCE: 382
gcttcgcgtc gttcg                                                        15

<210> SEQ ID NO 383
<211> LENGTH: 17
<212> TYPE: DNA
<213> ORGANISM: artificial sequence
<220> FEATURE:
<223> OTHER INFORMATION: Loop sequence WCR_miR-927b

<400> SEQUENCE: 383
ttaatttaaa atcacgg                                                      17

<210> SEQ ID NO 384
<211> LENGTH: 46
<212> TYPE: DNA
<213> ORGANISM: artificial sequence
<220> FEATURE:
<223> OTHER INFORMATION: Loop sequence GeCan_0510

<400> SEQUENCE: 384
atagattggt gaatgtatct tcttacactg tatgtttctt agatga                      46

<210> SEQ ID NO 385
<211> LENGTH: 18
<212> TYPE: DNA
<213> ORGANISM: artificial sequence
<220> FEATURE:
<223> OTHER INFORMATION: Loop sequence GeCan_1455

<400> SEQUENCE: 385
cctatattat ctacagtc                                                     18
```

```
<210> SEQ ID NO 386
<211> LENGTH: 24
<212> TYPE: DNA
<213> ORGANISM: artificial sequence
<220> FEATURE:
<223> OTHER INFORMATION: Loop sequence GeCan_1148

<400> SEQUENCE: 386
aaacaattca gttgttatat gggg                                          24

<210> SEQ ID NO 387
<211> LENGTH: 15
<212> TYPE: DNA
<213> ORGANISM: artificial sequence
<220> FEATURE:
<223> OTHER INFORMATION: Loop sequence WCR_miR-9d

<400> SEQUENCE: 387
tttattttta tatta                                                    15

<210> SEQ ID NO 388
<211> LENGTH: 17
<212> TYPE: DNA
<213> ORGANISM: artificial sequence
<220> FEATURE:
<223> OTHER INFORMATION: Loop sequence GeCan_1213

<400> SEQUENCE: 388
gctatatttg tgttgcc                                                  17

<210> SEQ ID NO 389
<211> LENGTH: 58
<212> TYPE: DNA
<213> ORGANISM: artificial sequence
<220> FEATURE:
<223> OTHER INFORMATION: Loop sequence GeCan_0352

<400> SEQUENCE: 389
ttaaaatcaa acaaggagag gttaacgcgt taacctctcc ttgtttgatt ttaaaacg     58

<210> SEQ ID NO 390
<211> LENGTH: 17
<212> TYPE: DNA
<213> ORGANISM: artificial sequence
<220> FEATURE:
<223> OTHER INFORMATION: Loop sequence WCR_miR-87

<400> SEQUENCE: 390
tgtcattaaa ctaggtg                                                  17

<210> SEQ ID NO 391
<211> LENGTH: 46
<212> TYPE: DNA
<213> ORGANISM: artificial sequence
<220> FEATURE:
<223> OTHER INFORMATION: Loop sequence GeCan_0032

<400> SEQUENCE: 391
ttttcctaac attttattat ataataaaat gttaggaaaa attaag                  46

<210> SEQ ID NO 392
<211> LENGTH: 45
<212> TYPE: DNA
<213> ORGANISM: artificial sequence
<220> FEATURE:
<223> OTHER INFORMATION: Loop sequence GeCan_1313
```

-continued

```
<400> SEQUENCE: 392
ctgagatcgg actgcccaag gggacgggca ctgccttaac agttg            45

<210> SEQ ID NO 393
<211> LENGTH: 44
<212> TYPE: DNA
<213> ORGANISM: artificial sequence
<220> FEATURE:
<223> OTHER INFORMATION: Loop sequence GeCan_0588

<400> SEQUENCE: 393
tataggagaa gcagaatata gggtctgctt ctcctatact ggcc             44

<210> SEQ ID NO 394
<211> LENGTH: 19
<212> TYPE: DNA
<213> ORGANISM: artificial sequence
<220> FEATURE:
<223> OTHER INFORMATION: Loop sequence WCR_miR-750b

<400> SEQUENCE: 394
aacatttcag aagtgccag                                         19

<210> SEQ ID NO 395
<211> LENGTH: 19
<212> TYPE: DNA
<213> ORGANISM: artificial sequence
<220> FEATURE:
<223> OTHER INFORMATION: Loop sequence WCR_miR-190

<400> SEQUENCE: 395
tgtagtttaa gaagcaccc                                         19

<210> SEQ ID NO 396
<211> LENGTH: 16
<212> TYPE: DNA
<213> ORGANISM: artificial sequence
<220> FEATURE:
<223> OTHER INFORMATION: Loop sequence GeCan_0843

<400> SEQUENCE: 396
acttctgaaa ctttcg                                            16

<210> SEQ ID NO 397
<211> LENGTH: 18
<212> TYPE: DNA
<213> ORGANISM: artificial sequence
<220> FEATURE:
<223> OTHER INFORMATION: loop sequence GeCan_1146

<400> SEQUENCE: 397
aaattctgaa actatccg                                          18

<210> SEQ ID NO 398
<211> LENGTH: 18
<212> TYPE: DNA
<213> ORGANISM: artificial sequence
<220> FEATURE:
<223> OTHER INFORMATION: Loop sequence GeCan_1322

<400> SEQUENCE: 398
attttatttt ttttattt                                          18

<210> SEQ ID NO 399
```

```
<211> LENGTH: 15
<212> TYPE: DNA
<213> ORGANISM: artificial sequence
<220> FEATURE:
<223> OTHER INFORMATION: Loop sequence GeCan_0826

<400> SEQUENCE: 399
tatattagct tcagt                                                    15

<210> SEQ ID NO 400
<211> LENGTH: 16
<212> TYPE: DNA
<213> ORGANISM: artificial sequence
<220> FEATURE:
<223> OTHER INFORMATION: Loop sequence WCR_miR-124b

<400> SEQUENCE: 400
tcaatatttt gtcata                                                   16

<210> SEQ ID NO 401
<211> LENGTH: 41
<212> TYPE: DNA
<213> ORGANISM: artificial sequence
<220> FEATURE:
<223> OTHER INFORMATION: Loop sequence GeCan_0360

<400> SEQUENCE: 401
ttttaattaa atctcttact aagagattta attaaaatag g                       41

<210> SEQ ID NO 402
<211> LENGTH: 21
<212> TYPE: DNA
<213> ORGANISM: artificial sequence
<220> FEATURE:
<223> OTHER INFORMATION: Minimal T7 RNA polymerase transcription binding
      site

<400> SEQUENCE: 402
ttaatacgac tcactatagg g                                             21

<210> SEQ ID NO 403
<211> LENGTH: 301
<212> TYPE: DNA
<213> ORGANISM: Artificial sequence
<220> FEATURE:
<223> OTHER INFORMATION: YFPv2 that was used as a control

<400> SEQUENCE: 403
catctggagc acttctcttt catgggaaga ttccttacgt tgtggagatg gaagggaatg   60
ttgatggcca cacctttagc atacgtggga aaggctacgg agatgcctca gtgggaaagg  120
ttgatgcaca gttcatctgc acaactggtg atgttcctgt gccttggagc acacttgtca  180
ccactctcac ctatggagca cagtgctttg ccaagtatgg tccagagttg aaggacttct  240
acaagtcctg tatgccagat ggctatgtgc aagagcgcac aatcaccttt gaaggagatg  300
g                                                                  301

<210> SEQ ID NO 404
<211> LENGTH: 107
<212> TYPE: DNA
<213> ORGANISM: artificial sequence
<220> FEATURE:
<223> OTHER INFORMATION: Diabrotica virgifera virgifera dsRNA sequence
      COPI?_v3

<400> SEQUENCE: 404
```

```
aggtgtaaac tgggcatctt tccatccaac tctgcctctt attgcctctg gtgctgatga    60
cagacaagta aaattatgga gaatgaatga ttctaaagca tgggaag                 107
```

<210> SEQ ID NO 405
<211> LENGTH: 60
<212> TYPE: DNA
<213> ORGANISM: artificial sequence
<220> FEATURE:
<223> OTHER INFORMATION: IRRNA.28112.3 - Diabrotica miR-1 backbone shRNA
      Diabrotica COPIalpha_v3

<400> SEQUENCE: 405

```
gaatgaatga ttctaaagcc atagtgttat taatcgtatg ctttagaatc attcattctc    60
```

<210> SEQ ID NO 406
<211> LENGTH: 60
<212> TYPE: DNA
<213> ORGANISM: artificial sequence
<220> FEATURE:
<223> OTHER INFORMATION: IRRNA.29794.3 - Diabrotica miR-1 backbone shRNA
      Diabrotica COPIbeta_v1

<400> SEQUENCE: 406

```
ccactttagt tacttccgac ttagtgttat taatcgtaat cggaagtaac taaagtggtg    60
```

<210> SEQ ID NO 407
<211> LENGTH: 60
<212> TYPE: DNA
<213> ORGANISM: artificial sequence
<220> FEATURE:
<223> OTHER INFORMATION: IRRNA.29796.3 - Diabrotica miR-1 backbone shRNA
      Diabrotica COPIbeta_v2

<400> SEQUENCE: 407

```
cgagtactgc ttccgatatc atagtgttat taatcgtata tatcggaagc agtactcgcg    60
```

<210> SEQ ID NO 408
<211> LENGTH: 60
<212> TYPE: DNA
<213> ORGANISM: Artificial sequence
<220> FEATURE:
<223> OTHER INFORMATION: IRRNA.29797.3 - Diabrotica miR-1 backbone shRNA
      Diabrotica COPIbeta_v2

<400> SEQUENCE: 408

```
ttccgatata gaagttatcc gtagtgttat taatcgtacg ataacttcta tatcggaagc    60
```

<210> SEQ ID NO 409
<211> LENGTH: 122
<212> TYPE: DNA
<213> ORGANISM: artificial sequence
<220> FEATURE:
<223> OTHER INFORMATION: Diabrotica virgifera virgifera COPI?_v1

<400> SEQUENCE: 409

```
gaagagaatg ctcctgcacc tgctgcaggc gccaccactt tagttacttc cgatggaaca    60
tatgctaccc aatcagcttt caacactgtc agccaaacca ctaaagaagc acgacctcct   120
ct                                                                  122
```

<210> SEQ ID NO 410
<211> LENGTH: 100
<212> TYPE: DNA
<213> ORGANISM: artificial sequence
<220> FEATURE:

-continued

<223> OTHER INFORMATION: Diabrotica virgifera virgifera COPI? dsRNA
    target v2

<400> SEQUENCE: 410
attttgggag aatacgcgag tactgcttcc gatatagaag ttatcgttgg agaaattaac    60
agattgttgg gtgaaggatc cctcgttgaa gctgagcaga                         100

<210> SEQ ID NO 411
<211> LENGTH: 60
<212> TYPE: DNA
<213> ORGANISM: artificial sequence
<220> FEATURE:
<223> OTHER INFORMATION: Diabrotica virgifera virgifera pre-miR-1
    backbone shRNA targeting Dvv V-ATPase C

<400> SEQUENCE: 411
ggtcgtcgaa gaattcaagc ttagtgttat taatcgtaac ttgaattctt cgacgacctt    60

<210> SEQ ID NO 412
<211> LENGTH: 2463
<212> TYPE: DNA
<213> ORGANISM: Artificial sequence
<220> FEATURE:
<223> OTHER INFORMATION: Diabrotica virgifera virgifera v-ATPase C

<400> SEQUENCE: 412
taaatgtcaa atgggtaggt ccatctaatg acaagtgacg gcaccaacaa tcacgtgaaa    60
cttcaataac gatcagctgg gctgactctg ttcattgggg agtggttgaa aggggtgttt   120
tttggagtta ttccattatt tgaaggagtg ataaagaaga tcttggaagc caccatagac   180
ttaattcaca tagaaccagc atactttctg atcaccaaga agaaatgact gagtattggt   240
tgatatctgc cccaggggat aagacctgtc aacagacatg ggacacgatg aataatatga   300
caagtaaaca gaataatttg tcaaccaact acaagtttca aatcccggac ttgaaagttg   360
gtactctgga tcagttagta ggactttctg atgatctggg caagcttgat gggttcgtgg   420
agcaggttac caggaaggta gctcagtacc ttggagaagt acttgaagaa cagagggaca   480
agtggtcaga aaacctgcag gccaataaca gcgatttgcc cacttattta acccgattta   540
cttgggacat cgccaaatat cccatcaagc aatcgctccg taacatcgcc gatataatca   600
gcaaacaagt tggccaaatt gacgctgatc tgaagaccaa atcgtctgcg tacaataact   660
tgaaaggaag tcttcagaat ttggagaaga aacagacagg aagtttacta acaagaaact   720
tggcagattt ggtgaaaaag gaacatttta ttttggattc tgaatatttg cagacattgt   780
tggttattgt tccaaaagcc caattcaacg aatggaatgc gacatacgaa aagattaccg   840
acatgatagt ccctcgttct tcacaactga ttaaacagga taacgaatac ggtctatata   900
ctgtatccct attcaaaaag gtcgtcgaag aattcaagtt acacgctaga gaaaagaagt   960
tcatcgttcg tgatttcata tataacgaag gaactggc agctggaaag aacgagataa   1020
ccaaactcgt caccgataaa aagaagcaat ttggtccatt agttagatgg cttaaagtca   1080
acttcagcga gtgtttctgc gcctggattc acgttaaagc gttgagggta tttgttgaat   1140
ctgttttaag atatgcctc cccgtcaatt tccaagctat tttaatccac cccaataaga   1200
aacaattaaa acgtttaaga gatgtcttga accaacttta cggccacctc gatagtagtg   1260
ctgccctttc aggacctaac gttgatagcg ttgacattcc aggcctcgga ttcggccaat   1320
cagagtatta cccatacgtt tactacaagc tgaacgtcga catgttagaa tcgaagatct   1380
aaactcacgc atcaatccaa gagtttgtta ttaataggtt ccaaacaatt ttaaaaaaac   1440

```
gtactacaga tacaaatagt atatttttga ttactcactc tttcgagggg ctgttttaat    1500
gtcggtattt ttaagttttg tccttactca atgtccattt agtaccccgt cattgtatgt    1560
aaattaatta aaaatgcgca acaaaaaatg tagaactttt ttttatttta aaatgcattt    1620
aaaattcgtt taacgatggt ataattgctt taatgtatca tgtaatactc cgattgaaca    1680
tataaatcgt tattaatatt atttcttgtt gataacacaa agagaccat  gttgttagaa    1740 attgcattcg aaaattaaa  aaaatgtata gatattatga cgcgtagatg agctgacaag    1800
tgacgtgtta agatgtattg atatctaagc ataaaatttc aacaaaccat ctatgttata    1860
gatgtacata tgtttcgtaa aattgacgaa aagctggaaa tagattacat ataatttgtc    1920
ataaaatatt tgcgtcagag acttgaggtt gtgatacaat atatatttac tcctacagaa    1980
tatttgttga atattaccga caccattaaa ataccttatc cgttatgatt gtagataaat    2040
aatttactct gaatttaata caaaacgatg tcataatttc aattgtactt gttctaataa    2100
tataactact tatcgaaaaa gaatagaaat ttattataaa attgtgtgaa atgactgggt    2160
attataggat tgccccaaca aaatattta  gatgtagtat gatgcttcat cagtgacaat    2220
atatttgacg tgttttatta tgggccactc tttaatgtaa accagtattg atttattgta    2280
aataaatatt gtatatatac tacaaaccaa taaaatattt tgccttttga atctatttat    2340
aaaagatgat tccatattgt aatatagttc aattagttga ctactttttt tgaatttatt    2400
tcagaaataa ttttaagtgg ttatttgttc aatgtaattg ttagaaaata aaaactattc    2460
caa                                                                 2463

<210> SEQ ID NO 413
<211> LENGTH: 60
<212> TYPE: DNA
<213> ORGANISM: artificial sequence
<220> FEATURE:
<223> OTHER INFORMATION: Diabrotica virgifera virgifera pre-miR-1
      backbone shRNA targeting Dvv COPI?_v4

<400> SEQUENCE: 413
ggaataccag attctgatgc atagtgttat taatcgtatc atcagaatct ggtattcccg     60

<210> SEQ ID NO 414
<211> LENGTH: 200
<212> TYPE: DNA
<213> ORGANISM: artificial sequence
<220> FEATURE:
<223> OTHER INFORMATION: Diabrotica virgifera virgifera COPI? dsRNA
      target v4

<400> SEQUENCE: 414
agttgcacta taacgaaacc ggtaccacat atgtagtagt taagttgcct gatgatgatc     60
tccccaactc tgttggtacg tgtggagccg tgttgaagtt cttagtgaaa gattgtgatc    120
catcaacggg aataccagat tctgatgagg gttacgatga tgaatataca ctggaagaca    180
tcgaaataac attaggggac                                               200

<210> SEQ ID NO 415
<211> LENGTH: 60
<212> TYPE: DNA
<213> ORGANISM: Artificial sequence
<220> FEATURE:
<223> OTHER INFORMATION: Diabrotica virgifera virgifera pre-miR-1
      backbone shRNA targeting Dvv COPI?_v1

<400> SEQUENCE: 415
```

```
cgaattattg ggacttgctc atagtgttat taatcgtata gcaagtccca ataattcgaa        60
```

<210> SEQ ID NO 416
<211> LENGTH: 100
<212> TYPE: DNA
<213> ORGANISM: artificial sequence
<220> FEATURE:
<223> OTHER INFORMATION: Diabrotica virgifera virgifera COPI? dsRNA
      target v1

<400> SEQUENCE: 416

```
aataggtcgt gatggtggcg tacaacaatt cgaattattg ggacttgcta ctttacacat        60
tggagatgag agatggggta ggatacgtgt gcaattggaa                             100
```

<210> SEQ ID NO 417
<211> LENGTH: 60
<212> TYPE: DNA
<213> ORGANISM: artificial sequence
<220> FEATURE:
<223> OTHER INFORMATION: Diabrotica virgifera virgifera pre-miR-1
      backbone shRNA targeting Dvv Rab5-1_v1 seq4

<400> SEQUENCE: 417

```
gtccgacgat cgtgatagct ctagtgttat taatcgtaag ctatcacgat cgtcggactg        60
```

<210> SEQ ID NO 418
<211> LENGTH: 444
<212> TYPE: DNA
<213> ORGANISM: artificial sequence
<220> FEATURE:
<223> OTHER INFORMATION: Diabrotica virgifera virgifera Rab5 dsRNA
      target region 1

<400> SEQUENCE: 418

```
ccacgaatac caggagagta ccataggagc agctttcctt acacaaacca tatgcctcga        60
cgatacaact gttaaatttg aaatttggga cacagcgggt caagaaaggt accacagttt       120
agctcctatg tactataggg gcgcacaggc agctatagtc gtctacgaca taaccaatca       180
agacacattc ggcagggcga aaacgtgggt gaaggaactt caaaggcagg ccagtccgac       240
gatcgtgata gctttggccg gcaacaagca ggatttggcc aacaaacgta tggtagaata       300
cgaagaggcg cagacgtatg ctgacgaaaa cggcttactt tttatggaaa cttccgcaaa       360
gacggcaatg aacgtcaacg atatattttt agcaatagct aagaaactgc caagaatga        420 acaaaccaca ggtcaaggcg gcag                                              444
```

<210> SEQ ID NO 419
<211> LENGTH: 60
<212> TYPE: DNA
<213> ORGANISM: Artificial sequence
<220> FEATURE:
<223> OTHER INFORMATION: Diabrotica virgifera virgifera pre-miR-1
      backbone shRNA targeting Dvv wupA-4 seq2

<400> SEQUENCE: 419

```
gccgccgaag aattaaagac atagtgttat taatcgtatt ctttaattct tcggcggctt        60
```

<210> SEQ ID NO 420
<211> LENGTH: 254
<212> TYPE: DNA
<213> ORGANISM: artificial sequence
<220> FEATURE:
<223> OTHER INFORMATION: Diabrotica virgifera virgifera wupA dsRNA
      target region 4

-continued

<400> SEQUENCE: 420

```
gaaagaaagc cgccgaagaa ttaaagaaag aacaagaacg caaagcagcc gaaaggaggc     60
gtatcattga agaaaggtgc ggtaaaccca aacttgtcga tgacgcaaat gaagggacac    120
ttaagaagat ttgcaaagac tattatgacc gcatgtatat atgtgaagaa cagaagtggg    180
atttggaacg tgaagttaga aaacgggatt gggagatctc cgaattgaac agccaagtaa    240
acgaccttag aggc                                                      254
```

<210> SEQ ID NO 421
<211> LENGTH: 60
<212> TYPE: DNA
<213> ORGANISM: artificial sequence
<220> FEATURE:
<223> OTHER INFORMATION: Diabrotica virgifera virgifera pre-miR-1 backbone shRNA targeting Dvv wupA-4 seq3

<400> SEQUENCE: 421

```
ttgtcgatga cgcaaatgac atagtgttat taatcgtatt catttgcgtc atcgacaagt     60
```

SHORT/SMALL HAIRPIN RNA MOLECULES

CROSS-REFERENCE TO RELATED APPLICATIONS

This application is a U.S. National Phase Application of International Application No. PCT/AU2019/050146, filed on 22 Feb. 2019, which claims priority to U.S. Provisional Application No. 62/773,355, filed on 30 Nov. 2018 and U.S. Provisional Application No. 62/633,720, filed on 22 Feb. 2018, the entire contents of which are incorporated by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 90.2 KB ASCII (Text) file named "77716 Sequence_ST25" created on Nov. 10, 2017.

TECHNICAL FIELD

The present invention relates generally to the field of molecular biology as applied to agricultural sciences. More particularly, certain embodiments concern compositions and methods for the use of a short/small hairpin RNA (shRNA) molecule to inhibit a target gene by suppressing the expression of the mRNA of the target gene. In some embodiments the shRNA molecule is used for insect control. Also disclosed are methods of making and using the shRNA molecule in the development of the novel insecticidal molecules in transgenic plant cells containing the polynucleotide sequences disclosed herein.

BACKGROUND

The transgenic expression of RNA inhibitory/interference (e.g., RNAi) molecules can be employed to regulate expression of target gene(s) by inhibiting RNA transcribed from an expressed target gene within a living cell of an organism. Small RNAs (sRNAs) are examples of RNAi Molecules. Further, microRNAs (miRNAs) are an example of such an sRNA molecule. These non-protein coding miRNAs guide cleavage of target mRNA transcripts thereby negatively regulating the expression of genes (Ambros (2001) Cell 107 (7):823-6; Bartel (2004) Cell 116 (2):281-97). Short/small hairpin RNAs (shRNAs) are engineered variants of miRNA. Applications of the transgenic expression of shRNA in animals and plants cells to inhibit a target gene by suppressing the expression of the mRNA of the target gene have been previously exemplified in human therapeutical applications. The usage of miRNA can be deployed for use in insect resistance management systems in crop fields. For instance, the use of shRNA in western corn rootworm shows a robust RNA interference response when fed these molecules.

Controlling insect populations in crop fields is economically necessary for modern agriculture practices. For example, the United States Department of Agriculture has estimated that corn rootworms (e.g., western corn rootworm) cause $1 billion in lost revenue each year. The deployment of transgenic plants for insect control provides an alternative to chemical insecticides. Chemical insecticide use is an imperfect insect control strategy. High populations of insect larvae, heavy rains, and improper application of the insecticide(s) may all result in inadequate insect control. Furthermore, the continual use of insecticide(s) may select for insecticide-resistant strains of insects, as well as raise significant environmental concerns due to toxicity to non-target species.

Accordingly, there remains a need for new novel shRNA structural molecules with different ranges of insecticidal activity against insect pests, for example shRNA molecules which are active against a variety of insects. Moreover, there remains a need for novel shRNA structural molecules with new modes of action that have activity against a variety of insect pests that have developed resistance to existing pesticides.

BRIEF SUMMARY

In embodiments of the subject disclosure, the disclosure relates to a small hairpin RNA (shRNA) polynucleotide comprising the following structures: a polynucleotide sequence comprising a hairpin structure of less than 25 nucleotides; a polynucleotide sequence comprising a DICER recognition and cleavage site structure; and, a polynucleotide sequence comprising a stem structure of 16-25 nucleotide pairs, wherein the stem structure is double stranded. In an aspect the shRNA comprises less than 70 nucleotides in length. In other aspects the shRNA comprises at least 2 alpha-helical turns. In further aspects the shRNA is not recognized by DROSHA. In some aspects the shRNA is not cleaved by DROSHA. In anaspect, the shRNA is not recognised and/or substantially cleaved by a plant DICER-like protein (e.g. DCL1, DCL2, DCL3 or DCL4) thus facilitating the shRNA to accumulate in the plant in an intact form such as in a pre-miRNA form, ready for subsequent recognition and cleavage by DICER in an insect cell after ingestion by the insect. In additional aspects, the hairpin structure comprises double-stranded nucleotides and single-stranded nucleotides. In further aspects the hairpin structure comprises a series of mismatches and/or bulges. In other aspects the hairpin structure comprises a polynucleotide obtained from an insect microRNA scaffold. In some aspects the hairpin structure comprises SEQ ID Nos:7-401 or any fragment thereof. In additional aspects the stem structure does not contain mismatches or bulges. In other aspects the stem structure comprises a polynucleotide that shares 70% to 100% sequence identity with a target polynucleotide of a plant pest. In further aspects the target polynucleotide of a plant pest is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In additional aspects the shRNA molecule has a free energy (AG) of less than −30 kcal/mol. In further aspects the shRNA comprises less than 80 nucleotides in length. In other aspects the shRNA comprises less than 90 nucleotides in length. In some aspects the shRNA molecule further comprises a polynucleotide overhang of at least 2 nucleotides and not more than 4 nucleotides. In additional aspects the first nucleotide of the polynucleotide overhang is double stranded. In other aspects the first nucleotide of the polynucleotide overhang is single stranded. In further aspects the second nucleotide of the polynucleotide overhang is single stranded. In additional aspects the third nucleotide of the polynucleotide overhang is single stranded. In some aspects the fourth nucleotide of the polynucleotide overhang is single stranded. In further aspects the polynucleotide overhang is on the 5' end of the shRNA molecule. In other aspects the polynucleotide overhang is on the 3' end of the shRNA molecule. In additional aspects the shRNA comprises less than 74 nucleotides in length. In further aspects the shRNA comprises less than 84 nucleotides in length. In some aspects the shRNA comprises less than 94 nucleotides in length. In other aspects the shRNA inhibits a target gene of an insect pest by suppressing the expression of the target mRNA of an insect pest. In additional aspects the shRNA comprises SEQ ID NOs:1-6, 405-408, 411, 413, 415, 417, 419, or 421.

In embodiments of the subject disclosure, the disclosure relates to a double stranded RNA (dsRNA) polynucleotide comprising less than 70 base pairs, wherein the dsRNA polynucleotide is not recognized and cleaved by DROSHA. In an aspect the dsRNA polynucleotide further comprising a hairpin structure. In other aspects the hairpin structure is less than 25 nucleotides in length. In some aspects the hairpin structure comprises double-stranded and single-stranded nucleotides. In additional aspects the hairpin structure comprises a series of mismatches and/or bulges. In further aspects the hairpin structure comprises a polynucleotide obtained from an insect microRNA scaffold. In other aspects the hairpin structure comprises SEQ ID Nos:7-401 or any fragment thereof. In additional aspects the hairpin structure the shRNA molecule has a free energy (AG) of less than −30 kcal/mol. In some aspects the dsRNA polynucleotide further comprising a stem structure. In other aspects the stem structure comprises is from 16-25 nucleotides in length. In further aspects the stem structure does not contain mismatches or bulges. In some aspects the stem structure comprises a polynucleotide that shares 70% to 100% sequence identity with a target polynucleotide of a plant pest. In additional aspects the target polynucleotide of a plant pest is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In further aspects the dsRNA polynucleotide further comprising a DICER recognition and cleavage site structure. In other aspects the dsRNA polynucleotide comprises at least two alpha-helical turns. In additional aspects the dsRNA polynucleotide further comprises a polynucleotide overhang of at least 2 nucleotides and not more than 4 nucleotides. In further aspects the polynucleotide overhang is double stranded. In some aspects the second nucleotide of the polynucleotide overhang is single stranded. In additional aspects the third nucleotide of the polynucleotide overhang is single stranded. In other aspects the fourth nucleotide of the polynucleotide overhang is single stranded. In further aspects the polynucleotide overhang is on the 5' end of the shRNA molecule. In some aspects the polynucleotide overhang is on the 3' end of the shRNA molecule. In an aspect the dsRNA polynucleotide and the polynucleotide overhang are less than 74 nucleotides in length. In another aspect the dsRNA polynucleotide and the polynucleotide overhang are less than 84 nucleotides in length. In a further aspect the dsRNA polynucleotide and the polynucleotide overhang are less than 94 nucleotides in length. In an additional aspect the the dsRNA polynucleotide inhibits a target gene of an insect pest by suppressing the expression of the target mRNA of an insect pest. In another aspect the dsRNA comprises SEQ ID NOs:1-6, 405-408, 411, 413, 415, 417, 419, or 421.

In embodiments of the subject disclosure, the disclosure relates to a small hairpin RNA (shRNA) polynucleotide comprising: a first RNA strand of 16-25 nucleotides; a second RNA strand of less than 25 nucleotides, wherein the second RNA strand comprises single stranded and double stranded polynucleotides; and a third RNA strand of 16-25 nucleotides, wherein the third RNA strand is substantially the reverse complement of the first RNA strand. In an aspect the first RNA strand is transcribed from a single polynucleotide. In another aspect the first RNA strand is linked to the second RNA strand and the second RNA strand is linked to the third RNA strand. In other aspects the third RNA strand is substantially the reverse complement of the first RNA strand, such that the first and the third RNA strands hybridize when transcribed into a ribonucleic acid to form the shRNA. In further aspects the DICER recognition and binding sequence is located between the second RNA strand and the hybridized first and third RNA strand. In some aspects the second RNA strand comprises a hairpin structure. In another aspect the second RNA strand is less than 25 nucleotides in length. In other aspects the second RNA strand comprises a series of mismatches and/or bulges. In some aspects the second RNA strand comprises a polynucleotide obtained from an insect microRNA scaffold. In another aspect the second RNA strand comprises SEQ ID Nos:7-401 or any fragment thereof. In an additional aspect the shRNA polynucleotide has a free energy (AG) of less than −30 kcal/mol. In further aspects the hybridized first and the third RNA strands comprise a stem structure. In other aspects the hybridized first and the third RNA strands do not contain mismatches or bulges. In some aspects the first RNA strands is from 16-25 nucleotides in length. In additional aspects the third RNA strands is from 16-25 nucleotides in length. In additional aspects the first RNA strand comprises a polynucleotide that shares 70% to 100% sequence identity with a target polynucleotide of a plant pest. In other aspects the target polynucleotide of a plant pest is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In some aspects the shRNA comprises at least two alpha-helical turns. In further aspects the shRNA further comprises a polynucleotide overhang of at least 2 nucleotides and not more than 4 nucleotides. In other aspects the first nucleotide of the polynucleotide overhang is double stranded. In an additional aspect the second nucleotide of the polynucleotide overhang is single stranded. In another aspect the third nucleotide of the polynucleotide overhang is single stranded. In a further aspect the fourth nucleotide of the polynucleotide overhang is single stranded. In some aspects the polynucleotide overhang is on the 5' end of the shRNA molecule. In other aspects the polynucleotide overhang is on the 3' end of the shRNA molecule. In further aspects the shRNA polynucleotide and the polynucleotide overhang are less than 74 nucleotides in length. In another aspect the shRNA polynucleotide and the polynucleotide overhang are less than 84 nucleotides in length. In additional aspects the shRNA polynucleotide and the polynucleotide overhang are less than 94 nucleotides in length. In some aspects the shRNA inhibits a target gene of an insect pest by suppressing the expression of the target mRNA of an insect pest. In a further aspect the shRNA comprises SEQ ID NOs:1-6, 405-408, 411, 413, 415, 417, 419, or 421.

In embodiments of the subject disclosure, the disclosure relates to a vector comprising a polynucleotide sequence encoding the shRNA polynucleotide. In an aspect the vector further comprises a heterologous promoter operably linked to the shRNA polynucleotide. In another aspect the vector is a plant transformation vector, and wherein the heterologous promoter is functional in a plant cell. In an additional aspect the vector further comprises at least one *Agrobacterium* border region. In yet another aspect the vector is selected from the group consisting of a plasmid, a cosmid, a bacterial artificial chromosome, a virus, and a bacteriophage. In some aspects the shRNA inhibits a target gene of an insect pest by suppressing the expression of the target mRNA of an insect pest. In an additional aspect the shRNA comprises SEQ ID NOs:1-6, 405-408, 411, 413, 415, 417, 419, or 421.

In embodiments of the subject disclosure, the disclosure relates to a gene expression cassette comprising a promoter operably linked to a heterologous coding sequence, wherein the heterologous coding sequences encodes the shRNA polynucleotide. In an aspect the gene expression cassette comprises one or more additional transgenic traits. In another aspect the one or more additional transgenic traits is selected from the group consisting of a heterologous coding sequence conferring insecticidal resistance, herbicide tolerance, a nucleic acid conferring nitrogen use efficiency, a nucleic acid conferring water use efficiency, a nucleic acid conferring nutritional quality, a nucleic acid encoding a DNA binding protein, and a nucleic acid encoding a selectable marker. In other aspects the heterologous coding sequence is operably linked to one or more heterologous regulatory sequences that drive expression of the shRNA. In other aspects the shRNA is orally active. In a further aspect the shRNA has insecticidal activity against an insect pest. In another aspect the insect pest is selected from the group consisting of the Orders Coleoptera, Diptera, Hymenoptera, Lepidoptera, Mallophaga, Homoptera, Hemiptera, Thysanoptera, Dermaptera, Isoptera, Anoplura, Siphonaptera, and Trichoptera. In some aspects the shRNA is contacted with the insect pest kills or inhibits the growth and/or feeding of the pest. In another aspect the shRNA inhibits a target gene of an insect pest by suppressing the expression of the target mRNA of an insect pest. In some aspects the shRNA comprises SEQ ID NOs:1-6, 405-408, 411, 413, 415, 417, 419, or 421.

In embodiments of the subject disclosure, the disclosure relates to a plant or progeny thereof, comprising the shRNA polynucleotide. In embodiments of the subject disclosure, the disclosure relates to a plant or progeny thereof stably transformed with the shRNA polynucleotide. In an aspect the plant is a monocotyledon. In another aspect the plant is a dicotyledon. In other aspects the plant is selected from is selected from the group consisting of *Zea mays*, wheat, rice, sorghum, oats, rye, bananas, sugar cane, *Glycine max*, cotton, *Arabidopsis*, tobacco, sunflower, and canola. In some aspects the plant further comprises one or more additional transgenic traits. In further aspects the transgenic trait is encodes a selectable marker protein, an insecticidal resistance protein, a herbicide tolerance protein, a nitrogen use efficiency protein, a water use efficiency protein, a small RNA molecule, a nutritional quality protein, or a DNA binding protein. In other aspects the plant produces a commodity product. In some aspects the commodity product is selected from the group consisting of protein concentrate, protein isolate, grain, meal, flour, oil, or fiber. In another aspect the shRNA is complementary to a target polynucleotide. In further aspects the target polynucleotide of a plant pest is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In additional aspects the insect pest ingests a plant part comprising the shRNA. In further aspects the insect pest contacts a plant part comprising the shRNA. In further aspects the insect pest results in decreased growth and/or survival, relative to the development of the same insect pest on a plant of the same host plant species that does not comprise the shRNA. In another aspect the shRNA inhibits a target gene of an insect pest by suppressing the expression of the target mRNA of an insect pest. In an additional aspect the the shRNA comprises SEQ ID NOs: 1-6, 405-408, 411, 413, 415, 417, 419, or 421.

In embodiments of the subject disclosure, the disclosure relates to a method for producing a plant cell, the method comprising the steps of: transforming a plant cell with a polynucleotide that expresses the shRNA polynucleotide; isolating the transformed plant cell comprising the polynucleotide that expresses the shRNA polynucleotide; and, producing a transgenic plant cell comprising the polynucleotide that expresses the shRNA. In an aspect transforming a plant cell is performed with a plant transformation method. In another aspect the plant transformation method is selected from the group consisting of an *Agrobacterium*-mediated transformation method, a biolistics transformation method, a silicon carbide transformation method, a protoplast transformation method, and a liposome transformation method. In an additional aspect the polynucleotide sequence of interest is constitutively expressed in a plant cell. In another aspect the polynucleotide sequence of interest is stably integrated into the genome of the transgenic plant cell. In other aspects the method for producing a plant cell, further comprises the steps of: regenerating the transgenic plant cell into a transgenic plant; and, obtaining the transgenic plant, wherein the transgenic plant comprises the polynucleotide that expresses the shRNA. In an aspect the transgenic plant cell is a monocotyledonous transgenic plant cell or a dicotyledonous transgenic plant cell. In another aspect dicotyledonous transgenic plant cell is selected from the group consisting of an *Arabidopsis* plant cell, a tobacco plant cell, a *Glycine max* plant cell, a canola plant cell, and a cotton plant cell. In some aspects the monocotyledonous transgenic plant cell is selected from the group consisting of a *Zea mays* plant cell, a rice plant cell, and a wheat plant cell. In another aspect the method comprises expressing in the plant or cell thereof the polynucleotide that expresses the shRNA polynucleotide. In some aspects the shRNA is complementary to a target polynucleotide. In other aspects the target polynucleotide of a plant pest is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase 11140, Sec23, Dre4, Gho, thread, ncm, RNA polymerase II-215, RNA polymerase I 1, RNA polymerase II 33, Kruppel, Spt5, Spt6, Snap25, and Prp8. In other aspects insect pest ingests a plant part comprising the shRNA polynucleotide. In additional aspects the insect pest contacts a plant part comprising the shRNA polynucleotide. In some aspects the insect pest results in decreased growth and/or survival, relative to the development of the same insect pest on a plant of the same host plant species that does not comprise the shRNA polynucleotide. In other aspects the shRNA polynucleotide inhibits a target gene of an insect pest by suppressing the expression of the target mRNA of an insect pest. In further aspects the shRNA comprises SEQ ID NOs:1-6, 405-408, 411, 413, 415, 417, 419, or 421.

In embodiments of the subject disclosure, the disclosure relates to a method for protecting a plant from an insect pest, comprising expressing in the plant or cell thereof the polynucleotide that expresses the shRNA polynucleotide.

In embodiments of the subject disclosure, the disclosure relates to a method for expressing a polynucleotide sequence of interest in a plant cell, the method comprising introducing into the plant cell a gene expression cassette comprising the polynucleotide that expresses the shRNA polynucleotide. In an aspect the gene expression cassette comprising the polynucleotide that expresses the shRNA polynucleotide is introduced into the plant cell by a plant transformation method. In another aspect the plant transformation method is selected from the group consisting of an *Agrobacterium*-mediated transformation method, a biolistics transformation method, a silicon carbide transformation method, a protoplast transformation method, and a liposome transformation method. In further aspects the polynucleotide sequence of interest is expressed constitutively in plant cell tissue. In other aspects the polynucleotide sequence of interest is stably integrated into the genome of the plant cell. In some aspects the transgenic plant cell is a monocotyledonous plant cell or a dicotyledonous plant cell. In an additional aspect the dicotyledonous plant cell is selected from the group consisting of an *Arabidopsis* plant cell, a tobacco plant cell, a *Glycine max* plant cell, a canola plant cell, and a cotton plant cell. In another aspect the monocotyledonous plant cell is selected from the group consisting of a *Zea mays* plant cell, a rice plant cell, and a wheat plant cell.

In embodiments of the subject disclosure, the disclosure relates to a method for protecting a plant from an insect pest, comprising expressing in the plant or cell thereof the polynucleotide that expresses the shRNA polynucleotide. In an aspect the shRNA is complementary to a target polynucleotide. In some aspects the target polynucleotide of a plant pest is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In another aspect the insect pest ingests a plant part comprising the shRNA. In a further aspect the insect pest contacts a plant part comprising the shRNA. In an additional aspect the insect pest results in decreased growth and/or survival, relative to the development of the same insect pest on a plant of the same host plant species that does not comprise the shRNA. In some aspects the shRNA inhibits a target gene of an insect pest by suppressing the expression of the target mRNA of an insect pest. In a further aspect the shRNA comprises SEQ ID NOs:1-6, 405-408, 411, 413, 415, 417, 419, or 421.

In embodiments of the subject disclosure, the disclosure relates to a recombinant microorganism, comprising a gene expression cassette containing the polynucleotide that expresses the shRNA polynucleotide. In an aspect the microorganism is selected from the group consisting of a bacteria, baculovirus, algae, yeast, and fungi. In another aspect the bacteria is selected from a *Pseudomonas*, an *Agrobacterium*, and *Escherichia*. In embodiments of the subject disclosure, the disclosure relates to a method for producing a shRNA with insecticidal activity, comprising culturing the recombinant microorganism comprising the shRNA polynucleotide under conditions which the shRNA polynucleotide is expressed. In another aspect the shRNA inhibits a target gene of an insect pest by suppressing the expression of the target mRNA of an insect pest. In further aspects the shRNA comprises SEQ ID NOs:1-6, 405-408, 411, 413, 415, 417, 419, or 421.

In embodiments of the subject disclosure, the disclosure relates to a transgenic cell comprising a gene expression cassette containing the polynucleotide that expresses the shRNA polynucleotide. In an aspect the transgenic cell is a transgenic plant cell. In another aspect the transgenic plant cell comprises the gene expression cassette containing the polynucleotide that expresses the shRNA polynucleotide. In a further aspect the transgenic plant is a monocotyledonous plant or dicotyledonous plant. In another aspect the monocotyledonous plant is selected from the group consisting of a maize plant, a rice plant, and a wheat plant. In an additional aspect the dicotyledonous plant is selected from the group consisting of a soybean plant, an *Arabidopsis* plant, an alfalfa plant, a sugar beet plant, a canola plant, and a cotton plant. In a further aspect the seed of the transgenic plant comprises the gene expression cassette containing the polynucleotide that expresses the shRNA polynucleotide. In another aspect the shRNA is complementary to a target polynucleotide. In other aspects the target polynucleotide of a plant pest is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In some aspects the insect pest ingests a plant part comprising the shRNA. In further aspects the insect pest contacts a plant part comprising the shRNA. In other aspects the insect pest results in decreased growth and/or survival, relative to the development of the same insect pest on a plant of the same host plant species that does not comprise the shRNA. In additional aspects the shRNA inhibits a target gene of an insect pest by suppressing the expression of the target mRNA of an insect pest. In other aspects the shRNA comprises SEQ ID NOs:1-6, 405-408, 411, 413, 415, 417, 419, or 421.

In embodiments of the subject disclosure, the disclosure relates to a method for controlling an insect pest population, comprising contacting the insect pest population with an insecticidally-effective amount of the shRNA polynucleotide. In another aspect the method for controlling an insect pest population comprises exposing the insect pest to a transgenic plant cell, plant or plant part, wherein said plant cell, plant or plant part expresses an insecticidally-effective amount of the shRNA. In another aspect the insect pest is from the Orders Coleoptera, Diptera, Hymenoptera, Lepidoptera, Mallophaga, Homoptera, Hemiptera, Thysanoptera, Dermaptera, Isoptera, Anoplura, Siphonaptera, or Trichoptera. In other aspects the shRNA inhibits a target gene of an insect pest by suppressing the expression of the target mRNA of an insect pest. In some aspects the shRNA comprises SEQ ID NOs:1-6, 405-408, 411, 413, 415, 417, 419, or 421.

In embodiments of the subject disclosure, the disclosure relates to a method of inhibiting growth or killing an insect pest, comprising contacting the insect pest with an insecticidally-effective amount of a recombinant shRNA polypeptide. In an aspect the method of inhibiting growth or killing an insect pest further comprises exposing the insect pest to a transgenic plant cell, plant or plant part, wherein said plant cell, plant or plant part expresses an insecticidally-effective amount of the recombinant shRNA polypeptide. In another aspect the insect pest is from the Orders Coleoptera, Diptera, Hymenoptera, Lepidoptera, Mallophaga, Homoptera, Hemiptera, Thysanoptera, Dermaptera, Isoptera, Anoplura, Siphonaptera, or Trichoptera. In another aspect the shRNA inhibits a target gene of an insect pest by suppressing the expression of the target mRNA of an insect pest. In further aspects the shRNA comprises SEQ ID NOs:1-6, 405-408, 411, 413, 415, 417, 419, or 421.

In embodiments of the subject disclosure, the disclosure relates to a method for controlling an insect pest population resistant to a pesticidal protein, comprising contacting the insect pest population with an insecticidally-effective amount of the shRNA polynucleotide. In an aspect the method further comprises contacting the population with a insecticidally-effective amount of the shRNA, wherein the pesticidal protein is selected from the group consisting of a Cry1Ac protein, a Cry1Ab protein, a Cry1A.105 protein, a Cry1Ac protein, a Cry1 F protein, a Cry1 Fa2 protein, a Cry1 F protein, a Cry2Ab protein, a Cry3A protein, a mCry3A protein, a Cry3Bb1 protein, a Cry34Ab1 protein, a Cry35Ab1 protein, a Vip3A protein, a Cry9c protein, a eCry3.1 Ab protein, a CBI-Bt protein, a patatin protein, a plant lectin protein, a phytoecdysteroid protein, a Xenorhabdus insecticidal protein, a *Photorhabdus* insecticidal protein, a *Bacillus* laterosporous insecticidal protein, and a *Bacillus sphaericus* insecticidal protein. In another aspect the method further comprises exposing the insect pest to a transgenic plant cell, plant or plant part, wherein said plant cell, plant or plant part expresses insecticidally-effective amount of the shRNA. In another aspect the insect pest is from the Orders Coleoptera, Diptera, Hymenoptera, Lepidoptera, Mallophaga, Homoptera, Hemiptera, Thysanoptera, Dermaptera, Isoptera, Anoplura, Siphonaptera, or Trichoptera. In an additional aspect the shRNA inhibits a target gene of an insect pest by suppressing the expression of the target mRNA of an insect pest. In a further aspect the shRNA comprises SEQ ID NOs:1-6, 405-408, 411, 413, 415, 417, 419, or 421.

In embodiments of the subject disclosure, the disclosure relates to a method for protecting a plant from an insect pest, comprising expressing in the plant or cell thereof an insecticidally-effective amount of the shRNA polynucleotide. In an aspect the method further comprises contacting the insect pest to a transgenic plant cell, plant or plant part, wherein said plant cell, plant or plant part expresses an insecticidally-effective amount of the shRNA. In another aspect the insect pest is from the Orders Coleoptera, Diptera, Hymenoptera, Lepidoptera, Mallophaga, Homoptera, Hemiptera, Thysanoptera, Dermaptera, Isoptera, Anoplura, Siphonaptera, or Trichoptera. In some aspects the plant is planted within a crop field. In additional aspects the shRNA inhibits a target gene of an insect pest by suppressing the expression of the target mRNA of an insect pest. In further aspects the shRNA comprises SEQ ID NOs:1-6, 405-408, 411, 413, 415, 417, 419, or 421.

In embodiments of the subject disclosure, the disclosure relates to a method of reducing likelihood of emergence of insect pests that are resistant to transgenic plants, comprising expressing the shRNA polynucleotide within a plant. In an aspect the shRNA is expressed in combination with an insecticidal protein that has a different mode of action as compared to the shRNA. In another aspect the insect pest is from the Orders Coleoptera, Diptera, Hymenoptera, Lepidoptera, Mallophaga, Homoptera, Hemiptera, Thysanoptera, Dermaptera, Isoptera, Anoplura, Siphonaptera, or Trichoptera. In a further aspect the plant is planted within a crop field. In some aspects the shRNA inhibits a target gene of an insect pest by suppressing the expression of the target mRNA of an insect pest. In an additional aspect the shRNA comprises SEQ ID NOs:1-6, 405-408, 411, 413, 415, 417, 419, or 421.

In embodiments of the subject disclosure, the disclosure relates to a method for insect resistance management, comprising expressing the shRNA polynucleotide. In an aspect the shRNA is co-expressed with one or more insecticidal molecules that are toxic to insect pests in a transgenic plant. In another aspect the shRNA and the other insecticidal molecules exhibit different modes of action of insecticidal activity against the insect pests. In further aspects the insecticidal activity is either insect mortality or growth inhibition. In other aspects the insect pest is from the Orders Coleoptera, Diptera, Hymenoptera, Lepidoptera, Mallophaga, Homoptera, Hemiptera, Thysanoptera, Dermaptera, Isoptera, Anoplura, Siphonaptera, or Trichoptera. In some aspects the other insecticidal molecule is a Cry protein. In further aspects the other insecticidal molecule is a VIP protein. In additional aspects the other insecticidal molecule is a small RNA molecule. In some aspects the transgenic plant is planted within a crop field. In some aspects the shRNA inhibits a target gene of an insect pest by suppressing the expression of the target mRNA of an insect pest. In further aspects the shRNA comprises SEQ ID NOs:1-6, 405-408, 411, 413, 415, 417, 419, or 421.

In embodiments of the subject disclosure, the disclosure relates to a composition, comprising an insecticidally-effective amount of the shRNA polynucleotide. In an aspect the method further comprises an agriculturally suitable carrier, a surfactant, an organosilicone, a safener, a fertilizer, a micronutrient, an insect attractant, and an insect growth regulator. In some aspects the carrier is selected from the group consisting of a powder, a dust, pellets, granules, spray, emulsion, colloid, and solution. In other aspects the composition further comprises one or more herbicides, insecticides or fungicides. In another aspect the composition further comprises one or more insecticides are pesticidal proteins. In additional aspects the one or more pesticidal proteins are selected from the group consisting of a Cry1 protein, a Cry2 protein, a Cry3 protein, a Cry4 protein, a Cry5 protein, a Cry6 protein, a Cry7 protein, a Cry8 protein, a Cry9 protein, a Cry15 protein, Cry22 protein, a Cry23 protein, a Cry32 protein, a Cry34 protein, a Cry35 protein, a Cry36 protein, a Cry37 protein, a Cry43 protein, a Cry46 protein, a Cry51 protein, a Cry55 protein, a Cry binary toxin, a Cyt protein, a VIP toxin, a SIP protein, an insecticidal lipase, an insecticidal chitinase, a snake venom protein, a patatin protein, a plant lectin protein, a phytoecdysteroid protein, a Xenorhabdus insecticidal protein, a *Photorhabdus* insecticidal protein, a *Bacillus* laterosporous insecticidal protein, and a *Bacillus sphaericus* insecticidal protein. In other aspects the one or more insecticides are pesticidal chemicals. In further aspects the one or more pesticidal chemicals are selected from the group consisting of pyrethrins and synthetic pyrethroids; oxadizine derivatives; chloronicotinyls; nitroguanidine derivatives; triazoles; organophosphates; pyrrols; pyrazoles; phenyl pyrazoles; diacylhydrazines; biological/fermentation products; and carbamates. In another aspect the shRNA inhibits a target gene of an insect pest by suppressing the expression of the target mRNA of an insect pest. In an additional aspect the shRNA comprises SEQ ID NOs:1-6, 405-408, 411, 413, 415, 417, 419, or 421.

In embodiments of the subject disclosure, the disclosure relates to a recombinant nucleic acid molecule comprising a first polynucleotide selected from the group consisting of: (a) a polynucleotide comprising the nucleic acid sequence of SEQ ID NOs: 1, 2, 3, 4, 5, 6, 404, 405, 406, 407, 408, 411, 413, 415, 417, 419 or 421; (b) a polynucleotide comprising at least 95% sequence identity to the nucleic acid sequence of SEQ ID NOs: 1, 2, 3, 4, 5, 6, 404, 405, 406, 407, 408, 411, 413, 415, 417, 419 or 421; (c) a polynucleotide comprising a fragment of at least 21 contiguous nucleotides of a nucleic acid sequence of SEQ ID NOs: 1, 2, 3, 4, 5, 6, 404, 405, 406, 407, 408, 411, 413, 415, 417, 419 or 421, wherein ingestion by an insect pest of a double stranded ribonucleotide sequence comprising at least one strand that is complementary to said fragment inhibits the growth of said pest; and, a polynucleotide comprising a complement of the sequence of (a), (b), or (c); wherein the polynucleotide is operably linked to a heterologous promoter. In an aspect the recombinant nucleic acid molecule is comprised on a plant transformation vector. In another embodiment of the subject disclosure, the disclosure relates to a double stranded ribonucleotide sequence produced from the expression of the nucleic acid molecule comprising the recombinant nucleic acid molecule comprising a first polynucleotide selected from the group consisting of: (a) a polynucleotide comprising the nucleic acid sequence of SEQ ID NOs: 1, 2, 3, 4, 5, 6, 404, 405, 406, 407, 408, 411, 413, 415, 417, 419 or 421; (b) a polynucleotide comprising at least 95% sequence identity to the nucleic acid sequence of SEQ ID NOs: 1, 2, 3, 4, 5, 6, 404, 405, 406, 407, 408, 411, 413, 415, 417, 419 or 421; (c) a polynucleotide comprising a fragment of at least 21 contiguous nucleotides of a nucleic acid sequence of SEQ ID NOs: 1, 2, 3, 4, 5, 6, 404, 405, 406, 407, 408, 411, 413, 415, 417, 419 or 421, wherein ingestion of said ribonucleotide sequence by an insect pest inhibits the growth of said pest. In an aspect the ingestion of the ribonucleotide sequence by the pest inhibits the expression of a nucleotide sequence complementary to a stem region of SEQ ID NOs: 1, 2, 3, 4, 5, 6, 404, 405, 406, 407, 408, 411, 413, 415, 417, 419 or 421. In another embodiment of the subject disclosure, the disclosure relates to a cell transformed with the recombinant nucleic acid molecule comprising the recombinant nucleic acid molecule comprising a first polynucleotide selected from the group consisting of: (a) a polynucleotide comprising the nucleic acid sequence of SEQ ID NOs: 1, 2, 3, 4, 5, 6, 404, 405, 406, 407, 408, 411, 413, 415, 417, 419 or 421; (b) a polynucleotide comprising at least 95% sequence identity to the nucleic acid sequence of SEQ ID NOs: 1, 2, 3, 4, 5, 6, 404, 405, 406, 407, 408, 411, 413, 415, 417, 419 or 421; (c) a polynucleotide comprising a fragment of at least 21 contiguous nucleotides of a nucleic acid sequence of SEQ ID NOs: 1, 2, 3, 4, 5, 6, 404, 405, 406, 407, 408, 411, 413, 415, 417, 419 or 421. In an aspect the cell is a prokaryotic cell, a eukaryotic cell, a bacterial cell or a plant cell.

In embodiments of the subject disclosure, the disclosure relates to a plant transformed with the recombinant nucleic acid molecule comprising a first polynucleotide selected from the group consisting of: (a) a polynucleotide comprising the nucleic acid sequence of SEQ ID NOs: 1, 2, 3, 4, 5, 6, 404, 405, 406, 407, 408, 411, 413, 415, 417, 419 or 421; (b) a polynucleotide comprising at least 95% sequence identity to the nucleic acid sequence of SEQ ID NOs: 1, 2, 3, 4, 5, 6, 404, 405, 406, 407, 408, 411, 413, 415, 417, 419 or 421; (c) a polynucleotide comprising a fragment of at least 21 contiguous nucleotides of a nucleic acid sequence of SEQ ID NOs: 1, 2, 3, 4, 5, 6, 404, 405, 406, 407, 408, 411, 413, 415, 417, 419 or 421. In an aspect the recombinant nucleic acid molecule is expressed in a cell of the plant as a double stranded ribonucleotide sequence and results in insecticidal activity against the insect pest. In another aspect the ingestion of the insect pest inhibitory amount of the double stranded ribonucleotide sequence kills or inhibits the growth and/or feeding of the insect pest. In embodiments of the subject disclosure, the disclosure relates to a commodity product produced from a plant, wherein said commodity product comprises the recombinant nucleic acid molecule comprising a first polynucleotide selected from the group consisting of: (a) a polynucleotide comprising the nucleic acid sequence of SEQ ID NOs: 1, 2, 3, 4, 5, 6, 404, 405, 406, 407, 408, 411, 413, 415, 417, 419 or 421; (b) a polynucleotide comprising at least 95% sequence identity to the nucleic acid sequence of SEQ ID NOs: 1, 2, 3, 4, 5, 6, 404, 405, 406, 407, 408, 411, 413, 415, 417, 419 or 421; (c) a polynucleotide comprising a fragment of at least 21 contiguous nucleotides of a nucleic acid sequence of SEQ ID NOs: 1, 2, 3, 4, 5, 6, 404, 405, 406, 407, 408, 411, 413, 415, 417, 419 or 421.

The foregoing and other features will become more apparent from the following detailed description of several embodiments, which proceeds with reference to the accompanying figures.

BRIEF DESCRIPTION OF THE FIGURES

FIG. 2A. Native miRNA. The precursor miRNA (pre-miRNA) sequence that is cleaved by the DROSHA protein is shown with the bracket. Insect DICER-1 cleaves the miRNA loop, releasing the mature miRNA which is highlighted to indicate the guide strand and STAR strand. FIG. 2B. shRNA. This molecule is not recognized or cleaved by the DROSHA protein as it is less than 70 base pairs in length. The insect DICER-1 enzyme cleaves the shRNA loop, releasing the mature shRNA which is highlighted to indicate the guide strand and STAR strand. The guide strand is designed to match a selected a target polynucleotide, for example the mRNA of an endogenous target gene.

SEQUENCE LISTING

Figure 1:
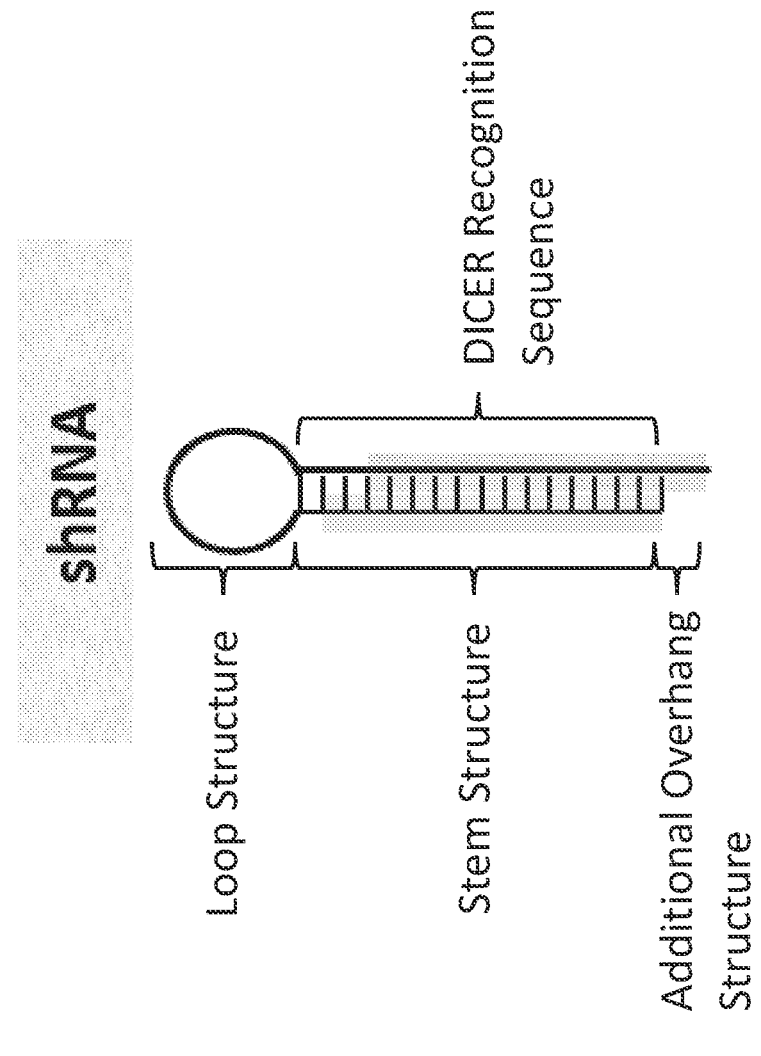
FIG. 1. This cartoon represents the structural components of the shRNA molecule. The "Hairpin Structure" of the shRNA molecule is an unpaired loop of the single stranded shRNA polynucleotide that is created when the shRNA polynucleotide folds and forms base pairs with another section of the same strand of the shRNA polynucleotide. The "Stem Structure" of the shRNA molecule is a predominantly double stranded polynucleotide sequence of the single stranded shRNA polynucleotide that is created when the shRNA polynucleotide folds and forms double stranded base pairs with another section of the same strand of the shRNA polynucleotide. The "DICER Recognition Sequence" is another structural component of the shRNA molecule. The DICER enzyme can recognize, bind and cleave the DICER recognition sequences of the shRNA molecule. A final structure that can be added and included onto the shRNA molecule is provided in this cartoon and labeled as an "Additional Overhang Structure".

The nucleic acid sequences listed in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). Furthermore, as it is understood in the art that the nucleotide sequence of a RNA strand is determined by the sequence of the DNA from which it was transcribed (but for the substitution of uracil (U) nucleobases for thymine (T)), a RNA sequence is included by any reference to the DNA sequence encoding it.

DETAILED DESCRIPTION

I. Overview of Several Embodiments

The small/short hairpin RNA (shRNA) of the subject disclosure provides a novel small RNA (sRNA) structural molecule to inhibit a target gene by suppressing the expression of the mRNA of the target gene. The deployment of RNA inhibition/interference has been applied through the use of shRNA in planta to confer resistance against insect species. Generally, this system results in the introduction of a shRNA molecule into a plant cell and the subsequent processing of the shRNA molecule by endogenous host proteins using a mechanism that is largely non-overlapping with the processing of double stranded RNA (dsRNA) molecules. The uptake of the shRNA molecule by an insect pest usually occurs when the insect pest comes into contact with the shRNA molecule through oral ingestion of the plant material that contains the shRNA molecule. Accordingly, the identification of novel pesticidal shRNA molecules to control insect species are beneficial for modern crop production systems.

Previous studies have indicated that a minimum length of ~70 nucleotides of double-stranded RNA is required for oral RNAi response in insect species such as western corn rootworm (Bolognesi et al. (2012) PLoS One 7 (10): e47534). Thus, it is likely that the processing of small RNA molecules such as microRNA results in an inefficient RNAi effect due to molecule's short length or low-level of base-paring within miRNA.

MicroRNAs (miRNAs) are non-protein coding RNAs, generally between about 19 to about 25 nucleotides in length, that guide cleavage in trans of target RNA transcripts, negatively regulating the expression of genes (Ambros (2001) Cell 107 (7):823-6; Bartel (2004) Cell 116 (2):281-97). Numerous miRNA genes have been identified and are made publicly available in a database ("miRBase" Griffiths-Jones et al. (2003) *Nucleic Acids Res.,* 31:439-441). MiRNAs were first reported in nematodes and have since been identified in other invertebrates; see, for example, Lee and Ambros (2001) *Science,* 294:862-864; Lim et al. (2003) *Genes Dev,* 17:991-1008; Stark et al. (2007) *Genome Res.,* 17:1865-1879. Transcription of miRNA genes may be under the control of a miRNA gene's own promoter. However, the biogenesis pathways of microRNAs can vary depending on their genomic origins, for example up to a third of animal miRNAs are thought to be derived from introns (mirtrons) (Okamura et al. (2008) Cell Cycle 7 (18):2840-5; Westholm and Lai (2011) Biochimie 93 (11): 1897-904). MiRNA genes may be isolated or appear in clusters in the genome; they can also be located entirely or partially within introns of both protein-coding and non-protein-coding, see Kim (2005) *Nature Rev Mol Cell Biol.,* 6:376-385; (Westholm and Lai (2011) Biochimie 93 (11): 1897-904). The primary transcript (pri-miRNA) can be quite long (several kilobases) and can be monocistronic or polycistronic, containing one or more precursor miRNAs (pre-miRNAs) (fold-back structures containing a stem-loop arrangement that is processed to the mature miRNA), as well as the usual 5' cap and polyadenylated tail of an mRNA. See, for example, FIG. 1 in Kim (2005) *Nature Rev. Mol. Cell Biol,* 6:376-385.

Biogenesis of a mature miRNA from its corresponding precursors differs significantly between animals and plants. In plant cells, microRNA precursor (pre-miRNA) molecules are believed to be largely processed to the mature miRNA entirely in the nucleus. Comparatively, in animal cells the pri-miRNA transcripts are processed in the nucleus by the animal-specific enzyme DROSHA (Lee et al (2003) Nature 425 (6956):415-9), followed by export of the pre-miRNA to the cytoplasm where it is further processed to the mature miRNA by DICER in mammals and *C. elegans* (Bernstein et al. (2001) Nature 409 (6818):363-6) or DICER-b 1 in insects (Lee et al. (2004) *Cell* 117 (1):69-81; Tsutsumi et al. (2011) Nat *Struct Mol Biol* 18 (10):1153-8), for an illustration see FIG. 1 in (Axtell et al. (2011) *Genome Biol* 12 (4):221). Animal miRNAs have many characteristics dissimilar to their plant counterparts. Animal miRNAs have shorter miRNA precursor (pre-miRNA) structures of about 60-80 nucleotides, versus plants having a more heterogeneous miRNA precursor structure, ranging from 70 to hundreds of nucleotides in length, for review see (Axtell, Westholm and Lai (2011) Genome Biol 12 (4):221). The stem region of animal miRNA generally has imperfect hybridization. Further, animal miRNAs precursors (pre-miRNAs) have mostly uniform structure, three helical turns (approximately 33 nucleotides) of mostly double-stranded RNA sequence connected by a small loop, and flanked by primarily single-stranded sequence (Zeng and Cullen (2005) J Biol Chem 280 (30):27595-603; Han et al. (2006) Cell 125 (5):887-901).

Typically, DROSHA, an RNase type III enzyme, cleaves the pri-miRNA within the nucleus of the cell, thereby releasing the pre-miRNA molecule. Empirical studies of the length and composition of the unstructured regions flaking pre-miRNA indicate that variable lengths of extensions are needed for efficient DROSHA recognition and cleavage, depending on the miRNA (~10-40 nt), while the sequence composition of the extensions was relatively unimportant (Chen et al. (2004) Science 303 (5654):83-6; Zeng and Cullen (2005) J Biol Chem 280 (30):27595-603). The three helical turns of double-stranded RNA followed by unstructured regions are required for DROSHA-DGCR8 complex recondition that liberates ~60-80 nucleotide-long pre-miRNA (Zeng and Cullen (2005) J Biol Chem 280 (30): 27595-603; Han et al (2006) Cell 125 (5):887-901). DGCR8 is also known as partner of DROSHA or PASHA (Denli et al. (2004) Nature 432 (7014):231-5). The released pre-miRNA molecule is about three helical turns of double stranded helix in length that is connected by a short loop. Animal pre-miRNAs are then exported to the cytoplasm by Exportin-5 Yi et al. (2003) Genes Dev 17 (24):3011-6), whereas plant pre-miRNAs are processed by DICER in the nucleus (Papp et al. (2003) Plant Physiol 132 (3):1382-90).

Next, animal pre-miRNA molecule is exported to the cytoplasm where it is processed by another type III RNase, DICER. The DICER molecule cleaves the pre-miRNA to liberate the loop sequence and produce a mature miRNA molecule. The resulting mature miRNA molecule is about 21 to 23 bp in length. This molecule is comprised of a guide and a STAR/passenger strand. The mature miRNA interacts with an Argonaute protein, predominantly Argonaute 1 (AGO1). The guide strand of the miRNA is subsequently integrated into the RNA-induced silencing complex (RISC). The resulting miRNA structural molecule and AGO-RISC then inhibits a target gene by suppressing the expression of the mRNA of the target gene.

A major distinction in miRNA vs. dsRNA processing between insects and other animals is that insects have two DICERs. DsRNAs are processed into small interfering RNAs (siRNAs) by insect type III ribonuclease, DICER-2. (Lee et al. (2004) Cell 117 (1):69-81). Studies in coleopteran insects also demonstrate that DICER-2 and AGO2 are involved in dsRNA pathways of *Tribolium castaneum* (Tomoyasu et al. (2008) Genome Biol 9 (1):R10) and *Diabrotica virgifera virgifera* (Miyata et al. (2014) PLoS One 9 (7):e101661; Velez et al. (2016) PLoS One 11 (6): e0157520). DICER-1 is specific for insect miRNA (Lee et al. (2004) Cell 117 (1):69-81; Tsutsumi et al. (2011) Nat Struct Mol Biol 18 (10):1153-8). DICER-1 substrate is a DROSHA product (pre-miRNA) that has the following characteristics: Insect DICER-1 recognizes an approximately 22 base pair RNA duplex; the RNA duplex or stem may have mismatched base pairing, but the mismatches are not necessary for efficient DICER-1 recognition (Tsutsumi et al. (2011) Nat Struct Mol Biol 18 (10):1153-8)). The efficiency of DICER-i processing decreases as the length of RNA duplex increases to 25 base pairs or above. The pre-miRNA stem has a two-nucleotide 5' overhang that may be paired or "frayed"; blunt paired or frayed ends are not effective DICER-1 substrates (Tsutsumi et al. (2011) Nat Struct Mol Biol 18 (10):1153-8)).

Unlike insect and other animal miRNAs, which are cleaved from their primary transcripts by two biogenesis enzymes first in the nucleus and then in the cytoplasm, plant miRNAs are processed by a single enzyme in the nucleus. Plant pre-miRNAs are generated by one of four DICER-like (DCL) proteins, with DCL1 being the major miRNA biogenesis protein. Unlike in animals, DCL1 protein can cleave both at the base and the loop. The processing usually initiates at the base of the pri-miRNA hairpin, but "loop-first" processing can also occur (Kurihara and Watanabe (2004) Proc Natl Acad Sci USA 101 (34):12753-8; Bologna et al. (2009) EMBO J 28 (23):3646-56; Addo-Quaye et al. (2009) RNA 15 (12):2112-21). Prior to plant miRNA transport from the nucleus, their 3' overhangs are methylated by an RNA methyltransferase protein, Hua-Enhancer1 (HEN1). The methylated miRNA is then transported from the nucleus into the cytoplasm by the Hasty (HST) protein, an Exportin 5 homolog. For a review of miRNA biogenesis in both plants and animals, see (Kim (2005) Nat Rev Mol Cell Biol 6 (5):376-85)(Axtell, Westholm and Lai (2011) Genome Biol 12 (4):221). Additional reviews on miRNA biogenesis and function are found, for example, in Ha and Kim (2014) Nat Rev Mol Cell Biol 15 (8):509-24; Bartel (2004) Cell, 116:281-297; Murchison and Hannon (2004) *Curr. Opin. Cell Biol.*, 16:223-229; and Dugas and Bartel (2004) *Curr. Opin. Plant Biol.*, 7:512-520.

The protein Arognaute-1 (AGO1) has been proposed to mediate an miRNA-guided repression of mRNA translation or accelerate the decay of mRNA (Valencia-Sanchez et al. (2006) Genes Dev 20 (5):515-24). Whereas, Arognaute-2 (AGO2) cleavage activity was assumed to be guided by dsRNA-derived siRNAs. In mammals, only AGO2 has mRNA cleavage/"slicer" activity (Rivas et al. (2005) Nat Struct Mol Biol 12 (4):340-9; Liu et al. (2004) Science 305 (5689):1437-41; Meister et al. (2004) Mol Cell 15 (2):185-97). In *Drosophila*, both AGO1 and AGO2 have "slicer" activity, but AGO1 is an inefficient nuclease (Forstemann et al. (2007) Cell 130 (2):287-97). While miRNAs may interact with AGO2, central mismatches with the miRNA duplex favor their loading onto AGO1-RISC complex (Tomari et al. (2007) Cell 130 (2):299-308). Lack of mismatches in the stem of miRNAs promotes their sorting onto AGO1-RISC complex (Tomari et al. (2007) Cell 130 (2):299-308). Thus, mismatches in the stem of miRNA, and by extension amiRNA, guide miRNA to AGO1, while perfect pairing/ hybridization within shRNA may guide them toward AGO2-RISC.

Animal miRNAs generally anneal imperfectly, with as little as seven nucleotide complementarity to their 5' ends, to the 3' untranslated region (UTR) of their target mRNA (Brennecke et al. (2005) PLoS Biol 3 (3):e85). On the other hand, most plant miRNAs are characterized by having perfect or near-perfect complementarity to their target sequence, which is usually in the coding region, with only a few examples of miRNAs having binding sites within the UTRs of the target mRNA; see Rhoades et al. (2002) *Cell*, 110:513-520; Jones-Rhoades et al. (2006) *Annu. Rev. Plant Biol.*, 57:19-53. These significant differences between plant and animal miRNAs make it generally unlikely that miRNAs will be processed and function across kingdoms.

Animal miRNAs have been utilized for transgenic regulation in animal cells; for example, the human miR-30 precursor has been expressed as a native miRNA sequence or as a modified miRNA (artificial miRNA or engineered miRNA, short hairpin RNAs/small hairpin RNA (shRNA), organic small hairpin RNA (OshR), shRNAmir, shRNA-miR, or shmiR) in cultured cells (Zeng et al. (2002) Mol. Cell, 9:1327-1333; Zeng et al. (2005) J. Biol. Chem., 280: 27595-27603; Chang et al. (2013) Cold Spring Harb Protoc 2013 (7):631-5; Zeng et al. (2013) Methods 63 (2):101-9). Additional miRNA backbones based on precursor miRNAs and primary miRNA transcripts have been optimized for efficient transgenic expression of shRNA and related molecules in mammalian systems (Chang et al. (2006) Nat Methods 3 (9):707-14; Yue et al. (2010) Biochem Biophys Res Commun 394 (3):667-72; Fellmann et al. (2013) Cell Rep 5 (6):1704-13; Lambeth and Smith (2013) Methods Mol Biol 942:205-32).

A single mature miRNA is precisely processed from a given precursor, and therefore such "artificial" miRNAs (engineered miRNA, short/small hairpin RNAs (shRNA), shRNAmir, shRNA-miR, shmiRs, etc.) offer an advantage over double-stranded RNA (dsRNA) in that only a specific miRNA sequence is expressed, limiting potential off-target effects. Although animal miRNAs typically interact with imperfect target sequences in the 3' UTR, artificial miRNAs with perfect target complernentarity will guide target cleavage (see Zeng et al. (2003) RNA, 9:112-123 and Zeng et al (2003) Proc. Natl. Acad. Sci. U.S.A., 100:9779-9784).

Approximately 150 miRNAs have been identified across Drosophila species (Lai et al. (2003) Genome Biol 4 (7): R42; Ruby et al. (2007) Genome Res 17 (12):1850-64; Stark et al. (2007) Genome Res 17 (12):1865-79). Numbers that range 100s to 500s of miRNAs have been identified in other insects, depending on the level of conservation examined and the confidence of the predictions (He et al. (2008) BMC Genomics 9:248; Luo et al. (2008) J Genet Genomics 35 (6):349-55; Chilana et al. (2013) Bioinformation 9 (2):79-83; Liang et al. (2013) PLoS One 8 (11):e78787; Lomate et al. (2014) Insect Biochem Mol Biol 54:129-37; Zhou et al. (2014) PLoS One 9 (7):e103041; Liu et al. (2014) Parasit Vectors 7:159; Kakumani et al. (2015) PLoS One 10 (2): e0116988). Conserved insect miRNAs fall within 65 families (Ylla et al. (2016) Sci Rep 6:37736). An even smaller number of insect miRNAs are known to be essential for insect's survival. These miRNAs include let-7, bantam, miR-1, miR-14, and miR-279 in Drosophila melanogaster (Smibert and Lai (2008) Cell Cycle 7 (16):2500-8). Alternatively, overexpression of miRNAs can lead to lethality or aberrant phenotypes in insects (Schertel et al. (2012) Genetics 192 (4):1543-52).

Drosophila melanogaster artificial miRNAs (amiRNAs), short/small hairpin RNAs (shRNA), or shmiRs are miRNA precursors where the mature miRNA portion has been replaced with an siRNA that targets a gene of interest. ShRNAs have high efficacy when transgenically expressed in Drosophila (Haley et al., 2008; Ni et al., 2011). Preferential processing of shRNAs/shmiRs with DICER-1 has been validated using DICER-1 and DICER-2 dsRNA in Drosophila cell culture in combination with northern blots (Ni et al. (2011) Nat Methods 8 (5):405-7). Thus, the transgenically expressed shRNAs have a biogenesis pathway that is distinct from dsRNA. Further, the Drosophila shmiR hairpins may interact with AGO2 and AGO1 (Ni et al. (2011) Nat Methods 8 (5):405-7).

Figure 2:
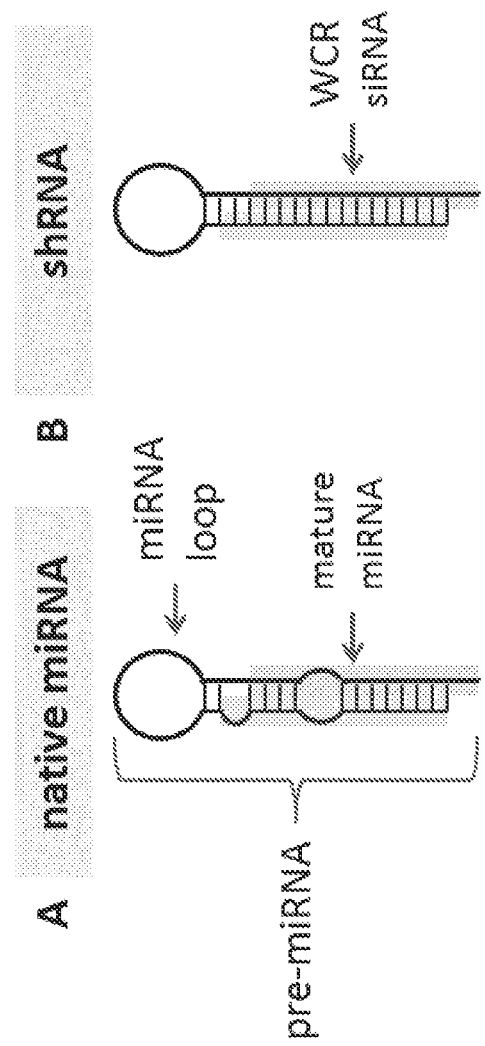
FIG. 2. Cartoon representation of native miRNA and short/small hairpin RNA (shRNA).

The present disclosure is drawn to compositions and methods for controlling insect pests through the use of shRNA polynucleotide sequences. Provided herein are novel shRNA molecules that are comprised of a hairpin structure and a stem structure (FIG. 1). These novel molecules are structurally distinct as compared to known miRNA molecules (FIG. 2). These structural modifications of the novel shRNA molecule provide significant improvements over known miRNA molecules. For instance, the shRNA molecule is less than 90 base pairs, less than 80 base pairs, or less than 70 base pairs in length and can forego processing by endogenous host proteins (e.g., DROSHA). Such an improvement results in the production of a mature shRNA molecule with less reliance upon processing by endogenous host proteins, such as DROSHA, of a phylogenetically unrelated organism. The similarity of the shRNA structure to that of pre-miRNA increases its likelihood of acting as a substrate for insect DICER-1. Further, shRNA molecules described herein lack central mismatches in their stems, predisposing them to association with AGO2. Moreover, the use of insect miRNA structure is likely to evade RNAi processing within a plant, to deliver intact insect pre-miRNAs or pri-miRNAs to be processed by insect's RNAi machinery.

Exemplary polynucleotides encoding the shRNA insecticidal molecules that confer insecticidal activity against the insect pests are provided. The biological molecules of the subject disclosure can be engineered into gene expression cassettes that are transformed into living organisms. In particular, the polynucleotide sequences are useful for preparing plants, plant cells, plant seeds, plant parts, compositions, and microorganisms that possess insecticidal activity as conferred by the shRNA polynucleotide. For instance the shRNA polynucleotide results in significant growth inhibition and mortality of insect pests. Moreover, the shRNA polynucleotide can be used to inhibit a target gene by suppressing the expression of the mRNA of the target gene. Various target polynucleotide sequences (e.g., that correspond to the mRNA of the target gene) can be incorporated into the stem region/structure of the shRNA polynucleotide for use in the suppression of target gene mRNA expression within another organism (e.g., the insect pest). The shRNA polynucleotide can be used for controlling, inhibiting growth or killing insect pests. Likewise, the resulting compositions that contain the novel insecticidal activity can be used to control an insect pest population or to reduce the emergence of insect resistance within transgenic plants. For the first time, novel insecticidal molecules that confer insecticidal activity against such insect pests are provided herein as a shRNA molecule.

II.. Terms and Abbreviations

Throughout the application, a number of terms are used. In order to provide a clear and consistent understanding of the specification and claims, including the scope to be given such terms, the following definitions are provided.

As used herein, the articles, "a," "an," and "the" include plural references unless the context clearly and unambiguously dictates otherwise.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendorf™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, introns and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene/heterologous coding sequence is an exogenous nucleic acid, where the transgene/heterologous coding sequence has been introduced into a host cell by genetic engineering (or the progeny thereof) where the transgene/heterologous coding sequence is not normally found. In one example, a transgene/heterologous coding sequence encodes an industrially or pharmaceutically useful compound, or a gene encoding a desirable agricultural trait (e.g., an herbicide-resistance gene). In yet another example, a transgene/heterologous coding sequence is an antisense nucleic acid sequence, wherein expression of the antisense nucleic acid sequence inhibits expression of a target nucleic acid sequence. In one embodiment the transgene/heterologous coding sequence is an endogenous nucleic acid, wherein additional genomic copies of the endogenous nucleic acid are desired, or a nucleic acid that is in the antisense orientation with respect to the sequence of a target nucleic acid in a host organism.

As used herein, "heterologous DNA coding sequence" means any coding sequence other than the one that naturally encodes the IRDIG37126 protein, or any homolog/variant of the expressed IRDIG37126 protein. The term "heterologous" is used in the context of this disclosure for any combination of nucleic acid sequences that is not normally found intimately associated in nature.

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, New York, 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

The terms "percent sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

Global sequence alignment programs calculate the percent identity of two sequences by comparing alignments end-to-end in order to find exact matches, dividing the number of exact matches by the length of the shorter sequences, and then multiplying by 100. Basically, the percentage of identical nucleotides in a linear polynucleotide sequence of a reference ("query) polynucleotide molecule as compared to a test ("subject") polynucleotide molecule when the two sequences are optimally aligned (with appropriate nucleotide insertions, deletions, or gaps).

Local sequence alignment programs are similar in their calculation, but only compare aligned fragments of the sequences rather than utilizing an end-to-end analysis. Local sequence alignment programs such as BLAST can be used to compare specific regions of two sequences. A BLAST comparison of two sequences results in an E-value, or expectation value, that represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GENBANK, have generally increased over time for any given query/entry match. In setting criteria for confidence of polypeptide function prediction, a "high" BLAST match is considered herein as having an E-value for the top BLAST hit of less than 1E-30; a medium BLASTX E-value is 1E-30 to 1E-8; and a low BLASTX E-value is greater than 1E-8. The protein function assignment in the present disclosure is determined using combinations of E-values, percent identity, query coverage and hit coverage. Query coverage refers to the percent of the query sequence that is represented in the BLAST alignment. Hit coverage refers to the percent of the database entry that is represented in the BLAST alignment. In one embodiment of the disclosure, function of a query polypeptide is inferred from function of a conserved protein sequence where either (1) hit_p<1e-30 or % identity>35% AND query_coverage>50% AND hit_coverage>50%, or (2) hit_p<1e-8 AND query_coverage>70% AND hit_coverage>70%. The following abbreviations are produced during a BLAST analysis of a sequence.

SEQ_NUM provides the SEQ ID NO for the listed recombinant polynucleotide sequences.

CONTIG_ID provides an arbitrary sequence name taken from the name of the clone from which the cDNA sequence was obtained.

PROTEIN_NUM provides the SEQ ID NO for the recombinant polypeptide sequence

NCBI_GI provides the GenBank ID number for the top BLAST hit for the sequence. The top BLAST hit is indicated by the National Center for Biotechnology Information GenBank Identifier number.

NCBI_GI_DESCRIPTION refers to the description of the GenBank top BLAST hit for the sequence.

E_VALUE provides the expectation value for the top BLAST match.

MATCH_LENGTH provides the length of the sequence which is aligned in the top BLAST match TOP_HIT_PCT_IDENT refers to the percentage of identically matched nucleotides (or residues) that exist along the length of that portion of the sequences which is aligned in the top BLAST match.

CAT_TYPE indicates the classification scheme used to classify the sequence. GO_BP=Gene Ontology Consortium–biological process; GO_CC=Gene Ontology Consortium–cellular component; GO_MF=Gene Ontology Consortium–molecular function; KEGG=KEGG functional hierarchy (KEGG=Kyoto Encyclopedia of Genes and Genomes); EC=Enzyme Classification from ENZYME data bank release 25.0; POI=Pathways of Interest.

CAT_DESC provides the classification scheme subcategory to which the query sequence was assigned.

PRODUCT_CAT_DESC provides the FunCAT annotation category to which the query sequence was assigned.

PRODUCT_HIT_DESC provides the description of the BLAST hit which resulted in assignment of the sequence to the function category provided in the cat_desc column.

HIT_E provides the E value for the BLAST hit in the hit_desc column.

PCT_IDENT refers to the percentage of identically matched nucleotides (or residues) that exist along the length of that portion of the sequences which is aligned in the BLAST match provided in hit_desc.

QRY_RANGE lists the range of the query sequence aligned with the hit.

HIT_RANGE lists the range of the hit sequence aligned with the query.

QRY_CVRG provides the percent of query sequence length that matches to the hit (NCBI). sequence in the BLAST match (% qry cvrg=(match length/query total length)×100).

HIT_CVRG provides the percent of hit sequence length that matches to the query sequence in the match generated using BLAST (% hit cvrg=(match length/hit total length)×100).

Methods for aligning sequences for comparison are well-known in the art. Various programs and alignment algorithms are described. In an embodiment, the subject disclosure relates to calculating percent identity between two polynucleotides or amino acid sequences using an AlignX alignment program of the Vector NTI suite (Invitrogen, Carlsbad, CA). The AlignX alignment program is a global sequence alignment program for polynucleotides or proteins. In an embodiment, the subject disclosure relates to calculating percent identity between two polynucleotides or amino acid sequences using the MegAlign program of the LASERGENE bioinformatics computing suite (MegAlign™ ©1993-2016). DNASTAR. Madison, WI). The MegAlign program is global sequence alignment program for polynucleotides or proteins. In an embodiment, the subject disclosure relates to calculating percent identity between two polynucleotides or amino acid sequences using the Clustal suite of alignment programs, including, but not limited to, ClustalW and ClustalV (Higgins and Sharp (1988) Gene. December 15;73(1):237-44; Higgins and Sharp (1989) CABIOS 5:151-3; Higgins et al. (1992) Comput. Appl. Biosci. 8:189-91). In an embodiment, the subject disclosure relates to calculating percent identity between two polynucleotides or amino acid sequences using the GCG suite of programs (Wisconsin Package Version 9.0, Genetics Computer Group (GCG), Madison, WI). In an embodiment, the subject disclosure relates to calculating percent identity between two polynucleotides or amino acid sequences using the BLAST suite of alignment programs, for example, but not limited to, BLASTP, BLASTN, BLASTX, etc. (Altschul et al. (1990) J. Mol. Biol. 215:403-10). Further examples of such BLAST alignment programs include Gapped-BLAST or PSI-BLAST (Altschul et al., 1997). In an embodiment, the subject disclosure relates to calculating percent identity between two polynucleotides or amino acid sequences using the FASTA suite of alignment programs, including, but not limited to, FASTA, TFASTX, TFASTY, SSEARCH, LALIGN etc. (Pearson (1994) Comput. Methods Genome Res. [Proc. Int. Symp.], Meeting Date 1992 (Suhai and Sandor, Eds.), Plenum: New York, NY, pp. 111-20). In an embodiment, the subject disclosure relates to calculating percent identity between two polynucleotides or amino acid sequences using the T-Coffee alignment program (Notredame, et. al. (2000) J. Mol. Biol. 302, 205-17). In an embodiment, the subject disclosure relates to calculating percent identity between two polynucleotides or amino acid sequences using the DIALIGN suite of alignment programs, including, but not limited to DIALIGN, CHAOS, DIALIGN-TX, DIALIGN-T etc. (Al Ait, et. al. (2013) DIALIGN at GOBICS Nuc. Acids Research 41, W3-W7). In an embodiment, the subject disclosure relates to calculating percent identity between two polynucleotides or amino acid sequences using the MUSCLE suite of alignment programs (Edgar (2004) Nucleic Acids Res. 32(5): 1792-1797). In an embodiment, the subject disclosure relates to calculating percent identity between two polynucleotides or amino acid sequences using the MAFFT alignment program (Katoh, et. al. (2002) Nucleic Acids Research 30(14): 3059-3066). In an embodiment, the subject disclosure relates to calculating percent identity between two polynucleotides or amino acid sequences using the Genoogle program (Albrecht, Felipe. arXiv150702987v1 [cs.DC] 10 Jul. 2015). In an embodiment, the subject disclosure relates to calculating percent identity between two polynucleotides or amino acid sequences using the HMMER suite of programs (Eddy. (1998) *Bioinformatics,* 14:755-63). In an embodiment, the subject disclosure relates to calculating percent identity between two polynucleotides or amino acid sequences using the PLAST suite of alignment programs, including, but not limited to, TPLASTN, PLASTP, KLAST, and PLASTX (Nguyen & Lavenier. (2009) *BMC Bioinformatics,* 10:329). In an embodiment, the subject disclosure relates to calculating percent identity between two polynucleotides or amino acid sequences using the USEARCH alignment program (Edgar (2010) *Bioinformatics* 26(19), 2460-61). In an embodiment, the subject disclosure relates to calculating percent identity between two polynucleotides or amino acid sequences using the SAM suite of alignment programs (Hughey & Krogh (January 1995) *Technical Report UCSC0CRL*-95-7, University of California, Santa Cruz). In an embodiment, the subject disclosure relates to calculating percent identity between two polynucleotides or amino acid sequences using the IDF Searcher (O'Kane, K. C., The Effect of Inverse Document Frequency Weights on Indexed Sequence Retrieval, *Online Journal of Bioinformatics*, Volume 6 (2) 162-173, 2005). In an embodiment, the subject disclosure relates to calculating percent identity between two polynucleotides or amino acid sequences using the Parasail alignment program. (Daily, Jeff. Parasail: SIMD C library for global, semi-global, and local pairwise sequence alignments. *BMC Bioinformatics*. 17:18. Feb. 10, 2016). In an embodiment, the subject disclosure relates to calculating percent identity between two polynucleotides or amino acid sequences using the ScalaBLAST alignment program (Oehmen C, Nieplocha J. "ScalaBLAST: A scalable implementation of BLAST for high-performance data-intensive bioinformatics analysis." *IEEE Transactions on Parallel & Distributed Systems* 17 (8): 740-749 August 2006). In an embodiment, the subject disclosure relates to calculating percent identity between two polynucleotides or amino acid sequences using the SWIPE alignment program (Rognes, T. Faster Smilth-Waterman database searches with inter-sequence SIMD parallelization. *BMC Bioinformatics.* 12, 221 (2011)). In an embodiment, the subject disclosure relates to calculating percent identity between two polynucleotides or amino acid sequences using the ACANA alignment program (Weichun Huang, David M. Umbach, and Leping Li, Accurate anchoring alignment of divergent sequences. *Bioinformatics* 22:29-34, Jan. 1, 2006). In an embodiment, the subject disclosure relates to calculating percent identity between two polynucleotides or amino acid sequences using the DOTLET alignment program (Junier, T. & Pagni, M. DOTLET: diagonal plots in a web browser. *Bioinformatics* 16(2): 178-9 Feb. 2000). In an embodiment, the subject disclosure relates to calculating percent identity between two polynucleotides or amino acid sequences using the G-PAS alignment program (Frohmberg, W., et al. G-PAS 2.0 —an improved version of protein alignment tool with an efficient backtracking routine on multiple GPUs. *Bulletin of the Polish Academy of Sciences Technical Sciences*, Vol. 60, 491 November 2012). In an embodiment, the subject disclosure relates to calculating percent identity between two polynucleotides or amino acid sequences using the GapMis alignment program (Flouri, T. et. al., Gap Mis: A tool for pairwise sequence alignment with a single gap. Recent Pat DNA Gene Seq. 7(2): 84-95 August 2013). In an embodiment, the subject disclosure relates to calculating percent identity between two polynucleotides or amino acid sequences using the EMBOSS suite of alignment programs, including, but not limited to: Matcher, Needle, Stretcher, Water, Wordmatch, etc. (Rice, P., Longden, I. & Bleasby, A. EMBOSS: The European Molecular Biology Open Software Suite. *Trends in Genetics* 16(6) 276-77 (2000)). In an embodiment, the subject disclosure relates to calculating percent identity between two polynucleotides or amino acid sequences using the Ngila alignment program (Cartwright, R. Ngila: global pairwise alignments with logarithmic and affine gap costs. *Bioinformatics.* 23(11): 1427-28. Jun. 1, 2007). In an embodiment, the subject disclosure relates to calculating percent identity between two polynucleotides or amino acid sequences using the probA, also known as propA, alignment program (Muckstein, U., Hofacker, IL, & Stadler, P F. Stochastic pairwise alignments. *Bioinformatics* 18 Suppl. 2:S153-60. 2002). In an embodiment, the subject disclosure relates to calculating percent identity between two polynucleotides or amino acid sequences using the SEQALN suite of alignment programs (Hardy, P. & Waterman, M. *The Sequence Alignment Software Library at USC.*

1997). In an embodiment, the subject disclosure relates to calculating percent identity between two polynucleotides or amino acid sequences using the SIM suite of alignment programs, including, but not limited to, GAP, NAP, LAP, etc. (Huang, X & Miller, W. A Time-Efficient, Linear-Space Local Similarity Algorithm. *Advances in Applied Mathematics*, vol. 12 (1991) 337-57). In an embodiment, the subject disclosure relates to calculating percent identity between two polynucleotides or amino acid sequences using the UGENE alignment program (Okonechnikov, K., Golosova, O. & Fursov, M. Unipro UGENE: a unified bioinformatics toolkit. *Bioinformatics.* 2012 28:1166-67). In an embodiment, the subject disclosure relates to calculating percent identity between two polynucleotides or amino acid sequences using the BAli-Phy alignment program (Suchard, MA & Redelings, BD. BAli-Phy: simultaneous Bayesian inference of alignment and phylogeny. Bioinformatics. 22:2047-48. 2006). In an embodiment, the subject disclosure relates to calculating percent identity between two polynucleotides or amino acid sequences using the Base-By-Base alignment program (Brodie, R., et. al. Base-By-Base: Single nucleotide-level analysis of whole viral genome alignments, *BMC Bioinformatics*, 5, 96, 2004). In an embodiment, the subject disclosure relates to calculating percent identity between two polynucleotides or amino acid sequences using the DECIPHER alignment program (ES Wright (2015) "DECIPHER: harnessing local sequence context to improve protein multiple sequence alignment." *BMC Bioinformatics*, doi:10.1186/si2859-015-0749-z.). In an embodiment, the subject disclosure relates to calculating percent identity between two polynucleotides or amino acid sequences using the FSA alignment program (Bradley, R K, et. al. (2009) Fast Statistical Alignment. *PLoS Computational Biology.* 5:e1000392). In an embodiment, the subject disclosure relates to calculating percent identity between two polynucleotides or amino acid sequences using the Geneious alignment program (Kearse, M., et. al. (2012). Geneious Basic: an integrated and extendable desktop software platform for the organization and analysis of sequence data. *Bioinformatics,* 28(12), 1647-49). In an embodiment, the subject disclosure relates to calculating percent identity between two polynucleotides or amino acid sequences using the Kalign alignment program (Lassmann, T. & Sonnhammer, E. Kalign—an accurate and fast multiple sequence alignment algorithm. *BMC Bioinformatics* 2005 6:298). In an embodiment, the subject disclosure relates to calculating percent identity between two polynucleotides or amino acid sequences using the MAVID alignment program (Bray, N. & Pachter, L. MAVID: Constrained Ancestral Alignment of Multiple Sequences. Genome Res. 2004 April; 14(4): 693-99). In an embodiment, the subject disclosure relates to calculating percent identity between two polynucleotides or amino acid sequences using the MSA alignment program (Lipman, D J, et.al. A tool for multiple sequence alignment. *Proc. Nat'l Acad. Sci. USA.* 1989; 86:4412-15). In an embodiment, the subject disclosure relates to calculating percent identity between two polynucleotides or amino acid sequences using the MultAlin alignment program (Corpet, F., Multiple sequence alignment with hierarchical clustering. *Nucl. Acids Res.,* 1988, 16(22), 10881-90). In an embodiment, the subject disclosure relates to calculating percent identity between two polynucleotides or amino acid sequences using the LAGAN or MLAGAN alignment programs (Brudno, et. al. LAGAN and Multi-LAGAN: efficient tools for large-scale multiple alignment of genomic DNA. Genome Research 2003 April; 13(4): 721-31). In an embodiment, the subject disclosure relates to calculating percent identity between two polynucleotides or amino acid sequences using the Opal alignment program (Wheeler, T. J., & Kececiouglu, J. D. Multiple alignment by aligning alignments. Proceedings of the 15$^{th}$ ISCB conference on Intelligent Systems for Molecular Biology. *Bioinformatics.* 23, i559-68, 2007). In an embodiment, the subject disclosure relates to calculating percent identity between two polynucleotides or amino acid sequences using the PicXAA suite of programs, including, but not limited to, PicXAA, PicXAA-R, PicXAA-Web, etc. (Mohammad, S., Sahraeian, E. & Yoon, B. PicXAA: greedy probabilistic construction of maximum expected accuracy alignment of multiple sequences. *Nucleic Acids Research.* 38(15):4917-28. 2010). In an embodiment, the subject disclosure relates to calculating percent identity between two polynucleotides or amino acid sequences using the PSAlign alignment program (SZE, S.-H., Lu, Y., & Yang, Q. (2006) A polynomial time solvable formulation of multiple sequence alignment *Journal of Computational Biology,* 13, 309-19). In an embodiment, the subject disclosure relates to calculating percent identity between two polynucleotides or amino acid sequences using the StatAlign alignment program (Novák, Á., et. al. (2008) StatAlign: an extendable software package for joint Bayesian estimation of alignments and evolutionary trees. *Bioinformatics,* 24(20):2403-04). In an embodiment, the subject disclosure relates to calculating percent identity between two polynucleotides or amino acid sequences using the Gap alignment program of Needleman and Wunsch (Needleman and Wunsch, *Journal of Molecular Biology* 48:443-453, 1970). In an embodiment, the subject disclosure relates to calculating percent identity between two polynucleotides or amino acid sequences using the BestFit alignment program of Smith and Waterman (Smith and Waterman, *Advances in Applied Mathematics,* 2:482-489, 1981, Smith et al., Nucleic Acids Research 11:2205-2220, 1983). These programs produces biologically meaningful multiple sequence alignments of divergent sequences. The calculated best match alignments for the selected sequences are lined up so that identities, similarities, and differences can be seen.

The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

The term "homology" is sometimes used to refer to the level of similarity between two or more nucleic acid or amino acid sequences in terms of percent of positional identity (i.e., sequence similarity or identity). Homology also refers to the concept of evolutionary relatedness, often evidenced by similar functional properties among different nucleic acids or proteins that share similar sequences.

As used herein, the term "variants" means substantially similar sequences. For nucleotide sequences, naturally occurring variants can be identified with the use of well-known molecular biology techniques, such as, for example, with polymerase chain reaction (PCR) and hybridization techniques as outlined herein.

For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the disclosure will have at least about 40%, 45%, 50%>, 55%, 60%, 65%, 70%, 75%, 80%, 85%, 90%, 91%, 92%, 93%, 94%, 95%, 96%, 97%, 98%0, 99% or more sequence identity to that particular nucleotide sequence as determined by sequence alignment programs and parameters described elsewhere herein. A biologically active variant of a nucleotide sequence of the disclosure may differ from that sequence by as few as 1-15 nucleic acid residues, as few as 1-10, such as 6-10, as few as 5, as few as 4, 3, 2, or even 1 nucleic acid residue.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "orally active" refers to a protein that inhibits the proliferation of insect pests when orally ingested by the insect pest.

As used herein, the term "insecticidal activity" refers to activity of an organism or a substance (such as, for example, a protein) that can be measured by, but is not limited to, insect mortality, insect weight loss, insect repellency, and other behavioral and physical changes of an insect after feeding and exposure for an appropriate length of time. Thus, an organism or substance having insecticidal activity adversely impacts at least one measurable parameter of insect fitness.

As used herein, the term "pest" refers to any insect that is unwanted and disruptive or destructive to the growth and development of agricultural crops. The term "insect pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Thysanoptera, Dermaptera, Isoptera, Anoplura, Siphonaptera, Trichoptera, etc., particularly Lepidoptera, and Hemiptera.

As used herein, the term "stable transformation" or "stably transformed" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or a polypeptide is introduced into a plant. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, and pollen).

As used herein, the term "regeneration" means the process of growing a plant from a plant cell (e.g., plant protoplast or explant).

As used herein, the term "culturing" refers to the in vitro propagation of cells or organisms on or in media of various kinds so that the maintenance or growth cell within a liquid culture medium are controlled under a set of physical conditions. It is understood that the descendants of a cell grown in culture may not be completely identical (i.e., morphologically, genetically, or phenotypically) to the parent cell.

As used herein, the term "controlling" (for instance as in "controlling an insect pest population"), as used herein refers to monitoring, treating, minimizing, exterminating, or preventing insect pests such as stink bugs. In specific instances the insect species are controlled to reducing the number of insects that cause reduced beneficial plant yield.

As used herein, the term "insecticidally-effective amount" refers to a quantity of a substance or organism that has insecticidal activity when present in the environment of an insect pest. For each substance or organism, the insecticidally-effective amount is determined empirically for each pest affected in a specific environment. Similarly, an "pesticidally effective amount" may be used to refer to a insecticidally-effective amount.

As used herein, the term "pesticidal protein" or "insecticidal protein" is intended to refer to a polypeptide that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., Xenorhabdus sp., *Clostridium bifermentans* and *Paenibacillus popilliae*. Pesticidal proteins include but are not limited to: insecticidal proteins from *Pseudomonas* sp. such as PSEEN3174 (Monalysin, (2011) *PLoS Pathogens,* 7:1-13), from *Pseudomonas protegens* strain CHAO and Pf-5 (previously *fluorescens*) (Pechy-Tarr, (2008) *Environmental Microbiology* 10:2368-2386: GenBank Accession No. EU400157); from *Pseudomonas Taiwanensis* (Liu, et al., (2010) *J. Agric. Food Chem.* 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and Xenorhabdus sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; and S-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of S-endotoxin genes and the *B. thuringiensis* cytolytic Cyt1 and Cyt2 genes. Members of these classes of *B. thuringiensis* insecticidal proteins include, but are not limited to Cry1Aa1 (Accession #Accession #M11250), Cry1Aa2 (Accession #M10917), Cry1Aa3 (Accession #D00348), Cry1Aa4 (Accession #X13535), Cry1Aa5 (Accession #D17518), Cry1Aa6 (Accession #U43605), Cry1Aa7 (Accession #AF081790), Cry1Aa8 (Accession #126149), Cry1Aa9 (Accession #AB026261), Cry1Aa10 (Accession #AF154676), Cry1Aa11 (Accession #Y09663), Cry1Aa12 (Accession #AF384211), Cry1Aa13 (Accession #AF510713), Cry1Aa14 (Accession #AY197341), Cry1Aa15 (Accession #DQ062690), Cry1Ab1 (Accession #M13898), Cry1Ab2 (Accession #M12661), Cry1Ab3 (Accession #M15271), Cry1Ab4 (Accession #D00117), Cry1Ab5 (Accession #X04698), Cry1Ab6 (Accession #M37263), Cry1Ab7 (Accession #X13233), Cry1Ab8 (Accession #M16463), Cry1Ab9 (Accession #X54939), Cry1Ab10 (Accession #A29125), Cry1Ab11 (Accession #I12419), Cry1Ab12 (Accession #AF059670), Cry1Ab13 (Accession #AF254640), Cry1Ab14 (Accession #U94191), Cry1Ab15 (Accession #AF358861), Cry1Ab16 (Accession #AF375608), Cry1Ab17 (Accession #AAT46415), Cry1Ab18 (Accession #AAQ88259), Cry1Ab19 (Accession #AY847289), Cry1Ab20 (Accession #DQ241675), Cry1Ab21 (Accession #EF683163), Cry1Ab22 (Accession #ABW87320), Cry1Ab-like (Accession #AF327924), Cry1Ab-like (Accession #AF327925), Cry1Ab-like (Accession #AF327926), Cry1Ab-like (Accession #DQ781309), Cry1Ac1 (Accession #M11068), Cry1Ac2 (Accession #M35524), Cry1Ac3 (Accession #X54159), Cry1Ac4 (Accession #M73249), Cry1Ac5 (Accession #M73248), Cry1Ac6 (Accession #U43606), Cry1Ac7 (Accession #U87793), Cry1Ac8 (Accession #U87397), Cry1Ac9 (Accession #U89872), Cry1Ac10 (Accession #AJ002514), Cry1Ac11 (Accession #AJ130970), Cry1Ac12 (Accession #I12418), Cry1Ac13 (Accession #AF148644), Cry1Ac14 (Accession #AF492767), Cry1Ac15 (Accession #AY122057), Cry1Ac16 (Accession #AY730621), Cry1Ac17 (Accession #AY925090), Cry1Ac18 (Accession #DQ023296), Cry1Ac19 (Accession #DQ195217), Cry1Ac20 (Accession #DQ285666), Cry1Ac21 (Accession #DQ062689), Cry1Ac22 (Accession #EU282379), Cry1Ac23 (Accession #AM949588), Cry1Ac24 (Accession #ABL01535), Cry1Ad1 (Accession #M73250), Cry1Ad2 (Accession #A27531), Cry1Ae1 (Accession #M65252), Cry1Af1 (Accession #U82003), Cry1Ag1 (Accession #AF081248), Cry1Ah1 (Accession #AF281866), Cry1Ah2 (Accession #DQ269474), Cry1Ai1 (Accession #AY174873), Cry1A-like (Accession #AF327927), Cry1Ba1 (Accession #X06711), Cry1Ba2 (Accession #X95704), Cry1Ba3 (Accession #AF368257), Cry1Ba4 (Accession #AF363025), Cry1Ba5 (Accession #AB020894), Cry1Ba6 (Accession #ABL60921), Cry1Bb1 (Accession #L32020), Cry1Bc1 (Accession #Z46442), Cry1Bd1 (Accession #U70726), Cry1Bd2 (Accession #AY138457), Cry1Be1 (Accession #AF077326), Cry1Be2 (Accession #AAQ52387), Cry1Bf1 (Accession #AX189649), Cry1Bf2 (Accession #AAQ52380), Cry1Bg1 (Accession #AY176063), Cry1Ca1 (Accession #X07518), Cry1Ca2 (Accession #X13620), Cry1Ca3 (Accession #M73251), Cry1Ca4 (Accession #A27642), Cry1Ca5 (Accession #X96682), Cry1Ca6 [1] (Accession #AF215647), Cry1Ca7 (Accession #AY015492), Cry1 Cab (Accession #AF362020), Cry1Ca9 (Accession #AY078160), Cry1Ca10 (Accession #AF540014), Cry1Ca11 (Accession #AY955268), Cry1Cb1 (Accession #M97880), Cry1Cb2 (Accession #AY007686), Cry1Cb3 (Accession #EU679502), Cry1 Cb-like (Accession #AAX63901), Cry1Da1 (Accession #X54160), Cry1Da2 (Accession #I76415), Cry1Db1 (Accession #Z22511), Cry1db2 (Accession #AF358862), Cry1Dc1 (Accession #EF059913), Cry1 Eat (Accession #X53985), Cry1Ea2 (Accession #X56144), Cry1Ea3 (Accession #M73252), Cry1Ea4 (Accession #U94323), Cry1Ea5 (Accession #A15535), Cry1Ea6 (Accession #AF202531), Cry1Ea7 (Accession #AAW72936), Cry1Ea8 (Accession #ABX11258), Cry1Eb1 (Accession #M73253), Cry1Fa1 (Accession #M63897), Cry1Fa2 (Accession #M73254), Cry1Fb1 (Accession #Z22512), Cry1Fb2 (Accession #AB012288), Cry1Fb3 (Accession #AF062350), Cry1Fb4 (Accession #I73895), Cry1Fb5 (Accession #AF336114), Cry1Fb6 (Accession #EU679500), Cry1Fb7 (Accession #EU679501), Cry1Ga1 (Accession #Z22510), Cry1Ga2 (Accession #Y09326), Cry1Gb1 (Accession #U70725), Cry1Gb2 (Accession #AF288683), Cry1Gc (Accession #AAQ52381), Cry1Ha1 (Accession #Z22513), Cry1Hb1 (Accession #U35780), Cry1H-like (Accession #AF182196), Cry1Ia1 (Accession #X62821), Cry1Ia2 (Accession #M98544), Cry1Ia3 (Accession #L36338), Cry1Ia4 (Accession #L49391), Cry1Ia5 (Accession #Y08920), Cry1Ia6 (Accession #AF076953), Cry1Ia7 (Accession #AF278797), Cry1Ia8 (Accession #AF373207), Cry1Ia9 (Accession #AF521013), Cry1Ia10 (Accession #AY262167), Cry1Ia11 (Accession #AJ315121), Cry1Ia12 (Accession #AAV53390), Cry1Ia13 (Accession #ABF83202), Cry1Ia14 (Accession #EU887515), Cry1Ib1 (Accession #U07642), Cry1Ib2 (Accession #ABW88019), Cry1Ib3 (Accession #EU677422), Cry1Ic1 (Accession #AF056933), Cry1Ic2 (Accession #AAE71691), Cry1Id1 (Accession #AF047579), Cry1Ie1 (Accession #AF211190), Cry1If1 (Accession #AAQ52382), Cry1I-like (Accession #I90732), Cry1I-like (Accession #DQ781310), Cry1Ja1 (Accession #L32019), Cry1Jb1 (Accession #U31527), Cry1Jc1 (Accession #I90730), Cry1Jc2 (Accession #AAQ52372), Cry1Jd1 (Accession #AX189651), Cry1 Kat (Accession #U28801), Cry1La1 (Accession #AAS60191), Cry1-like (Accession #I90729), Cry2Aa1 (Accession #M31738), Cry2Aa2 (Accession #M23723), Cry2Aa3 (Accession #D86064), Cry2Aa4 (Accession #AF047038), Cry2Aa5 (Accession #AJ132464), Cry2Aa6 (Accession #AJ132465), Cry2Aa7 (Accession #AJ132463), Cry2Aa8 (Accession #AF252262), Cry2Aa9 (Accession #AF273218), Cry2Aa10 (Accession #AF433645), Cry2Aa11 (Accession #AAQ52384), Cry2Aa12 (Accession #DQ977646), Cry2Aa13 (Accession #ABL01536), Cry2Aa14 (Accession #ACF04939), Cry2Ab1 (Accession #M23724), Cry2Ab2 (Accession #X55416), Cry2Ab3 (Accession #AF164666), Cry2Ab4 (Accession #AF336115), Cry2Ab5 (Accession #AF441855), Cry2Ab6 (Accession #AY297091), Cry2Ab7 (Accession #DQ119823), Cry2Ab8 (Accession #DQ361266), Cry2Ab9 (Accession #DQ341378), Cry2Ab10 (Accession #EF157306), Cry2Ab11 (Accession #AM691748), Cry2Ab12 (Accession #ABM21764), Cry2Ab13 (Accession #EU909454), Cry2Ab14 (Accession #EU909455), Cry2Ac1 (Accession #X57252), Cry2Ac2 (Accession #AY007687), Cry2Ac3 (Accession #AAQ52385), Cry2Ac4 (Accession #DQ361267), Cry2Ac5 (Accession #DQ341379), Cry2Ac6 (Accession #DQ359137), Cry2Ac7 (Accession #AM292031), Cry2Ac8 (Accession #AM421903), Cry2Ac9 (Accession #AM421904), Cry2Ac10 (Accession #BI 877475), Cry2Ac11 (Accession #AM689531), Cry2Ac12 (Accession #AM689532), Cry2Ad1 (Accession #AF200816), Cry2Ad2 (Accession #DQ358053), Cry2Ad3 (Accession #AM268418), Cry2Ad4 (Accession #AM490199), Cry2Ad5 (Accession #AM765844), Cry2Ae1 (Accession #AAQ52362), Cry2Af1 (Accession #EF439818), Cry2Ag (Accession #ACH91610), Cry2Ah (Accession #EU939453), Cry3Aa1 (Accession #M22472), Cry3Aa2 (Accession #J02978), Cry3Aa3 (Accession #Y00420), Cry3Aa4 (Accession #M30503), Cry3Aa5 (Accession #M37207), Cry3Aa6 (Accession #U10985), Cry3Aa7 (Accession #AJ237900), Cry3Aa8 (Accession #AAS79487), Cry3Aa9 (Accession #AAW05659), Cry3Aa10 (Accession #AAU29411), Cry3Aa11 (Accession #AY882576), Cry3Aa12 (Accession #ABY49136), Cry3Ba1 (Accession #X17123), Cry3Ba2 (Accession #A07234), Cry3Bb1 (Accession #M89794), Cry3Bb2 (Accession #U31633), Cry3Bb3 (Accession #I15475), Cry3Ca1 (Accession #X59797), Cry4Aa1 (Accession #Y00423), Cry4Aa2 (Accession #D00248), Cry4Aa3 (Accession #AL731825), Cry4A-like (Accession #DQ078744), Cry4Ba1 (Accession #X07423), Cry4Ba2 (Accession #X07082), Cry4Ba3 (Accession #M20242), Cry4Ba4 (Accession #D00247), Cry4Ba5 (Accession #AL731825), Cry4Ba-like (Accession #ABC47686), Cry4Ca1 (Accession #EU646202), Cry5Aa1 (Accession #L07025), Cry5Ab1 (Accession #L07026), Cry5Ac1 (Accession #I34543), Cry5Ad1 (Accession #EF219060), Cry5Ba1 (Accession #U19725), Cry5Ba2 (Accession #EU121522), Cry6Aa1 (Accession #L07022), Cry6Aa2 (Accession #AF499736), Cry6Aa3 (Accession #DQ835612), Cry6Ba1 (Accession #L07024), Cry7Aa1 (Accession #M64478), Cry7Ab1 (Accession #U04367), Cry7Ab2 (Accession #U04368), Cry7Ab3 (Accession #BI 1015188), Cry7Ab4 (Accession #EU380678), Cry7Ab5 (Accession #ABX79555), Cry7Ab6 (Accession #FJ194973), Cry7Ba1 (Accession #ABB70817), Cry7Ca1 (Accession #EF486523), Cry8Aa1 (Accession #U04364), Cry8Ab1 (Accession #EU044830), Cry8Ba1 (Accession #U04365), Cry8Bb1 (Accession #AX543924), Cry8Bc1 (Accession #AX543926), Cry8Ca1 (Accession #U04366), Cry8Ca2 (Accession #AAR98783), Cry8Ca3 (Accession #EU625349), Cry8Da1 (Accession #AB089299), Cry8Da2 (Accession #BD133574), Cry8Da3 (Accession #BD133575), Cry8 Db1 (Accession #AB303980), Cry8Ea1 (Accession #AY329081), Cry8Ea2 (Accession #EU047597), Cry8Fa1 (Accession #AY551093), Cry8Ga1 (Accession #AY590188), Cry8Ga2 (Accession #DQ318860), Cry8Ga3 (Accession #FJ198072), Cry8Ha1 (Accession #EF465532), Cry8Ia1 (Accession #EU381044), Cry8Ja1 (Accession #EU625348), Cry8 like (Accession #ABS53003), Cry9Aa1 (Accession #X58120), Cry9Aa2 (Accession #X58534), Cry9Aa like (Accession #AAQ52376), Cry9Ba1 (Accession #X75019), Cry9Bb1 (Accession #AY758316), Cry9Ca1 (Accession #Z37527), Cry9Ca2 (Accession #AAQ52375), Cry9Da1 (Accession #D85560), Cry9Da2 (Accession #AF042733), Cry9 Db1 (Accession #AY971349), Cry9Ea1 (Accession #AB011496), Cry9Ea2 (Accession #AF358863), Cry9Ea3 (Accession #EF157307), Cry9Ea4 (Accession #EU760456), Cry9Ea5 (Accession #EU789519), Cry9Ea6 (Accession #EU887516), Cry9Eb1 (Accession #AX189653), Cry9Ec1 (Accession #AF093107), Cry9Ed1 (Accession #AY973867), Cry9 like (Accession #AF093107), Cry10Aa1 (Accession #M12662), Cry10Aa2 (Accession #E00614), Cry10Aa3 (Accession #AL731825), Cry10A like (Accession #DQ167578), Cry11Aa1 (Accession #M31737), Cry11Aa2 (Accession #M22860), Cry11Aa3 (Accession #AL731825), Cry11Aa-like (Accession #DQ166531), Cry1 Ba1 (Accession #X86902), Cry11Bb1 (Accession #AF017416), Cry12Aa1 (Accession #L07027), Cry13Aa1 (Accession #L07023), Cry14Aa1 (Accession #U13955), Cry15Aa1 (Accession #M76442), Cry16Aa1 (Accession #X94146), Cry17Aa1 (Accession #X99478), Cry18Aa1 (Accession #X99049), Cry18Ba1 (Accession #AF169250), Cry18Ca1 (Accession #AF169251), Cry19Aa1 (Accession #Y07603), Cry19Ba1 (Accession #D88381), Cry20Aa1 (Accession #U82518), Cry21Aa1 (Accession #I32932), Cry21Aa2 (Accession #I66477), Cry21Ba1 (Accession #AB088406), Cry22Aa1 (Accession #I34547), Cry22Aa2 (Accession #AX472772), Cry22Aa3 (Accession #EU715020), Cry22Ab1 (Accession #AAK50456), Cry22Ab2 (Accession #AX472764), Cry22Ba1 (Accession #AX472770), Cry23Aa1 (Accession #AAF76375), Cry24Aa1 (Accession #U88188), Cry24Ba1 (Accession #BAD32657), Cry24Ca1 (Accession #AM158318), Cry25Aa1 (Accession #U88189), Cry26Aa1 (Accession #AF122897), Cry27Aa1 (Accession #AB023293), Cry28Aa1 (Accession #AF132928), Cry28Aa2 (Accession #AF285775), Cry29Aa1 (Accession #AJ251977), Cry30Aa1 (Accession #AJ251978), Cry30Ba1 (Accession #BAD00052), Cry30Ca1 (Accession #BAD67157), Cry30Da1 (Accession #EF095955), Cry30 Db1 (Accession #BAE80088), Cry30Ea1 (Accession #EU503140), Cry30Fa1 (Accession #EU751609), Cry30Ga1 (Accession #EU882064), Cry31Aa1 (Accession #AB031065), Cry31Aa2 (Accession #AY081052), Cry31Aa3 (Accession #AB250922), Cry31Aa4 (Accession #AB274826), Cry31Aa5 (Accession #AB274827), Cry31Ab1 (Accession #AB250923), Cry31Ab2 (Accession #AB274825), Cry31Ac1 (Accession #AB276125), Cry32Aa1 (Accession #AY008143), Cry32Ba1 (Accession #BAB78601), Cry32Ca1 (Accession #BAB78602), Cry32Da1 (Accession #BAB78603), Cry33Aa1 (Accession #AAL26871), Cry34Aa1 (Accession #AAG50341), Cry34Aa2 (Accession #AAK64560), Cry34Aa3 (Accession #AY536899), Cry34Aa4 (Accession #AY536897), Cry34Ab1 (Accession #AAG41671), Cry34Ac1 (Accession #AAG50118), Cry34Ac2 (Accession #AAK64562), Cry34Ac3 (Accession #AY536896), Cry34Ba1 (Accession #AAK64565), Cry34Ba2 (Accession #AY536900), Cry34Ba3 (Accession #AY536898), Cry35Aa1 (Accession #AAG50342), Cry35Aa2 (Accession #AAK64561), Cry35Aa3 (Accession #AY536895), Cry35Aa4 (Accession #AY536892), Cry35Ab1 (Accession #AAG41672), Cry35Ab2 (Accession #AAK64563), Cry35Ab3 (Accession #AY536891), Cry35Ac1 (Accession #AAG50117), Cry35Ba1 (Accession #AAK64566), Cry35Ba2 (Accession #AY536894), Cry35Ba3 (Accession #AY536893), Cry36Aa1 (Accession #AAK64558), Cry37Aa1 (Accession #AAF76376), Cry38Aa1 (Accession #AAK64559), Cry39Aa1 (Accession #BAB72016), Cry40Aa1 (Accession #BAB72018), Cry40Ba1 (Accession #BAC77648), Cry40Ca1 (Accession #EU381045), Cry40Da1 (Accession #EU596478), Cry41Aa1 (Accession #AB116649), Cry41Ab1 (Accession #AB116651), Cry42Aa1 (Accession #AB116652), Cry43Aa1 (Accession #AB115422), Cry43Aa2 (Accession #AB176668), Cry43Ba1 (Accession #AB115422), Cry43-like (Accession #AB115422), Cry44Aa (Accession #BAD08532), Cry45Aa (Accession #BAD22577), Cry46Aa (Accession #BAC79010), Cry46Aa2 (Accession #BAG68906), Cry46Ab (Accession #BAD35170), Cry47Aa (Accession #AY950229), Cry48Aa (Accession #AJ841948), Cry48Aa2 (Accession #AM237205), Cry48Aa3 (Accession #AM237206), Cry48Ab (Accession #AM237207), Cry48Ab2 (Accession #AM237208), Cry49Aa (Accession #AJ841948), Cry49Aa2 (Accession #AM237201), Cry49Aa3 (Accession #AM237203), Cry49Aa4 (Accession #AM237204), Cry49Ab1 (Accession #AM237202), Cry50Aa1 (Accession #AB253419), Cry51Aa1 (Accession #DQ836184), Cry52Aa1 (Accession #EF613489), Cry53Aa1 (Accession #EF633476), Cry54Aa1 (Accession #EU339367), Cry55Aa1 (Accession #EU121521), Cry55Aa2 (Accession #AAE33526).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8.304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) Applied and Environmental Microbiology 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080r12, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103,247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as Xenorhabdus, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus*, Xenorhabdus or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

As used herein, the term "inhibiting growth" or "growth inhibition" means a reduction or inhibition in the growth of an insect organism, in some embodiments by at least 10%, 15%, 20%, 25%, 30%, 40%, 45%, 50%, 55%, 60%, 65%, 70%, 75%, 80%, 85%, 90% or 95%. The inhibition of growth of insect can be determined by measuring the weight or size of the insect.

As used herein, the term "mortality" refers to the death of the insects.

As used herein, the term "resistant", "resistance" and "host plant resistance" refers the ability of a host plant to prevent or reduce infestation and damage of a pest from the group comprising insects, nematodes, pathogens, fungi, viruses, and diseases.

As used herein, the term "insect resistance transgene product", can mean a "pesticide", a "Bt" or "Bt polypeptide" where the plant protectant is a protein, or a variant thereof, derived from *Bacillus thuringiensis*, a "non-Bt" or "non-Bt polypeptide", where the plant protectant is a protein, or a variant thereof, derived from a bacterium other than *Bacillus thuringiensis* or a plant, particularly from a fern or other primitive plant, or "RNA" where the plant protectant is an RNA molecule, particularly a RNAi or dsRNA. Transgenic insecticidal products can be expressed from a transgenic event that comprises a transgene encoding the transgenic insect resistance trait.

As used herein, the term "protecting" refers to the avoidance of, or minimizing the amount of attack of plant by a soil pest to a point where it no longer poses a threat to plant vitality, selective plant death, quality loss and/or reduced yields.

As used herein, the term "crop field" refers to a cultivated expanse of land that a farmer uses to grow a crop species. A crop field ranges in size depending on crop species and purpose. In one example, a crop field can include rows and can be planted at various lengths. In another example, a crop field can be planted by broadcasting the seed throughout the crop field. In a further example, a crop field can be planted by drilling the seed throughout the crop field.

As used herein, the term "modes of action" means the biological or biochemical means by which a pest control strategy or compound inhibits pest feeding and/or increases pest mortality.

As used herein, the term "co-expressing" refers to two or more gene products which are produced at the same time within the same host organism.

As used herein, the term "degenerate" refers to a primer or probe nucleic acid in which certain positions are not defined by a single, specific nucleotide. Thus, in such a degenerate position, the primer or probe sequence can be either one of at least two different nucleotides. Such positions often represent difference in genotypes of the target nucleic acid. A degenerate sequence may also be represented as a mixture of multiple non-degenerate individual sequences which, for the purpose of this disclosure, differ in at least two positions.

As used herein, the term "enzymatically active fragment", "fragment" or "biologically active portion" include polypeptide fragments comprising amino acid sequences sufficiently identical to a polypeptide and that exhibit insecticidal activity. "Fragments" or "biologically active portions" include polypeptide fragments comprising amino acid sequences sufficiently identical to the amino acid sequence that exhibit insecticidal activity. A biologically active portion of a polypeptide can be a polypeptide that is, for example, 8, 10, 25, 50, 100, 150, 200, 250 or more amino acids in length. Such biologically active portions can be prepared by recombinant techniques and evaluated for insecticidal activity. As used here, a fragment comprises at least 8 contiguous amino acids of a polypeptide. The embodiments encompass other fragments, however, such as any fragment in the protein greater than about 10, 20, 30, 50, 100, 150, 200, 250 or more amino acids.

As used herein, the term "peptide segment" refers to a protein molecule that has been isolated free of other protein sequences and amino acid residues.

As used herein, the term "DNA segment" refers to a DNA molecule that has been isolated free of total genomic DNA of a particular species. Therefore, a DNA segment encoding a protein or peptide refers to a DNA segment that contains protein coding sequences yet is isolated away from, or purified free from, total genomic DNA of the species from which the DNA segment is obtained, which in the instant case is the genome of the Gram-positive bacterial genus, *Bacillus*, and in particular, the species known as *B. thuringiensis*. Included within the term "DNA segment", are DNA segments and smaller fragments of such segments, and also recombinant vectors, including, for example, plasmids, cosmids, phagemids, phage, viruses, and the like.

As used herein, the term "formulated insecticidal protein" refers to a purified or isolated insecticidal protein that has been expressed or placed into a synthetic composition suitable for agricultural application, including but not limited to transgenic plants, sprayable liquid formulations, powdered solid formulations, or granular formulations.

As used herein, the term "expression" refers to the combination of intracellular processes, including transcription and translation undergone by a coding DNA molecule such as a structural gene to produce a polypeptide.

As used herein, the term "transgenic cell" means any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

As used herein, the term "transgenic plant" means a plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5' UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) *Genes & Dev.*, 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

As used herein, the terms "5' untranslated region" or "5' UTR" is defined as the untranslated segment in the 5' terminus of pre-mRNAs or mature mRNAs. For example, on mature mRNAs, a 5' UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

As used herein, the terms "transcription terminator" or "terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

As used herein, the term "3' untranslated region" or "3' UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3' UTR is considered to include the polyadenylation signal and transcription terminator.

on the polyadenylation site, for example, located 10 to 30 bases downstream of the poly-(A) signal. Many polyadenylation signals are known in the art and are useful for the present disclosure. An exemplary sequence includes AAUAAA and variants thereof, as described in Loke J., et al., (2005) Plant Physiology 138(3); 1457-1468.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) Cell 15:579-85); *Agrobacterium*-mediated transfer; direct DNA uptake; WIISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

An exogenous nucleic acid sequence. In one example, a transgene/heterologous coding sequence is a gene sequence (e.g., an herbicide-resistance gene), a gene encoding an industrially or pharmaceutically useful compound, or a gene encoding a desirable agricultural trait. In yet another example, the transgene/heterologous coding sequence is an antisense nucleic acid sequence, wherein expression of the antisense nucleic acid sequence inhibits expression of a target nucleic acid sequence. A transgene/heterologous coding sequence may contain regulatory sequences operably linked to the transgene/heterologous coding sequence (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the term a transgenic "event" is produced by transformation of plant cells with heterologous DNA, i.e., a nucleic acid construct that includes a transgene/heterologous coding sequence of interest, regeneration of a population of plants resulting from the insertion of the transgene/heterologous coding sequence into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene/heterologous coding sequence DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene/heterologous coding sequence of interest as the result of a sexual cross of one parental line that includes the inserted DNA (e.g., the original transformant and progeny resulting from selfing) and a parental line that does not contain the inserted DNA.

As used herein, the terms "Polymerase Chain Reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51:263 (1987); Erlich, ed., PCR Technology, (Stockton Press, N Y, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is typically a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red®, Fluorescein isothiocyanate, etc.). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™ etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector.

The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other.

Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. In other instances the term "polylinker" as used herein refers to a stretch of nucleotides that are targeted for joining two sequences via any known seamless cloning method (i.e., Gibson Assembly®, NEBuilder HiFiDNA Assembly®, Golden Gate Assembly, BioBrick® Assembly, etc.). Constructs comprising a polylinker are utilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present disclosure is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "small RNA" refers to several classes of non protein-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease DICER in animals or DCL1 in plants.

Many types of small RNA exist either naturally or produced artificially, including microRNAs (miRNAs), small interfering RNAs (siRNAs), antisense RNA, short/small hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)," "tmRNA" (a.k.a. "10S RNA," Muto et al., (1998) *Trends Biochem Sci.* 23:25-29; and Gillet et al., (2001) *Mol Microbiol.* 42:879-885); RNAi molecules including without limitation "small interfering RNA (siRNA)," "endoribonuclease-prepared siRNA (e-siRNA)," "short/small hairpin RNA (shRNA)," and "small temporally regulated RNA (stRNA)," "diced siRNA (d-siRNA)," and aptamers, oligonucleotides and other synthetic nucleic acids that comprise at least one uracil base.

As used herein, the term DICER recognition sequence is any stretch of polynucleotides that are recognized and bound by the DICER enzyme for subsequent cleavage. The double-stranded molecule generated by DICER activity upon the shRNA molecule may be separated into two single-stranded shRNAs; the "STAR/passenger strand" and the "guide strand." The STAR/passenger strand may be degraded, and the guide strand may be incorporated into the RISC complex. Post-transcriptional inhibition occurs by specific hybridization of the guide strand with a specifically complementary polynucleotide of an mRNA molecule, and subsequent cleavage by the enzyme, Argonaute (e.g., a catalytic component of the RISC complex).

As used herein, the term DROSHA recognition sequence, is any stretch of polynucleotides that are recognized and bound by the DROSHA enzyme for subsequent cleavage.

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

III. Novel Small Hairpin RNA (shRNA) Molecules

Provided are methods and compositions disclosing the shRNA polynucleotide. In an embodiment the shRNA polynucleotide may be a DNA or an RNA polynucleotide. In an aspect of this embodiment, the shRNA polynucleotide is less than 70 nucleotides in length. In an example of this aspect, the shRNA may be less than 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15 polynucleotides in length. In another aspect of this embodiment, the shRNA polynucleotide is less than 80 nucleotides in length. In an example of this aspect, the shRNA may be less than 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15 polynucleotides in length. In an aspect of this embodiment, the shRNA polynucleotide is less than 90 nucleotides in length. In an example of this aspect, the shRNA may be less than 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15 polynucleotides in length. In further aspects, the shRNA polynucleotide is initially a single stranded polynucleotide sequence (e.g., ribonucleic acid sequence) that may fold back upon itself and self-hybridize under appropriate conditions. In an aspect, the shRNA comprises a first RNA strand, a second RNA strand, and a third RNA strand. Accordingly, the first RNA strand comprises from 16-25 nucleotides. The second RNA strand comprises less than 25 nucleotides. In addition, the third RNA strand comprises from 16-25 nucleotides. In some aspects, the third RNA strand is the reverse complement of the first RNA strand. In other aspects the first and third RNA strands may self-hybridize when the shRNA polynucleotide folds back upon itself. In such an aspect the shRNA polynucleotide may form a stem-loop type structure that is comprised of a hairpin structure and a stem structure. Accordingly, aspects of the disclosure include a shRNA molecule that is comprised of a hairpin structure and a stem structure. Other aspects include a shRNA molecule that consists of a hairpin structure and a stem structure. In other aspects the shRNA molecule has a free energy ($\Delta G°$ 37) of less than −30 kcal/mol. In additional aspects the shRNA molecule comprises SEQ ID NO:1, SEQ ID NO:2, SEQ ID NO:3, SEQ ID NO:4, SEQ ID NO:5, SEQ ID NO:6, SEQ ID NO:405, SEQ ID NO:406, SEQ ID NO:407, SEQ ID NO:408, SEQ ID NO:411, SEQ ID NO:413, SEQ ID NO:415, SEQ ID NO:417, SEQ ID NO:419, or SEQ ID NO421. In some aspects the shRNA inhibits a target gene of an insect pest by suppressing the expression of the target mRNA of an insect pest. In other aspects the shRNA inhibits a target gene of a living organism by suppressing the expression of the target mRNA of a living organism.

In further embodiments of the subject disclosure the shRNA polynucleotide does not comprise a DROSHA recognition sequence. In other aspects the shRNA polynucleotide is not cleaved by the DROSHA enzyme. The pri-miRNA is transcribed in the nucleus and processed by a complex of the DROSHA ribonuclease and DGCR8 (e.g., PASHA) to produce a pre-miRNA molecule of ~70 nucleotides in length. In other embodiments the pre-miRNA molecule is ~80 nucleotides in length. In further embodiments the pre-miRNA molecule is ~90 nucleotides in length. In an aspect of this embodiment, a DROSHA enzyme is an enzyme of the RNase III family that does not function in cleaving the shRNA molecule. In other aspects, the DROSHA enzyme is an enzyme of the RNase III family that does not recognize or bind to the shRNA molecule. Comparatively, the DROSHA enzyme does recognize, bind and cleave miRNA molecules within the nucleus of a cell. Exemplary DROSHA enzymes include members of the Enzyme Class:3.1.26.3 (i.e., EC:3.1.26.3).

In other embodiments of the subject disclosure the shRNA polynucleotide comprises a DICER recognition sequence. In further aspects the shRNA polynucleotide is cleaved by the DICER enzyme. Typically, the pre-miRNA is processed into a pri-miRNA through cleavage of the loop feature (e.g., hairpin structure) of the stem-loop structure by DICER in collaboration with other cofactors (e.g., TRBP and PACT). The resulting cleavage produces an imperfect ~22 nucleotide miRNA duplex with 2 nucleotide overhangs on the 3' end of the molecule. In an aspect of this embodiment, a DICER enzyme is an enzyme of the RNase III family that cleaves shRNA molecule to produce short double-stranded RNA fragments called small interfering RNA (siRNA) and mature miRNA. In other aspects, the DICER enzyme processes a shRNA molecule into fragments of approximately 19-25 nucleotide lengths. As such, aspects of this embodiment include the processing of a shRNA molecule by DICER into a 19 nucleotide shRNA molecule. Other aspects of this embodiment include the processing of a shRNA molecule by DICER into a 20 nucleotide shRNA molecule. Further aspects of this embodiment include the processing of a shRNA molecule by DICER into a 21 nucleotide shRNA molecule. Aspects of this embodiment include the processing of a shRNA molecule by DICER into a 22 nucleotide shRNA molecule. Additional aspects of this embodiment include the processing of a shRNA molecule by DICER into a 23 nucleotide shRNA molecule. Other aspects of this embodiment include the processing of a shRNA molecule by DICER into a 24 nucleotide shRNA molecule. Further aspects of this embodiment include the processing of a shRNA molecule by DICER into a 25 nucleotide shRNA molecule. In other aspects the DICER enzyme recognizes and cleaves a shRNA molecule thereby activating the RNA-induced silencing complex (RISC). Accordingly, aspects of this embodiment include a DICER processed shRNA molecule that activates RISC. In further aspects, the DICER enzyme of the subject disclosure encompasses any orthologous DICER enzyme from a living organism. In most examples the DICER enzyme contains both a helicase and a PAZ (Piwi/Argonaute/Zwille) domain. Further examples of DICER enzymes include members of the Enzyme Class: 3.1.26.-(i.e., EC:3.1.26.-). In other aspects the DICER enzyme includes a DICER enzyme obtained from an insect (e.g., DICER-1). Accordingly, the insect DICER enzyme can recognize a shRNA and process the shRNA by processing shRNA molecule into mature shRNA which is an siRNA molecule. Subsequently these mature shRNA molecules are loaded onto RISC (e.g., AGO2-RISC) and result in the inhibition of a target gene via cleavage of the target mRNA. In further aspects the DICER enzyme includes a DICER enzyme or fragment thereof obtained from a plant (e.g., DCL-1, DCL-2, DCL-3, or DCL-4). Accordingly, the plant DICER enzyme or fragment thereof can recognize a shRNA and process the shRNA by cleaving the shRNA molecule into 19-25 bp fragments. Subsequently these cleaved shRNA may be loaded onto RISC and result in the inhibition of a target gene by suppressing the expression of the mRNA of the target gene.

In other embodiments of the subject disclosure the shRNA polynucleotide comprises a hairpin structure. In an aspect, the hairpin structure may be less than 25, 24, 23, 22, 21, 20, 19, 18, 17, 16, 15, 14, 13, 12, 11, 10, 9, 8, 7, 6, or 5 polynucleotides in length. In an aspect, the hairpin structure may be any polynucleotide sequence of less than 25 polynucleotides in length. In a further aspect, the hairpin structure may be any polynucleotide sequence of less than 24 polynucleotides in length. In an additional aspect, the hairpin structure may be a polynucleotide sequence obtained from an insect microRNA scaffold. In additional aspects the stem structure may comprise base pairs 24-38 of SEQ ID No:1, base pairs 23-36 of SEQ ID No:6, base pairs 23-38 of SEQ ID No:2, base pairs 24-38 of SEQ ID No:3, base pairs 25-37 of SEQ ID No:4, base pairs 38-60 of SEQ ID No:4, base pairs 24-37 of SEQ ID No:5, base pairs 25-34 of SEQ ID No:5, base pairs 1-23 of SEQ ID No:405, base pairs 39-60 of SEQ ID No:405, base pairs 39-60 of SEQ ID No:406, base pairs 24-38 of SEQ ID No:407, base pairs 24-38 of SEQ ID No:408, base pairs 24-38 of SEQ ID No:411, base pairs 24-38 of SEQ ID No:413, base pairs 24-38 of SEQ ID No:415, base pairs 24-38 of SEQ ID No:417 base pairs 24-38 of SEQ ID No:419, or base pairs 24-38 of SEQ ID No:421. In other aspects, the a hairpin structure may comprise any polynucleotide of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO: 142, SEQ ID NO:143, SEQ ID NO:144, SEQ ID NO:145, SEQ ID NO:146, SEQ ID NO:147, SEQ ID NO:148, SEQ ID NO:149, SEQ ID NO:150 SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO: 161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193 SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250 SEQ ID NO:251, SEQ ID NO:252, SEQ ID NO:253, SEQ ID NO:254, SEQ ID NO:255, SEQ ID NO:256, SEQ ID NO:257, SEQ ID NO:258, SEQ ID NO:259, SEQ ID NO:260, SEQ ID NO:261, SEQ ID NO:262, SEQ ID NO:263, SEQ ID NO:264, SEQ ID NO:265, SEQ ID NO:266, SEQ ID NO:267, SEQ ID NO:268, SEQ ID NO:269, SEQ ID NO:270, SEQ ID NO:271, SEQ ID NO:272, SEQ ID NO:273, SEQ ID NO:274, SEQ ID NO:275, SEQ ID NO:276, SEQ ID NO:277, SEQ ID NO:278, SEQ ID NO:279, SEQ ID NO:280, SEQ ID NO:281, SEQ ID NO:282, SEQ ID NO:283, SEQ ID NO:284, SEQ ID NO:285, SEQ ID NO:286, SEQ ID NO:287, SEQ ID NO:288, SEQ ID NO:289, SEQ ID NO:290, SEQ ID NO:291, SEQ ID NO:292, SEQ ID NO:293 SEQ ID NO:294, SEQ ID NO:295, SEQ ID NO:296, SEQ ID NO:297, SEQ ID NO:298, SEQ ID NO:299, SEQ ID NO:300, SEQ ID NO:301, SEQ ID NO:302, SEQ ID NO:303, SEQ ID NO:304, SEQ ID NO:305, SEQ ID NO:306, SEQ ID NO:307, SEQ ID NO:308, SEQ ID NO:309, SEQ ID NO:310, SEQ ID NO:311, SEQ ID NO:312, SEQ ID NO:313, SEQ ID NO:314, SEQ ID NO:315, SEQ ID NO:316, SEQ ID NO:317, SEQ ID NO:318, SEQ ID NO:319, SEQ ID NO:320, SEQ ID NO:321, SEQ ID NO:322, SEQ ID NO:323, SEQ ID NO:324, SEQ ID NO:325, SEQ ID NO:326, SEQ ID NO:327, SEQ ID NO:328, SEQ ID NO:329, SEQ ID NO:330, SEQ ID NO:331, SEQ ID NO:332, SEQ ID NO:333, SEQ ID NO:334, SEQ ID NO:335, SEQ ID NO:336, SEQ ID NO:337, SEQ ID NO:338, SEQ ID NO:339, SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:350 SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:361, SEQ ID NO:362, SEQ ID NO:363, SEQ ID NO:364, SEQ ID NO:365, SEQ ID NO:366, SEQ ID NO:367, SEQ ID NO:368, SEQ ID NO:369, SEQ ID NO:370, SEQ ID NO:371, SEQ ID NO:372, SEQ ID NO:373, SEQ ID NO:374, SEQ ID NO:375, SEQ ID NO:376, SEQ ID NO:377, SEQ ID NO:378, SEQ ID NO:379, SEQ ID NO:380, SEQ ID NO:381, SEQ ID NO:382, SEQ ID NO:383, SEQ ID NO:384, SEQ ID NO:385, SEQ ID NO:386, SEQ ID NO:387, SEQ ID NO:388, SEQ ID NO:389, SEQ ID NO:390, SEQ ID NO:391, SEQ ID NO:392, SEQ ID NO:393 SEQ ID NO:394, SEQ ID NO:395, SEQ ID NO:396, SEQ ID NO:397, SEQ ID NO:398, SEQ ID NO:399, SEQ ID NO:400, or SEQ ID NO:401. In additional aspects the hairpin structure may comprise a fragment of any of SEQ ID Nos:7-401. In an example of this aspect, the fragment length of any of SEQ ID Nos:7-401 may be less than 25, 24, 23, 22, 21, 20, 19, 18, 17, 16, 15, 14, 13, 12, 11, 10, 9, 8, 7, 6, or 5 polynucleotides in length. The polynucleotide sequences of the subject disclosure can be used to isolate corresponding hairpin microRNA scaffold structures from other organisms, particularly other insect species. In this manner, methods such as PCR, hybridization, bioinformatics analysis, and the like can be used to identify such sequences based on their sequence identity to the sequences set forth herein.

In further aspects, the shRNA polynucleotide comprising the hairpin structure may fold back upon itself and self-hybridize. In such an aspect the shRNA polynucleotide may form a stem-loop type structure that is comprised of a hairpin structure and a stem structure. In such an aspect the hairpin structure may be comprised of single-stranded nucleotides that do not self-hybridize. In another aspect the hairpin structure may be comprised of a combination of single stranded nucleotides that do not self-hybridize and double stranded nucleotides that do self-hybridize. In such an example, the double stranded nucleotides that do self-hybridize make up a minority of the hairpin structure, wherein the hairpin structure is observed as the loop feature within the stem-loop type structure. In an aspect, the hairpin structure comprises double stranded fragments of a length of 1, 2, 3, 4, or 5 nucleotides. In other aspects there may be multiple double stranded fragments/polynucleotides within the hairpin structure. Accordingly, the result of double stranded nucleotides that do self-hybridize within a stem structure may be observed as a series of bulges and/or mismatches within the stem structure. In an aspect, the bulges/mismatches are unbound, single stranded nucleotides that resulted from the formation of double stranded sequences directly upstream and downstream of the unstructured bulges/mismatches of the polynucleotide sequence. In further aspects the hairpin structure has a free energy (ΔG) of less than −20 kcal/mol. As provided herein are methods and compositions disclosing the hairpin structure of the shRNA polynucleotide of the subject disclosure.

In other embodiments of the subject disclosure the shRNA polynucleotide comprises a stem structure. In an aspect, the stem structure may be 25, 24, 23, 22, 21, 20, 19, 18, 17, or 16 polynucleotides in length. In a further aspect, the stem structure may be from 25 to 16 polynucleotides in length. In another aspect, the stem structure may be from 23 to 16 polynucleotides in length. In other aspects, the stem structure of the shRNA contains target polynucleotide sequences that specifically inhibit transcribed RNA from an expressed gene within a living organism. For example, the target polynucleotide of the shRNA molecule inhibits a target gene by suppressing the expression of the mRNA of the target gene. In a further aspect, the stem structure of the shRNA polynucleotide may be any polynucleotide sequence that shares at least 70% to 100% sequence identity with a target polynucleotide of a plant pest. For instance the polynucleotide may share at least 70% sequence identity, 71% sequence identity, 72% sequence identity, 73% sequence identity, 74% sequence identity, 75% sequence identity, 76% sequence identity, 77% sequence identity, 78% sequence identity, 79% sequence identity, 80% sequence identity, 81% sequence identity, 82% sequence identity, 83% sequence identity, 84% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity, 99.5% sequence identity, 99.9% sequence identity or 100% sequence identity with a target polynucleotide of an insect pest. In examples of this aspect the target polynucleotide may be an essential gene of the insect pest. Accordingly, the target polynucleotide sequence is obtained from a plant pest and is incorporated as a stem structure of 16-23 polynucleotides in length within the shRNA molecule. Similarly, the target polynucleotide sequence is obtained from a plant pest and is incorporated as a stem structure of 16-25 polynucleotides in length within the shRNA molecule. In other aspects, the stem structure may be a target polynucleotide that is selected from the group consisting of a Caf1-180 gene, RPA70 gene, V-ATPase H gene, Rho1 gene, V-ATPase C gene, Reptin gene, PPI-87B gene, RPS6 gene, COPI gamma gene, COPI alpha gene, COPI beta gene, COPI delta gene, Brahma gene, ROP gene, Hunchback gene, RNA polymerase II 140 gene, Sec23 gene, Dre4 gene, Gho gene, thread gene, ncm gene, RNA polymerase II-215 gene, RNA polymerase I 1 gene, RNA polymerase II 33 gene, Kruppel gene, Spt5 gene, Spt6 gene, Snap25 gene, and Prp8 gene. In further examples of this aspect the target polynucleotide sequences of the stem structure are selected from target gene homologs that were identified in the transcriptome sequence database as described in the following patent applications: U.S. Patent Application No. 20120174258; U.S. Patent Application No. 20130091601; U.S. Patent Application No. 20120198586; U.S. Patent Application No. US20120174260; U.S. Patent Application No. 20120174259; U.S. Patent Application No. 20140298536; U.S. Patent Application No. 20130091600; U.S. Patent Application No. 20130097730; Patent Application No. WO2016060911; Patent Application No. WO2016060912; Patent Application No. WO2016060913; Patent Application No. WO2016060914; U.S. Patent Application No. 20160208251; U.S. Patent Application No. 20160222408; U.S. Patent Application No. 20150176025; U.S. Patent Application No. 20160222407; U.S. Patent Application No. 20160208252; U.S. Patent Application No. 20150176009; U.S. Patent Application No. 20150322455; U.S. Patent Application No. 20150322456; U.S. Patent Application No. 20160186203; Patent Application No. WO2016191357; U.S. Patent Application No. 20160194658; U.S. Patent Application No. 20160264992; U.S. Patent Application No. 20160264991; U.S. Patent Application No. 20160355841; U.S. Patent Application No. 20160208253; U.S. Patent Application No. 20160369296; U.S. Patent Application No. 20160348130; U.S. Patent Application No. 2016196241; U.S. Patent Application No. 2017011764; and, U.S. Patent Application No. 2017011771, the disclosures of which are herein incorporated by reference in their entirety. In additional aspects the stem structure may comprise base pairs 1-23 of SEQ ID No:1, base pairs 39-60 of SEQ ID No:1, base pairs 1-22 of SEQ ID No:6, base pairs 37-58 of SEQ ID No:6, base pairs 1-22 of SEQ ID No:2, base pairs 39-60 of SEQ ID No:2, base pairs 1-23 of SEQ ID No:3, base pairs 1-24 of SEQ ID No:4, base pairs 38-60 of SEQ ID No:4, base pairs 1-23 of SEQ ID No:5, base pairs 38-60 of SEQ ID No:5, base pairs 1-24 of SEQ ID No:5, base pairs 36-60 of SEQ ID No:5, base pairs 1-23 of SEQ ID No:405, base pairs 39-60 of SEQ ID No:405, base pairs 1-23 of SEQ ID No:406, base pairs 39-60 of SEQ ID No:406, base pairs 1-23 of SEQ ID No:407, base pairs 39-60 of SEQ ID No:407, base pairs 1-23 of SEQ ID No:408, base pairs 39-60 of SEQ ID No:408, base pairs 1-23 of SEQ ID No:411, base pairs 39-60 of SEQ ID No:411, base pairs 1-23 of SEQ ID No:413, base pairs 39-70 of SEQ ID No:413, base pairs 1-23 of SEQ ID No:415, base pairs 39-60 of SEQ ID No:415, base pairs 1-23 of SEQ ID No:417, base pairs 39-60 of SEQ ID No:417, base pairs 1-23 of SEQ ID No:419, base pairs 39-60 of SEQ ID No:419, base pairs 1-23 of SEQ ID No:421, or base pairs 39-60 of SEQ ID No:421. In other aspects the stem structure may comprise a 16, 17, 18, 19, 20, 12, 22, 23, 24, or 25 base pair fragment of SEQ ID NO:404, SEQ ID NO:409, SEQ ID NO:410, SEQ ID NO:412, SEQ ID NO:414, SEQ ID NO:416, SEQ ID NO:418, or SEQ ID NO:420. In other aspects the stem structure may comprise a 16, 17, 18, 19, 20, 12, 22, 23, 24, or 25 base pair fragment of the reverse complement sequence of SEQ ID NO:404, SEQ ID NO:409, SEQ ID NO:410, SEQ ID NO:412, SEQ ID NO:414, SEQ ID NO:416, SEQ ID NO:418, or SEQ ID NO:420. In other aspects the stem structure may comprise a 16, 17, 18, 19, 20, 12, 22, 23, 24, or 25 base pair fragment of the complementary sequence of SEQ ID NO:404, SEQ ID NO:409, SEQ ID NO:410, SEQ ID NO:412, SEQ ID NO:414, SEQ ID NO:416, SEQ ID NO:418, or SEQ ID NO:420.

In further aspects, the shRNA polynucleotide may fold back upon itself and self-hybridize. In such an aspect the shRNA polynucleotide may form a stem-loop type structure that is comprised of a hairpin structure and a stem structure. In such an aspect the stem structure may be comprised of paired or double-stranded nucleotides that self-hybridize. In another aspect, the stem structure of the shRNA molecule does not contain a single stranded polynucleotide sequence within the stem structure. Accordingly, the stem structure of the shRNA molecule is free of any mismatches and/or bulges of base pairs within the stem structure. In further aspects the stem structure has a free energy ($\Delta G°_{37}$) of less than −30 kcal/mol. As provided herein are methods and compositions disclosing the stem structure of the shRNA polynucleotide of the subject disclosure.

Another aspect of the subject disclosure comprises a functional variant which differs in one or more nucleotides from those of the polynucleotide encoding the target polynucleotides of the stem structure within the shRNA polynucleotide, as provided herein. Such a variant is produced as the result of one or more modifications (e.g., deletion, substitution, or addition) of the nucleotide sequences comprising the sequences encoding the target polynucleotides of the stem structure. In some embodiments, the target polynucleotide of the stem structure is altered to produce a variant target polynucleotides sequence. In an aspect of this embodiment, the variant target polynucleotides of the stem structure shares at least 80%, 82.5%, 85%, 87.5%, 90%, 91%, 92%, 93%, 94%, 95%, 96%, 97%, 98%, 99%, 99.5% or 99.9% sequence identity with a 16, 17, 18, 19, 20, 12, 22, 23, 24, or 25 base pair fragment of SEQ ID NO:404, SEQ ID NO:409, SEQ ID NO:410, SEQ ID NO:412, SEQ ID NO:414, SEQ ID NO:416, SEQ ID NO:418, or SEQ ID NO:420. In an aspect of this embodiment, the variant target polynucleotides of the stem structure shares at least 80%, 82.5%, 85%, 87.5%, 90%, 91%, 92%, 93%, 94%, 95%, 96%, 97%, 98%, 99%, 99.5% or 99.9% sequence identity with base pairs 1-23 of SEQ ID No:1, base pairs 39-60 of SEQ ID No:1, base pairs 1-22 of SEQ ID No:6, base pairs 37-58 of SEQ ID No:6, base pairs 1-22 of SEQ ID No:2, base pairs 39-60 of SEQ ID No:2, base pairs 1-23 of SEQ ID No:3, base pairs 1-24 of SEQ ID No:4, base pairs 38-60 of SEQ ID No:4, base pairs 1-23 of SEQ ID No:5, base pairs 38-60 of SEQ ID No:5, base pairs 1-24 of SEQ ID No:5, base pairs 36-60 of SEQ ID No:5, base pairs 1-23 of SEQ ID No:405, base pairs 39-60 of SEQ ID No:405, base pairs 1-23 of SEQ ID No:406, base pairs 39-60 of SEQ ID No:406, base pairs 1-23 of SEQ ID No:407, base pairs 39-60 of SEQ ID No:407, base pairs 1-23 of SEQ ID No:408, base pairs 39-60 of SEQ ID No:408, base pairs 1-23 of SEQ ID No:411, base pairs 39-60 of SEQ ID No:411, base pairs 1-23 of SEQ ID No:413, base pairs 39-70 of SEQ ID No:413, base pairs 1-23 of SEQ ID No:415, base pairs 39-60 of SEQ ID No:415, base pairs 1-23 of SEQ ID No:417, base pairs 39-60 of SEQ ID No:417, base pairs 1-23 of SEQ ID No:419, base pairs 39-60 of SEQ ID No:419, base pairs 1-23 of SEQ ID No:421, or base pairs 39-60 of SEQ ID No:421.

The degree of complementarity between the stem region's first segment of at least 16, 17, 18, 19, 20, 12, 22, 23, 24, or 25 contiguous nucleotides to a segment of equivalent length in the target polynucleotide is readily selected by one of skill in the art. It will be appreciated by those with skill in the art that base pairing between nucleotides located towards the 5' end of the mature s4RNA to the target polynucleotide is comparatively important in the ability of a shRNA to silence expression of the target polynucleotide. Furthermore, it is expected that high complementarity between the 5' end of the shRNA to the target polynucleotide can allow a relatively higher degree of mismatch between nucleotides closer to the 3' end of the shRNA and the target polynucleotide (and vice versa). Thus, in a preferred embodiment, the nucleotide sequence of the stem region's first segment of at least 16, 17, 18, 19, 20, 12, 22, 23, 24, or 25 contiguous nucleotides is selected so that the mature miRNA processed from the stem-loop is perfectly complementary to the target polynucleotide at the 5'-most segment of nucleotides of the shRNA. In another preferred embodiment, the nucleotide sequence of the stem region's first segment of at least 16, 17, 18, 19, 20, 12, 22, 23, 24, or 25 contiguous nucleotides is selected so that the shRNA processed from the stem-loop is perfectly complementary to the target polynucleotide at nucleotide positions 2, 3, 4, 5, 6, and 7 (from the 5' end) of the shRNA. In another preferred embodiment, the nucleotide sequence of the stem region's first segment's at least 16, 17, 18, 19, 20, 12, 22, 23, 24, or 25 contiguous nucleotides is designed so that the shRNA processed from the stem-loop structure has few or no G:U wobble base pairs.

The polynucleotide sequences of the present disclosure, regardless of the length of the coding sequence itself, may be combined with other DNA sequences, such as promoters, polyadenylation signals, additional restriction enzyme sites, multiple cloning sites, other coding regions, and the like, such that their overall length may vary considerably. It is therefore contemplated that a polynucleotide sequence of almost any length may be employed, with the total length preferably being limited by the ease of preparation and use in the intended recombinant DNA protocol. For example, polynucleotide sequence fragments may be prepared that include a short contiguous stretch of polynucleotides encoding the whole or a portion of the shRNA polynucleotides of the subject disclosure.

The polynucleotide sequences of the present disclosure encompass biologically-functional, equivalent shRNA molecules. Changes designed by the hand of man may be introduced through the application of site-directed mutagenesis techniques, e.g., to introduce improvements to the toxicity of the shRNA polynucleotide or to test variant shRNA polynucleotides in order to improve insecticidal activity of the shRNA polynucleotide against an insect pest.

Variant nucleotide sequences also encompass sequences derived from a mutagenic and recombinogenic procedure such as DNA shuffling. With such a procedure, the polynucleotide sequences encoding the shRNA stem structure of the following target polynucleotides; Caf1-180 gene, RPA70 gene, V-ATPase H gene, Rho1 gene, V-ATPase C gene, Reptin gene, PPI-87B gene, RPS6 gene, COPI gamma gene, COPI alpha gene, COPI beta gene, COPI delta gene, Brahma gene, ROP gene, Hunchback gene, RNA polymerase II 140 gene, Sec23 gene, Dre4 gene, Gho gene, thread gene, ncm gene, RNA polymerase II-215 gene, RNA polymerase I 1 gene, RNA polymerase II 33 gene, Kruppel gene, Spt5 gene, Spt6 gene, Snap25 gene, or Prp8 gene can be manipulated to create a new target polynucleotide encoding the stem structure of the shRNA polynucleotide. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) Proc. Natl. Acad. Sci. USA i: 10747-10751; Stemmer (1994) Nature 570:389-391; Crameri et al. (1997) Nature Biotech. 75:436-438; Moore et al. (1997) J. Mol. Biol. 272:336-347; Zhang et al. (1997) Proc. Natl. Acad. Sci. USA 4:4504-4509; Crameri et al. (1998) Nature 527:288-291; and U.S. Pat. Nos. 5,605,793 and 5,837,458.

In other embodiments of the subject disclosure the shRNA polynucleotide comprises a combination of a hairpin structure and a stem structure.

In an aspect of this embodiment the shRNA polynucleotide comprises a hairpin structure comprising a polynucleotide sequence of less than 25, 24, 23, 22, 21, 20, 19, 18, 17, 16, 15, 14, 13, 12, 11, 10, 9, 8, 7, 6, or 5 base pairs in length in combination with a stem structure comprising base pairs 1-23 of SEQ ID No:1, base pairs 39-60 of SEQ ID No:1, base pairs 1-22 of SEQ ID No:6, base pairs 37-58 of SEQ ID No:6, base pairs 1-22 of SEQ ID No:2, base pairs 39-60 of SEQ ID No:2, base pairs 1-23 of SEQ ID No:3, base pairs 1-24 of SEQ ID No:4, base pairs 38-60 of SEQ ID No:4, base pairs 1-23 of SEQ ID No:5, base pairs 38-60 of SEQ ID No:5, base pairs 1-24 of SEQ ID No:5, base pairs 36-60 of SEQ ID No:5, base pairs 1-23 of SEQ ID No:405, base pairs 39-60 of SEQ ID No:405, base pairs 1-23 of SEQ ID No:406, base pairs 39-60 of SEQ ID No:406, base pairs 1-23 of SEQ ID No:407, base pairs 39-60 of SEQ ID No:407, base pairs 1-23 of SEQ ID No:408, base pairs 39-60 of SEQ ID No:408, base pairs 1-23 of SEQ ID No:411, base pairs 39-60 of SEQ ID No:411, base pairs 1-23 of SEQ ID No:413, base pairs 39-70 of SEQ ID No:413, base pairs 1-23 of SEQ ID No:415, base pairs 39-60 of SEQ ID No:415, base pairs 1-23 of SEQ ID No:417, base pairs 39-60 of SEQ ID No:417, base pairs 1-23 of SEQ ID No:419, base pairs 39-60 of SEQ ID No:419, base pairs 1-23 of SEQ ID No:421, or base pairs 39-60 of SEQ ID No:421. In an additional aspect, the shRNA polynucleotide comprises a hairpin structure comprising a polynucleotide sequence obtained from an insect microRNA scaffold in combination with a stem structure comprising base pairs 1-23 of SEQ ID No:1, base pairs 39-60 of SEQ ID No:1, base pairs 1-22 of SEQ ID No:6, base pairs 37-58 of SEQ ID No:6, base pairs 1-22 of SEQ ID No:2, base pairs 39-60 of SEQ ID No:2, base pairs 1-23 of SEQ ID No:3, base pairs 1-24 of SEQ ID No:4, base pairs 38-60 of SEQ ID No:4, base pairs 1-23 of SEQ ID No:5, base pairs 38-60 of SEQ ID No:5, base pairs 1-24 of SEQ ID No:5, base pairs 36-60 of SEQ ID No:5, base pairs 1-23 of SEQ ID No:405, base pairs 39-60 of SEQ ID No:405, base pairs 1-23 of SEQ ID No:406, base pairs 39-60 of SEQ ID No:406, base pairs 1-23 of SEQ ID No:407, base pairs 39-60 of SEQ ID No:407, base pairs 1-23 of SEQ ID No:408, base pairs 39-60 of SEQ ID No:408, base pairs 1-23 of SEQ ID No:411, base pairs 39-60 of SEQ ID No:411, base pairs 1-23 of SEQ ID No:413, base pairs 39-70 of SEQ ID No:413, base pairs 1-23 of SEQ ID No:415, base pairs 39-60 of SEQ ID No:415, base pairs 1-23 of SEQ ID No:417, base pairs 39-60 of SEQ ID No:417, base pairs 1-23 of SEQ ID No:419, base pairs 39-60 of SEQ ID No:419, base pairs 1-23 of SEQ ID No:421, or base pairs 39-60 of SEQ ID No:421. In additional aspects the shRNA polynucleotide comprises a hairpin structure of base pairs 24-38 of SEQ ID No:1, base pairs 23-36 of SEQ ID No:6, base pairs 23-38 of SEQ ID No:2, base pairs 24-36 of SEQ ID No:3, base pairs 25-37 of SEQ ID No:4, base pairs 38-60 of SEQ ID No:4, base pairs 24-37 of SEQ ID No:5, base pairs 25-34 of SEQ ID No:5, base pairs 1-23 of SEQ ID No:405, base pairs 39-60 of SEQ ID No:405, base pairs 39-60 of SEQ ID No:406, base pairs 24-38 of SEQ ID No:407, base pairs 24-38 of SEQ ID No:408, base pairs 24-38 of SEQ ID No:411, base pairs 24-38 of SEQ ID No:413, base pairs 24-38 of SEQ ID No:415, base pairs 24-38 of SEQ ID No:417 base pairs 24-38 of SEQ ID No:419, or base pairs 24-38 of SEQ ID No:421 in combination with a stem structure comprising base pairs 1-23 of SEQ ID No:1, base pairs 39-60 of SEQ ID No:1, base pairs 1-22 of SEQ ID No:6, base pairs 37-58 of SEQ ID No:6, base pairs 1-22 of SEQ ID No:2, base pairs 39-60 of SEQ ID No:2, base pairs 1-23 of SEQ ID No:3, base pairs 1-24 of SEQ ID No:4, base pairs 38-60 of SEQ ID No:4, base pairs 1-23 of SEQ ID No:5, base pairs 38-60 of SEQ ID No:5, base pairs 1-24 of SEQ ID No:5, base pairs 36-60 of SEQ ID No:5, base pairs 1-23 of SEQ ID No:405, base pairs 39-60 of SEQ ID No:405, base pairs 1-23 of SEQ ID No:406, base pairs 39-60 of SEQ ID No:406, base pairs 1-23 of SEQ ID No:407, base pairs 39-60 of SEQ ID No:407, base pairs 1-23 of SEQ ID No:408, base pairs 39-60 of SEQ ID No:408, base pairs 1-23 of SEQ ID No:411, base pairs 39-60 of SEQ ID No:411, base pairs 1-23 of SEQ ID No:413, base pairs 39-70 of SEQ ID No:413, base pairs 1-23 of SEQ ID No:415, base pairs 39-60 of SEQ ID No:415, base pairs 1-23 of SEQ ID No:417, base pairs 39-60 of SEQ ID No:417, base pairs 1-23 of SEQ ID No:419, base pairs 39-60 of SEQ ID No:419, base pairs 1-23 of SEQ ID No:421, or base pairs 39-60 of SEQ ID No:421. In an example of this aspect, the shRNA comprises a hairpin structure comprising a fragment of 5-24 polynucleotides in length of any of SEQ ID Nos:7-401 in combination with a stem structure comprising base pairs 1-23 of SEQ ID No:1, base pairs 39-60 of SEQ ID No:1, base pairs 1-22 of SEQ ID No:6, base pairs 37-58 of SEQ ID No:6, base pairs 1-22 of SEQ ID No:2, base pairs 39-60 of SEQ ID No:2, base pairs 1-23 of SEQ ID No:3, base pairs 1-24 of SEQ ID No:4, base pairs 38-60 of SEQ ID No:4, base pairs 1-23 of SEQ ID No:5, base pairs 38-60 of SEQ ID No:5, base pairs 1-24 of SEQ ID No:5, base pairs 36-60 of SEQ ID No:5, base pairs 1-23 of SEQ ID No:405, base pairs 39-60 of SEQ ID No:405, base pairs 1-23 of SEQ ID No:406, base pairs 39-60 of SEQ ID No:406, base pairs 1-23 of SEQ ID No:407, base pairs 39-60 of SEQ ID No:407, base pairs 1-23 of SEQ ID No:408, base pairs 39-60 of SEQ ID No:408, base pairs 1-23 of SEQ ID No:411, base pairs 39-60 of SEQ ID No:411, base pairs 1-23 of SEQ ID No:413, base pairs 39-70 of SEQ ID No:413, base pairs 1-23 of SEQ ID No:415, base pairs 39-60 of SEQ ID No:415, base pairs 1-23 of SEQ ID No:417, base pairs 39-60 of SEQ ID No:417, base pairs 1-23 of SEQ ID No:419, base pairs 39-60 of SEQ ID No:419, base pairs 1-23 of SEQ ID No:421, or base pairs 39-60 of SEQ ID No:421.

In an aspect of this embodiment the shRNA polynucleotide comprises a hairpin structure comprising a polynucleotide sequence of less than 25, 24, 23, 22, 21, 20, 19, 18, 17, 16, 15, 14, 13, 12, 11, 10, 9, 8, 7, 6, or 5 base pairs in length in combination with a stem structure comprising a target polynucleotide that is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In an additional aspect, the shRNA polynucleotide comprises a hairpin structure comprising a polynucleotide sequence obtained from an insect microRNA scaffold in combination with a stem structure comprising a target polynucleotide that is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In additional aspects the shRNA polynucleotide comprises a hairpin structure of base pairs 24-38 of SEQ ID No:1, base pairs 23-36 of SEQ ID No:6, base pairs 23-38 of SEQ ID No:2, base pairs 24-36 of SEQ ID No:3, base pairs 25-37 of SEQ ID No:4, base pairs 38-60 of SEQ ID No:4, base pairs 24-37 of SEQ ID No:5, base pairs 25-34 of SEQ ID No:5, base pairs 1-23 of SEQ ID No:405, base pairs 39-60 of SEQ ID No:405, base pairs 39-60 of SEQ ID No:406, base pairs 24-38 of SEQ ID No:407, base pairs 24-38 of SEQ ID No:408, base pairs 24-38 of SEQ ID No:411, base pairs 24-38 of SEQ ID No:413, base pairs 24-38 of SEQ ID No:415, base pairs 24-38 of SEQ ID No:417 base pairs 24-38 of SEQ ID No:419, or base pairs 24-38 of SEQ ID No:421 in combination with a stem structure comprising a target polynucleotide that is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8. In an example of this aspect, the shRNA comprises a hairpin structure comprising a fragment of 5-24 polynucleotides in length of any of SEQ ID Nos:7-401 in combination with a stem structure comprising a target polynucleotide that is selected from the group consisting of Caf1-180, RPA70, V-ATPase H, Rho1, V-ATPase C, Reptin, PPI-87B, RPS6, COPI gamma, COPI alpha, COPI beta, COPI delta, Brahma, ROP, Hunchback, RNA polymerase II 140, Sec23, Dre4, Gho, thread, ncm, RNA polymerase II-215, RNA polymerase I 1, RNA polymerase II 33, Kruppel, Spt5, Spt6, Snap25, and Prp8.

In an aspect of this embodiment the shRNA polynucleotide comprises a hairpin structure comprising a polynucleotide sequence of less than 25, 24, 23, 22, 21, 20, 19, 18, 17, 16, 15, 14, 13, 12, 11, 10, 9, 8, 7, 6, or 5 base pairs in length in combination with a stem structure comprising a 16, 17, 18, 19, 20, 12, 22, 23, 24, or 25 base pair fragment of SEQ ID NO:404, SEQ ID NO:409, SEQ ID NO:410, SEQ ID NO:412, SEQ ID NO:414, SEQ ID NO:416, SEQ ID NO:418, or SEQ ID NO:420. In an additional aspect, the shRNA polynucleotide comprises a hairpin structure comprising a polynucleotide sequence obtained from an insect microRNA scaffold in combination with a stem structure comprising a 16, 17, 18, 19, 20, 12, 22, 23, 24, or 25 base pair fragment of SEQ ID NO:404, SEQ ID NO:409, SEQ ID NO:410, SEQ ID NO:412, SEQ ID NO:414, SEQ ID NO:416, SEQ ID NO:418, or SEQ ID NO:420. In additional aspects the shRNA polynucleotide comprises a hairpin structure of base pairs 24-38 of SEQ ID No:1, base pairs 23-36 of SEQ ID No:6, base pairs 23-38 of SEQ ID No:2, base pairs 24-36 of SEQ ID No:3, base pairs 25-37 of SEQ ID No:4, base pairs 38-60 of SEQ ID No:4, base pairs 24-37 of SEQ ID No:5, base pairs 25-34 of SEQ ID No:5, base pairs 1-23 of SEQ ID No:405, base pairs 39-60 of SEQ ID No:405, base pairs 39-60 of SEQ ID No:406, base pairs 24-38 of SEQ ID No:407, base pairs 24-38 of SEQ ID No:408, base pairs 24-38 of SEQ ID No:411, base pairs 24-38 of SEQ ID No:413, base pairs 24-38 of SEQ ID No:415, base pairs 24-38 of SEQ ID No:417 base pairs 24-38 of SEQ ID No:419, or base pairs 24-38 of SEQ ID No:421 in combination with a stem structure comprising a 16, 17, 18, 19, 20, 12, 22, 23, 24, or 25 base pair fragment of SEQ ID NO:404, SEQ ID NO:409, SEQ ID NO:410, SEQ ID NO:412, SEQ ID NO:414, SEQ ID NO:416, SEQ ID NO:418, or SEQ ID NO:420. In an example of this aspect, the shRNA comprises a hairpin structure comprising a fragment of 5-24 polynucleotides in length of any of SEQ ID Nos:7-401 in combination with a stem structure comprising a 16, 17, 18, 19, 20, 12, 22, 23, 24, or 25 base pair fragment of SEQ ID NO:404, SEQ ID NO:409, SEQ ID NO:410, SEQ ID NO:412, SEQ ID NO:414, SEQ ID NO:416, SEQ ID NO:418, or SEQ ID NO:420.

In other embodiments of the subject disclosure the shRNA polynucleotide comprises a polynucleotide overhang of 2 to 4 nucleotides. For example, the polynucleotide overhang comprises a polynucleotide sequence of 2 base pairs in length. In another example, the polynucleotide overhang comprises a polynucleotide sequence of 3 base pairs in length. In an additional example, the polynucleotide overhang comprises a polynucleotide sequence of 4 base pairs in length. In an aspect the combination of the shRNA polynucleotide and the polynucleotide overhang comprise a polynucleotide sequence of less than 74 nucleotides in length. In a further aspect the combination of the shRNA polynucleotide and the polynucleotide overhang comprise a polynucleotide sequence of less than 84 nucleotides in length. In another aspect the combination of the shRNA polynucleotide and the polynucleotide overhang comprise a polynucleotide sequence of less than 94 nucleotides in length. In an aspect the first nucleotide of the polynucleotide overhang is double stranded. In another aspect, the first nucleotide of the polynucleotide overhang is single stranded. In an additional aspect, the second nucleotide of the polynucleotide overhang is single stranded. In a further aspect the third nucleotide of the polynucleotide overhang is single stranded. In another aspect, the fourth nucleotide of the polynucleotide overhang is single stranded. In some aspects, the polynucleotide overhang is on the 5' end of the shRNA molecule. In other aspects the polynucleotide overhang is on the 3' end of the shRNA molecule. In an aspect, the 1 base pair over hang is comprised of one of the following nucleotide sequences 5'-A-3', 5'-G-3', 5'-C-3', or 5'-T-3'. In some aspects the 2 base pair overhang is comprised of one of the following polynucleotide sequences 5'-AA-3', 5'-AC-3', 5'-AG-3', 5'-AT-3', 5'-CA-3', 5'-CC-3', 5'-CG-3', 5'-CT-3', 5'-GA-3', 5'-GC-3', 5'-GG-3', 5'-GT-3', 5'-TA-3', 5'-TC-3', 5'-TG-3', or 5'-TT-3'. In other aspects the 3 base pair overhang is comprised of one of the following polynucleotide sequences 5'-AAA-3', 5'-AAC-3', 5'-AAG-3', 5'-AAT-3', 5'-ACA-3', 5'-ACC-3', 5'-ACG-3', 5'-ACT-3', 5'-AGA-3', 5'-AGC-3', 5'-AGG-3', 5'-AGT-3', 5'-ATA-3', 5'-ATC-3', 5'-ATG-3', 5'-ATT-3', 5'-CAA-3', 5'-CAC-3', 5'-CAG-3', 5'-CAT-3', 5'-CCA-3', 5'-CCC-3', 5'-CCG-3', 5'-CCT-3', 5'-CGA-3', 5'-CGC-3', 5'-CGG-3', 5'-CGT-3', 5'-CTA-3', 5'-CTC-3', 5'-CTG-3', 5'-CTT-3', 5'-GAA-3', 5'-GAC-3', 5'-GAG-3', 5'-GAT-3', 5'-GCA-3', 5'-GCC-3', 5'-GCG-3', 5'-GCT-3', 5'-GGA-3', 5'-GGC-3', 5'-GGG-3', 5'-GGT-3', 5'-GTA-3', 5'-GTC-3', 5'-GTG-3', 5'-GTT-3', 5'-TAA-3', 5'-TAC-3', 5'-TAG-3', 5'-TAT-3', 5'-TCA-3', 5'-TCC-3', 5'-TCG-3', 5'-TCT-3', 5'-TGA-3', 5'-TGC-3', 5'-TGG-3', 5'-TGT-3', 5'-TTA-3', 5'-TTC-3', 5'-TTG-3', or 5'-TTT-3'. In other aspects the 4 base pair overhang is comprised of one of the following polynucleotide sequence 5'-AAAA-3', 5'-AACA-3', 5'-AAGA-3', 5'-AATA-3', 5'-ACAA-3', 5'-ACCA-3', 5'-ACGA-3', 5'-ACTA-3', 5'-AGAA-3', 5'-AGCA-3', 5'-AGGA-3', 5'-AGTA-3', 5'-ATAA-3', 5'-ATCA-3', 5'-ATGA-3', 5'-*ATTA*-3', 5'-ACAA-3', 5'-CACA-3', 5'-CAGA-3', 5'-CATA-3', 5'-CCAA-3', 5'-CCCA-3', 5'-CCGA-3', 5'-CCTA-3', 5'-CGAA-3', 5'-CGCA-3', 5'-CGGA-3', 5'-CGTA-3', 5'-CTAA-3', 5'-CTCA-3', 5'-CTGA-3', 5'-CTTA-3', 5'-GAAA-3', 5'-GACA-3', 5'-GAGA-3', 5'-GATA-3', 5'-GCAA-3', 5'-GCCA-3', 5'-GCGA-3', 5'-GCTA-3', 5'-GGAA-3', 5'-GGCA-3', 5'-GGGA-3', 5'-GGTA-3', 5'-GTAA-3', 5'-GTCA-3', 5'-GTGA-3', 5'-GTTA-3', 5'-TAAA-3', 5'-TACA-3', 5'-TAGA-3', 5'-TATA-3', 5'-TCAA-3', 5'-TCCA-3', 5'-TCGA-3', 5'-TCTA-3', 5'-TGAA-3', 5'-TGCA-3', 5'-TGGA-3', 5'-TGTA-3', 5'-TTAA-3', 5'-TTC-3', 5'-TTGA-3', 5'-TTTA-3', 5'-AAAG-3', 5'-AACG-3', 5'-AAGG-3', 5'-AATG-3', 5'-ACAG-3', 5'-ACCG-3', 5'-ACGG-3', 5'-ACTG-3', 5'-AGAG-3', 5'-AGCG-3', 5'-AGGG-3', 5'-AGTG-3', 5'-ATAG-3', 5'-ATCG-3', 5'-ATGG-3', 5'-ATTG-3', 5'-CAAG-3', 5'-CACG-3', 5'-CAGG-3', 5'-CATG-3', 5'-CCAG-3', 5'-CCCG-3', 5'-CCGG-3', 5'-CCTG-3', 5'-CGAG-3', 5'-CGCG-3', 5'-CGGG-3', 5'-CGTG-3', 5'-CTAG-3', 5'-CTCG-3', 5'-CTGG-3', 5'-CTTG-3', 5'-GAAG-3', 5'-GACG-3', 5'-GAGG-3', 5'-GATG-3', 5'-GCAG-3', 5'-GCCG-3', 5'-GCGG-3', 5'-GCTG-3', 5'-GGAG-3', 5'-GGCG-3', 5'-GGGG-3', 5'-GGTG-3', 5'-GTAG-3', 5'-GTCG-3', 5'-GTGG-3', 5'-GTTG-3', 5'-TAAG-3', 5'-TACG-3', 5'-TAGG-3', 5'-TATG-3', 5'-TCAG-3', 5'-TCCG-3', 5'-TCGG-3', 5'-TCTG-3', 5'-TGAG-3', 5'-TGCG-3', 5'-TGGG-3', 5'-TGTG-3', 5'-TTAG-3', 5'-TTCG-3', 5'-TTGG-3', 5'-TTTG-3', 5'-AAAC-3', 5'-AACC-3', 5'-AAGC-3', 5'-AATC-3', 5'-ACAC-3', 5'-ACCC-3', 5'-ACGC-3', 5'-ACTC-3', 5'-AGAC-3', 5'-AGCC-3', 5'-AGGC-3', 5'-AGTC-3', 5'-ATAC-3', 5'-ATCC-3', 5'-ATGC-3', 5'-ATTC-3', 5'-CAAC-3', 5'-CACC-3', 5'-CAGC-3', 5'-CATC-3', 5'-CCAC-3', 5'-CCCC-3', 5'-CCGC-3', 5'-CCTC-3', 5'-CGAC-3', 5'-CGCC-3', 5'-CGGC-3', 5'-CGTC-3', 5'-CTAC-3', 5'-CTCC-3', 5'-CTGC-3', 5'-CTTC-3', 5'-GAAC-3', 5'-GACC-3', 5'-GAGC-3', 5'-GATC-3', 5'-GCAC-3', 5'-GCCC-3', 5'-GCGC-3', 5'-GCTC-3', 5'-GGAC-3', 5'-GGCC-3', 5'-GGGC-3', 5'-GGTC-3', 5'-GTAC-3', 5'-GTCC-3', 5'-GTGC-3', 5'-GTTC-3', 5'-TAAC-3', 5'-TACC-3', 5'-TAGC-3', 5'-TATC-3', 5'-TCAC-3', 5'-TCCC-3', 5'-TCGC-3', 5'-TCTC-3', 5'-TGAC-3', 5'-TGCC-3', 5'-TGGC-3', 5'-TGTC-3', 5'-TTAC-3', 5'-TTCC-3', 5'-TTGC-3', 5'-TTTC-3', 5'-AAAT-3', 5'-AACT-3', 5'-AAGT-3', 5'-AATT-3', 5'-ACAT-3', 5'-ACCT-3', 5'-ACGT-3', 5'-ACTT-3', 5'-AGAT-3', 5'-AGCT-3', 5'-AGGT-3', 5'-AGTT-3', 5'-ATAT-3', 5'-ATCT-3', 5'-ATGT-3', 5'-ATTT-3', 5'-CAAT-3', 5'-CACT-3', 5'-CAGT-3', 5'-CATT-3', 5'-CCAT-3', 5'-CCCT-3', 5'-CCGT-3', 5'-CCTT-3', 5'-CGAT-3', 5'-CGCT-3', 5'-CGGT-3', 5'-CGTT-3', 5'-CTAT-3', 5'-CTCT-3', 5'-CTGT-3', 5'-CTTT-3', 5'-GAAT-3', 5'-GACT-3', 5'-GAGT-3', 5'-GATT-3', 5'-GCAT-3', 5'-GCCT-3', 5'-GCGT-3', 5'-GCTT-3', 5'-GGAT-3', 5'-GGCT-3', 5'-GGGT-3', 5'-GGTT-3', 5'-GTAT-3', 5'-GTCT-3', 5'-GTGT-3', 5'-GTTT-3', 5'-TAAT-3', 5'-TACT-3', 5'-TAGT-3', 5'-TATT-3', 5'-TCAT-3', 5'-TCCT-3', 5'-TCGT-3', 5'-TCTT-3', 5'-TGAT-3', 5'-TGCT-3', 5'-TGGT-3', 5'-TGTT-3', 5'-TTAT-3', 5'-TTCT-3', 5'-TTGT-3', or 5'-TTTT-3'.

Another aspect of the subject disclosure includes a nucleic acid vector that comprises a polynucleotide encoding the shRNA polynucleotide as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

Recombinant vectors containing the polynucleotide that encodes the shRNA polynucleotide can be further engineered to contain regulatory elements such as promoters, 5'UTR's, introns, 3' UTR's and terminators. In some embodiments the sequences that make up these regulatory elements may be operably linked to the polynucleotide that encodes the shRNA polynucleotide. In an embodiment, the polynucleotide that encodes the shRNA polynucleotide is provided as a gene expression cassette. In preparing the gene expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

In some aspects of this embodiment, the polynucleotide that encodes the shRNA polynucleotide is positioned under the control of a promoter. In such embodiments, it is contemplated that certain advantages will be gained by positioning the polynucleotide that encodes the shRNA polynucleotide under the control of a recombinant, or heterologous, promoter. As used herein, a recombinant or heterologous promoter is intended to refer to a promoter that is not normally associated with a DNA segment encoding a shRNA in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even the organism, chosen for expression. The use of promoter and cell type combinations for shRNA expression is generally known to those of skill in the art of molecular biology, for example, see Sambrook et al., 1989. The promoters employed may be constitutive, inducible, or tissue preferred, and can be used under the appropriate conditions to direct high level expression of the introduced DNA segment within the gene expression cassette, such as is advantageous in the production of recombinant shRNA molecules within transgenic plants or in the heterologous expression of recombinant shRNA molecules within a microorganism.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the shRNA polynucleotide from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4:645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a shRNA molecule in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize ln 2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Tissue-preferred promoters can be utilized to target enhanced shRNA expression within a particular plant tissue. Tissue-preferred promoters include those discussed in Yamamoto, et al., (1997) *Plant J.* 12(2)255-265; Kawamata, et al., (1997) *Plant Cell Physiol.* 38(7):792-803; Hansen, et al., (1997) *Mol. Gen. Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443

(root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, Plant Science (Limerick) 79(1):69-76). They concluded that enhancer and tissue-preferred DNA determinants are dissociated in those promoters. Teen, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, EMBO J. 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) BioEssays 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku, K. D. and Goldberg, R. B. Plant Cell 1:1079-1093, 1989), bean 0-phaseolin, napin, 0-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611, herein incorporated by reference.

The above list of promoters is not meant to be limiting. Any appropriate promoter can be used in the embodiments.

In some embodiments, the termination region may be native with the transcriptional initiation region, may be native with the promoter regulatory element, may be native with the plant host or may be derived from another source (i.e., foreign or heterologous to the promoter, the sequence of interest, the plant host or any combination thereof). Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

In other embodiments the recombinant gene expression cassette is operably linked to an *Agrobacterium* T-DNA border. In accordance with one embodiment the recombinant gene cassette further comprises a first and second T-DNA border, wherein the first T-DNA border is operably linked to one end of a gene construct, and the second T-DNA border is operably linked to the other end of a gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence of the polynucleotide encoding the shRNA polynucleotide. In another embodiment, the first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In an embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence of the polynucleotide encoding the shRNA polynucleotide. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence of the polynucleotide encoding the shRNA polynucleotide. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence of the polynucleotide encoding the shRNA polynucleotide.

Transgenes of interest may be stacked with the shRNA polynucleotide of the subject disclosure. Exemplary transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene/heterologous coding sequence of the polynucleotide encoding the shRNA polynucleotide is further stacked with at least one other transgene/heterologous coding sequence encoding a selectable marker or a gene product conferring insecticidal resistance, herbicide tolerance, small RNA expression, nitrogen use efficiency, water use efficiency, or nutritional quality.

1. Insect Resistance

Various insect resistance genes can be further stacked with the polynucleotide encoding the shRNA polynucleotide. The gene expression cassette encoding the polynucleotide encoding the shRNA polynucleotide can be operably linked with at least one other gene expression cassette containing an insect resistance gene. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: crylA; crylA.105; crylAb; cry1Ab(truncated); crylAb-Ac (fusion protein); cry1Ac (marketed as Widestrike®); cry1C; cry1F (marketed as Widestrike®); cry1Fa2; cry2Ab2; cry2Ae; cry9C; mocryiF; pinI (protease inhibitor protein); vip3A(a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance genes can be can be further stacked with the polynucleotide encoding the shRNA polynucleotide. The gene expression cassette encoding the polynucleotide encoding the shRNA polynucleotide can be operably linked with at least one other gene expression cassette containing a herbicide tolerance gene. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-I genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csrl-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83.), the *B. subtilis* PPO gene (Li, X. and Nicholl D. 2005. Development of PPO inhibitor-resistant cultures and crops. Pest Manag. Sci. 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. Biosci Biotechnol Biochem 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), Is+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait genes can be can be can be further stacked with the polynucleotide encoding the shRNA polynucleotide. The gene expression cassette encoding the polynucleotide encoding the shRNA polynucleotide can be operably linked with at least one other gene expression cassette containing an agronomic trait gene. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and transcription. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding transgene/heterologous coding sequence genes/heterologous coding sequences can be can be further stacked with the polynucleotide encoding the shRNA polynucleotide. The gene expression cassette encoding the polynucleotide encoding the shRNA polynucleotide can be operably linked with at least one other gene expression cassette containing a DNA binding gene. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, TALENS, CRISPRS, and meganucleases. The above list of DNA binding protein coding sequences is not meant to be limiting. Any DNA binding protein coding sequences is encompassed by the present disclosure.

5. Small RNA

Various small RNA sequences can be can be further stacked with the polynucleotide encoding the shRNA polynucleotide. The gene expression cassette encoding the polynucleotide encoding the shRNA polynucleotide can be operably linked with at least one other gene expression cassette containing a small RNA sequence. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pRi small RNA (degrades R1 transcripts to limit the formation of reducing sugars through starch degradation). Additional, benefits such as reduced acrylamide resulting from the asni small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be can be further stacked with the polynucleotide encoding the shRNA polynucleotide. The gene expression cassette encoding the polynucleotide encoding the shRNA polynucleotide can be operably linked with at least one other gene expression cassete containing a reporter gene. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), redfluorescent protein (DsRFP, RFP, etc), β-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces* viridichromogenes, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvylshikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene/heterologous coding sequence can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, heterologous coding sequence or transgene/heterologous coding sequence is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166, 302, and 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al. (1987) Nature 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-*Agrobacterium* bacteria or viruses such as *Rhizobium* sp. NGR234, Sinorhizoboium me/iloti, *Mesorhizobium loti*, potato virus X, cauliflower mosaic virus and cassava vein mosaic virus and/or tobacco mosaic virus, See, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming *Zea mays* are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

Molecular Confirmation

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or green fluorescent protein genes) that may be present on the recombinant nucleic acid constructs. Such selection and screening methodologies are well known to those skilled in the art. Molecular confirmation methods that can be used to identify transgenic plants are known to those with skill in the art. Several exemplary methods are further described below.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene/heterologous coding sequence and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar® assays are a method of detecting and quantifying the presence of a DNA sequence. Briefly, the genomic DNA sample comprising the integrated gene expression cassette polynucleotide is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. In one embodiment, a second fluorescent DNA dye is SYTO13® used at less than 10 μM, less than 4 μM, or less than 2.7 μM.

In further embodiments, Next Generation Sequencing (NGS) can be used for detection. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX™ from 454 Life Sciences/Roche, the Illumina Genome Analyser™ from Solexa and Applied Biosystems' SOLiD™ (acronym for: 'Sequencing by Oligo Ligation and Detection'). In addition, there are two single molecule sequencing methods that are currently being developed. These include the true Single Molecule Sequencing (tSMS) from Helicos Bioscience™ and the Single Molecule Real Time™ sequencing (SMRT) from Pacific Biosciences.

The Genome Sequencher FLX™ which is marketed by 454 Life Sciences/Roche is a long read NGS, which uses emulsion PCR and pyrosequencing to generate sequencing reads. DNA fragments of 300-800 bp or libraries containing fragments of 3-20 kb can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser™ which is marketed by Solexa™ is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems™ is a short read technology. This NGS technology uses fragmented double stranded DNA that are up to 10 kb in length. The system uses sequencing by ligation of dye-labelled oligonucleotide primers and emulsion PCR to generate one billion short reads that result in a total sequence output of up to 30 gigabases per run.

tSMS of Helicos Bioscience™ and SMRT of Pacific Biosciences™ apply a different approach which uses single DNA molecules for the sequence reactions. The tSMS Helicos™ system produces up to 800 million short reads that result in 21 gigabases per run. These reactions are completed using fluorescent dye-labelled virtual terminator nucleotides that is described as a 'sequencing by synthesis' approach.

The SMRT Next Generation Sequencing system marketed by Pacific Biosciences™ uses a real time sequencing by synthesis. This technology can produce reads of up to 1,000 bp in length as a result of not being limited by reversible terminators. Raw read throughput that is equivalent to one-fold coverage of a diploid human genome can be produced per day using this technology.

In another embodiment, the detection can be completed using blotting assays, including Western blots, Northern blots, and Southern blots. Such blotting assays are commonly used techniques in biological research for the identification and quantification of biological samples. These assays include first separating the sample components in gels by electrophoresis, followed by transfer of the electrophoretically separated components from the gels to transfer membranes that are made of materials such as nitrocellulose, polyvinylidene fluoride (PVDF), or Nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers.

In a further embodiment the detection can be completed using an ELISA assay, which uses a solid-phase enzyme immunoassay to detect the presence of a substance, usually an antigen, in a liquid sample or wet sample. Antigens from the sample are attached to a surface of a plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate.

Transgenic Plants

In an embodiment, a plant, plant tissue, plant seed, or plant cell comprises a polynucleotide encoding the shRNA polynucleotide. In one embodiment a plant, plant tissue, or plant cell comprises the polynucleotide encoding the shRNA polynucleotide of a sequence selected from SEQ ID NOs: 1, 2, 3, 4, 5, 6, 404, 405, 406, 407, 408, 411, 413, 415, 417, 419 or 421 or a sequence that has at least 90%, 91%, 92%, 93%, 94%, 95%, 96%, 97%, 98%, 99% or 99.5% sequence identity with a sequence selected from SEQ ID NOs: 1, 2, 3, 4, 5, 6, 404, 405, 406, 407, 408, 411, 413, 415, 417, 419 or 421. In an embodiment, a plant, plant tissue, plant seed, or plant cell comprises a gene expression cassette comprising the polynucleotide encoding the shRNA polynucleotide of a sequence selected from SEQ ID NOs: 1, 2, 3, 4, 5, 6, 404, 405, 406, 407, 408, 411, 413, 415, 417, 419 or 421, or a sequence that has at least 90%, 91%, 92%, 93%, 94%, 95%, 96%, 97%, 98%, 99% or 99.5% sequence identity with a sequence selected from SEQ ID NOs: 1, 2, 3, 4, 5, 6, 404, 405, 406, 407, 408, 411, 413, 415, 417, 419 or 421. In an embodiment, a plant, plant tissue, or plant cell comprises the shRNA polynucleotide. In an embodiment, a plant, plant tissue, or plant cell consists of the shRNA polynucleotide. In an illustrative embodiment, a plant, plant tissue, plant seed, or plant cell comprises a gene expression cassette comprising the polynucleotide encoding the shRNA polynucleotide further comprising at least one other transgene or heterologous coding sequence. Such examples of the transgene or heterologous coding sequence can include an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In some instances, more than one transgene/heterologous coding sequence may be incorporated into the genome of the transformed host plant cell. Such is the case when more than one protein or shRNA-encoding DNA segment is incorporated into the genome of such a plant. In certain situations, it may be desirable to have one, two, three, four, or even more insecticidal proteins or other insecticidal proteins or nucleic acids (e.g., shRNA or miRNA or dsRNA) incorporated and stably expressed in the transformed transgenic plant.

In another embodiment the plant, plant tissue, plant seed, or plant cell comprising the polynucleotide encoding the shRNA polynucleotide is a dicotyledonous or monocotyledonous plant, seed, cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*).

In an embodiment, a plant, plant tissue, or plant cell according to the methods disclosed herein can be a dicotyledonous plant. The dicotyledonous plant, plant tissue, or plant cell can be, but is not limited to alfalfa, rapeseed, canola, Indian mustard, Ethiopian mustard, soybean, sunflower, cotton, beans, broccoli, cabbage, cauliflower, celery, cucumber, eggplant, lettuce; melon, pea, pepper, peanut, potato, pumpkin, radish, spinach, sugarbeet, sunflower, tobacco, tomato, and watermelon.

In an embodiment, a plant, plant tissue, or plant cell according to the methods disclosed herein can be a monocotyledonous plant. The monocotyledonous plant, plant tissue, or plant cell can be, but is not limited to various turf grasses, wheat, corn, rice, barley, oats, and species of the genus brachypodium.

In accordance with one embodiment the gene expression cassette comprising the polynucleotide encoding the shRNA polynucleotide is incorporated into the genome of the plant, plant tissue, plant seed, or plant cell. One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed. For example, two different transgenic plants can be mated to produce offspring that contain two independently segregating transgenes/heterologous shRNA coding sequences. Selfing of appropriate progeny can produce plants that are homozygous for both transgenes/heterologous coding sequences that encode a shRNA of interest. Back-crossing to a parental plant and out-crossing with a non-transgenic plant are also contemplated. The result of back-crossing produces a transgenic progeny plant that is homozygous for transgenes/heterologous coding sequences. A homozygous transgenic plant can be obtained by sexually mating (selfing) an independent segregant transgenic plant that contains a single added gene, germinating some of the seed produced and analyzing the resulting plants produced for enhanced insecticidal activity resulting in insect growth inhibition and mortality relative to a control (native, non-transgenic) or an independent segregant transgenic plant.

The present disclosure also encompasses seeds of the transgenic plants described above, wherein the seed has the transgene/heterologous coding sequence of the shRNA polynucleotide as provided in the subject disclosure. The present disclosure further encompasses the progeny, clones, callous cultures, cell lines or cells of the transgenic plants described above wherein said progeny, clone, callous cultures, cell line or cell has the transgene/heterologous coding sequence or gene construct containing the shRNA polynucleotide of the subject disclosure.

The present disclosure also encompasses the regeneration, development, and production of plants from transformants or from various transformed explants. Such methodology is well known in the art. This regeneration and growth process typically includes the steps of selection of transformed cells, culturing those individualized cells through the usual stages of embryonic development through the rooted plantlet stage. Transgenic embryos and seeds can also be similarly regenerated. The resulting transgenic rooted shoots are thereafter planted in an appropriate plant growth medium such as soil.

The development or regeneration of plants containing the transgene/heterologous coding sequence of the polynucleotide encoding the shRNA polynucleotide can be achieved by methods well known in the art. In this procedure, transformants are cultured in the presence of a selection agent and in a medium that induces the regeneration of shoots in the plant being transformed as described. This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant employed, such variations being well known in the art.

In some instances the regenerated plants are self-pollinated to provide homozygous transgenic plants, as discussed before. Otherwise, pollen obtained from the regenerated plants is crossed to seed-grown plants of agronomically important lines, such as elite inbred lines. Conversely, pollen from plants of those agronomically important lines is used to pollinate regenerated plants. A transgenic plant of the subject disclosure containing the transgene/heterologous coding sequence of the polynucleotide encoding the shRNA polynucleotide is produced using methods well known to one skilled in the art.

A transgenic plant of the subject disclosure contains a stably integrated transgene/heterologous coding sequence that encodes the polynucleotide encoding the shRNA molecule. In an embodiment the transgenic plant is an independent segregant and can transmit that gene and its activity to its progeny. In further embodiments the transgenic plant is homozygous for that gene, and transmits that gene to all of its offspring through sexual mating. Seed from a transgenic plant may be grown in the crop field or greenhouse, and resulting sexually mature transgenic plants are self-pollinated to generate true breeding plants. The progeny from these plants become true breeding lines that are evaluated for, by way of example, increased insecticidal activity against insect pests resulting in insect growth inhibition and mortality, for example in the crop field, under a range of environmental conditions. Such methodology will find particular utility in the creation of transgenic plants of commercial interest.

The present disclosure also encompasses the cultivation of transgenic plants described above, wherein the transgenic plant has the transgene/heterologous coding sequence of the polynucleotide encoding the shRNA molecule as provided in the subject disclosure. Accordingly, such transgenic plants may be engineered to, inter alia, have one or more desired traits or transgenic events containing the gene regulatory elements of the subject disclosure, by being transformed with nucleic acid molecules according to the disclosure, and may be cropped or cultivated by any method known to those of skill in the art.

Method of Expressing a Transgene

In an embodiment, a method of expressing the polynucleotide sequence of interest within a plant comprises growing a plant containing a gene encoding the shRNA polynucleotide operably linked to at least one regulatory element or a polylinker sequence. In an embodiment the gene encoding the shRNA polynucleotide consists of a sequence selected from SEQ ID NOs: 1, 2, 3, 4, 5, 6, 404, 405, 406, 407, 408, 411, 413, 415, 417, 419 or 421 or a sequence that has at least 90%, 91%, 92%, 93%, 94%, 95%, 96%, 97%, 98%, 99% or 99.5% sequence identity with a sequence selected from SEQ ID NOs: 1, 2, 3, 4, 5, 6, 404, 405, 406, 407, 408, 411, 413, 415, 417, 419 or 421. In an embodiment, a method of expressing at least one polynucleotide sequence of interest in a plant tissue or plant cell comprising culturing a plant tissue or plant cell containing a gene encoding the shRNA polynucleotide operably linked to at least one transgene. In a further embodiment, a method of expressing a gene encoding the shRNA polynucleotide contained within a plant results in protecting the plant from an insect pest.

In an embodiment, a method of expressing the polynucleotide sequence of interest within a plant comprises growing a plant containing a gene expression cassette comprising a gene encoding the shRNA polynucleotide operably linked to at least one regulatory element or a polylinker sequence. In an embodiment the gene expression cassette comprising a gene encoding the shRNA polynucleotide comprises a sequence selected from SEQ ID NOs: 1, 2, 3, 4, 5, 6, 404, 405, 406, 407, 408, 411, 413, 415, 417, 419 or 421 or a sequence that has at least 90%, 91%, 92%, 93%, 94%, 95%, 96%, 97%, 98%, 99% or 99.5% sequence identity with a sequence selected from shRNA molecule of SEQ ID NOs: 1, 2, 3, 4, 5, 6, 404, 405, 406, 407, 408, 411, 413, 415, 417, 419 or 421. In an embodiment the gene expression cassette comprising a gene encoding the shRNA polynucleotide consists of a sequence selected from SEQ ID NOs: 1, 2, 3, 4, 5, 6, 404, 405, 406, 407, 408, 411, 413, 415, 417, 419 or 421 or a sequence that has at least 90%, 91%, 92%, 93%, 94%, 95%, 96%, 97%, 98%, 99% or 99.5% sequence identity with a sequence selected from shRNA molecule of SEQ ID NOs: 1, 2, 3, 4, 5, 6, 404, 405, 406, 407, 408, 411, 413, 415, 417, 419 or 421. In an embodiment, a method of expressing at least one polynucleotide sequence of interest in a plant tissue or plant cell comprises culturing a plant tissue or plant cell containing a gene expression cassette comprising a gene encoding the shRNA polynucleotide operably linked to at least one transgene. In a further embodiment, the method of expressing a gene encoding the shRNA polynucleotide from a gene expression cassette contained within a plant results in protecting the plant from an insect pest by inhibiting growth or killing the insect pest.

In an embodiment, a method of expressing the polynucleotide sequence of interest within a microorganism comprises growing a microorganism containing a gene expression cassette comprising a gene encoding the shRNA polynucleotide operably linked to at least one regulatory element or a polylinker sequence. In an embodiment the gene expression cassette comprising a gene encoding the shRNA polynucleotide comprises a sequence selected from SEQ ID NOs: 1, 2, 3, 4, 5, 6, 404, 405, 406, 407, 408, 411, 413, 415, 417, 419 or 421 or a sequence that has at least 90%, 91%, 92%, 93%, 94%, 95%, 96%, 97%, 98%, 99% or 99.5% sequence identity with a sequence selected from a SEQ ID NOs: 1, 2, 3, 4, 5, 6, 404, 405, 406, 407, 408, 411, 413, 415, 417, 419 or 421. In an embodiment the gene expression cassette comprising a gene encoding the shRNA polynucleotide consists of a sequence selected from SEQ ID NOs: 1, 2, 3, 4, 5, 6, 404, 405, 406, 407, 408, 411, 413, 415, 417, 419 or 421 or a sequence that has at least 90%, 91%, 92%, 93%, 94%, 95%, 96%, 97%, 98%, 99% or 99.5% sequence identity with a sequence selected from a SEQ ID NOs: 1, 2, 3, 4, 5, 6, 404, 405, 406, 407, 408, 411, 413, 415, 417, 419 or 421. In an embodiment, a method of expressing at least one polynucleotide sequence of interest in a plant comprises culturing a plant tissue or plant cell containing a gene expression cassette comprising a gene encoding the shRNA polynucleotide operably linked to at least one transgene. In a further embodiment, the method of expressing a gene encoding the shRNA polynucleotide from a gene expression cassette contained within a microorganism results in producing a shRNA with insecticidal activity.

In some embodiment the gene encoding the shRNA polynucleotide is expressed in the plant, plant cell, plant part, or plant seed in a constitutive manner. In an aspect of such an embodiment, the constitutive expression directs transcription in most or all tissues at all time. Accordingly, the constitutive expression is more or less at a steady state level throughout development. In other embodiments, the gene encoding the shRNA polynucleotide is expressed in the plant, plant cell, plant part, or plant seed in a tissue preferred manner. In an aspect of such an embodiment, the tissue preferred expression is expressed in only certain tissue types or at certain times during development.

In a Microbial Cell

In an embodiment, a microbial cell comprises a polynucleotide encoding the shRNA polynucleotide. In one embodiment a microbial cell comprises the polynucleotide encoding the shRNA polynucleotide of a sequence selected from SEQ ID NOs: 1, 2, 3, 4, 5, 6, 404, 405, 406, 407, 408, 411, 413, 415, 417, 419 or 421 or a sequence that has at least 90%, 91%, 92%, 93%, 94%, 95%, 96%, 97%, 98%, 99% or 99.5% sequence identity with a sequence selected from SEQ ID NOs: 1, 2, 3, 4, 5, 6, 404, 405, 406, 407, 408, 411, 413, 415, 417, 419 or 421. In an embodiment, a microbial cell comprises a gene expression cassette comprising the polynucleotide encoding the shRNA polynucleotide of a sequence selected from SEQ ID NOs: 1, 2, 3, 4, 5, 6, 404, 405, 406, 407, 408, 411, 413, 415, 417, 419 or 421, or a sequence that has at least 90%, 91%, 92%, 93%, 94%, 95%, 96%, 97%, 98%, 99% or 99.5% sequence identity with a sequence selected from SEQ ID NOs: 1, 2, 3, 4, 5, 6, 404, 405, 406, 407, 408, 411, 413, 415, 417, 419 or 421. In an embodiment, a microbial cell comprises the shRNA polynucleotide. In further embodiments, the microbial cell may be a bacteria, baculovirus, algae, yeast, or a fungi cell. Non-limiting examples of bacterial cells include *Pseudomonas*, *Bacillus* (including *B. megaterium*, *B. subtilis*, and *B. thuringiensis*), *Agrobacterium*, *Escherichia*, or other species of the Enterobacteraceae.

The present disclosure also encompasses microbial host cells which express a polynucleotide encoding the shRNA polynucleotide, in the soluble fraction, inclusion bodies or crystals, culture supernatant, disrupted cells, cell extracts, lysates, homogenates, and the like. The bacterial host cells may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing the shRNA polynucleotide are well-known to those of skill in the art of microbial shRNA isolation and purification. In certain embodiments, the shRNA molecules may be purified, concentrated, admixed with other reagents, or processed to a desired final form. In some embodiments, the composition will comprise from about 1% to about 90% by weight of the cell lysate, and in other embodiments from about 5%, to about 50% by weight.

The present disclosure also encompasses shRNA compositions that are prepared by a process which comprises the steps of culturing a microbial cell. The microbial cells are engineered to express a polynucleotide encoding the shRNA polynucleotide under conditions effective to produce such a shRNA, and then obtaining the shRNA from the cell. The obtaining of such a shRNA may further include purifying, concentrating, processing, or mixing the shRNA with one or more reagents. In some embodiments, the shRNA polynucleotide is obtained in an amount of from between about 1% to about 90% by weight and in other embodiments from about 5% to about 50% by weight.

Composition

In an embodiment, the subject disclosure includes a composition comprising the shRNA polynucleotide. In one embodiment a composition comprises the polynucleotide encoding the shRNA polynucleotide of a sequence selected from SEQ ID NOs: 1, 2, 3, 4, 5, 6, 404, 405, 406, 407, 408, 411, 413, 415, 417, 419 or 421 or a sequence that has at least 90%, 91%, 92%, 93%, 94%, 95%, 96%, 97%, 98%, 99% or 99.5% sequence identity with a sequence selected SEQ ID NOs: 1, 2, 3, 4, 5, 6, 404, 405, 406, 407, 408, 411, 413, 415, 417, 419 or 421. In an embodiment, a composition comprises a gene expression cassette comprising the polynucleotide encoding the shRNA polynucleotide of a sequence selected from SEQ ID NOs: 1, 2, 3, 4, 5, 6, 404, 405, 406, 407, 408, 411, 413, 415, 417, 419 or 421, or a sequence that has at least 90%, 91%, 92%, 93%, 94%, 95%, 96%, 97%, 98%, 99% or 99.5% sequence identity with a sequence selected from SEQ ID NOs: 1, 2, 3, 4, 5, 6, 404, 405, 406, 407, 408, 411, 413, 415, 417, 419 or 421. In an embodiment, a composition comprises the shRNA polynucleotide.

In certain embodiments, the subject disclosure relates to a method of preparing a composition comprising the shRNA polynucleotide. Such a method generally involves the steps of culturing a microbial cell which expresses the shRNA polynucleotide under conditions effective to produce the shRNA, and then obtaining the shRNA so produced. Prokaryotic host cells including Gram-negative cells such as *E. coli, Pseudomonas fluorescens* and related Enterobacteraceae, or Gram-positive cells such as *Bacillus* spp. (including *B. megaterium, B. subtilis,* and *B. thuringiensis*) and the like are all contemplated to be useful in the preparation of the shRNA polynucleotide of the subject disclosure.

Alternatively, the compositions may be prepared by native or recombinant bacterial expression systems in vitro and isolated for subsequent crop field application. Such shRNA may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the shRNA polynucleotide and apply solutions, suspensions, or colloidal preparations of such crystals and/or spores as the active bioinsecticidal composition.

The compostion comprising the shRNA polynucleotide described herein may be made by formulating the bacterial cell, crystal and/or spore suspension, or isolated shRNA component with the desired agriculturally-acceptable carrier. The compostion comprising the shRNA polynucleotide may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques. Likewise the formulation may be mixed with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

In some embodiments the compostion comprising the shRNA polynucleotide can be applied in the form of compositions and can be applied to the crop field or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying the compostion comprising the shRNA polynucleotide include leaf application, seed coating and soil application. Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art. The compositions of the subject disclosure are applied to the environment of the target insect, typically onto the foliage and in the rhizosphere (the soil surrounding plant roots) of the plant or crop to be protected, by conventional methods, for example by spraying.

In further embodiments of the subject disclosure, the compositions comprising the shRNA polynucleotide of the subject disclosure will find particular utility as insecticides for topical or systemic application to crops, grasses, fruits and vegetables, and ornamental plants. In an embodiment, the composition comprises an oil flowable suspension of bacterial cells which expresses a novel shRNA polynucleotide as disclosed herein. For example, the bacterial host cell expresses the novel nucleic acid segments disclosed herein and produce a shRNA polynucleotide.

In another embodiment, the compostion comprising the shRNA polynucleotide is provided as a water dispersible granule. This granule comprises bacterial cells which expresses a novel shRNA polynucleotide as disclosed herein. Exemplary bacterial cells include *B. thuringiensis, B. megaterium, B. subtilis, E. coli*, or *Pseudomonas* spp. cells that have been transformed with a DNA segment disclosed herein and expressing the shRNA are also contemplated to be useful.

In a further embodiment, the compostion comprising the shRNA polynucleotide is provided as a powder, dust, pellet, or collodial concentrate. This form of composition comprises bacterial cells which expresses a novel shRNA polynucleotide as disclosed herein. Such dry forms of the insecticidal compositions may be formulated to dissolve immediately upon wetting, or alternatively, dissolve in a controlled-release, sustained release, or other time-dependent manner. Exemplary bacterial cells include *B. thuringiensis, B. megaterium, B. subtilis, E. coli*, or *Pseudomonas* spp. cells that have been transformed with a DNA segment disclosed herein and expressing the shRNA polynucleotide are also contemplated to be useful.

In yet another embodiment, the compostion comprising the shRNA polynucleotide is provided as an aqueous suspension of bacterial cells such as those described above which express the shRNA polynucleotide. Such aqueous suspensions may be provided as a concentrated stock solution which is diluted prior to application, or alternatively, as a diluted solution ready-to-apply.

The composition of the subject disclosure may be employed in the method of the disclosure singly or in combination with other compounds, including and not limited to other pesticides. These methods may also be used in conjunction with other treatments such as surfactants, detergents, polymers or time-release formulations. The insecticidal compositions of the present disclosure may be formulated for either systemic or topical use.

In other embodiments of the subject disclosure, the plants can also be treated by the shRNA polynucleotide with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus* thuriengiensis, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinetofuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, lndoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, 1provalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, loxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, 2,4-D, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, lndoxacarb, Spinosad, Sulfoxaflor, Oxamyl or combinations thereof.

Regardless of the method of application or the content of the composition, the amount of the active component(s) are applied at an insecticidally-effective amount, which will vary depending on such factors as, for example, the specific insects to be controlled, the specific plant or crop to be treated, the environmental conditions, and the method, rate, and quantity of application of the insecticidally-active composition. Such that the shRNA polynucleotide inhibits a target gene of an insect pest by suppressing the expression of the target mRNA of an insect pest. The number of applications and the rate of application depend on the intensity of infestation by the corresponding pest. Likewise, the strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the composition, as well as the particular formulation contemplated.

The concentration of composition which is used for environmental, systemic, or soil application will vary widely depending upon the nature of the particular formulation, means of application, environmental conditions, and degree of biocidal activity. Typically, the composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. In other instances, the composition may be administered to a particular plant or target area in one or more applications as needed, with a typical crop field application rate per hectare ranging on the order of from about 50 g to about 500 g of active ingredient, or of from about 500 g to about 1000 g, or of from about 1000 g to about 5000 g or more of active ingredient.

Commodity Product

In an embodiment, the subject disclosure includes a commodity product. In certain aspects the commodity product is produced within the transgenic plant of the subject disclosure. Exemplary commodity products include protein concentrate, protein isolate, grain, meal, flour, oil, or fiber. In other examples such commodity products may include whole or processed seeds, animal feed containing transgenic plants of the subject disclosure or transgenic plant by-products, oil, meal, flour, starch, flakes, bran, biomass and stover, and fuel products and fuel by-products when made from transgenic plants or plant parts.

Furthermore, the commodity products may be sold to consumers and may be viable or nonviable. Nonviable commodity products include but are not limited to nonviable seeds; processed seeds, seed parts, and plant parts; seeds and plant parts processed for feed or food, oil, meal, flour, flakes, bran, biomasses, and fuel products. Viable commodity products include but are not limited to seeds, plants, and plant cells. The plants comprising the polynucleotides and shRNA molecules of the subject disclosure can thus be used to manufacture any commodity product typically acquired from such a transgenic crop plant.

Insecticidal Activity

In an embodiment, the subject disclosure provides the shRNA polynucleotide which confers insecticidal activity. Also provided are the polynucleotide sequences that encode the shRNA polynucleotide. The shRNA polynucleotide resulting from transcription of these polynucleotide sequences allows for the control or death of insect pests that ingest the shRNA polynucleotide. In an aspect of this embodiment the shRNA polynucleotide is orally active in providing insecticidal activity. In further aspects, the shRNA polynucleotide may be utilized to provide insecticidal activity against insect pests, in economically important agronomic, forest, greenhouse, nursery ornamentals, food and fiber, public and animal health, domestic and commercial structure, household and stored product pests. In other aspects the shRNA polynucleotide provides toxic insecticidal activity against one or more insect pests. Examples of such insect pests include, but is not limited to, members of the Lepidoptera, Diptera, Hemiptera and Coleoptera orders or the Nematoda phylum. In some embodiments, the insecticidal activity is provided against Lepidopteran, Dipteran, Heteropteran, Nematode, Hemiptera or Coleopteran pests. In further aspects of this embodiment, the Lepidopteran, Dipteran, Heteropteran, Nematode, Hemiptera or Coleopteran pests may be killed or reduced in numbers by the methods of the disclosure.

In other embodiment of the subject disclosure, methods are provided for producing the shRNA polynucleotide and for using shRNA polynucleotide to control, inhibit growth or kill a Lepidopteran, Coleopteran, Nematode, Hemipteran and/or Dipteran pest. In some embodiments, the transgenic plants of the subject disclosure are engineered to express one or more polynucleotides encoding the shRNA polynucleotide as disclosed herein. In various embodiments, the transgenic plants further comprise one or more additional genes for insect resistance, for example, one or more additional genes for controlling Coleopteran, Lepidopteran, Hemipteran, Dipteran, and/or Nematode pests.

Exemplary shRNA polynucleotides find use in controlling, inhibiting growth or killing Lepidopteran, Dipteran, Heteropteran, Nematode, Hemiptera or Coleopteran pest populations and for producing compositions with insecticidal activity against such insects. Included as insect pests of interest are adults and nymphs.

Agronomically important species of interest from the order Lepidoptera include, but are not limited to, armyworms, cutworms, loopers, and heliothines in the family Noctuidae *Spodoptera frugiperda* JE Smith (fall arnyworm); X. exigna iHibner (beet armyworm); S. iunra Fabricius (tobacco cutworm, cluster caterpillar); *Mamestra* configuata Walker (bertha armyworm); MV *brassicae* Linnaeus (cabbage moth); Agrolis ip,silon Hufnagel (black cutworm); A. orthogonia Morrison (western cutworm); A. *subterranea* Fabricius (granulate cutworm); *Alabama argillacea* Hübner (cotton leaf worm); Triichoplusia ni Hübner (cabbage looper); *Pseudoplusia includens* Walker (soybean looper); *Anticarsia* gemnmatalis Hibner (velvetbean caterpillar); Hyypena scabra Fabricius (green cloverworm); IleIothis' virescens Fabricius (tobacco budworm); Pseudletia unipuncta I-laworth (arnyworm); Athetis inindara Barnes and Mcdunnough (rough skinned cutworm); *Euxoa* messoria Harris (darksided cutworm); *Earias insulana* Boisduval (spiny bollworm); *E. vittella* Fabricius (spotted bollworm); *Helicoverpa armigera* Hibner (American bollworm); *H. zea* Boddie (corn earworm or cotton bollworm); Melanchra picta Harris (zebra caterpillar); Egira (Xvlomny,ge,s) curialis Grote (citrus cutworm); borers, casebearers, webworms, coneworms, and skeletonizers from the family Pyralidae Ostrini nubiais Hubner (European corn borer); *Amyelois transitella* Walker (naval orangeworm); Anagasta knehniella Zeller (Mlediterranean flour moth); Cadra cautella Walker (almond moth); *Chilo suppressalis* Walker (rice stem borer); C. partellus, (sorghum borer); Corcyra cephalonica Stainton (rice nmoth); *Crambus* caliginosetlus Clemens (corn root webworm); *C. teterrellus* Zincken (bluegrass webworm); Cnaphalocrocis *medinalis* Guenee (rice leaf roller); Desina fineralis Hübner (grape leaffolder); *Diaphania* hyalinata Linnaeus (melon worm); *D. nitidalis* Stoll (pickleworm); *Diatraea grandiosella* Dyar (southwestern corn borer), 1). saccharalis Fabricius (surgarcane borer); Eoreuma loftini Dyar (Mexican rice borer); Ephestia elutella Hubner (tobacco (cacao) moth); *Galleria mellonella* Linnaeus (greater wax moth); Herpetogranmma *licarsisalis* Walker (sod webworm); Nomoeosoma electelum Hulst (sunflower moth); *Elasmopalpus lignosellus* Zeller (lesser cornstalk borer); Achroia grisella Fabriicius (lesser wax moth); Loxosege sticlicalis Linnaeus (beet webworm); Or1haga thyrisalis Walker (tea tree web moth); Maruca testulalis Geyer (bean pod borer); P/odia inteipunctella Hübner (Indian meal moth); Scirpophaga incertulas Walker (yellow stem borer); Udea rubigalis Guenee (celery leaftier); and leafrollers, budworms, seed worms, and fruit worms in the family Tortricidae Acleris gloverana Walsingham (Western blackheaded budworm); A. variana Fernald (Eastern blackheaded budworm); Arc/ips *argyrospila* Walker (fruit tree leaf roller); A. rosana Linnaeus (European leaf roller); and other *Archips* species, *Adoxophyes orana* Fischer von Rosslerstamm (summer fruit *tortrix* moth); *Cochylis hospes* Walsingham (banded sunflower moth); *Cydia* latiferreana Walsingham (filbertworm); *C. pomonella* Linnaeus (coding moth); Platynota fkavedana Clemens (variegated leafroller); P. s/ultana Walsingham (omnivorous leafroller); *Lobesia botrana* Denis & Schiffermuller (European grape vine moth); Spi/onota ocellana Denis & Schiffermuller (eyespotted bud moth); *Endopiza viteana* Clemens (grape berry moth); *Eupoecilia ambiguella* Hibner (vine moth): Bonagota salubricola Neyrick (Brazilian apple leafroller); *Grapholita molesta* Busck (oriental fruit moth); Suleima helianthana Riley (sunflower bud moth); Argrotaenia spp.; *Choristoneura* spp.

Other selected agronomic pests in the order Lepidoptera include, but are not limited to, Alsophilapometaria Harris (fall cankerworm); *Anarsia* linea/ella Zeller (peach twig borer); *Anisota* senatoria J. E Smith (orange striped oakworm); Antheraea pernyi Guerin-Meneville (Chinese Oak Tussah Moth); *Bombyx mori* Linnaeus (Silkworm); *Bucculatrix thurberiella* Busck (cotton leaf perforator); Collas eurythene Boisduval (alfalfa caterpillar); Datana infegerrima Grote & Robinson (walnut caterpillar); *Dendrolimus* s/biricus Tschetwerikov (Siberian silk moth), Ennomos subsignaria Hübner (elm spanworm); Erannis tiliaria Harris (linden looper); *Euproctis chrysorrhoea* Linnaeus (browntail moth); Harrisina americana Guerin-Meneville (grapeleaf skeletonizer); Hemileuca oliv/ae Cockrell (range caterpillar); *Hyphantria cunea* Drury (fall webworm); *Keiferia*/vcopersicella Walsingham (tomato pinworm); *Lambdina fiscellaria* fiscellaria iulst (Eastern hemlock looper); *L. fiscellaria lugubrosa* Hulst (Western hemlock looper); *Leucomca salicis* Linnaeus (satin moth); *Lymantria dispar* Linnaeus (gypsy moth); *Manduca quinquemaculata* laworth (five spotted hawk moth, tomato hornworm); *M. sexta* Haworth (tomato hornworm, tobacco hornworm); *Operophtera brumata* Linnaeus (winter moth): *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenee (omnivorous looper); *Schizura concinna* J. E Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenee; *Malacosoma* spp. and *Orgyia* spp.

Agronomically important species of interest from the order Coleoptera including weevils from the families Anthribidae, Bruchidae, and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles, and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith & Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (corn flea beetle); *Colaspis brunnea* Fabricius (grape colaspis); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)), chafers and other beetles from the family Scarabaeidae (including, but not limited to: *Popillia japonica* Newman (Japanese beetle); *Cyclocephala borealis* Arrow (northern masked chafer, white grub); *C. immaculate* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Agronomically important species from the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldfiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly); and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other *Brachycera*, mosquitoes *Aedes* spp.; *Anopheles* spp.; *Culex* spp.; black flies *Prosimulium* spp.; *Simulium* spp.; biting midges, sand flies, sciarids, and other Nematocera.

Agronomically important species of interest from the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae ortheziidae, Phoenicococcidae and Mlargarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae, and red bugs and cotton stainers from the family Pyrrhocoridae.

Other agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjurmov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid); and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolli* Bellows & Perring (silverleaf whitefly); *Dialeurodes citri* Ashmead (citrus whitefly); *Trialeurodes abutiloneus* (bandedwinged whitefly) and *T vaporariorum* Westwood (greenhouse whitefly); *Empoasca fabae* Harris (potato leafhopper); *Laodelphax striatellus* Fallen (smaller brown planthopper); *Macrolestes quadrilneatus* Forbes (aster leafhopper); *Nephotettix cinticeps* Uhler (green leafhopper); *N. nigropictus* Stçl (rice leafhopper); *Nilaparvata lugens* Stçl (brown planthopper); *Peregrinus maidis* Ashmead (corn planthopper); *Sogatella furcifera* Horvath (white-backed planthopper); *Sogatodes orizicola* Muir (rice delphacid); *Typlocyba pomaria* McAtee (white apple leafhopper); *Erythroneoura* spp. (grape leafhoppers); *Magicicada septendecim* Linnaeus (periodical cicada): *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schaffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezcra viridula* Linnaeus (southern green stink bug); *Oebalus pugnax* Fabricius (rice stink bug); *Oncopeltusfasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciafus* Reuter (whitemarked fleahopper); *Diaphnocoris chlorionis* Say (boneylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysuis ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp.; and *Cimicidae* spp.

Agronomically important species of interest from the order Acari (mites) such as *Aceria tosichella* Keifer (wheat curl mite): *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *L. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede).

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for measuring insecticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743, 477, all of which are herein incorporated by reference in their entirety. Generally, the shRNA is mixed and used in feeding assays. See, for example Marrone, et al., (1985) *J. of Economic Entomology* 78:290-293. Such assays can include contacting plants with one or more pests and determining the plant's ability to survive and/or cause the death of the pests. For each substance or organism, the insecticidally effective amount is determined empirically for each pest affected in a specific environment.

Methods for Inhibiting Growth or Killing an Insect Pest and Controlling an Insect Population. In some embodiments methods are provided for inhibiting growth or killing an insect pest, comprising contacting the insect pest with an insecticidally-effective amount of a recombinant shRNA polynucleotide. In some embodiments methods are provided for inhibiting growth or killing an insect pest, comprising contacting the insect pest with an insecticidally-effective amount of a recombinant pesticidal shRNA molecule of SEQ ID NOs: 1, 2, 3, 4, 5, 6, 404, 405, 406, 407, 408, 411, 413, 415, 417, 419 or 421 or a variant thereof.

In some embodiments methods are provided for controlling an insect pest population, comprising contacting the insect pest population with an insecticidally-effective amount of a recombinant shRNA polynucleotide. In some embodiments methods are provided for controlling an insect pest population, comprising contacting the insect pest population with an insecticidally-effective amount of a recombinant pesticidal shRNA molecule of SEQ ID NOs: 1, 2,3, 4, 5,6, 404,405,406,407,408,411,413,415,417,419 or 421 or a variant thereof.

In some embodiments methods are provided for controlling an insect pest population resistant to a pesticidal shRNA, comprising contacting the insect pest population with an insecticidally-effective amount of a recombinant shRNA polynucleotide. In some embodiments methods are provided for controlling an insect pest population resistant to a pesticidal shRNA, comprising contacting the insect pest population with an insecticidally-effective amount of a recombinant pesticidal shRNA polynucleotide of SEQ ID NOs: 1, 2, 3, 4, 5, 6, 404, 405, 406, 407, 408, 411, 413, 415, 417, 419 or 421 or a variant thereof.

In some embodiments methods are provided for protecting a plant from an insect pest, comprising expressing in the plant or cell thereof a recombinant shRNA polynucleotide. In some embodiments methods are provided for protecting a plant from an insect pest, comprising expressing in the plant or cell thereof a recombinant pesticidal shRNA molecule of SEQ ID NOs: 1, 2, 3, 4, 5, 6, 404, 405, 406, 407, 408, 411, 413, 415, 417, 419 or 421 or variants thereof.

Insect Resistance Management (IRM) Strategies

One way to increase the effectiveness of transgenic insect resistance traits against target insect pests and contemporaneously reduce the development of insecticide-resistant pests is to use or provide non-transgenic (i.e., non-insecticidal protein or shRNA) refuges (a section of non-insecticidal crops/corn). The United States Environmental Protection Agency (epa.gov/oppbppdl/biopesticides/pips/bt_corn_refuge-2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insect pests within the refuge area, larger refuges may reduce overall yield.

Another way to increase the effectiveness of the transgenic insect resistance traits against target insect pests and contemporaneously reduce the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of insect resistance to transgenic plants. This is based on the principle that evolution of resistance against two separate modes of action is far more unlikely than only one. Roush for example, outlines two-toxin strategies, also called "pyramiding" or "stacking," for management of insecticidal transgenic crops. (The Royal Society. Phil. Trans. R. Soc. Lond. B. (1998) 353:777-1786). Stacking or pyramiding of two different insecticidal molecules each effective against the target pests and with little or no cross-resistance can allow for use of a smaller refuge. The U.S. Environmental Protection Agency requires significantly less (generally 5%) structured refuge of non-Bt corn be planted than for single trait products (generally 20%). There are various ways of providing the insect resistance management effects of a refuge, including various geometric planting patterns in the crop fields and in-bag seed mixtures, as discussed further by Roush.

In some embodiments the shRNA polynucleotide of the subject disclosure is useful as an insect resistance management strategy in combination (i.e., pyramided) with other insecticidal molecules include but are not limited to Bt toxins, Xenorhabdus sp. or *Photorhabdus* sp. insecticidal proteins, small RNA molecules, and the like. In such an embodiment, the yield of the plant is significantly increased.

Provided are methods of controlling Lepidopteran, Dipteran, Heteropteran, Nematode, Hemiptera or Coleopteran insect infestation(s) in a transgenic plant that promote insect resistance management, comprising expressing in the plant at least two different insecticidal molecules having different modes of action. In such an embodiment, the yield of the plant is significantly increased.

In some embodiments the methods of controlling Lepidopteran, Dipteran, Heteropteran, Nematode, Hemiptera and/or Coleopteran insect infestation in a transgenic plant and promoting insect resistance management wherein at least one of the insecticidal molecules comprise a shRNA polynucleotide with insecticidal activity to insects in the Order Lepidopteran, Dipteran, Heteropteran, Nematode, Hemiptera and/or Coleopteran. In such an embodiment, the yield of the plant is significantly increased.

In some embodiments the methods of controlling Lepidopteran, Dipteran, Heteropteran, Nematode, Hemiptera and/or Coleopteran insect infestation in a transgenic plant and promoting insect resistance management at least one of the insecticidal molecules comprises a shRNA molecule of SEQ ID NOs: 1, 2, 3, 4, 5, 6, 404, 405, 406, 407, 408, 411, 413, 415, 417, 419 or 421 or variants thereof, with insecticidal activity to insects in the order Lepidopteran, Dipteran, Heteropteran, Nematode, Hemiptera and/or Coleopteran. In such an embodiment, the yield of the plant is significantly increased.

In some embodiments the methods of controlling Lepidopteran, Dipteran, Heteropteran, Nematode, Hemiptera and/or Coleopteran insect infestation in a transgenic plant and promoting insect resistance management comprise expressing in the transgenic plant a shRNA polynucleotide and a Cry protein with insecticidal activity to insects in the order Lepidopteran, Dipteran, Heteropteran, Nematode, Hemiptera and/or Coleopteran having different modes of action. In such an embodiment, the yield of the plant is significantly increased.

In some embodiments the methods of controlling Lepidopteran, Dipteran, Heteropteran, Nematode, Hemiptera and/or Coleopteran insect infestation in a transgenic plant and promoting insect resistance management comprise in the transgenic plant a shRNA molecule of SEQ ID NOs: 1, 2, 3, 4, 5, 6, 404, 405, 406, 407, 408, 411, 413, 415, 417, 419 or 421 or variants thereof and a Cry protein with insecticidal activity to insects in the order Lepidopteran, Dipteran, Heteropteran, Nematode, Hemiptera and/or Coleopteran having different modes of action. In such an embodiment, the yield of the plant is significantly increased.

Also provided are methods of reducing likelihood of emergence of Lepidopteran, Dipteran, Heteropteran, Nematode, Hemiptera and/or Coleopteran insect resistance to transgenic plants expressing in the plants insecticidal molecules to control the insect species, comprising expression of a shRNA polynucleotide with insecticidal activity to the insect species in combination with a second insecticidal molecule to the insect species having different modes of action. In such an embodiment, the yield of the plant is significantly increased.

Also provided are methods of reducing likelihood of emergence of Lepidopteran, Dipteran, Heteropteran, Nematode, Hemiptera and/or Coleopteran insect resistance to transgenic plants expressing in the plants insecticidal molecules to control the insect species, comprising expression of a shRNA molecule of SEQ ID NOs: 1, 2, 3, 4, 5, 6, 404, 405, 406, 407, 408, 411, 413, 415, 417, 419 or 421 or variants thereof, with insecticidal activity to the insect species in combination with a second insecticidal molecule to the insect species having different modes of action. In such an embodiment, the yield of the plant is significantly increased.

Also provided herein are means for effective Lepidopteran, Dipteran, Heteropteran, Nematode, Hemiptera and/or Coleopteran insect resistance management of transgenic plants, comprising co-expressing at in the plants two or more insecticidal molecules toxic to Lepidoptera and/or Hemiptera insects but each exhibiting a different mode of effectuating its inhibiting growth or killing activity, wherein the two or more insecticidal molecules comprise a shRNA polynucleotide and a Cry protein. Also provided are means for insect resistance management of transgenic plants, comprising co-expressing in the plants two or more insecticidal molecules toxic to Lepidopteran, Dipteran, Heteropteran, Nematode, Hemiptera and/or Coleopteran insects but each exhibiting a different mode of effectuating its inhibiting growth or activity, wherein the two or more insecticidal molecules comprise a shRNA molecule of SEQ ID NOs: 1, 2, 3, 4, 5, 6, 404, 405, 406, 407, 408, 411, 413, 415, 417, 419 or 421 or variants thereof and a Cry protein. In such an embodiment, the yield of the plant is significantly increased.

In addition, methods are provided for obtaining regulatory approval for planting or commercialization of plants expressing molecules insecticidal to insects in the order Lepidopteran, Dipteran, Heteropteran, Nematode, Hemiptera and/or Coleopteran, comprising the step of referring to, submitting or relying on insect assay binding data showing that the shRNA polynucleotide does not compete with binding sites for Cry proteins in such insects. In addition, methods are provided for obtaining regulatory approval for planting or commercialization of plants expressing molecules insecticidal to insects in the order Lepidopteran, Dipteran, Heteropteran, Nematode, Hemiptera and/or Coleopteran, comprising the step of referring to, submitting or relying on insect assay binding data showing that the shRNA molecule of SEQ ID NOs: 1, 2, 3, 4, 5, 6, 404, 405, 406, 407, 408, 411, 413, 415, 417, 419 or 421 or a variant thereof does not compete with binding sites for Cry proteins in such insects. In such an embodiment, the yield of the plant is significantly increased.

The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) Plant Biotech Journal 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one insecticidal molecules well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Insecticidal molecules also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Insecticidal molecules also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Insecticidal molecules also include toxin complex (TC) proteins, obtainable from organisms such as Xenorhabdus, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus*, Xenorhabdus or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Insecticidal molecules also include spider, snake and scorpion venom proteins. Examples of spider venom peptides include but are not limited to lycotoxin-1 peptides and mutants thereof (U.S. Pat. No. 8,334,366). In such an embodiment, the yield of the plant is significantly increased.

In a further embodiment, a method of expressing a gene encoding the shRNA polynucleotide within a plant results in protecting the plant from an insect pest via suppressing the expression of the target mRNA of an insect pest. In such an embodiment, the yield of the plant is significantly increased.

The following examples are provided to illustrate certain particular features and/or embodiments. The examples should not be construed to limit the disclosure to the particular features or embodiments exemplified.

EXAMPLES

Example 1: shRNA Molecules Contain Novel Structural Features

A novel short/small hairpin (shRNA) molecule was designed and developed to inhibit RNA transcribed from an expressed gene within a living cell of an organism. In some embodiments, the shRNA molecule is a single stranded polynucleotide molecule that is less than 70 nucleotides (i.e., <70 nt) in length. In other embodiments, the shRNA molecule is a single stranded polynucleotide molecule that is less than 80 nucleotides (i.e., <80 nt) in length. In further embodiments, the shRNA molecule is a single stranded polynucleotide molecule that is less than 90 nucleotides (i.e., <90 nt) in length. The single stranded shRNA molecule forms a secondary structure known as a stem-loop structure (e. g., hairpin-loop structure). The shRNA stem-loop structure results from intramolecular nucleotide base pairing so that the single stranded shRNA molecule folds and forms base pairs with another section of the same shRNA polynucleotide strand.

The shRNA molecule contains a combination of structural features that are being described for the first time in this disclosure. The combination of the structural features that make up the shRNA molecule result to inhibit RNA within a living cell. The structural features of the shRNA are graphically depicted in FIG. 1. The first structural feature of the shRNA molecule is a hairpin structure. The second structural feature of the shRNA molecule is a polynucleotide sequence that may be recognized, bound and cleaved by the DICER enzyme. Although the shRNA molecule does contain at least one DICER recognition site, it should be noted that the shRNA molecule may not contain a DROSHA recognition site. Accordingly, the shRNA molecule may not contain a polynucleotide sequence that is recognized, bound and cleaved by the DROSHA enzyme. The third structural feature of the shRNA molecule is a double stranded stem structure. The resulting stem-loop shRNA molecule structure comprises two complete alpha-helical turns. Each of these structural features is described in further detail below.

Example 2: shRNA Molecules Contain a Hairpin Structure

The hairpin structure of the shRNA is a stretch of predominantly unpaired or single stranded nucleotides of the shRNA polynucleotide that was created when the shRNA polynucleotide folds and forms base pairs with another section of the same strand of the shRNA polynucleotide. Although the hairpin structure remains predominantly unpaired or single stranded, there may be some formation of double stranded binding between nucleotides of the shRNA within the hairpin structure. It is not improbable for double stranded fragments of a length of 1, 2, 3, 4, or 5 nucleotides to be observed within the hairpin structure of the shRNA molecule. Furthermore, there may be multiple double stranded fragments observed within the hairpin structure of the shRNA molecule. In some aspects the hairpin structure of the shRNA molecule contained unstructured polynucleotide sequences. These unstructured polynucleotide sequences within the loop structure were single-stranded bulges/mismatches of a single or multiple nucleotide(s) that did not bind to the polynucleotides of the opposite strand of the loop sequence. The single stranded bulges/mismatches presented as unbound, single stranded nucleotides that resulted from the formation of double stranded sequences directly upstream and downstream of the unstructured polynucleotide sequence. In other aspects the hairpin structure of the shRNA molecule was an unpaired, single stranded structure. The shRNA hairpin structure was designed to be less than or equal to 25 nucleotides in length (i.e., ≤25 bp). In other words the shRNA hairpin structure was designed to be a length of up to or equal to 25 nucleotides in length (i.e., ≤25 bp).

Figure 3:
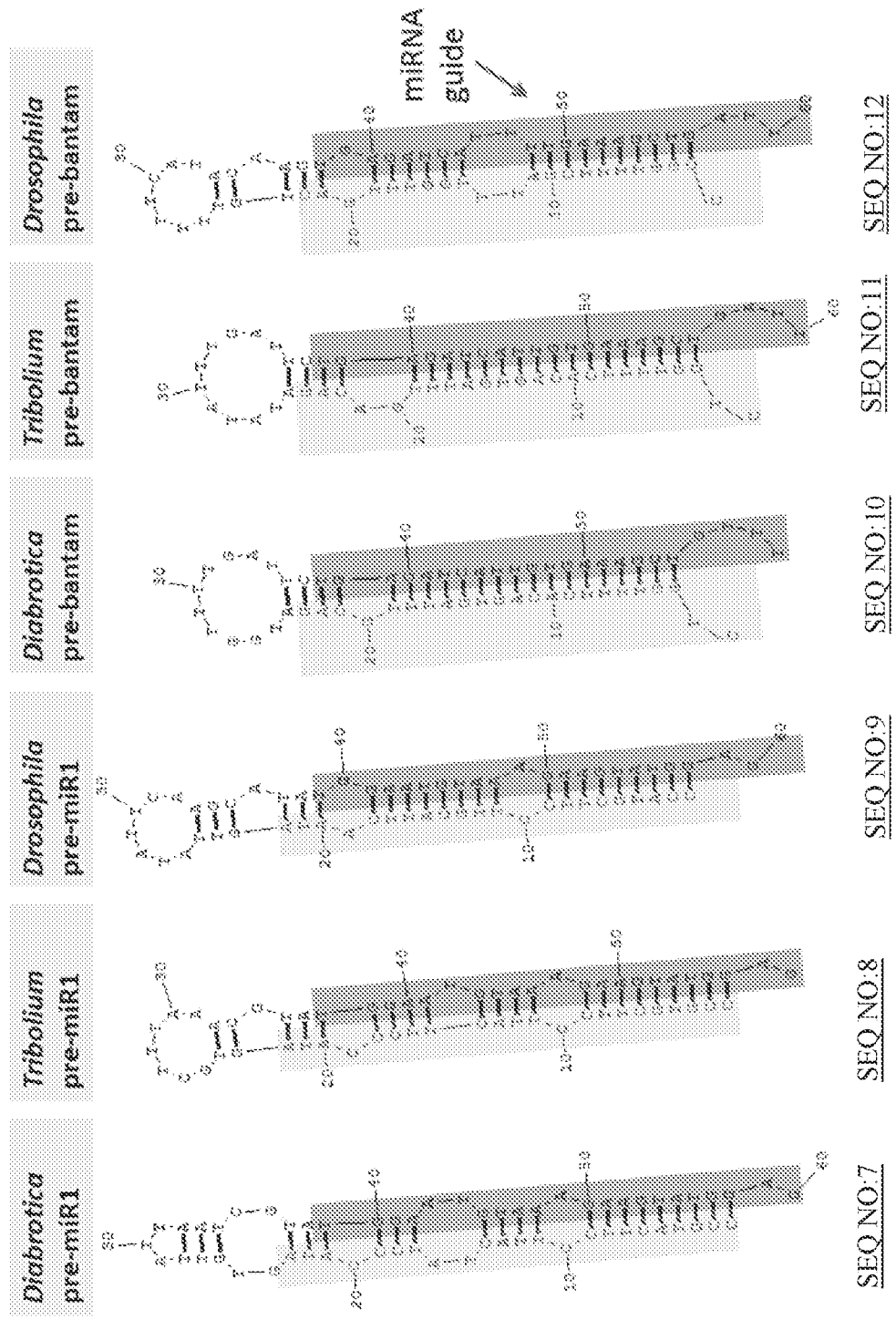
FIG. 3. This cartoon provides a schematic of the miR-1 and bantam pre-miRNA sequences from *Diabrotica, Tribolium*, and *Drosophila* that were used to identify scaffolds for the hairpin structure of the shRNA design. The sequences were identified as described in the Examples. Guide and STAR/passenger strands are highlighted. These strands were predicted based on small RNAseq abundance in miRBase (mirbase.org/which can be accessed on the world-wide web using the "www" prefix; also see Griffiths-Jones et al. (2003) *Nucleic Acids Res.*, 31:439-441). The structure of IRRNA.27482.8 is provided as SEQ ID NO:1. The structure of IRRNA.25074.6 is provided as SEQ ID NO:6. The structure of IRRNA.27480.2 is provided as SEQ ID NO:2. The structure of IRRNA.28297.1 is provided as SEQ ID NO:3. The structure of IRRNA.28298.1 is provided as SEQ ID NO:4. The structure of IRRNA.28299.1 is provided as SEQ ID NO:5. The sequences were folded using the RNA-Structure Version 5.5 computer program J. S. Reuter and D. H. Mathews (2010) *BMC Bioinformatics,* 11:129.

In some aspects the polynucleotide sequence that constitutes a portion of the shRNA loop is a shRNA scaffold. In an aspect the shRNA scaffold is identified and obtained from an insect polynucleotide sequence. In embodiments of this aspect the shRNA scaffold is identified and obtained from an insect miRNA polynucleotide sequence. For example, the shRNA scaffolds from *Diabrotica virgifera virgifera* LeConte (i.e., WCR) were identified and isolated by screening the primary transcripts of WCR with orthologous gene sequences of conserved insect miRNAs. The primary transcripts of these miRNAs were identified using a combination of small RNA sequencing, sequences from the WCR transcriptome and genome, and sequence homology to other insect species in the same subphylum (e. g., SEQ ID NOs:7-12). The small RNA sequencing data obtained from WCR were mapped to the WCR transcriptome and genome contigs to extract primary transcripts. A custom in-house pipeline was used to identify stem-loop structures that were probable pre-miRNA sequences. Conserved miRNAs in WCR were identified by sequence alignments with miRNAs from other insect species. The sequences of the other insect species were obtained from miRBase (Kozomara A, Griffiths-Jones S. "miRBase: annotating high confidence microRNAs using deep sequencing data." NAR 2014 42:D68-D73; available at mirbase.org/, which can be accessed on the world-wide web using the "www" prefix). The *Drosophila melanogaster*, Tribolium castaneum, and other arthropod miRNA precursors were obtained from mirbase.org/(which can be accessed on the world-wide web using the "www" prefix). FIG. 3 provides a graphical representation of the miRNA sequences for the miR-1 and bantam miRNA's that were obtained using this disclosed method (SEQ ID NOs:7-12). The shRNA scaffolds were identified from the folded sequences. The loop portions of scaffolds obtained from WCR (SEQ ID NOs:13-401), *Drosophila* and Tribolium were then incorporated into the hairpin structure of the shRNA polynucleotides.

Example 3: shRNA Molecules Contain a Stem Structure

The stem structure of the shRNA is a double stranded polynucleotide sequence of the single stranded shRNA polynucleotide that is created when the shRNA polynucleotide folds and forms double stranded base pairs with another section of the same strand of the shRNA polynucleotide. The stem structure remains primarily paired or double stranded, with no formation of single stranded polynucleotide sequence between nucleotides of the shRNA within the stem structure due to non-binding of the nucleotides. In some aspects the stem structure of the shRNA molecule may contain unstructured polynucleotide sequences. In other aspects the stem structure of the shRNA molecule may present entirely as a paired, double stranded structure. In further aspects the shRNA stem structure was designed to be greater than 16 nucleotides in length (i.e., >16 bp). In other aspects the shRNA stem structure was designed to be less than or equal to 25 nucleotides in length (i.e., ≤25 bp). In other words the shRNA stem structure was designed to be a length up to or equal to 25 nucleotides in length (i.e., ≤25 bp). The stem structure of the shRNA contains target polynucleotide sequences that specifically inhibit transcribed RNA from an expressed gene within a living organism.

Example 4: Identification of Candidate Target Genes

Target polynucleotide sequences that were incorporated into the stem structure of the shRNA polynucleotides were selected from dsRNA transcript regions that had been previously exemplified in alternative forms of RNAi molecules (e. g., dsRNA). These target sequences were tested to determine whether the novel shRNA structure could function to inhibit the transcribed RNA from an expressed gene within the cell of a living organism. For instance, a non-limiting list of target polynucleotide sequences include: Caf1-180 (U.S. Patent Application No. 20120174258); RPA70 (U.S. Patent Application No. 20130091601); V-ATPase H (U.S. Patent Application No. 20120198586); Rho1 (U.S. Patent Application No. US20120174260); V-ATPase C (U.S. Patent Application No. 20120174259); Reptin (U.S. Patent Application No. 20140298536); PPI-87B (U.S. Patent Application No. 20130091600); RPS6 (U.S. Patent Application No. 20130097730); COPI gamma (Patent Application No. WO2016060911); COPI alpha (Patent Application No. WO2016060912); COPI beta (Patent Application No. WO2016060913); COPI delta (Patent Application No. WO2016060914); Brahma (U.S. Patent Application Nos. 20160208251 and 20160222408); ROP (U.S. Patent Application No. 20150176025); Hunchback (U.S. Patent Application Nos. 20160222407 and 20160208252); RNA polymerase II 140 (U.S. Patent Application No. 20150176009); Sec23 (U.S. Patent Application No. 20150322455); Dre4 (U.S. Patent Application No. 20150322456); Gho (U.S. Patent Application No. 20160186203); thread (Patent Application No. WO2016191357); ncm (U.S. Patent Application No. 20160194658); RNA polymerase II-215 (U.S. Patent Application No. 20160264992); RNA polymerase I 1 (U.S. Patent Application No. 20160264991); RNA polymerase 1133 (U.S. Patent Application No. 20160355841); Kruppel (U.S. Patent Application Nos. 20160208253 and 20160369296); Spt5 (U.S. Patent Application No. 20160348130); Spt6 (U.S. Patent Application No. 2016196241); Snap25 (U.S. Patent Application No. 2017011764); and Prp8 (U.S. Patent Application No. 2017011771).

The exemplary target sequences were used to identify target sequences for the shRNA polynucleotides by analyzing the expressed target sequence present at different stages of insect development. For example, a specific target sequence would be obtained from WCR insects of different stages of development by pooling the transcriptome analysis to identify candidate target gene sequences. Candidate genes for shRNA targeting were those hypothesized to be essential for survival and growth in WCR. Selected target gene homologs were identified in the transcriptome sequence database as described in the following patent applications (U.S. Patent Application No. 20120174258; U.S. Patent Application No. 20130091601; U.S. Patent Application No. 20120198586; U.S. Patent Application No. US20120174260; U.S. Patent Application No. 20120174259; U.S. Patent Application No. 20140298536; U.S. Patent Application No. 20130091600; U.S. Patent Application No. 20130097730; Patent Application No. WO2016060911; Patent Application No. WO2016060912; Patent Application No. WO2016060913; Patent Application No. WO2016060914; U.S. Patent Application No. 20160208251; U.S. Patent Application No. 20160222408; U.S. Patent Application No. 20150176025; U.S. Patent Application No. 20160222407; U.S. Patent Application No. 20160208252; U.S. Patent Application No. 20150176009; U.S. Patent Application No. 20150322455; U.S. Patent Application No. 20150322456; U.S. Patent Application No. 20160186203; Patent Application No. WO2016191357; U.S. Patent Application No. 20160194658; U.S. Patent Application No. 20160264992; U.S. Patent Application No. 20160264991; U.S. Patent Application No. 20160355841; U.S. Patent Application No. 20160208253; U.S. Patent Application No. 20160369296; U.S. Patent Application No. 20160348130; U.S. Patent Application No. 2016196241; U.S. Patent Application No. 2017011764; and, U.S. Patent Application No. 2017011771), the disclosures of which are herein incorporated by reference in their entirety.

In one exemplification, total RNA was isolated from about 0.9 gm whole first-instar WCR larvae; (4 to 5 days post-hatch; held at 16° C.), and purified using the following phenol/TRI REAGENT®-based method (MOLECULAR RESEARCH CENTER, Cincinnati, OH). Larvae were homogenized at room temperature in a 15 mL homogenizer with 10 mL of TRI REAGENT® until a homogenous suspension was obtained. Following 5 minutes incubation at room temperature, the homogenate processed according to manufacturer's protocol. The ethanol-washed RNA pellet was allowed to air-dry for 3 to 5 minutes, and then was dissolved in nuclease-free sterile water. The RNA concentration was determined by measuring the absorbance (A) at 260 nm and 280 nm. A typical extraction from about 0.9 gm of larvae yielded over 1 mg of total RNA, with an $A_{260}/A_{280}$ ratio of 1.9. The extracted RNA was stored at −80° C. until further processed. The RNA quality was determined by running an aliquot on a 1% agarose 1×TAE gel.

A normalized cDNA library was prepared from the total larval RNA by a commercial service provider (EUROFINS MWG Operon, Huntsville, AL), using random priming. The normalized larval cDNA library was sequenced at 1/2 plate scale by GS FLX 454 Titanium™ series chemistry at EUROFINS MWG Operon, which resulted in over 600,000 reads with an average read length of 348 bp About 350,000 reads were assembled into over 50,000 contigs. Both, the unassembled reads and the contigs were converted into BLASTable databases using the publicly available program, FORMATDB (available from NCBI).

Total RNA and normalized cDNA libraries were similarly prepared from materials harvested at other WCR developmental stages. A pooled transcriptome library for target gene screening was constructed by combining cDNA library members representing the various developmental stages.

Candidate genes for shRNA targeting were those hypothesized to be essential for survival and growth in WCR. Selected target gene homologs were identified in the transcriptome sequence database as described below. TBLASTN searches using candidate protein coding sequences were run against BLASTable databases containing the unassembled WCR sequence reads or the assembled contigs. Significant hits to a WCR sequence (defined as better than $e^{-20}$ for contig homologies and better than $e^{-10}$ for unassembled sequence read homologies) were confirmed using BLASTX against the NCBI non-redundant database. The results of this BLASTX search confirmed that the WCR homolog candidate gene sequences identified in the TBLASTN search indeed comprised WCR genes, or were the best hit to the non-WCR candidate gene sequence present in the WCR sequences. In a few cases, it was clear that some of the WCR contigs or unassembled sequence reads selected by homology to a non-WCR candidate gene overlapped, and that the assembly of the contigs had failed to join these overlaps. In those cases, Sequencher™ v4.9 (GENE CODES CORPORATION, Ann Arbor, MI) was used to assemble the sequences into longer contigs.

Example 5: In Vitro Synthesis of shRNAs

The RNA synthesis for applications such as insect diet bioassays and topical plant application can be achieved by in vitro transcription of RNA from specific short promoter sequences using bacteriophage DNA-dependent RNA polymerases such as T7, T3, or Sp6. The conventional method for in vitro generation of single-stranded and double-stranded RNA involves transcription from double-stranded or partially double-stranded DNA templates (Stump and Hall (1993) Nucleic Acids Research 21 (23):5480-84). Previously, at least 18 bp of double-stranded DNA sequence within a bacteriophage promoter was believed necessary for efficient synthesis of RNA (Stump and Hall (1993) Nucleic Acids Research 21 (23):5480-84). Generation of these double-stranded DNA templates requires a PCR reaction or at least annealing of oligonucleotides.

The following approach uses single-stranded DNA templates for efficient transcription of single-stranded RNA products of up to 180 bp in length. The advantages of this approach include the elimination of PCR or a hybridization step, which saves time with similar or better comparative yield. Additionally, the use of commercially synthesized oligonucleotide DNA templates (up to 200 bp) enables the production of hairpins that are prohibitive for gene synthesis and can be problematic during PCR amplification (i.e., mispriming of the fold-back sequences).

An exemplary 200 bp single-stranded DNA includes a minimal T7 21-nucleotide promoter: (SEQ ID NO:402 TTAATACGACTCACTATAGGG), the single-stranded DNA oligonucleotide template is a reverse-and-compliment of the desired product sequence. The T7 promoter initiates transcription from the last C of the template promoter/RNA polymerase binding site, incorporating a single G into the transcript and yielding the 180 bp RNA product. In some applications the forward (F) and reverse (R) oligonucleotides were used as primers to amplify a double-stranded DNA template via PCR.

The T7 primer (SEQ ID NO:402) was incorporated into shRNA templates to enable in vitro synthesis of the shRNA. The shRNAs were synthesized using MEGAscript RNAi® kit with T7 RNA polymerase (Life Technologies, AM1626) using DNA oligonucleotide sequences for the COPIα target genes in WCR. The concentrations of shRNA molecules were measured using a NANODROP™ 8000 spectrophotometer (THERMO SCIENTIFIC, Wilmington, DE) using RNA settings. The synthesized shRNA molecules were then diluted in 0.1×TE buffer for bioassay applications.

A negative control dsRNA, of the yfp gene was synthesized with MEGAscript RNAi T7 Kit™, using PCR-amplified product as a template. The YFP template was amplified from a DNA clone comprising the coding region for yellow fluorescent protein (YFPv2; SEQ ID NO:403) (Shagin et al. (2004) Mol. Biol. Evol. 21(5):841-50). The primers designed to amplify dsRNA contained the T7 primer (SEQ ID NO:402) at their 5' ends.

Example 6: Diet-Based Insect Larval Bioassay

Samples were tested for insect activity in bioassays conducted with neonate insect larvae on artificial insect diet.

The WCR bioassays were conducted in 48-well cell culture plates Costar 3548 (Cole-Parmer|, Vernon Hills, IL). Each well contained approximately 750 µl of an artificial diet designed for growth of coleopteran insects. The shRNA samples were applied at 500 ng/cm² to the surface area of 0.95 cm² in each well (a 40 µl aliquot of shRNA sample at 11.88 ng/l was delivered by pipette onto the surface of the diet of each well). The trays were sealed with Breathe-Easy® adhesive microplate sealing membrane (Diversified Biotech). Alternatively, WCR bioassays were conducted in 128-well plastic bioassay trays (C-D International, Pitman, NJ). Each well contained approximately 1.5 ml of an artificial diet designed for growth of coleopteran insects. The dsRNA samples were applied at 500 ng/cm² to the surface area of 1.5 cm² in each well (a 60 µl aliquot of dsRNA sample at 12.5 ng/µl was delivered by sheets (C-D International, Pitman, NJ). pipette onto the surface of the diet of each well). The trays were then sealed with Pull N' Peel Tab vented adhesive plastic.

In addition to experimental samples, the samples included; YFPv2 dsRNA, 0.1×TE (Tris HCl (0.1 mM) plus EDTA (0.01 mM) buffer, pH7.2.), and water as negative controls or "Background Check" samples. Within a few hours of eclosion, individual larvae were picked up with a moistened paint brush and deposited on the treated diet (two to three larvae per well). Bioassay trays were held under controlled environmental conditions (28° C., ~40% Relative Humidity) for 9 days, after which time the total number of insects exposed to each sample, the number of dead insects, and the weight of surviving insects were recorded. Average percent mortality and average growth inhibition were calculated for each treatment. Growth inhibition (GI) was calculated as follows: $GI=[1-(TWIT/TNIT)/(TWIBC/TNIBC)]$, where TWIT is the Total Weight of live Insects in the Treatment; TNIT is the Total Number of Insects in the Treatment; TWIBC is the Total Weight of live Insects in the Background Check (Buffer control); and TNIBC is the Total Number of Insects in the Background Check (Buffer control).

Means comparisons were performed for all pairs using Tukey-Kramer HSD method in JMP®Pro 11.1.1 (SAS, Cary, NC). In some cases, $LC_{50}$ and $GI_{50}$ values were calculated. The $LC_{50}$ (Lethal Concentration) is defined as the dosage at which 50% of the test insects are killed. The $GI_{50}$ (Growth Inhibition) is defined as the dosage at which the mean growth (e. g., live weight) of the test insects is 50% of the mean value seen in Background Check samples.

Example 7: shRNA Sequences Result in Mortality and Growth Inhibition of Insects

The delivery of novel shRNAs molecules to insects via bioassay resulted in mortality and growth inhibition of the insects. It was observed that the oral delivery of the shRNA molecule caused growth inhibition of WCR in bioassay. The data generated from the bioassay experiments showed that shRNAs of less than 70 nucleotides (i.e., <70 bp) can cause both morality and growth inhibition in WCR. These results contrasted from the established precedent that dsRNA sequences of greater than 70 nucleotides (i.e., >70 bp) were necessary for oral activity in WCR. For the first time, these bioassay experiments indicated that shRNA molecules of less than 70 nucleotides are efficacious in insect species.

The following shRNA molecules contained two nucleotide 3' overhang. SEQ ID NO:1 contained the following fragments of a shRNA molecule: nucleotide position 1-23 was the stem region of COPIα sense strand which may not be identical to COPIα sequence; nucleotide position 24-38 was the loop from *Diabrotica* miR-1; nucleotide position 39-60 was the stem region of COPIα antisense strand that matched siRNA4 within COPIα v3 region (SEQ ID NO:404). SEQ ID NO:6 contained the following fragments of a shRNA molecule: nucleotide position 1-22 was the stem region of COPIα sense strand which may not be identical to COPIα sequence; nucleotide position 23-36 was the loop from Tribolium miR-1; nucleotide position 37-58 was the stem region of COPIα antisense strand that matched siRNA4 within COPIα v3 region SEQ ID NO:404).

Figure 4:
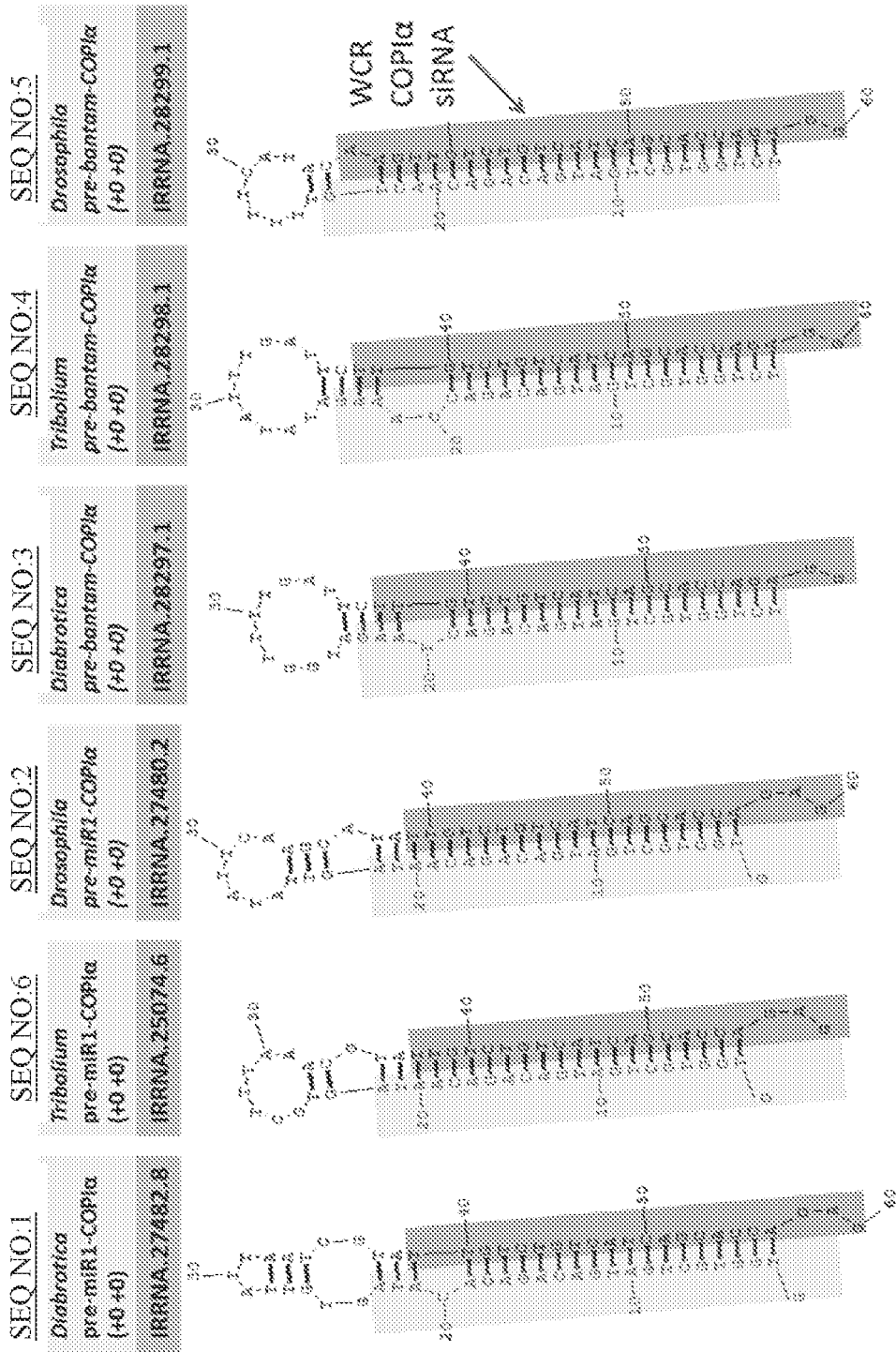
FIG. 4. This cartoon provides a schematic of the shRNA sequences designed to include the hairpin structures that were described in FIG. 3. These shRNA sequences contain a stem structure that was designed to target the endogenous COPIα gene of Western Corn Rootworm (e.g., WCR). Regarding the stem structure; the STAR strand and the antisense strand of the COPIα siRNA4 are highlighted. The hairpin structure polynucleotide sequences are not highlighted. The sequences were folded in RNAStructure Version 5.5 computer program J. S. Reuter and D. H. Mathews (2010) *BMC Bioinformatics,* 11:129.

Provided in FIG. 4 are the novel shRNA molecules that were synthesized to inhibit the COPIα target genes in WCR. The shRNA molecules contained hairpin structures comprising shRNA scaffolds obtained from the miR-1 of WCR. The data provided in Table 1 show that the shRNAs molecules caused both significant morality and growth inhibition in WCR. The shRNA molecules containing the COPIα target gene inhibited COPIα mRNA in WCR, thereby causing statistically significant growth inhibition (as indicated by the connecting letters report as shown in Table 1).

Table 1. Oral efficacy of miR-1-based shRNAs in WCR larvae. Bioassay results from diet surface treatment with 500 ng/cm² shRNA or negative control (YFPv2 dsRNA; SEQ ID NO:403) nine days after exposure. Abbreviations are as follows; N: number of replicates (each replicate represents eight wells in a 128-well rearing tray, 17 insects/replicate); SEM: standard error or the mean; GI: growth inhibition; connecting letter report from Tukey-Kramer HSD method (CLR): levels not connected by same letter are significantly different.

| SEQ ID NO | Design ID | Sample Name | N | % mortality ± SEM | GI ± SEM |
|---|---|---|---|---|---|
| 6 | IRRNA.25074.6 | Tribolium miR-1 WCR-COPIα_v3 siRNA4 + 0 + 0 | 6 | 51.02 ± 6.29 (A) | 0.87 ± 0.03 (A) |
| 1 | IRRNA.27482.8 | WCR miR-1 WCR-COPIα_v3 siRNA4 + 0 + 0 | 6 | 36.79 ± 6.42 (AB) | 0.78 ± 0.02 (A) |
| — | Control | 0.1X TE buffer | 2 | 23.53 ± 11.77 (AB) | 0.13 ± 0.12 (B) |
| — | Control | WATER | 2 | 20.59 ± 20.59 (AB) | −0.02 ± 0.25 (B) |
| 403 | Control | YFPv2 dsRNA | 2 | 2.94 ± 2.94 (B) | −0.13 ± 0.11 (B) |

In additional experiments, a set of six different shRNA molecules that contained different shRNA scaffolds were tested in bioassay. The shRNA molecules contained hairpin structures comprising shRNA scaffolds obtained from the miR-1 and bantam miRNAs of WCR, Tribolium and *Drosophila*. SEQ ID NO:2 contained the following fragments of a shRNA molecule: nucleotide position 1-22 was the stem region of COPIα sense strand, which may not be identical to COPIα sequence; nucleotide position 23-38 was the loop from *Drosophila* miR-1; nucleotide position 39-60 was the stem region of COPIα antisense strand that matched siRNA4 within COPIα v3 region (SEQ ID NO:404). SEQ ID NO:3 contained the following fragments of a shRNA molecule: nucleotide position 1-23 was the stem region of COPIα sense strand, which may not be identical to COPIα sequence; nucleotide position 24-36 was the loop from *Diabrotica* bantam; nucleotide position 37-59 was the stem region of COPIα antisense strand that matched siRNA4 within COPIα v3 region (SEQ ID NO:404). SEQ ID NO:4 contained the following fragments of a shRNA molecule: nucleotide position 1-24 was the stem region of COPIα sense strand, which may not be identical to COPIα sequence; nucleotide position 25-37 was the loop from Tribolium bantam; nucleotide position 38-60 was the stem region of COPIα antisense strand that matched siRNA4 within COPIα v3 region (SEQ ID NO:404). SEQ ID NO:5 contained the following fragments of a shRNA molecule: nucleotide position 1-23 or 1-24 was the stem region of COPIα sense strand, which may not be identical to COPIα sequence; nucleotide position 24-37 or 25-34 was the loop from Drosophila bantam; nucleotide position 36-60 or 38-60 was the stem region of COPIα antisense strand that matched COPIα v3 region (SEQ ID NO:404).

The bioassay data as shown in Table 2 indicated that the shRNA molecules produced statistically significant growth inhibition and variable levels of mortality for five out of six shRNAs tested. These results further support that the novel shRNAs molecules inhibit target RNA and result in growth inhibition of insects.

Table 2. Oral efficacy of miR-1—and bantam-based shRNAs in WCR larvae. Bioassay results [% mortality and growth inhibition (GI)] from diet surface treatment with 500 ng/cm$^2$ shRNA, dsRNA, or negative control (YFPv2 dsRNA) nine days after exposure. Abbreviations are as follows; N: number of replicates (each replicate represents eight wells in a 128-well rearing tray, 17 insects/replicate); SEM: standard error or the mean; and GI: growth inhibition. Connecting letter report from Tukey-Kramer HSD method: levels not connected by same letter are significantly different.

| SEQ ID NO | Design ID | Sample Name | N | % mortality ± SEM | Mean GI ± SEM |
|---|---|---|---|---|---|
| 1 | IRRNA.27482.8 | WCR miR-1 WCR-COPIα_v3 siRNA4 + 0 + 0 | 6 | 10.73 ± 2.83 (BC) | 0.64 ± 0.03 (B) |
| 2 | IRRNA.27480.2 | Dm miR-1 WCR-COPIα_v3 siRNA4 + 0 + 0 | 6 | 5.88 ± 2.15 (C) | 0.25 ± 0.05 (C) |
| 3 | IRRNA.28297.1 | WCR bantam WCR-COPIα_v3 siRNA4 + 0 + 0 | 6 | 19.61 ± 4.47 (ABC) | 0.71 ± 0.03 (AB) |
| 4 | IRRNA.28298.1 | Tribolium bantam WCR-COPIα_v3 siRNA4 + 0 + 0 | 6 | 16.85 4.91 (ABC) | 0.62 ± 0.06 (B) |
| 5 | IRRNA.28299.1 | Drosophila bantam WCR-COPIα_v3 siRNA4 + 0 + 0 | 6 | 35.9 ± 4.34 (A) | 0.82 ± 0.02 (AB) |
| 6 | IRRNA.25074.6 | Tribolium miR-1 WCR-COPIα_v3 siRNA4 + 0 + 0 | 6 | 27.45 ± 7.7 (AB) | 0.79 ± 0.04 (AB) |
| — | Control | 0.1 X TE Buffer | 4 | 4.41 ± 1.47 (C) | 0.05 ± 0.05 (CD) |
| — | Control | WATER | 3 | 5.88 3.39 (BC) | −0.02 ± 0.01 (D) |
| 403 | Control | YFPv2 dsRNA | 5 | 3.53 ± 1.44 (C) | −0.02 ± 0.04 (D) |

Example 8: Additional shRNA Target Sequences Result in Growth Inhibition in WCR To demonstrate efficacy of multiple shRNA targets, an additional target sequence within COPIα as well as three COPIβ target sequences were tested resulting in shRNA SEQ ID NOs:405-408. The guide sequences included COPIα region v3 siRNA1 (within SEQ ID NO:404), COPIβ region v1 siRNA1 (within SEQ ID NO:409) and COPIβ region v2 siRNA1 and siRNA2 (within SEQ ID NO:410). SEQ ID NO:405 contained the following fragments of an shRNA molecule: nucleotide position 1-23 was the stem region of COPIα sense strand, which may not be identical to COPIα sequence; nucleotide position 24-38 was the loop from *Diabrotica* miR-1; nucleotide position 39-60 was the stem region of COPIα antisense strand that matched siRNA1 within COPIα v3 region (SEQ ID NO:404). SEQ ID NO:406 contained the following fragments of an shRNA molecule: nucleotide position 1-23 was the stem region of COPIβ sense strand, which may not be identical to COPIβ sequence; nucleotide position 24-38 was the loop from *Diabrotica* miR-1; nucleotide position 39-60 was the stem region of COPIβ antisense strand that matched siRNA1 within COPIβ v1 region (SEQ ID NO:409). SEQ ID NO:407 contained the following fragments of an shRNA molecule: nucleotide position 1-23 was the stem region of COPIβ sense strand, which may not be identical to COPIβ sequence; nucleotide position 24-38 was the loop from *Diabrotica* miR-1; nucleotide position 39-60 was the stem region of COPIβ antisense strand that matched siRNA1 within COPIβ v2 region (SEQ ID NO:410). SEQ ID NO:408 contained the following fragments of an shRNA molecule: nucleotide position 1-23 was the stem region of COPIβ sense strand, which may not be identical to COPIβ sequence; nucleotide position 24-38 was the loop from *Diabrotica* miR-1; nucleotide position 39-60 was the stem region of COPIβ antisense strand that matched siRNA2 within COPIβ v2 region (SEQ ID NO:410).

Additionally, SEQ ID NO:411 can be designee to contain the following fragments of a shRNA: nucleotide position 1-23 is the stem region of v-ATPase C sense strand which may not be identical to v-ATPase C sequence; nucleotide position 24-38 is the loop from *Diabrotica* miR-1; nucleotide position 39-60 is the stem region of v-ATPase C antisense strand that matches siRNA1 within v-ATPase C (SEQ ID NO:412). SEQ ID NO:413 can be designee to contain the following fragments of a shRNA molecule: nucleotide position 1-23 is the stem region of COPIγ sense strand which may not be identical to COPIγ sequence; nucleotide position 24-38 is the loop from *Diabrotica* miR-1; nucleotide position 39-70 is the stem region of COPIγ antisense strand that matches siRNA1 within COPIγ region v4 (SEQ ID NO:414). SEQ ID NO:415 can be designee to contain the following fragments of a shRNA molecule: nucleotide position 1-23 is the stem region of COPIδ sense strand which may not be identical to COPIδ sequence; nucleotide position 24-38 is the loop from *Diabrotica* miR-1; nucleotide position 39-60 is the stem region of COPIδ antisense strand that matches siRNA2 within COPIδ region v1 (SEQ ID NO:416). SEQ ID NO:417 can be designee to contain the following fragments of a shRNA molecule: nucleotide position 1-23 is the stem region of Rab5 sense strand which may not be identical to Rab5 sequence; nucleotide position 24-38 is the loop from *Diabrotica* miR-1; nucleotide position 39-60 is the stem region of Rab5 antisense strand that matches seq4 within Rab5 region 1_v1 (SEQ ID NO:418). SEQ ID NO:419 can be designee to contain the following fragments of a shRNA molecule: nucleotide position 1-23 is the stem region of wupA sense strand which may not be identical to wupA sequence; nucleotide position 24-38 is the loop from *Diabrotica* miR-1; nucleotide position 39-60 is the stem region of wupA antisense strand that matches seq2 within wupA region 4 (SEQ ID NO:420). SEQ ID NO:421 can be designee to contain the following fragments of a shRNA molecule: nucleotide position 1-23 is the stem region of wupA sense strand which may not be identical to wupA sequence; nucleotide position 24-38 is the loop from *Diabrotica* miR-1; nucleotide position 39-60 is the stem region of wupA antisense strand that matches seq3 within wupA region 4 (SEQ ID NO:420). Additional shRNAs are designed to target sequences in EXAMPLE 4, and other essential genes from arthropod species.

Of the additional sequences tested, SEQ ID NO:406 (IRRNA.29794.3) showed both significant WCR larval mortality and growth inhibition (Table 3).

Table 3. Oral efficacy of shRNAs targeting COPIα, and COPIβ WCR larvae. Bioassay results [N mortality and growth inhibition (GI)] from diet surface treatment with 500 ng/cm$^2$ shRNA, dsRNA, or negative control (YFPv2 dsRNA) nine days after exposure. Abbreviations are as follows; N: number of replicates (each replicate represents eight wells in a 48-well format, 16 insects/replicate); SEM: standard error of the mean; and GI: growth inhibition. Connecting letter report from Tukey-Kramer HSD method: levels not connected by same letter are significantly different.

| SEQ ID NO | Design ID | Sample Name | N | % mortality ± SEM | Mean GI ± SEM |
|---|---|---|---|---|---|
| 405 | IRRNA.28112.3 | Dvv miR-1 Dvv-COPIα_v3 siRNA1 + 0 + 0 | 6 | 33.7 ± 8.4 (AB ) | 0.41 ± 0.19 (AB) |
| 1 | IRRNA.27482.8 | Dvv miR-1 Dvv-COPIα_v3 siRNA4 + 0 + 0 | 6 | 11.6 ± 3.2 (B ) | 0.14 ± 0.16 (AB) |
| 406 | IRRNA.29794.3 | Dvv miR-1 Dvv-COPIβ_v1 siRNA1 + 0 + 0 | 6 | 48.5 ± 5.2 (A ) | 0.69 ± 0.08 (A) |
| 407 | IRRNA.29796.3 | Dvv miR-1 Dvv-COPIβ_v2 siRNA1 + 0 + 0 | 6 | 12.1 ± 4.2 (B) | 0.012 ± 0.19 (B) |
| 408 | IRRNA.29797.3 | Dvv miR-1 Dvv-COPIβ_v2 siRNA2 + 0 + 0 | 5 | 24.1 ± 3.1 (AB) | 0.12 ± 0.22 (AB) |
| — | — | TE buffer | 6 | 22.8 ± 10.4 (AB) | 0.17 ± 0.10 (AB) |
| — | — | water | 6 | 17.5 ± 5.3 (B) | −0.11 ± 0.07 (B ) |
| 403 | — | YFPv2 dsRNA | 6 | 15.3 ± 4.0 (B) | −0.19 ± 0.14 (B) |

Example 9: Transgenic Plants Containing shRNA Molecules

Construction of plant transformation vectors. Gene expression cassettes containing the shRNA molecules (e.g. SEQ TD NOs:1-6, 405-408, 411, 413, 415, 417, 419, and 421) are assembled onto plasmid vectors using standard molecular cloning methods. The shRNAs comprise a stem structure separated by a hairpin structure. In some instances the shRNA is flanked by a 5' overhang and/or a 3' overhang. A promoter is cloned in directly upstream of the shRNA molecule (e.g. maize ubiquitin 1 promoter, 35S Cauliflower Mosaic Virus; Sugarcane bacilliform badnavirus promoter; promoters from rice actin genes; ubiquitin gene promoters; pEMU promoters; MAS promoter; maize H3 histone promoter; ALS promoter; phaseolin gene promoter; CAB promoter; RUBISCO promoter; LAT52 promoter; Zm13 promoter; and/or APG promoter are non-limiting examples of promoters known in the art that may be selected to drive expression of the shRNA molecule) is used to drive production of the primary mRNA shRNA molecule. Next, a 3' untranslated region (e.g., a ZmPER5 3'UTR; AtUbi103'UTR; AtEfl 3'UTR; or StPinII 3'UTR are non-limiting examples of 3'UTRs known in the art that may be selected to terminate expression of the shRNA molecule) is used to terminate transcription of the shRNA molecule. The completion of the gene expression cassettes are performed using standard molecular cloning methods and may include additional gene expression cassettes linked in trans or in cis to other gene expression cassettes that express other agronomically important traits and/or selectable markers.

Plant transformation. Further provided are non-limiting examples of plant transformation protocols for transformation of the gene expression cassettes containing the shRNA molecule. In light of the subject disclosure, additional crops can be transformed according to embodiments of the subject disclosure using techniques that are known in the art. Plant transformation of monocot plant species can be achieved. For *Agrobacterium*-mediated transformation of rye, see, e. g., Popelka J C, Xu J, Altpeter F., "Generation of rye with low transgene copy number after biolistic gene transfer and production of (*Secale cereale* L.) plants instantly marker-free transgenic rye," Transgenic Res. 2003 October; 12(5): 587-96.). For *Agrobacterium*-mediated transformation of sorghum, see, e. g., Zhao et al., "*Agrobacterium*-mediated sorghum transformation," Plant Mol Biol. 2000 December; 44(6):789-98. For *Agrobacterium*-mediated transformation of barley, see, e. g., Tingay et al., "*Agrobacterium tumefaciens*-mediated barley transformation," The Plant Journal, (1997) 11: 1369-1376. For *Agrobacterium*-mediated transformation of wheat, see, e. g., Cheng et al., "Genetic Transformation of Wheat Mediated by *Agrobacterium tumefaciens*," Plant Physiol. 1997 November; 115(3):971-980. For *Agrobacterium*-mediated transformation of tobacco, see, e. g., U.S. Pat. App. Pub. No. US 2013/0157369 A1. For *Agrobacterium*-mediated transformation of rice, see, e. g., Hiei et al., "Transformation of rice mediated by *Agrobacterium tumefaciens*," Plant Mol. Biol. 1997 September; 35(1-2):205-18. Plant transformation of dicot plant species can be achieved. For *Agrobacterium*-mediated transformation of *Arabidopsis*, see, e. g., Clough, S. J., & Bent, A. F. (1998). Floral dip: a simplified method for *Agrobacterium*-mediated transformation of *Arabidopsis thaliana*. The plant journal, 16(6), 735-743. For *Agrobacterium*-mediated transformation of cotton, see, e. g., Tohidfar, M., Mohammadi, M., & Ghareyazie, B. (2005). *Agrobacterium*-mediated transformation of cotton (*Gossypium hirsutum*) using a heterologous bean chitinase gene. Plant cell, tissue and organ culture, 83(1), 83-96. For *Agrobacterium*-mediated transformation of soybean, see, e. g., U.S. Pat. App. Pub. No. US 2014/0173780 A1. For *Agrobacterium*-mediated transformation of tobacco, see, e. g., An, G. (1985). High efficiency transformation of cultured tobacco cells. Plant Physiology, 79(2), 568-570.

Corn may be transformed with gene expression cassettes containing the shRNA molecule by utilizing the same techniques previously described in Example #8 of patent application WO 2007/053482.

Soybean may be transformed with gene expression cassettes containing the shRNA molecule by utilizing the same techniques previously described in Example #11 or Example #13 of patent application WO 2007/053482.

Cotton may be transformed gene expression cassettes containing the shRNA molecule by utilizing the same techniques previously described in Examples #14 of U.S. Pat. No. 7,838,733 or Example #12 of patent application WO 2007/053482 (Wright et al.).

Canola may be transformed with gene expression cassettes containing the shRNA molecule by utilizing the same techniques previously described in Example #26 of U.S. Pat. No. 7,838,733 or Example #22 of patent application WO 2007/053482 (Wright et al.).

Wheat may be transformed with gene expression cassettes containing the shRNA molecule by utilizing the same techniques previously described in Example #23 of patent application WO 2013/116700A1 (Lira et al.).

Rice may be transformed with gene expression cassettes containing the shRNA molecule by utilizing the same techniques previously described in Example #19 of patent application WO 2013/116700A1 (Lira et al.).

Arabidopsis may be transformed with gene expression cassettes containing the shRNA molecule by utilizing the same techniques previously described in Example #7 of patent application WO 2013/116700A1 (Lira et al.).

Tobacco may be transformed with gene expression cassettes containing the shRNA molecule by utilizing the same techniques previously described in Example #10 of patent application WO 2013/116700A1 (Lira et al.).

The Latin names for these and other plants are given below. It should be clear that other (non-*Agrobacterium*) transformation techniques can be used to transform gene expression cassettes containing the shRNA molecule, for example, into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Saccharum officinarum*), Tomato (*Lycopersicon esculentum* and other spp., *Physalis ixocarpa, Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense,* and *frutescens*), Lettuce (*Lactuca sativa, perennis,* and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (*Pisum, Vigna,* and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynodon,* and other genera), Clover (*Trifolium*), Vetch (*Vicia*). Transformation of such plants, with gene expression cassettes containing the shRNA molecule, for example, is contemplated in embodiments of the subject disclosure.

Use of the gene expression cassettes containing the shRNA molecule can be deployed in many deciduous and evergreen timber species. Such applications are also within the scope of embodiments of this disclosure. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp.), and pine (*Pinus* spp.).

Use of the gene expression cassettes containing the shRNA molecule can be deployed in ornamental and fruit-bearing species. Such applications are also within the scope of embodiments of this disclosure. Examples include, but are not limited to; rose (*Rosa* spp.), burning bush (*Euonymus* spp.), petunia (*Petunia* spp.), begonia (*Begonia* spp.), rhododendron (*Rhododendron* spp.), crabapple or apple (*Malus* spp.), pear (*Pyrus* spp.), peach (*Prunus* spp.), and marigolds (*Tagetes* spp.).

Molecular analyses. Molecular analysis of transformed plant tissues are performed on samples obtained from plants materials transformed with gene expression cassettes containing the shRNA molecule to confirm the presence and copy number of a stably integrated shRNA molecule and to quantitate the expressed quantity of shRNA being produced in the plant cell. Various assays are known in the art and can be utilized for molecular analysis of the shRNA molecule within plant material.

Insect bioassays. Bioactivity of transgenic plant material expressing the shRNA molecules of the subject disclosure is demonstrated by known bioassay methods. See, e.g., Baum et al. (2007) Nat. Biotechnol. 25(11):1322-1326. The completion of these assays allows one to demonstrate efficacy of the shRNA molecule, for example, by feeding various plant tissues or tissue pieces derived from a plant producing an insecticidal shRNA to target insects in a controlled feeding environment. Alternatively, extracts are prepared from various plant tissues derived from a plant producing the insecticidal shRNA, and the extracted nucleic acids are dispensed on top of artificial diets for bioassays. The results of such feeding assays are compared to similarly conducted bioassays that employ appropriate control tissues from host plants that do not produce a shRNA molecule, or to other control samples. Growth and survival of target insects on the transgenic plant material expressing the shRNA molecules is determined and compared to that of the control group.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

That which is claimed:

1. A small hairpin RNA (shRNA) polynucleotide less than 70 nucleotides in length, the polynucleotide comprising the following structures:

a) a hairpin structure consisting of less than or equal to 25 nucleotides, obtained from an insect microRNA scaffold, that comprises double-stranded nucleotides and single-stranded nucleotides;

b) a DICER-1 recognition and cleavage site structure; and c) a double-stranded stem structure consisting of 16-25 nucleotide pairs, wherein the two strands of the double-stranded stem structure are 100% complementary to one another;

wherein the two strands of the double-stranded stem structure (c) are connected at one end of the double-stranded stem structure via the hairpin structure (a); wherein the stem structure comprises a polynucleotide that shares 70% to 100% sequence identity with a target polynucleotide of a plant pest;

wherein the shRNA is unable to be cleaved by insect DROSHA.

2. The shRNA polynucleotide of claim 1, wherein the shRNA comprises 2 alpha-helical turns.

3. The shRNA polynucleotide of claim 1, wherein the shRNA is not recognized by insect DROSHA.

4. The shRNA polynucleotide of claim 1, wherein the hairpin structure comprises mismatches and/or bulges.

5. The shRNA polynucleotide of claim 1, wherein the insect microRNA scaffold is SEQ ID NO:7.

6. The shRNA polynucleotide of claim 1, wherein the target polynucleotide of a plant pest is selected from the group consisting of: COPI gamma, COPI alpha, COPI beta, and COPI delta.

7. The shRNA polynucleotide of claim 1, wherein the shRNA has a free energy ($\Delta G°_{37}$) of less than −30 kcal/mol.

8. The shRNA polynucleotide of claim 1, wherein the shRNA further comprises a polynucleotide overhang of at least 2 nucleotides and not more than 4 nucleotides.

9. The shRNA polynucleotide of claim 8, wherein the first nucleotide of the polynucleotide overhang is double stranded.

10. The shRNA polynucleotide of claim 8, wherein the first nucleotide of the polynucleotide overhang is single stranded.

11. The shRNA polynucleotide of claim 8, wherein the second nucleotide of the polynucleotide overhang is single stranded.

12. The shRNA polynucleotide of claim 8, wherein the third nucleotide of the polynucleotide overhang is single stranded.

* * * * *